United States Patent
Su et al.

(10) Patent No.: US 11,498,903 B2
(45) Date of Patent: Nov. 15, 2022

(54) 2-(1,1'-BIPHENYL)-1H-BENZODIMIDAZOLE DERIVATIVES AND RELATED COMPOUNDS AS APELIN AND APJ AGONISTS FOR TREATING CARDIOVASCULAR DISEASES

(71) Applicant: BRISTOL-MYERS SQUIBB COMPANY, Princeton, NJ (US)

(72) Inventors: Shun Su, Pennington, NJ (US); Hannguang J. Chao, Nashua, NH (US); Adam James Clarke, Pennington, NJ (US); R. Michael Lawrence, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/639,145

(22) PCT Filed: Aug. 16, 2018

(86) PCT No.: PCT/US2018/000311
§ 371 (c)(1),
(2) Date: Feb. 14, 2020

(87) PCT Pub. No.: WO2019/036024
PCT Pub. Date: Feb. 21, 2019

(65) Prior Publication Data
US 2020/0231547 A1    Jul. 23, 2020

Related U.S. Application Data

(60) Provisional application No. 62/546,693, filed on Aug. 17, 2017.

(51) Int. Cl.
| | | |
|---|---|---|
| *C07D 235/16* | (2006.01) | |
| *C07D 413/12* | (2006.01) | |
| *C07D 413/10* | (2006.01) | |
| *C07D 471/04* | (2006.01) | |
| *C07D 491/056* | (2006.01) | |
| *C07D 473/00* | (2006.01) | |
| *C07D 235/18* | (2006.01) | |

(52) U.S. Cl.
CPC ......... *C07D 235/16* (2013.01); *C07D 235/18* (2013.01); *C07D 413/10* (2013.01); *C07D 413/12* (2013.01); *C07D 471/04* (2013.01); *C07D 473/00* (2013.01); *C07D 491/056* (2013.01)

(58) Field of Classification Search
None
See application file for complete search history.

(56) References Cited

U.S. PATENT DOCUMENTS

| | | |
|---|---|---|
| 2004/0029920 A1 | 2/2004 | Kuduk et al. |
| 2004/0034064 A1 | 2/2004 | Kuduk et al. |
| 2004/0044041 A1 | 3/2004 | Kuduk et al. |
| 2004/0063761 A1 | 4/2004 | Kuduk et al. |
| 2005/0187277 A1 | 8/2005 | Mjalli et al. |
| 2007/0299086 A1 | 12/2007 | Kawamoto |
| 2010/0113512 A1 | 5/2010 | Ignar |

FOREIGN PATENT DOCUMENTS

| | | |
|---|---|---|
| CA | 2155275 C | 2/1996 |
| CN | 103664878_AB A | 3/2014 |
| CN | 101591299 A | 12/2019 |
| EP | 0702012 B1 | 3/1996 |
| EP | 1164135 A1 | 12/2001 |
| EP | 1903052 A2 | 3/2008 |
| EP | 2002838 A1 | 12/2008 |
| JP | 9149797 A2 | 6/1997 |
| WO | WO199415920 A1 | 7/1994 |
| WO | WO199511243 A1 | 4/1995 |
| WO | WO199515954 A1 | 6/1995 |
| WO | WO199532967 A1 | 12/1995 |
| WO | WO199619477 A1 | 6/1996 |
| WO | WO199503305 A1 | 2/1999 |
| WO | WO199938533 A1 | 8/1999 |
| WO | WO200059506 A1 | 10/2000 |
| WO | WO2001016120 A1 | 3/2001 |
| WO | WO2001049685 A1 | 7/2001 |
| WO | WO200212224 A2 | 2/2002 |
| WO | WO2002079145 A1 | 10/2002 |

(Continued)

OTHER PUBLICATIONS

Chemical Abstract Registry No. 1349265-30-0, indexed in the Registry File on STN CAS Online Dec. 5, 2011.*

*Primary Examiner* — Po-Chih Chen
(74) *Attorney, Agent, or Firm* — Hong Liu; Shrikant M. Kulkarni

(57) ABSTRACT

The present invention provides compounds of Formula (I): wherein all variables are as defined in the specification. The compounds are apelin and APJ agonists for treating cardiovascular diseases. Preferred compounds are 2-(1,1'-biphe-1H-benzo[d]imidazole derivatives. The invention further provides compositions comprising the compounds and the compounds for use in methods of medical treatment.

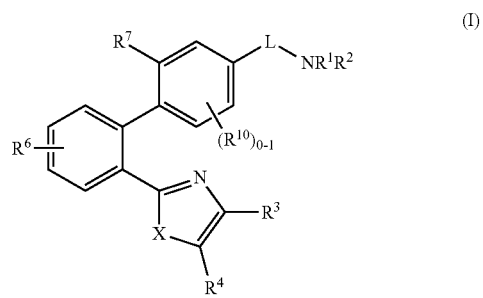

15 Claims, No Drawings

(56) References Cited

FOREIGN PATENT DOCUMENTS

| | | |
|---|---|---|
| WO | WO2003062248 A2 | 7/2003 |
| WO | WO2003062252 A1 | 7/2003 |
| WO | WO2003068756 A1 | 8/2003 |
| WO | WO2004/052488 A2 | 6/2004 |
| WO | WO2005048948 A2 | 6/2005 |
| WO | WO2005048953 A2 | 6/2005 |
| WO | WO2006002099 A2 | 1/2006 |
| WO | WO2007002563 A1 | 1/2007 |
| WO | WO2007077457 A3 | 7/2007 |
| WO | WO2008021849 A2 | 2/2008 |
| WO | WO2010091876 A2 | 8/2010 |
| WO | WO2012129562 A2 | 9/2012 |
| WO | WO2012151355 A1 | 11/2012 |
| WO | WO2013100672 A1 | 7/2013 |
| WO | WO2013106761 A2 | 7/2013 |
| WO | WO2014039042 A1 | 3/2014 |
| WO | WO2014152518 A3 | 9/2014 |
| WO | WO2014152536 A3 | 9/2014 |
| WO | WO2016109501 A1 | 7/2016 |
| WO | WO2017031213 A1 | 2/2017 |
| WO | WO2017117447 A1 | 7/2017 |

* cited by examiner

2-(1,1'-BIPHENYL)-1H-BENZODIMIDAZOLE DERIVATIVES AND RELATED COMPOUNDS AS APELIN AND APJ AGONISTS FOR TREATING CARDIOVASCULAR DISEASES

CROSS REFERENCE TO RELATED APPLICATIONS

This application is a 371 application of PCT/US2018/000311 filed Aug. 16, 2018, which is entitled to priority pursuant to 35 U.S.C. § 119(e) to U.S. provisional patent application No. 62/546,693, filed Aug. 17, 2017, which is incorporated herein in its entirety.

FIELD OF THE INVENTION

The present invention provides novel biaryl compounds, and their analogues thereof, compositions containing them, and methods of using them, for example, for the treatment or prophylaxis of heart failure, atherosclerosis, ischemic heart disease and related conditions.

BACKGROUND OF THE INVENTION

Heart failure (HF) and related complications constitute major health burden in developed countries with an estimated prevalence of 5,700,000 in the United States alone (Roger, V. L. et al., *Circulation*, 125(1):e2-e220 (2012)). Despite considerable advances in recent two decades, the prognosis remains very poor, with survival rates of only ~50% within 5-years of diagnosis (Roger, V. L. et al., *JAMA*, 292(3):344-350 (2004)). In addition to poor survival, the impaired quality of life and recurrent hospitalizations constitute clear unmet medical need for development of novel treatment options.

HF is a clinical syndrome characterized by the inability of the heart to deliver sufficient supply of blood and oxygen to meet the metabolic demands of organs in the body. Main symptoms associated with HF include shortness of breath due to pulmonary edema, fatigue, reduced tolerance to exercise and lower extremity edemas. The etiology of HF is highly complex with multiple associated risk factors and potential causes. Among the leading causes of HF are coronary artery disease and cardiac ischemia, acute myocardial infarction, intrinsic cardiomyopathies and chronic uncontrolled hypertension. HF can develop either acutely (functional impairment post myocardial infarction) or as a chronic condition, characterized by long-term maladaptive cardiac tissue remodeling, hypertrophy and cardiac dysfunction (for example due to uncontrolled long-term hypertension). According to the diagnostic criteria and type of ventricular dysfunction, HF is classified to two major groups, HF with "reduced ejection fraction" (HFrEF) or HF with "preserved ejection fraction" (HFpEF). Both types are associated with similar signs and symptoms, but differ in the type of ventricular functional impairment (Borlaug, B. A. et al., *Eur. Heart J.*, 32(6):670-679 (2011)).

APJ receptor (APLNR) and its endogenous peptidic ligand apelin have been implicated as important modulators of cardiovascular function and candidates for therapeutic intervention in HF (for review see Japp, A. G. et al., *Biochem. Pharmacol.*, 75(10): 1882-1892 (2008)).

Accumulated evidence from preclinical disease models and human heart failure patients have implicated apelin and APJ agonism as beneficial in the setting of HF. Mice lacking Apelin or APJ gene have impaired myocyte contractility (Charo, D. N. et al., *Am. J. Physiol. Heart Circ. Physiol.*, 297(5):H1904-H1913 (2009)). Apelin knockout (KO) mice develop progressive cardiac dysfunction with aging and are more susceptible to HF in the model of trans-aortic constriction (ITAC) (Kuba, K. et al., *Circ. Res.*, 101(4):e32-42 (2007)). The functional impairment in chronic HF is a result of prolonged demand on the heart and is associated with maladaptive cardiac remodeling, manifested by the cardiac hypertrophy, increased inflammation and interstitial fibrosis which eventually lead to decrease in cardiac performance. Acute administration of apelin increases cardiac output in rodents under normal conditions and also in models of heart failure (Berry, M. F., *Circulation*, 110(11 Suppl. 1):11187-11193 (2004)). Increased cardiac output is a result of direct augmentation of cardiac contractility and reduced peripheral vascular resistance in the arterial and venous beds (Ashley, E. A., *Cardiovasc. Res.*, 65(1):73-82 (2005)). Reduction in the vascular resistance leads to lower pre-load and after-load on the heart and thus lesser work load (Cheng, X. et al., *Eur. J. Pharmacol.*, 470(3):171-175 (2003)). Similar to rodent studies, acute infusion of apelin to healthy human subjects and patients with heart failure produces similar hemodynamic responses with increased cardiac output and increased vasodilatory response in peripheral and coronary arteries (Japp, A. G. et al., *Circulation*, 121(16):1818-1827 (2010)). The mechanisms underlying inotropic action of apelin are not well understood, but appear to be distinct from clinically used $\beta_1$-adrenergic agonists (dobutamine) due to lack of increase in heart rate. The vasodilatory action of apelin is primarily mediated via endothelial nitric oxide synthase pathways (Tatemoto, K., *Regul. Pept.*, 99(2-3):87-92 (2001)). Apelin is induced under hypoxic conditions, promotes angiogenesis and has been shown to limit the infarct size in ischemia-reperfusion models (Simpkin, J. C., *Basic Res. Cardiol.*, 102(6):518-528 (2007)). In addition to aforementioned studies evaluating acute administration of apelin, several studies have clearly demonstrated beneficial effects of prolonged administration of apelin in a number of chronic rodent models of HF, including the angiotensin 11 model, TAC model and rat Dahl salt-sensitive model (Siddiquee, K. et al., *J. Hypertens.*, 29(4):724-731 (2011); Scimia, M. C. et al., *Nature*, 488(7411):394-398 (2012); Koguchi, W. et al., *Circ. J.*, 76(1):137-144 (2012)). In these studies, prolonged apelin infusion reduced cardiac hypertrophy and cardiac fibrosis, and was associated with improvement in cardiac performance. Genetic evidence is also emerging that polymorphisms in the APJ gene are associated with slower progression of HF (Sarzani, R. et al., *J. Card. Fail.*, 13(7): 521-529 (2007)). Importantly, while expression of APJ and apelin can be reduced or vary considerably with HF progression, the cardiovascular hemodynamic effects of apelin are sustained in patients with developed HF and receiving standard of care therapy (Japp, A. G. et al., *Circulation*, 121(16):1818-1827 (2010)). In summary, there is a significant amount of evidence to indicate that APJ receptor agonism plays a cardioprotective role in HF and would be of potential benefit to HF patients. Apelin's very short half life in circulation limits its therapeutic utility, and consequently, there is a need for APJ receptor agonists with improved pharmacokinetic and signaling profile while maintaining or enhancing the beneficial effects of endogenous APJ agonist apelin.

SUMMARY OF THE INVENTION

The present invention provides biaryl compounds, and their analogues thereof, which are useful as APJ agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with APJ, such as heart failure, coronary artery disease, cardiomyopathy, diabetes and related conditions including but not limited to acute coronary syndrome, myocardial ischemia, hypertension, pulmonary hypertension, coronary vasospasm, cerebral vasospasm, ischemia/reperfusion injury, angina, renal disease, metabolic syndrome and insulin resistance.

The compounds of the invention may be used in therapy.

The compounds of the invention may be used for the manufacture of a medicament for the treatment and/or prophylaxis of multiple diseases or disorders associated with APJ.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

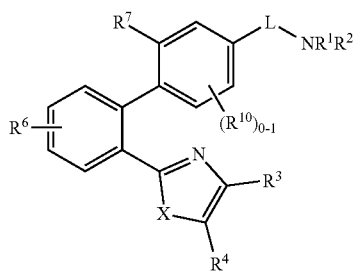

(I)

or a stereoisomer, a tautomer, a pharmaceutically acceptable salt, or a solvate thereof, wherein:

X is independently selected from: $NR^5$, O, and S;

L is independently selected from: C=O, $CH_2$, and $CHCF_3$;

$R^1$ is independently selected from: H and $C_{1-4}$ alkyl substituted with 0-1 $R^b$;

$R^2$ is independently selected from: $C_{1-4}$ alkyl substituted with 0-1 $R^b$, and —$(CHR^8)_{0-2}$—$R^9$;

alternatively, $R^1$ and $R^2$, together with the nitrogen atom to which they are attached, combine to form a 5- to 10-membered heterocyclic ring comprising carbon atoms and additional 1-3 heteroatoms selected from N, $NR^5$, O, and S, and substituted with 0-3 $R^c$;

$R^3$ and $R^4$ are independently selected from: H, $C_{1-4}$ alkyl, phenyl, and pyridyl, wherein said phenyl and pyridyl are substituted with 0-2 $R^a$;

alternatively, $R^3$ and $R^4$, together with the carbon atoms to which they are attached, combine to form a 5- to 10-membered fused carbocyclic ring or a 5- to 10-membered fused heterocyclic ring comprising carbon atoms and 1-3 heteroatoms selected from N, $NR^5$, O, and S; wherein said fused carbocyclic ring and fused heterocyclic ring are substituted with 0-2 $R^a$;

$R^5$ is, independently at each occurrence, selected from: H and $C_{1-4}$ alkyl;

$R^6$ is independently selected from: H, halogen, $C_{1-4}$ alkyl, $C_{1-4}$ haloalkyl, $C_{1-4}$ alkoxy, and $C_{1-4}$ haloalkoxy;

$R^7$ is independently selected from: OH, $CO_2H$, $CH_2OH$, $CO_2(C_{1-4}$ alkyl), CN, CONHCN, CONHOH, $CONHO(C_{1-4}$ alkyl), $CONHCH_2CO_2H$, $CONHSO_2(C_{1-4}$ alkyl), $CONHSO_2$(4-halo-Ph), $CONHSO_2N(C_{1-4}$ alkyl$)_2$, and a 5-membered heterocyclic ring comprising carbon atoms and 1-4 heteroatoms selected from N, $NR^5$, O, and S; wherein said heterocyclic ring is substituted with 0-2 $R^d$;

$R^8$ is independently selected from: $C_{1-6}$ alkyl substituted with 0-1 $R^b$, $C_{3-6}$ cycloalkyl, phenyl, and a 5- or 6-membered heterocyclic ring comprising carbon atoms and 1-4 heteroatoms selected from N, $NR^5$, O, and S;

$R^9$ is independently selected from: $C_{3-10}$ carbocycle, phenyl, and 5- to 6-membered heterocyclic ring comprising carbon atoms and 1-4 heteroatoms selected from N, $NR^5$, O, and S; wherein each moiety is substituted with 0-3 $R^c$;

$R^{10}$ is independently selected from: halogen and $C_{1-4}$ alkyl;

$R^a$ is, independently at each occurrence, selected from: OH, CN, halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), $C_{3-6}$ cycloalkyl, Bn, and phenyl;

$R^b$ is independently selected from: $N(C_{1-4}$ alkyl$)_2$, $C_{1-4}$ alkoxy, $C_{1-4}$ haloalkyl, phenyl, and a 5- or 6-membered heterocyclic ring comprising carbon atoms and 1-4 heteroatoms selected from N, $NR^5$, O, and S; wherein said heterocyclic ring is substituted with 0-2 $R^d$;

$R^c$ is, independently at each occurrence, selected from: OH, halogen, $C_{1-4}$ alkyl, $C_{1-4}$ alkoxy, and $C_{1-4}$ haloalkoxy; and $R^d$ is, independently at each occurrence, selected from: =O, =S, OH, halogen, $C_{1-4}$ alkyl, and $C_{1-4}$ alkoxy.

In a second aspect, the present disclosure provides a compound of Formula (II):

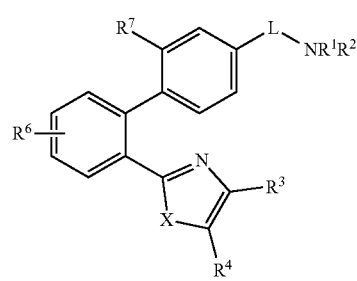

(II)

or a stereoisomer, a tautomer, a pharmaceutically acceptable salt, or a solvate thereof, within the scope of the first aspect.

In a third aspect, the present disclosure provides a compound of Formula (III):

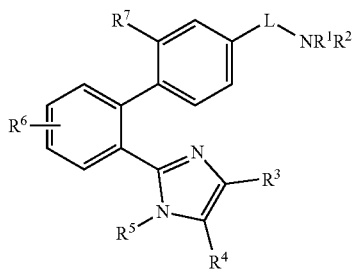

or a stereoisomer, a tautomer, a pharmaceutically acceptable salt, or a solvate thereof, within the scope of the first or second aspect.

In a fourth aspect, the present disclosure provides a compound of Formula (I), (II) or (III), or a stereoisomer, a tautomer, a pharmaceutically acceptable salt, or a solvate thereof, within the scope of any of the above aspects, wherein:

L is C=O;
$R^1$ is independently selected from: H and methyl;
$R^2$ is —(CHR$^8$)$_{0-1}$—R$^9$;
alternatively, $R^1$ and $R^2$, together with the nitrogen atom to which they are attached, combine to form a 5- to 10-membered heterocyclic ring comprising carbon atoms and additional 1-3 heteroatoms selected from N, NR$^5$, O, and S and substituted with 0-3 R$^c$;
$R^3$ and $R^4$ are independently selected from: H, C$_{1-4}$ alkyl, phenyl, and pyridyl, wherein said phenyl and pyridyl are substituted with 0-2 R$^a$;
alternatively, $R^3$ and $R^4$, together with the carbon atoms to which they are attached, combine to form a 5- to 10-membered fused carbocyclic ring or a 5- to 10-membered fused heterocyclic ring comprising carbon atoms and 1-3 heteroatoms selected from N, NR$^5$, O, and S; wherein said fused carbocyclic ring and fused heterocyclic ring are substituted with 0-2 R$^a$;
$R^7$ is independently selected from: OH, CO$_2$H, CH$_2$OH, CO$_2$(C$_{1-4}$ alkyl), CN, CONHCN, CONHOH, CONHO(C$_{1-4}$ alkyl), CONHCH$_2$CO$_2$H, CONHSO$_2$(C$_{1-4}$ alkyl), CONHSO$_2$(4-halo-Ph), CONHSO$_2$N(C$_{1-4}$ alkyl)$_2$, tetrazolyl,

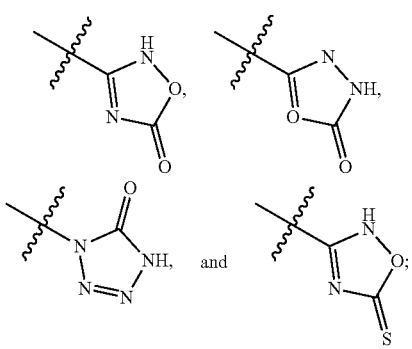

$R^8$ is independently selected from: C$_{1-6}$ alkyl substituted with 0-1 R$^b$, C$_{3-6}$ cycloalkyl, phenyl, and a 5- or 6-membered heterocyclic ring comprising carbon atoms and 1-4 heteroatoms selected from N, NR$^5$, O, and S;
$R^9$ is independently selected from: C$_{3-10}$ cycloalkyl, phenyl, and 5- to 6-membered heteroaryl comprising carbon atoms and 1-4 heteroatoms selected from N, NR$^5$, O, and S; wherein each moiety is substituted with 0-3 Re.

In a fifth aspect, the present disclosure provides a compound of Formula (IV):

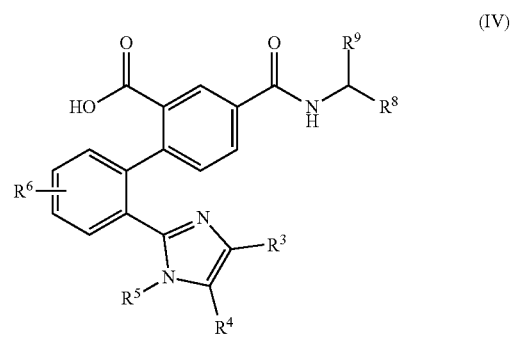

or a stereoisomer, a tautomer, a pharmaceutically acceptable salt, or a solvate thereof, within the scope of any of the above aspects.

In a sixth aspect, the present disclosure provides a compound of Formula (I), (II) (III) or (IV), or a stereoisomer, a tautomer, a pharmaceutically acceptable salt, or a solvate thereof, within the scope of any of the above aspects, wherein:

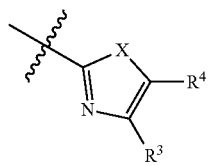

is independently selected from:

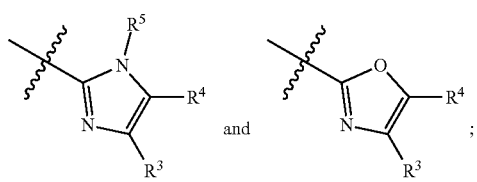

$R^3$ and $R^4$ are independently selected from: H, C$_{1-4}$ alkyl and phenyl substituted with 0-2 R$^a$.

In a seventh aspect, the present disclosure provides a compound of Formula (I), (II), (III), or (IV), or a stereoisomer, a tautomer, a pharmaceutically acceptable salt, or a solvate thereof, within the scope of any of the above aspects, wherein:

$R^3$ and $R^4$, together with the carbon atoms to which they are attached, combine to form a 5- to 10-membered fused carbocyclic ring or a 5- to 6-membered fused heterocyclic ring comprising carbon atoms and 1-3 heteroatoms selected from N, NR$^5$, O, and S; wherein said fused carbocyclic ring and fused heterocyclic ring are substituted with 0-2 R$^a$.

In an eighth aspect, the present disclosure provides a compound of Formula (I), (II) (III) or (IV), or a stereoisomer, a tautomer, a pharmaceutically acceptable salt, or a solvate thereof, within the scope of any of the first, second, third, and fourth aspects, wherein:

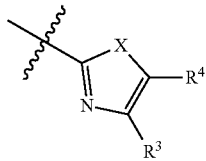

is independently selected from:

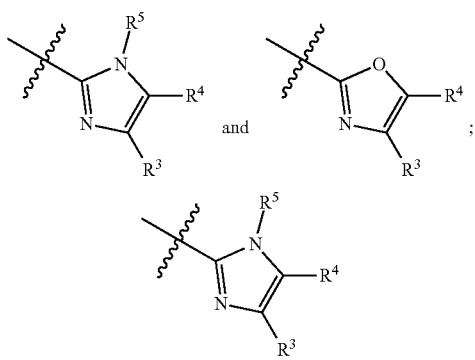

is independently selected from:

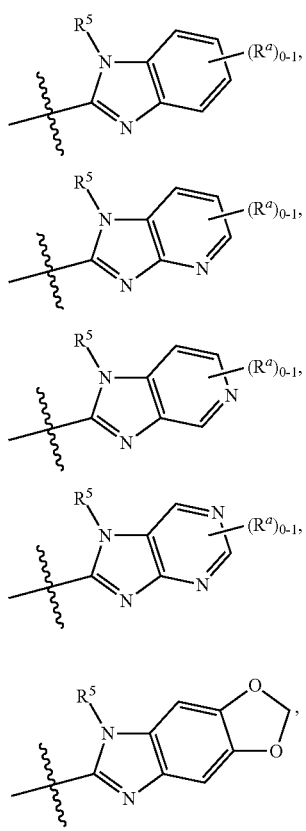

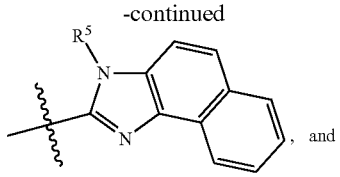

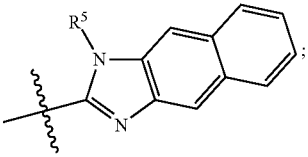

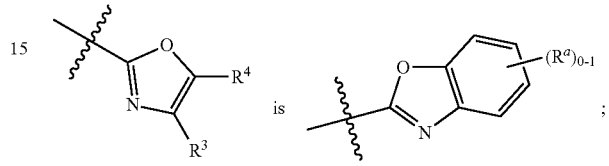

$R^5$ is, independently at each occurrence, selected from: H and $C_{1-4}$ alkyl;

$R^6$ is, independently at each occurrence, selected from: H, halogen, $C_{1-4}$ alkyl, $C_{1-4}$ haloalkyl, and $C_{1-4}$ alkoxy;

$R^8$ is independently selected from: $C_{1-6}$ alkyl substituted with 0-1 $R^b$ and cyclopropyl;

$R^9$ is independently selected from: phenyl substituted with 0-2 $R^c$, naphthyl substituted with 0-1 $R^c$ and pyridyl substituted with 0-1 $R^c$;

$R^a$ is, independently at each occurrence, selected from: OH, CN, halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), and $C_{3-6}$ cycloalkyl;

$R^b$ is independently selected from: $C_{1-4}$ alkoxy, $C_{1-4}$ haloalkyl and morpholinyl; and $R^c$ is, independently at each occurrence, selected from: halogen, $C_{1-4}$ alkyl, and $C_{1-4}$ alkoxy.

In a ninth aspect, the present disclosure provides a compound of Formula (I), (II), (III), or (IV) or a stereoisomer, a tautomer, a pharmaceutically acceptable salt, or a solvate thereof, within the scope of any of the above aspects, wherein:

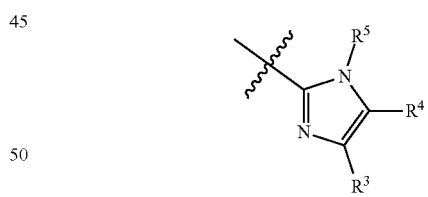

is independently selected from:

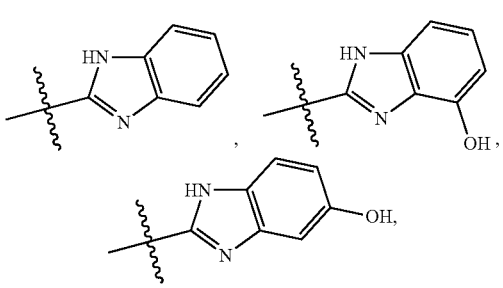

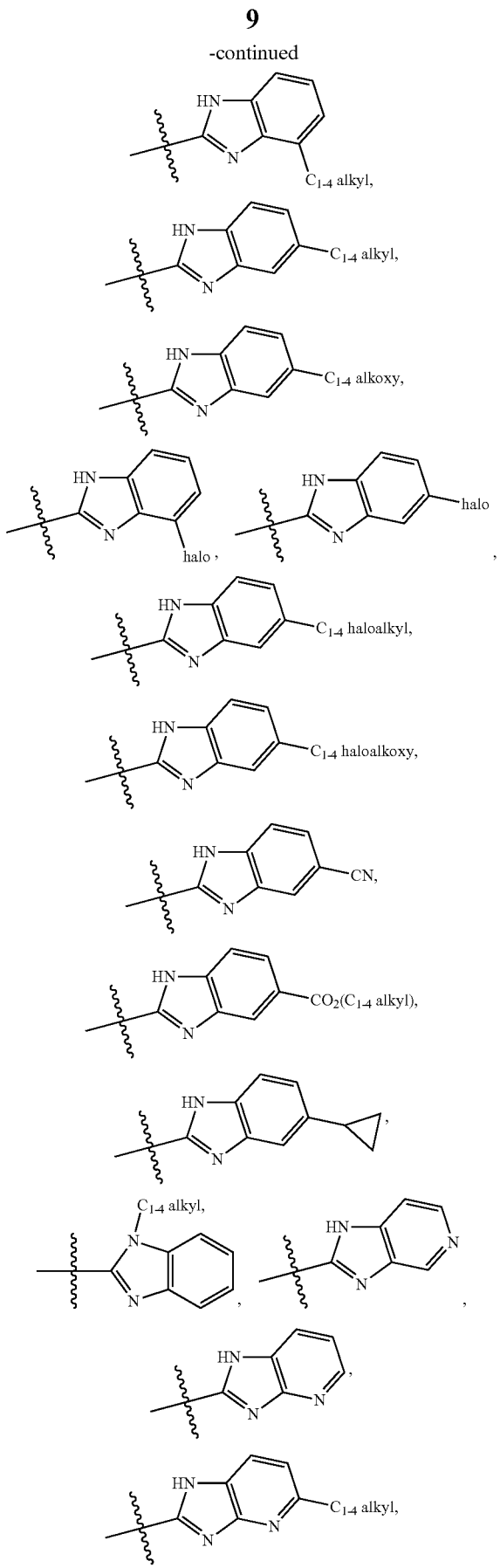

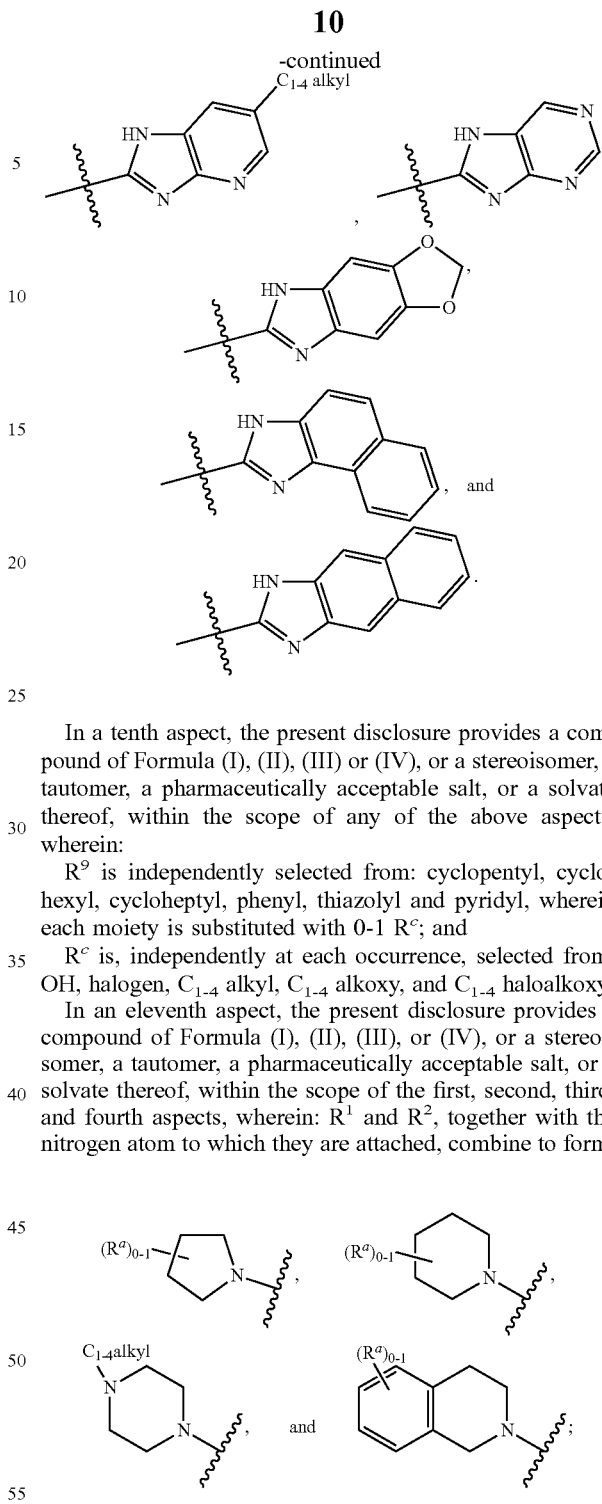

In a tenth aspect, the present disclosure provides a compound of Formula (I), (II), (III) or (IV), or a stereoisomer, a tautomer, a pharmaceutically acceptable salt, or a solvate thereof, within the scope of any of the above aspects, wherein:

$R^9$ is independently selected from: cyclopentyl, cyclohexyl, cycloheptyl, phenyl, thiazolyl and pyridyl, wherein each moiety is substituted with 0-1 $R^c$; and $R^c$ is, independently at each occurrence, selected from: OH, halogen, $C_{1-4}$ alkyl, $C_{1-4}$ alkoxy, and $C_{1-4}$ haloalkoxy.

In an eleventh aspect, the present disclosure provides a compound of Formula (I), (II), (III), or (IV), or a stereoisomer, a tautomer, a pharmaceutically acceptable salt, or a solvate thereof, within the scope of the first, second, third, and fourth aspects, wherein: $R^1$ and $R^2$, together with the nitrogen atom to which they are attached, combine to form;

and $R^a$ is, independently at each occurrence, selected from: $C_{1-4}$ alkyl, $C_{1-4}$ alkoxy, $C_{1-4}$ haloalkyl, $C_{1-4}$ haloalkoxy, $CO_2(C_{1-4}$ alkyl), $C_{3-6}$ cycloalkyl, Bn, and phenyl.

In a twelfth aspect, the present disclosure provides a compound selected from the exemplified examples or a stereoisomer, a tautomer, a pharmaceutically acceptable salt, or a solvate thereof.

In another aspect, the present disclosure provides a compound selected from any subset list of compounds within the scope of the eleventh aspect.

In another embodiment, the compounds of the present invention have $EC_{50}$ values ≤10 µM, using the APJ hcAMP assay disclosed herein, preferably, $EC_{50}$ values ≤1 µM, more preferably, $IC_{50}$ values ≤0.5 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, β-adrenergic receptor blocker, angiotensin II receptor blocker, diuretic, aldosterone antagonist and digitalis compound.

In another embodiment, the present invention provides a method for the treatment and/or prophylaxis of multiple diseases or disorders associated with APJ or apelin activity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the APJ and apelin that can be prevented, modulated, or treated according to the present invention include, but are not limited to heart failure, coronary artery disease, peripheral vascular disease, atherosclerosis, diabetes, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, peripheral vascular disease, atherosclerosis, diabetes, metabolic syndrome, hypertension, pulmonary hypertension, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes and obesity, comprising administering to a patient in need 1.0 of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of pulmonary hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of acute coronary syndrome and cardiac ischemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with APJ and apelin.

In another embodiment, the present invention also provides the use of a compound of the present invention for the manufacture of a medicament for the treatment and/or prophylaxis of multiple diseases or disorders associated with APJ and apelin.

In another embodiment, the present invention provides a method for the treatment and/or prophylaxis of multiple diseases or disorders associated with APJ and apelin, comprising administering to a patient in need thereof a therapeutically effective amount of a first and second therapeutic agent, wherein the first therapeutic agent is a compound of the present invention. Preferably, the second therapeutic agent, for example selected inotropic agent such as 3-adrenergic agonist (for example dobutamine).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with APJ and apelin.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the APJ agonist of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent(s) selected from one or more, preferably one to three, of the following therapeutic agents: anti-hypertensive agents, ACE inhibitors, mineralocorticoid receptor antagonists, angiotensin receptor blockers, calcium channel blockers, β-adrenergic receptor blockers, diuretics, vasorelaxation agents such as nitrates, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, 3-blockers, diuretics, mineralocorticoid receptor antagonists, renin inhibitors, calcium channel blockers, angiotensin II receptor antagonists, nitrates, digitalis compounds, inotropic agents.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Certain compounds of the present invention can exhibit a chirality resulting from the presence of bulky substituents that hinder the otherwise free rotation about a bond. These rotational stereoisomers are named atropisomers, and the interconversion can be sufficiently slow to allow for their separation and characterization. See, e.g., March, J. ed., *Advanced Organic Chemistry*, pp. 101-102, 4th Edition, John Wiley & Sons, (1992); and LaPlante, S. R. et al., *J. Med. Chem.*, 54: 7005-7022 (2011). The present invention includes atropisomers of compounds embraced by Formula (I), singly and in mixtures. Additionally, separation, enrichment and/or selective preparation of atropisomers can be achieved by methods known to one skilled in the art.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct build.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4'-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1.991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

All measurements are subject to experimental error and are within the contemplation of the invention.

When the invention is described or characterized by any of the disclosed figures or tables, it is understood that all variations within limitations and/or error margins of the experiments and technology are contemplated.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "IL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

$Ac_2O$ acetic anhydride
AcOH or HOAc acetic acid
Bn Benzyl
Boc tert-butyloxycarbonyl
$Boc_2O$ di-tert-butyl dicarbonate
Bu Butyl
$CDCl_3$ deutero-chloroform
$CH_2Cl_2$ dichloromethane
$CH_3CN$ or ACN acetonitrile
$CHCl_3$ chloroform
$Cs_2CO_3$ cesium carbonate
DCC N,N'-dicyclohexylcarbodiimide
DMA dimethylamine
DMAP 4-dimethylaminopyridine
DME dimethylether
DMF dimethyl formamide
DMSO dimethyl sulfoxide
EDTA ethylenediaminetetraacetic acid
Et Ethyl
$Et_2O$ diethyl ether
EtOAc ethyl acetate
EtOH Ethanol
$H_2SO_4$ sulfuric acid
HATU O-(7-azabenzotriazol-1-yl)-N,N,N',N'-tetramethyluronium hexafluorophosphate
HCl hydrochloric acid
Hex hexanes
i-Bu isobutyl
i-Pr isopropyl
i-$Pr_2$NEt diisopropylethylamine
i-PrOH or I'A isopropanol
$K_2CO_3$ potassium carbonate
KOAc potassium acetate
Me Methyl
MeOH methanol
$MgSO_4$ magnesium sulfate
Ms Mesylate
$Na_2SO_4$ sodium sulfate
NaCl sodium chloride
$NaHCO_3$ sodium bicarbonate
$NH_3$ ammonia
$NH_4Cl$ ammonium chloride
$NH_4OH$ ammonium hydroxide Pd(dppf)C$_2$·CH$_2$Cl$_2$ [1,1'-Bis(diphenylphosphino)ferrocene]dichloropalladium(II), complex with dichloromethane
Pd$_2$dba$_3$ tris(dibenzylideneacetone)dipalladium(0)
Ph Phenyl
Pr Propyl
SFC Supercritical Fluid Chromatography
SiO$_2$ silica oxide
T$_3$P propylphosphonic anhydride
t-Bu tert butyl
TEA triethylamine
Tf$_2$O trifluoromethanesulfonic anhydride
TFA trifluoroacetic acid
THF tetrahydrofuran
Zn Zinc The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (1) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 6th Edition, Wiley & Sons, New York, N.Y. (2007); Katritzky, A. R. et al, eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

For example, compounds of Formula (II), where R$^3$ and R$^4$ combined to form a benzene ring, can be made according to Scheme 1.

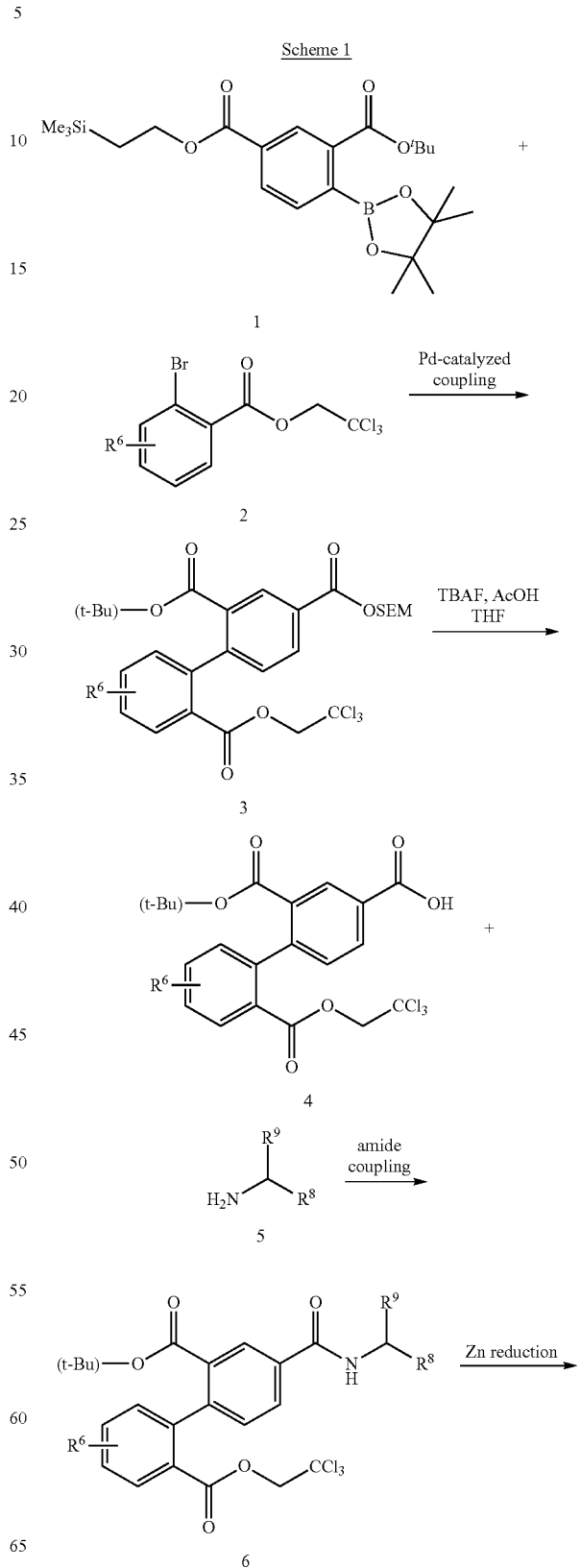

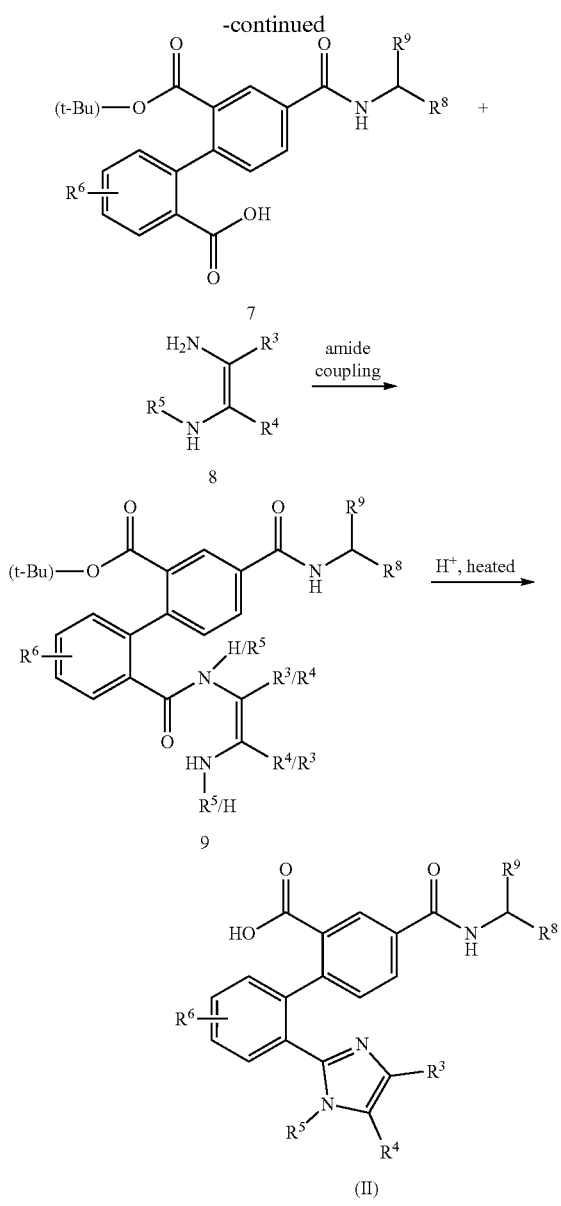

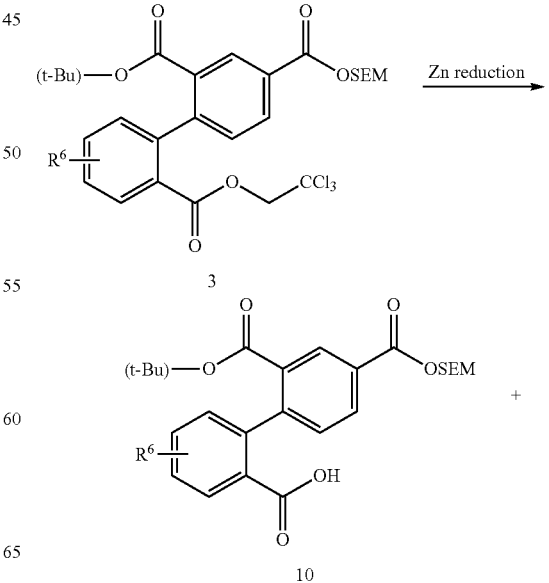

reduction condition is carried out with saturated $NH_4Cl$ as activator in a suitable solvent such as THF or 1,4-dioxane. Acid 7 is coupled to diamine 8 under typical amide bond formation condition such as HATU/DIEA or EDC/HOAt/DIEA in a solvent such as DCM or DMF to produce amide 9. Other amide bond forming reaction known to those skilled in the art may be employed. Without further purification, 9 is heated at 75-95° C. under acidic condition to deliver compounds of Formula (II). A mixture of AcOH and $H_2O$ is used to perform this transformation. Other proton source such as TFA, TsOH, or PPTS may also be employed in combination with a suitable solvent, for example, toluene.

Alternatively, compounds of Formula (II), where $R^3$ and $R^4$ combined to form a benzene ring, can be made according to Scheme 2. Tri-carboxylic ester 3 is subjected to selective ester deprotection condition mediated by Zn to generate acid 10. Suitable solvent such as THF or 1,4-dioxane may be used for this transformation and an activator such as sat $NH_4Cl$ may be used to promote the reaction. Acid 10 is coupled to diamine 8 under typical amide bond formation condition such as HATU/DIEA or EDC/HOAt/DIEA in a proper solvent such as DCM or DMF to produce amide 11. Other amide bond forming reaction known to those skilled in the art may be employed. Amide 11 is subsequently reacted with $Boc_2O$ in a suitable solvents such as DCM, THF, or 1,4-dioxane under room temperature or at 50° C. to generate 12. Ester deprotection of 12 using a suitable fluoride source such as TBAF in THF reveals carboxylic acid 13. Acid 13 is subsequently coupled to primary amine 5 under typical amide bond formation condition to generate amide 14. The combination of HATU/DIEA/DCM or EDC/HOAt/DIEA/DCM are generally reliable and effective for this transformation. Other amide bond forming reaction known to those skilled in the art may be employed. Without further purification, crude amide 14 was heated at 75-95° C. under acidic condition to deliver compounds of Formula (II). A mixture of AcOH and $H_2O$ is used to perform this transformation. Other proton source such as TFA, TsOH, or PPTS may also be employed in combination with a suitable solvent, for example, toluene.

Boronic ester 1 is heated with bromide 2 in the presence of a palladium catalyst and base using a suitable solvent such as THF, toluene, DMF with or without water to produce tri-ester 3. Boronic ester 1 may be substituted with alternative analogs such as boronate acids, trifluoroborates, and others known to those skilled in the art. Palladium catalyst commonly employed include, but are not restricted to, $Pd(PPh_3)_4$ and $PdCl_2(dppf) \cdot CH_2Cl_2$. Other palladium catalyst known to those skilled in the art may be employed. Bases commonly employed include, but are not restricted to, $Na_2CO_3$ and $K_2CO_3$. Other bases known to those skilled in the art may also be employed. Selective ester deprotection of 3 using a suitable fluoride source such as TBAF in THF reveals carboxylic acid 4. Acid 4 is subsequently coupled to primary amine 5 under typical amide bond formation condition to generate amide 6. The combination of HATU/DIEA/DCM or EDC/HOAt/DIEA/DCM are generally reliable and effective for this transformation. Other amide bond forming reaction known to those skilled in the art may be employed. In order to form carboxylic acid 7, a Zn mediated

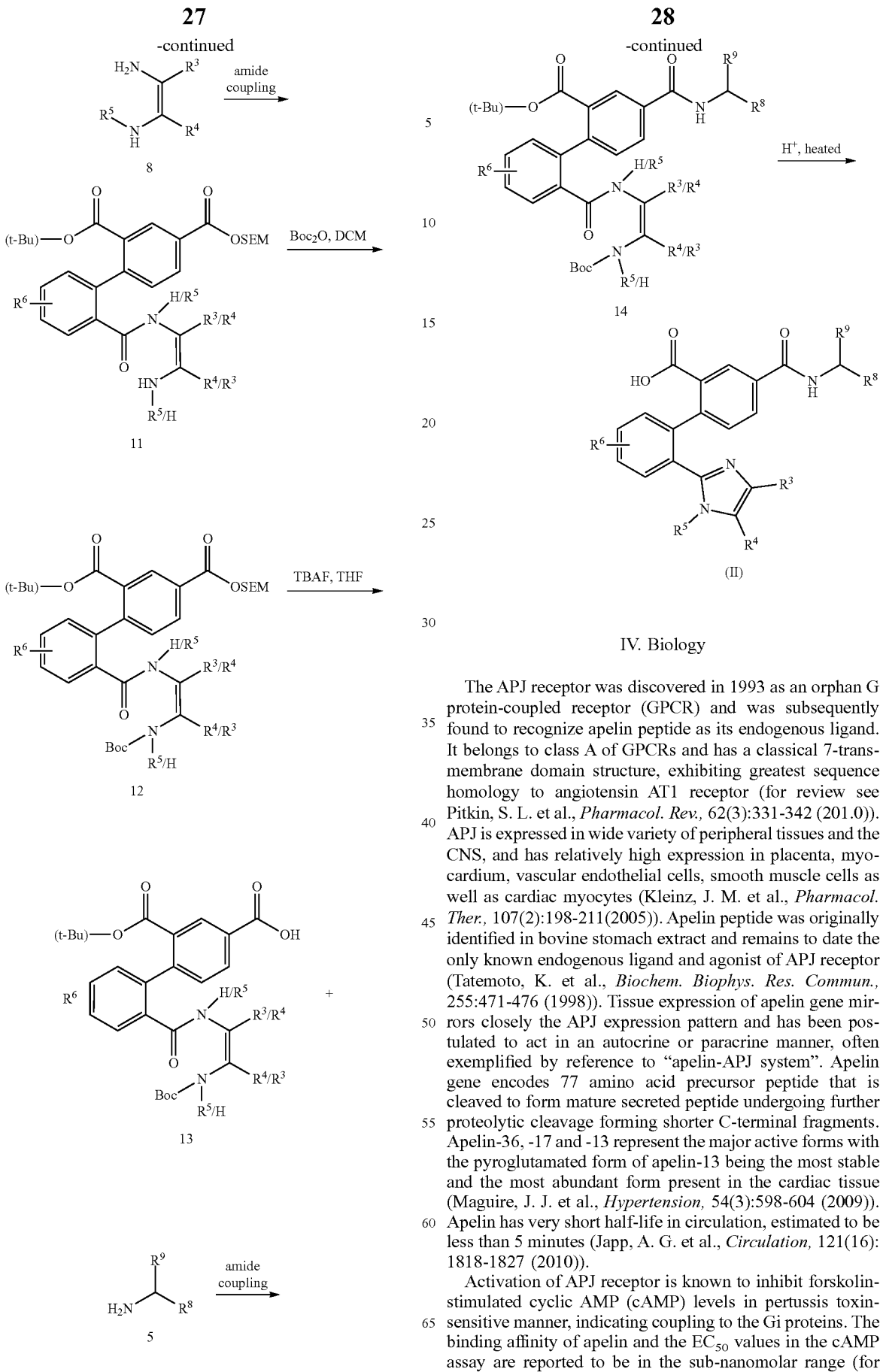

IV. Biology

The APJ receptor was discovered in 1993 as an orphan G protein-coupled receptor (GPCR) and was subsequently found to recognize apelin peptide as its endogenous ligand. It belongs to class A of GPCRs and has a classical 7-transmembrane domain structure, exhibiting greatest sequence homology to angiotensin AT1 receptor (for review see Pitkin, S. L. et al., *Pharmacol. Rev.*, 62(3):331-342 (201.0)). APJ is expressed in wide variety of peripheral tissues and the CNS, and has relatively high expression in placenta, myocardium, vascular endothelial cells, smooth muscle cells as well as cardiac myocytes (Kleinz, J. M. et al., *Pharmacol. Ther.*, 107(2):198-211(2005)). Apelin peptide was originally identified in bovine stomach extract and remains to date the only known endogenous ligand and agonist of APJ receptor (Tatemoto, K. et al., *Biochem. Biophys. Res. Commun.*, 255:471-476 (1998)). Tissue expression of apelin gene mirrors closely the APJ expression pattern and has been postulated to act in an autocrine or paracrine manner, often exemplified by reference to "apelin-APJ system". Apelin gene encodes 77 amino acid precursor peptide that is cleaved to form mature secreted peptide undergoing further proteolytic cleavage forming shorter C-terminal fragments. Apelin-36, -17 and -13 represent the major active forms with the pyroglutamated form of apelin-13 being the most stable and the most abundant form present in the cardiac tissue (Maguire, J. J. et al., *Hypertension*, 54(3):598-604 (2009)). Apelin has very short half-life in circulation, estimated to be less than 5 minutes (Japp, A. G. et al., *Circulation*, 121(16): 1818-1827 (2010)).

Activation of APJ receptor is known to inhibit forskolin-stimulated cyclic AMP (cAMP) levels in pertussis toxin-sensitive manner, indicating coupling to the Gi proteins. The binding affinity of apelin and the $EC_{50}$ values in the cAMP assay are reported to be in the sub-nanomolar range (for review see Pitkin, S. L. et al., *Pharmacol. Rev.*, 62(3):331-342(2010)). In addition to cAMP inhibition, APJ receptor activation also leads to β-arrestin recruitment, receptor internalization and activation of extracellular-regulated kinases (ERKs) (for review see Kleinz, J. M. et al., *Pharmacol. Ther.*, 107(2):198-211 (2005)). Which of these signaling mechanisms contribute to modulation of downstream physiological effects of apelin is not clear at present. APJ receptor has been shown to interact with the AT1 receptor. While apelin does not bind AT1 and angiotensin II does not bind APJ, it has been postulated that certain physiological actions of apelin are mediated at least in part, via functional antagonism of the angintensin II and AT1 receptor pathway (Chun, A. J. et al., *J. Clin. Invest.*, 118(10):3343-3354 (2008)).

It is also desirable and preferable to find compounds with advantageous and improved characteristics compared with known HF treatment agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an APJ agonist. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate APJ and/or to prevent or treat the disorders listed herein. When applied to a combination, the term refers to combined amounts of the active ingredients that result in the preventive or therapeutic effect, whether administered in combination, serially, or simultaneously.

A. Assay Methods

Intracellular cAMP Accumulation Assay

HEK293 cells stably expressing human APJ receptor were used to assess the activity of compounds. Cultured cells were detached and resuspended in the cAMP Homogeneous Time-Resolved Fluorescence (HTRF) assay buffer (Cisbio cat; #62AM4PEJ). The assay was performed in 384-well assay plates (Perkin-Elmer; cat #6008289) according to assay protocol provided by the manufacturer. Serial dilutions of a compound together with assay buffer containing 0.2 nM IBMX and 2 μM forskolin were added to each well containing 5,000 cells and incubated for 30 minutes at room temperature. Subsequently, cAMP D2 reagent was added in the lysis buffer followed by the EuK antibody (Cisbio; cat #62AM4PEJ) and incubated for 60 min. The fluorescence emission ratio was measured using fluorometer. The intracellular cAMP concentrations (compound-stimulated inhibition of forskolin-mediated cAMP production) were calculated by extrapolation from a standard curve using known cAMP concentrations. The $EC_{50}$ values were obtained by fitting the data to a sigmoidal concentration-response curve with variable slope. The maximal achievable inhibition of forskolin-induced cAMP levels ($Y_{max}$) for each compound was expressed as relative percentage of inhibition attained using pyroglutamated apelin-13 ((Pyrl)apelin-13) peptide, which was set to 100%.

The exemplified Examples disclosed below were tested in the APJ in vitro assays described above and were found having human APJ cyclic AMP (hcAMP) activity. Table 1 lists hcAMP $EC_{50}$ values measured for the following examples. Ranges are as followε: A=0.0-10 nM; B=10.01-100 nM; C=101-500 nM.

TABLE 1

| Example No. | APJ hcAMP $EC_{50}$ (nM) |
|---|---|
| 1 | A |
| 2 | A |
| 3 | A |
| 4 | A |
| 5 | B |
| 6 | C |
| 7 | B |
| 8 | B |
| 9 | B |
| 10 | C |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | B |
| 23 | B |
| 24 | B |
| 25 | B |
| 26 | B |
| 27 | B |
| 28 | B |
| 29 | B |
| 30 | B |
| 31 | B |
| 32 | A |
| 33 | A |
| 34 | A |

TABLE 1-continued

| Example No. | APJ hcAMP EC$_{50}$ (nM) |
|---|---|
| 35 | A |
| 36 | A |
| 37 | A |
| 38 | A |
| 39 | B |
| 40 | B |
| 41 | B |
| 42 | B |
| 43 | C |
| 44 | B |
| 45 | C |
| 46 | C |
| 47 | A |
| 48 | A |
| 49 | B |
| 50 | B |
| 51 | A |
| 52 | A |
| 53 | A |
| 54 | B |
| 55 | C |
| 56 | A |
| 57 | A |
| 58 | A |
| 59 | A |
| 60 | A |
| 61 | A |
| 62 | B |
| 63 | B |
| 64 | A |
| 65 | A |
| 66 | B |
| 67 | A |
| 68 | A |
| 69 | A |
| 70 | A |
| 71 | B |
| 72 | B |
| 73 | B |
| 74 | B |
| 75 | B |
| 76 | B |
| 77 | B |
| 78 | C |
| 79 | A |
| 80 | A |
| 81 | A |
| 82 | A |
| 83 | A |
| 84 | B |
| 85 | B |
| 86 | A |
| 87 | A |
| 88 | C |
| 89 | A |
| 90 | A |
| 91 | A |
| 92 | A |
| 93 | A |
| 94 | A |
| 95 | A |
| 96 | A |
| 97 | A |
| 98 | A |
| 99 | B |
| 100 | B |
| 101 | B |
| 102 | A |
| 103 | A |
| 104 | A |
| 105 | A |
| 106 | A |
| 107 | A |
| 108 | B |
| 109 | B |
| 110 | A |
| 111 | B |
| 112 | A |
| 113 | A |
| 114 | A |
| 115 | A |
| 116 | A |
| 117 | B |
| 118 | B |
| 119 | B |
| 120 | B |
| 121 | B |
| 122 | B |
| 123 | B |
| 124 | B |
| 125 | B |
| 126 | B |
| 127 | B |
| 128 | V |
| 129 | A |
| 130 | B |
| 131 | A |
| 132 | A |
| 133 | B |
| 134 | A |
| 135 | A |
| 136 | A |
| 137 | B |
| 138 | C |
| 139 | B |
| 140 | C |
| 141 | A |
| 142 | A |
| 143 | B |
| 144 | A |
| 145 | A |
| 146 | A |
| 147 | A |
| 148 | A |
| 149 | C |
| 150 | A |
| 151 | A |
| 152 | A |
| 153 | A |
| 154 | B |
| 155 | B |
| 156 | A |
| 157 | A |
| 158 | B |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | B |
| 190 | B |

TABLE 1-continued

| Example No. | APJ hcAMP EC$_{50}$ (nM) |
|---|---|
| 191 | B |
| 192 | B |
| 193 | B |
| 194 | B |
| 195 | A |
| 196 | A |
| 197 | A |
| 198 | A |
| 199 | A |
| 200 | A |
| 201 | A |
| 202 | A |
| 203 | B |
| 204 | C |
| 205 | B |
| 206 | B |
| 207 | A |
| 208 | A |
| 209 | A |
| 210 | A |
| 211 | A |
| 212 | B |
| 213 | B |
| 214 | B |
| 215 | C |
| 216 | C |
| 217 | C |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | B |
| 230 | C |
| 231 | A |
| 232 | A |
| 233 | A |
| 234 | A |
| 235 | A |
| 236 | A |
| 237 | A |
| 238 | A |
| 239 | A |
| 240 | A |
| 241 | A |

The compounds of the present invention possess activity as agonists of APJ receptor, and, therefore, may be used in the treatment of diseases associated with APJ activity. Accordingly, the compounds of the present invention can be administered to mammals, preferably humans, for the treatment of a variety of conditions and disorders, including, but not limited to, treating, preventing, or slowing the progression of heart failure, coronary artery disease, peripheral vascular disease, atherosclerosis, diabetes, metabolic syndrome and the sequelae of thereof, hypertension, pulmonary hypertension, cerebrovascular disorders, angina, ischemia, stroke, myocardial infarction, acute coronary syndrome, reperfusion injury, angioplastic restenosis, vascular complications of diabetes and obesity.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012), The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with other APJ agonists or one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors, β-blockers, diuretics, mineralocorticoid receptor antagonists, renin inhibitors, calcium channel blockers, angiotensin II receptor antagonists, nitrates, digitalis compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the APJ receptor and apelin activity. Such compounds may be provided in a commercial kit, for example, for use in pharmaceutical research involving APJ and apelin or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving APJ and apelin.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with APJ and apelin (as defined previously). In another embodiment, the package insert states that the pharmaceutical composition can be used in combination (as defined previously) with a second therapeutic agent for the treatment and/or prophylaxis of multiple diseases or disorders associated with APJ and apelin. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

Description of Analytical LCMS Methods:

Method A: Waters Acquity UPLC; Column: BEH C18, 2.1×50 mm, 1.7 µm particles; Mobile Phase A: ACN with 0.05% TFA; Mobile Phase B: water with 0.05% TFA; Temperature: 50° C.; Gradient: 2-98% B over 1.0 minutes, then a 0.5 minute hold at 98% B, followed by 98-2% B over 0.1 min; Flow: 0.80 mL/min; Detection: UV at 220 nm.

Method B: Shimadzu Analytical HPLC system; Column: PHENOMENEX® Luna $C_{18}$ column, 4.6×50 mm, 5 µm particles, Mobile Phase A: 10% methanol, 89.9% water, 0.1% TFA; Mobile Phase B: 10% water, 89.9% methanol, 0.1% TFA; Temperature: 40° C.; Gradient: 0-100% B over 2 minutes, with 1 minute hold at 100% B; Flow: 1.0 mL/min; Detection: UV 220 nm.

Method C: Method B: Shimadzu Analytical HPLC system; Column: PHENOMENEX® Luna C18 column, 4.6×50 mm, 5 µm particles, Mobile Phase A: 10% methanol, 89.9% water, 0.1% TFA; Mobile Phase B: 10% water, 89.9% methanol, 0.1% TFA; Temperature: 40° C.; Gradient:

0-100% B over 4 minutes, with 1 minute hold at 100% B; Flow: 0.8 mL/min; Detection: UV 220 nm.

NMR Employed in Characterization of Examples $^1$H NMR spectra (unless otherwise noted) were obtained with JEOL® or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Intermediate 1A. 3-tert-Butyl 1-methyl 4-hydroxyisophthalate

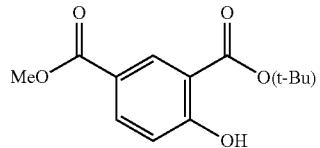

Into the reaction vessel was added pyridine (50 mL) and dimethyl 4-hydroxyisophthalate (3.6 g, 17 mmol). The mixture was stirred at reflux for 17 h and concentrated. The residue was acidified with 1M HCl (50 mL) and extracted with EtOAc (30 mL×3). The organic phase was dried over $Na_2SO_4$, concentrated, and dissolved in DCM (10 mL). 1,1-Di-tert-butoxy-N,N-dimethylmethanamine (10.45 g, 51.40 mmol) was then added and the reaction was stirred at rt for 12 h. After diluted with EtOAc (30 mL), the organic phase was washed with sat $NaHCO_3$ (20 mL×3), dried over $Na_2SO_4$, and concentrated to produce 1A (2.62 g, 10.40 mmol, 60.7% yield) as a white solid which was used for next step without further purification. LCMS Anal. Calc'd for $C_{13}H_{16}O_5$ 252.10, found [M+14] 253.1; $^1$H NMR (500 MHz, chloroform-d) δ 11.56 (s, 1H), 8.58-8.46 (m, 1H), 8.16-8.08 (m, 1H), 7.02 (s, 1H), 3.93 (s, 3H), 1.66 (s, 9H).

Intermediate 1B. 3-tert-Butyl 1-(2-(trimethylsilyl)ethyl) 4-hydroxyisophthalate

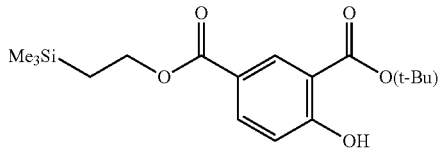

Into a reaction vessel was added 2-(trimethylsilyl)ethanol (4.30 g, 36.4 mmol) and toluene (50 mL). The reaction mixture was cooled to 0° C. and NaH (1.248 g, 31.20 mmol) was added. After 5 min, the reaction mixture was allowed to warm to rt and stirred for additional 50 min. 1A (2.623 g, 10.40 mmol) was then added and the reaction mixture was heated at 50° C. for 30 min. The reaction mixture was allowed to cool to rt, washed with sat $NH_4Cl$ (containing 31.2 mmol HCl), and extracted with EtOAc. The organic layer was dried over $Na_2SO_4$ and concentrated under reduced pressure. Silica gel chromatography afforded 1B (2.18 g, 6.44 mmol, 61.9% yield) as a colorless oil. $^1$H NMR (500 MHz, chloroform-d) δ 11.52 (s, 1H), 8.47 (d, J=2.2 Hz, 1H), 8.08 (dd, J=8.8, 2.2 Hz, 1H), 6.98 (d, J=8.8 Hz, 1H), 4.44-4.38 (m, 2H), 1.63 (s, 9H), 1.15-1.09 (m, 2H), 0.09 (s, 9H).

Intermediate 1C. 3-tert-Butyl 1-(2-(trimethylsilyl)ethyl) 4-(((trifluoromethyl)sulfonyl) oxy)isophthalate

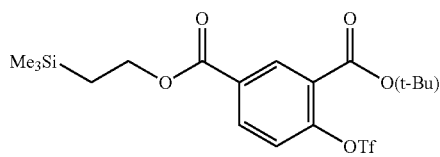

Into the reaction vessel was added 1B (2180 mg, 6.44 mmol), DCM (20 mL), and pyridine (2.60 mL, 32.2 mmol). The reaction mixture was cooled to 0° C. and $Tf_2O$ (1.63 mL, 9.66 mmol) was added. The reaction mixture was allowed to warm to rt, stirred at rt for 30 min, cooled to 0° C., and 30 mL DCM and 50 mL water were added. The organic phase was collected, dried over $Na_2SO_4$, concentrated under reduced pressure, and subjected to silica gel chromatography purification to produce 1C (3000 mg, 6.4 mmol, 99% yield) as a colorless oil. $^1$H NMR (500 MHz, chloroform-d) δ 8.52-8.47 (m, 1H), 8.14-8.09 (m, 1H), 7.25-7.22 (m, 1H), 4.39-4.32 (m, 2H), 1.53 (s, 9H), 1.05 (d, J=17.1 Hz, 2H), 0.00 (s, 9H).

Intermediate 1D. 3-tert-Butyl 1-(2-(trimethylsilyl)ethyl) 4-(4,4,5,5-tetramethyl-1,3,2-dioxaborolan-2-yl)isophthalate

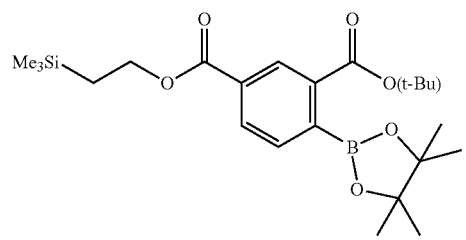

Into the reaction vessel was added 1C (2300 mg, 4.89 mmol), 4,4,4',4',5,5, 5',5'-octamethyl-2,2'-bi(1,3,2-dioxaborolane) (1341 mg, 5.280 mmol), and 1,4-dioxane (30 mL). $PdCl_2(dppf)$-$CH_2Cl_2$ (200 mg, 0.244 mmol) and KOAc (1199 mg, 12.22 mmol) were subsequently added and the reaction mixture was degassed by bubbling $N_2$ for 10 min. The reaction mixture was stirred at 65° C. for 3 h, allowed to cool to rt, diluted with 1:1:0.01 EtOAc/hexane/$Et_3N$ (50 mL), filtered through $SiO_2$ (15 g, 200 mL 1:1:0.01 EtOAc/hexane/$Et_3N$ as eluent), and concentrated under reduced pressure to afford 1D (2.1 g, 96%) as a brown solid. This intermediate was used for next step without further purification. $^1$H NMR (500 MHz, chloroform-d) δ 8.35 (d, J=1.1 Hz, 1H), 8.05-7.99 (m, 1H), 7.45 (d, J=7.7 Hz, 1H), 4.40-4.30 (m, 2H), 1.51 (s, 9H), 1.34 (s, 12H), 1.06 (dd, J=8.8, 7.7 Hz, 2H), 0.04 (s, 9H).

Intermediate 1E. 2,2,2-Trichloroethyl 2-bromo-4-chlorobenzoate

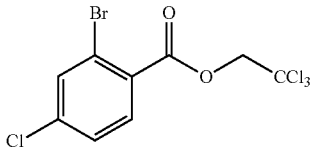

Into the reaction vessel was added 2-bromo-4-chlorobenzoyl chloride (310 mg, 1.22 mmol), DCM (2.5 mL), and Et$_3$N (681 µl, 4.88 mmol). The reaction mixture was cooled to 0° C. followed by the addition of 2,2,2-trichloroethanol (365 mg, 2.44 mmol). The reaction mixture was allowed to warm to rt and stirred at rt for 24 h. Concentration under reduced pressure and silica gel chromatography purification produced 1E (355 mg, 0.968 mmol, 79%) as a colorless oil. 1H NMR (500 MHz, chloroform-d) δ 7.95 (d, J=8.5 Hz, 1H), 7.76 (d, J=1.9 Hz, 1H), 7.42 (dd, J=8.5, 1.9 Hz, 1H), 4.98 (s, 2H).

Intermediate 1F. 2-tert-Butyl 2'-(2,2,2-trichloroethyl) 4-(2-(trimethylsilyl)ethyl) 5'-chloro-[1,1'-biphenyl]-2,2',4-tricarboxylate

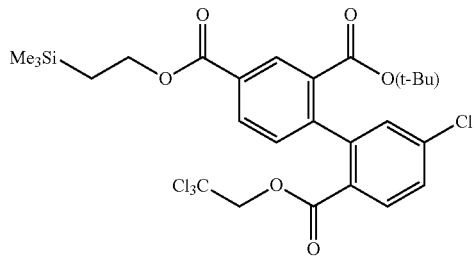

To the reaction vessel containing 1D (1553 mg, 3.460 mmol) was added 1E (1588 mg, 4.330 mmol), toluene (42 mL), PdCl$_2$(dppf)-CH$_2$Cl$_2$ (127 mg, 0.173 mmol), and Na$_2$CO$_3$ (2M, 6.61 mL, 13.2 mmol). The reaction mixture was degassed by bubbling N$_2$ for 10 min, stirred at 65° C. for 12 h, allowed to cool to rt, concentrated under reduced pressure, and subjected to silica gel chromatography purification to produce 1F (1.196 g, 1.966 mmol, 56.80% yield) as a white solid. LCMS Anal. Calc'd for C$_{26}$H$_{30}$Cl$_4$O$_6$Si 606.06, found [M+H] 607.1; $^1$H NMR (500 MHz, chloroform-d) δ 8.52 (d, J=1.7 Hz, 1H), 8.06-8.00 (m, 2H), 7.38 (dd, J=8.5, 1.7 Hz, 1H), 7.16 (s, 5H), 7.14 (s, 2H), 4.60 (s, 2H), 4.42-4.32 (m, 2H), 1.15 (s, 9H), 1.07-1.04 (m, 2H), 0.00 (s, 9H).

Intermediate 1G. (R)-2-tert-Butyl 2'-(2,2,2-trichloroethyl) 5'-chloro-4-((1-phenylbutyl)carbamoyl)-[1,1'-biphenyl]-2,2'-dicarboxylate

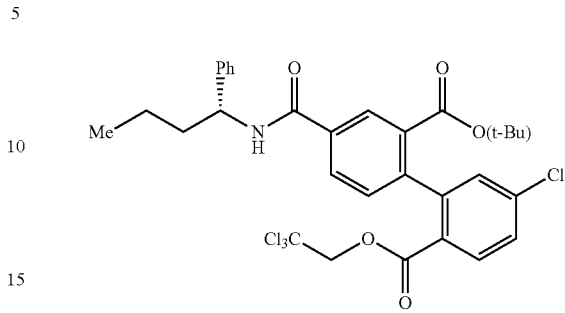

Into the reaction vessel was added 1F (600 mg, 0.986 mmol), THF (9.86 mL), and TBAF (4.931 mL, 4.930 mmol). The reaction mixture was stirred at rt for 30 min, quenched by the addition of sat NH$_4$Cl (20 mL), and extracted with EtOAc (25 mL×3). The combined organic phase was dried over sodium sulfate, filtered and concentrated under reduced pressure to yield the corresponding acid. Into the reaction vessel containing the intermediate acid was added (R)-1-phenylbutan-1-amine (147 mg, 0.986 mmol), DIEA (0.517 mL, 2.96 mmol), DCM (10 mL), and HATU (487 mg, 1.28 mmol). The reaction mixture was stirred at rt for 12 h and concentrated under reduced pressure. Purification by silica gel chromatography produced 1G (475 mg, 0.743 mmol, 75%) as a white solid. LCMS Anal. Calc'd for C$_{31}$H$_{31}$Cl$_4$NO$_5$ 637.10, found [M+H] 637.1; $^1$H NMR (500 MHz, chloroform-d) δ 8.38-8.28 (m, 1H), 8.22-8.13 (m, 1H), 8.08-7.98 (m, 1H), 7.58-7.48 (m, 1H), 7.39 (d, J=5.0 Hz, 2H), 7.29 (s, 5H), 6.51-6.40 (m, 1H), 5.27-5.15 (m, 1H), 4.74 (d, J=6.3 Hz, 2H), 1.94 (d, J=7.7 Hz, 2H), 1.59 (s, 9H), 1.46 (br. s., 2H), 1.00 (t, J=7.3 Hz, 3H).

Intermediate 1H. (R)-2'-(tert-Butoxycarbonyl)-5-chloro-4'-((1-phenylbutyl)carbamoyl)-[1,1'-biphenyl]-2-carboxylic acid

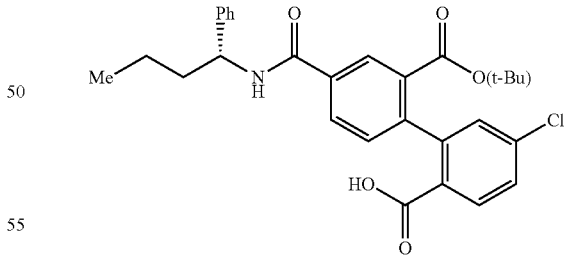

Into the reaction vessel was added 1G (475 mg, 0.743 mmol), THF (7.429 mL), sat NH$_4$Cl solution (3 mL), and Zn (243 mg, 3.71 mmol). The reaction mixture was stirred vigorously at rt for 1 h and extracted with EtOAc (20 mL×3). The combined organic layer was dried over Na$_2$SO$_4$ and concentrated under reduced pressure to produce 1H as a white solid (339 mg, 0.667 mmol, 90%), which was used for subsequent steps without further purification. LCMS Anal. Calc'd for C$_{29}$H$_{30}$ClNO$_5$ 507.18, found [M+H] 508.1.

Example 1. (R)-5'-Chloro-2'-(5-methoxy-1H-benzo[d]imidazol-2-yl)-4-((1-phenylbutyl)carbamoyl)-[1,1'-biphenyl]-2-carboxylic acid

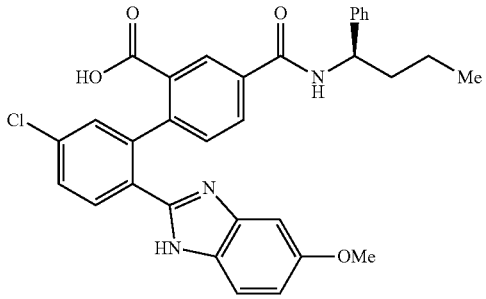 [SMILES: CCC[C@@H](NC(=O)c1ccc(-c2cc(Cl)ccc2-c2nc3cc(OC)ccc3[nH]2)c(C(=O)O)c1)c1ccccc1]

Into the reaction vessel was added 1H (18 mg, 0.035 mmol), 4-methoxy-benzene-1,2-diamine (9.79 mg, 0.0710 mmol), DIEA (0.031 mL, 0.18 mmol), DCM (1 mL), and HATU (20.21 mg, 0.05300 mmol). The reaction mixture was stirred at rt for 12 h, concentrated under reduced pressure, dissolved in AcOH (1 mL)/water (0.1 mL). After stirring at 85° C. for 12 h, the reaction mixture was allowed to cool to rt, concentrated under reduced pressure, and subjected to preparative HPLC purification to produce example 1 (16.3 mg, 0.024 mmol, 68.9% yield) as a brown film. LCMS Anal. Calc'd for $C_{32}H_{28}ClN_3O_4$ 553.18, found [M+H] 554.1; $^1$H NMR (500 MHz, methanol-$d_4$) δ 8.98 (d, J=8.0 Hz, 1H), 8.39 (dd, J=5.8, 1.7 Hz, 1H), 8.11-8.02 (m, 1H), 7.87 (d, J=8.3 Hz, 1H), 7.77 (dd, J=8.4, 2.1 Hz, 1H), 7.61 (d, J=1.7 Hz, 1H), 7.55 (d, J=9.1 Hz, 1H), 7.51 (dd, J=8.0, 4.4 Hz, 1H), 7.41-7.38 (m, 2H), 7.37-7.32 (m, 2H), 7.28-7.23 (m, 1H), 7.19 (dd, J=9.1, 2.2 Hz, 1H), 7.10 (d, J=2.2 Hz, 1H), 5.19-5.04 (m, 1H), 2.05-1.76 (m, 2H), 1.56-1.32 (m, 2H), 0.99 (t, J=7.4 Hz, 3H).

Example 2. (R)-2'-(1H-Benzo[d]imidazol-2-yl)-5'-chloro-4-((1-phenylbutyl)carbamoyl)-[1,1'-biphenyl]-2-carboxylic acid

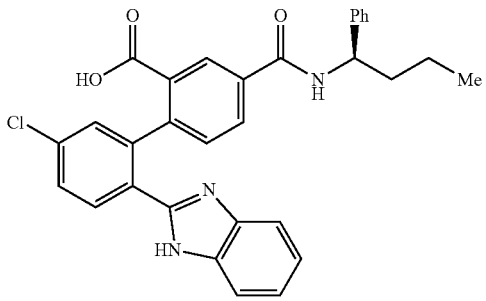 [SMILES: CCC[C@@H](NC(=O)c1ccc(-c2cc(Cl)ccc2-c2nc3ccccc3[nH]2)c(C(=O)O)c1)c1ccccc1]

Intermediate 2A. 2'-(tert-Butoxycarbonyl)-5-chloro-4'-((2-(trimethylsilyl)ethoxy) carbonyl)-[1,1'-biphenyl]-2-carboxylic acid

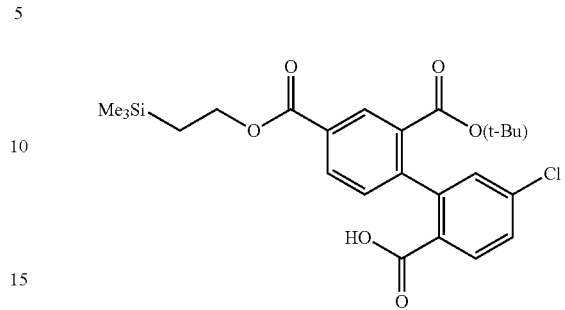

Into the reaction vessel was added 1F (250 mg, 0.411 mmol), THF (5 mL), sat NH$_4$Cl solution (2.5 mL), and Zn (134 mg, 2.06 mmol). The reaction mixture was stirred vigorously at rt for 1 h and extracted with EtOAc (10 mL×3). The combined organic layer was dried over Na$_2$SO$_4$ and concentrated under reduced pressure. The residue was dissolved in DCM (10 mL) and filtered to remove insoluble impurities. After concentration under reduced pressure, 2A (white foam, 190 mg, 97%) was used for subsequent step without further purification. LCMS Anal. Calc'd for $C_{24}H_{29}ClO_6Si$ 476.14, found [M+H] 477.1.

Intermediate 2B. 2-tert-Butyl 4-(2-(trimethylsilyl)ethyl)2'-((2-((tert-butoxycarbonyl)amino)phenyl)carbamoyl)-5'-chloro-[1,1'-biphenyl]-2,4-dicarboxylate

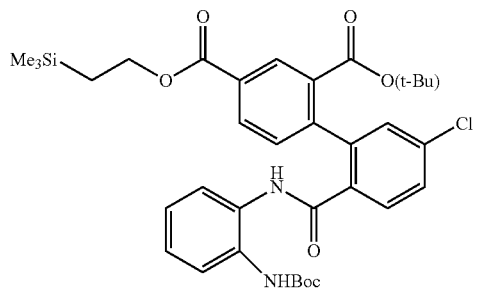

Into the reaction vessel was added 2A (190 mg, 0.398 mmol), benzene-1,2-diamine (95 mg, 0.88 mmol), DIEA (0.348 mL, 1.99 mmol), DCM (7.5 mL), and HATU (189 mg, 0.498 mmol). The reaction mixture was stirred at rt for 12 h, and BOC$_2$O (0.388 mL, 1.673 mmol) was added. After stirring at 50° C. for 12 h, the reaction mixture was allowed to cool to rt, concentrated under reduced pressure, and purified by silica gel chromatography to produce 2B (292 mg, 0.362 mmol, 91.0%) as a colorless oil. LCMS Anal. Calc'd for $C_{35}H_{43}ClN_2O_7Si$ 666.25, found [M+H] 667.1; $^1$H NMR (500 MHz, chloroform-d) δ 8.47-8.37 (m, 1H), 8.14 (dd, J=7.8, 1.8 Hz, 1H), 7.78 (d, J=8.3 Hz, 1H), 7.67 (br. s., 1H), 7.50 (dd, J=8.3, 2.2 Hz, 1H), 7.37 (d, J=7.7 Hz, 1H), 7.17-7.09 (m, 2H), 6.97-6.88 (m, 1H), 6.65 (d, J=8.0 Hz, 1H), 4.52-4.37 (m, 2H), 1.52 (s, 9H), 1.41 (s, 9H), 1.18-1.11 (m, 2H), 0.09 (s, 9H).

Intermediate 2C. 2-(tert-Butoxycarbonyl)-2'-((2-((tert-butoxycarbonyl)amino)phenyl)carbamoyl)-5'-chloro-[1,1'-biphenyl]-4-carboxylic acid

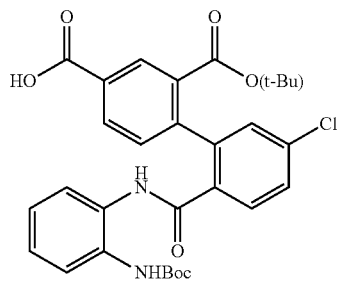

Intermediate 2B (292 mg, 0.362 mmol) was dissolved in THF (5 mL) and TBAF (1.992 mL, 1.992 mmol) was added at 0° C. The ice bath was removed and the reaction mixture was allowed to stir at rt for 1 h. After quenching by the addition of sat NH$_4$Cl (20 mL), the reaction mixture was extracted with EtOAc (20 mL×3), dried with Na$_2$SO$_4$, and concentrated under reduced pressure to generate 2C (205 mg, 0.362 mmol, 100% yield), which was used for subsequent steps without further purification. LCMS Anal. Calc'd for C$_{30}$H$_{31}$ClN$_2$O$_7$ 566.18, found [M+H] 567.1.

Example 2

Into the reaction vessel was added 2C (50 mg, 0.088 mmol), (R)-1-phenylbutan-1-amine (26.3 mg, 0.176 mmol), DIEA (0.077 mL, 0.44 mmol), DCM (2 mL), and HATU (50.3 mg, 0.132 mmol). The reaction mixture was stirred at rt for 12 h, concentrated under reduced pressure, and the residue was dissolved in AcOH (1.5 mL)/H$_2$O (0.15 mL). After stirring at 85° C. for 12 h, the reaction mixture was allowed to cool to rt, concentrated under reduced pressure, and subjected to preparative HPLC purification to produce example 2 (44 mg, 0.069 mmol, 78% yield) as a yellow foam. LCMS Anal. Calc'd for C$_{31}$H$_{26}$ClN$_3$O$_3$ 523.17, found [M+H] 524.1; $^1$H NMR (500 MHz, DMSO-d$_6$) δ 8.98 (d, J=8.3 Hz, 1H), 8.34 (d, J=1.9 Hz, 1H), 8.02 (dd, J=8.0, 1.7 Hz, 1H), 7.90 (d, J=8.5 Hz, 1H), 7.72 (dd, J=8.4, 2.1 Hz, 1H), 7.49 (dd, J=5.8, 3.3 Hz, 2H), 7.44 (d, J=1.7 Hz, 1H), 7.42-7.37 (m, 2H), 7.36-7.31 (m, 3H), 7.26-7.20 (m, 3H), 5.08-5.00 (m, 1H), 1.94-1.83 (m, 1H), 1.78-1.68 (m, 1H), 1.44-1.35 (m, 1H), 1.33-1.25 (m, 1H), 0.91 (t, J=7.4 Hz, 3H).

Examples 12-40, 47-49, 51-66, 69-76, and 78-80 may be synthesized by one skilled in the art by appropriate application of the procedures described for Examples 1-2.

Example 3. (R)-5'-Chloro-2'-(5-hydroxy-1H-benzo[d]imidazol-2-yl)-4-((1-phenylbutyl)carbamoyl)-[1,1'-biphenyl]-2-carboxylic acid

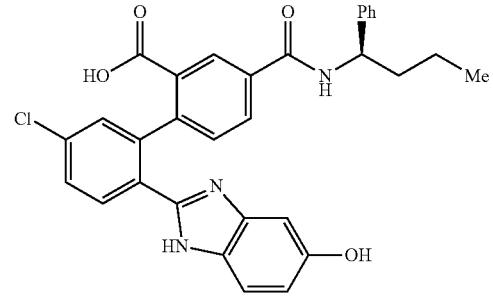

Intermediate 3A. 1 Amino 3 Nitrophenyl Acetate

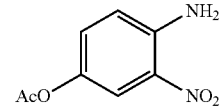 [SMILES: CC(=O)Oc1ccc(N)c([N+](=O)[O-])c1]

Into the reaction vessel containing 4-amino-3-nitrophenol (121 mg, 0.785 mmol) was added DCM (3 mL), Ac$_2$O (0.074 mL, 0.79 mmol), and DMAP (4.80 mg, 0.039 mmol). The reaction mixture was stirred at rt for 12 h, concentrated under reduced pressure, and subjected to silica gel chromatography purification to produce 3A (99 mg, 0.51 mmol, 64% yield) as a yellow solid. LCMS Anal. Calc'd for C$_8$H$_8$N$_2$O$_4$ 196.05, found [M+H] 197.0; $^1$H NMR (500 MHz, chloroform-d) δ 8.01-7.81 (m, 1H), 7.22-7.09 (m, 1H), 6.83 (d, J=9.1 Hz, 1H), 6.17-5.96 (m, 2H), 2.32 (s, 3H).

Intermediate 3B. 3,4-Diaminophenyl Acetate

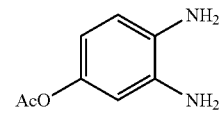

Into the reaction vessel containing 3A (99 mg, 0.51 mmol) was added THF (2 mL), water (2 mL), NH$_4$Cl (500 mg, 9.35 mmol), and zinc (264 mg, 4.04 mmol). The reaction mixture was stirred vigorously at rt for 30 min and extracted with EtOAc (15mLX3). The combined organic layer was dried over Na$_2$SO$_4$, concentrated under reduced pressure, and subjected to silica gel chromatography purification to produce 3B (58 mg, 0.35 mmol, 69% yield) as pale pink solid. LCMS Anal. Calc'd for C$_8$H$_{10}$N$_2$O$_2$ 166.07, found [M+H] 167.1; 1H NMR (500 MHz, chloroform-d) δ 6.74-6.62 (m, 1H), 6.53-6.20 (m, 2H), 3.61-3.37 (m, 2H), 3.32-3.11 (m, 2H), 2.25 (s, 3H).

Example 3

Into the reaction vessel was added 1H (15 mg, 0.030 mmol), 3,4-diamino-phenyl acetate (9.81 mg, 0.0590 mmol), DIEA (0.026 mL, 0.15 mmol), DCM (1 mL), and HATU (16.84 mg, 0.04400 mmol). The reaction mixture was stirred at rt for 12 h, concentrated under reduced pressure, and dissolved in AcOH (1 mL)/water (0.1 mL). After stirring at 85° C. for 48 h, the reaction mixture was allowed to cool to rt, concentrated under reduced pressure, and subjected to preparative HPLC purification to produce example 3 (13.9 mg, 0.0210 mmol, 72.0% yield) as a brown solid. LCMS Anal. Calc'd for $C_{31}H_{26}ClN_3O_4$ 539.16, found [M+H] 540.1; $^1$H NMR (500 MHz, methanol-$d_4$) δ 8.98 (d, J=8.3 Hz, 1H), 8.43-8.29 (m, 1H), 8.03 (t, J=7.2 Hz, 1H), 7.83 (d, J=8.3 Hz, 1H), 7.73 (dd, J=8.4, 2.1 Hz, 1H), 7.58 (s, 1H), 7.52-7.42 (m, 2H), 7.41-7.35 (m, 2H), 7.34-7.28 (m, 2H), 7.26-7.18 (m, 1H), 7.03 (dd, J=8.9, 2.1 Hz, 1H), 6.93 (d, J=1.9 Hz, 1H), 5.15-5.05 (m, 1H), 1.98-1.78 (m, 2H), 1.50-1.27 (m, 2H), 0.96 (t, J=7.4 Hz, 3H).

Example 4. (R)-5'-Chloro-2'-(4-phenyl-1H-imidazol-2-yl)-4-((1-phenylbutyl)carbamoyl)-[1,1'-biphenyl]-2-carboxylic acid

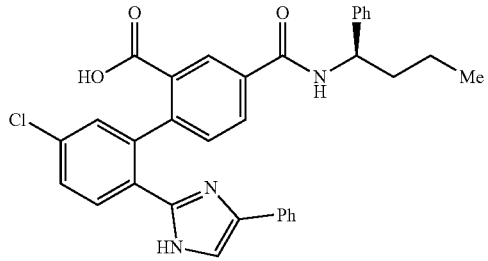 [SMILES: CCC[C@@H](NC(=O)c1ccc(-c2cc(Cl)ccc2-c2nc(-c3ccccc3)c[nH]2)c(C(=O)O)c1)c1ccccc1]

Into the reaction vessel was added 1H (20 mg, 0.039 mmol), $Cs_2CO_3$ (13.47 mg, 0.04100 mmol), and DMF (1 mL). The reaction mixture was stirred for 10 min and 2-bromo-1-phenylethanone (7.84 mg, 0.0390 mmol) was added. After stirring at rt for 1 h, the reaction mixture was concentrated under reduced pressure, dissolved with EtOAc (20 mL), and filtered. After concentration, the residue was dissolved in AcOH (1.5 mL) and ammonium acetate (60.7 mg, 0.787 mmol) was added. The reaction mixture was heated at 150° C. for 5 h, concentrated under reduced pressure, and subjected to preparative HPLC purification to produce 5 (7 mg, 10 μmol, 20% yield) as pale yellow solid. LCMS Anal. Calc'd for $C_{33}H_{28}ClN_3O_3$ 549.18, found [M+H] 550.1; $^1$H NMR (500 MHz, methanol-$d_4$) δ 8.98 (d, J=8.3 Hz, 1H), 8.41 (br. s., 1H), 8.11 (t, J=7.3 Hz, 1H), 7.84-7.79 (m, 1H), 7.76-7.71 (m, 2H), 7.64-7.56 (m, 3H), 7.54-7.44 (m, 4H), 7.43-7.39 (m, 2H), 7.34 (t, J=7.6 Hz, 2H), 7.29-7.24 (m, 1H), 5.18-5.08 (m, 1H), 2.03-1.81 (m, 2H), 1.54-1.32 (m, 2H), 1.00 (t, J=7.3 Hz, 3H).

Examples 50 and 102-107 may be synthesized by one skilled in the art by appropriate application of the procedures described for Examples 4.

Example 5. (S)-2'-(1H-benzo[d]imidazol-2-yl)-5'-chloro-4-((2-morpholino-1-phenylethyl)carbamoyl)-[1,1'-biphenyl]-2-carboxylic acid

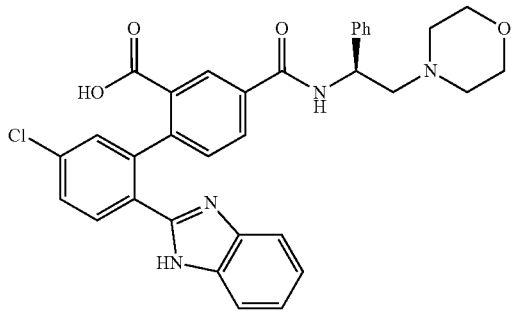 [SMILES: O=C(N[C@H](CN1CCOCC1)c1ccccc1)c1ccc(-c2cc(Cl)ccc2-c2nc3ccccc3[nH]2)c(C(=O)O)c1]

Intermediate 5A. (S)-2-((tert-butoxycarbonyl)amino)-2-phenylethyl methanesulfonate

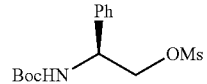

Into the reaction vessel was added (S)-tert-butyl (2-hydroxy-1-phenylethyl)carbamate (354 mg, 1.49 mmol), DCM (5 mL), and $Et_3N$ (0.624 mL, 4.48 mmol). The reaction mixture was cooled to 0° C. and MsCl (0.140 mL, 1.790 mmol) was added. The reaction mixture was allowed to warm to rt, stirred at rt for 30 min, cooled to 0° C., and 20 mL DCM and 20 mL water were added. The organic phase was collected, dried over $Na_2SO_4$, concentrated under reduced pressure, and subjected to silica gel chromatography purification to produce 5A (466 mg, 1.48 mmol, 99.0% yield). LCMS Anal. Calc'd for $C_{14}H_{21}NO_5S$ 315.11, found [M+H] 316.1; $^1$H NMR (500 MHz, chloroform-d) δ 7.43-7.39 (m, 2H), 7.37-7.33 (m, 3H), 5.16 (br. s., 1H), 5.04 (br. s., 1H), 4.56-4.38 (m, 2H), 2.91 (s, 3H), 1.46 (s, 9H).

Intermediate 5B. (S)-2-morpholino-1-phenylethan-1-amine

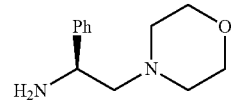

Into the reaction vessel was added 5A (45.5 mg, 0.144 mmol) and morpholine (37.7 mg, 0.433 mmol). The reaction mixture was stirred at rt for 12 h, concentrated, and subjected to preparative HPLC purification to provide the corresponding tert-butyl (S)-(2-morpholino-1-phenylethyl)carbamate which was treated with 3:1 DCM/TFA (1 mL) for 2 h at rt. The resulting reaction mixture was concentrated under reduced pressure and washed with a mixture of DCM/sat $NaHCO_3$(10 mL/10 mL). The organic phase was collected, dried over $Na_2SO_4$, and concentrated to produce 5B (17.6 mg, 0.085 mmol, 59.1% yield). $^1$H NMR (500 MHz, chloroform-d) δ 7.34-7.29 (m, 2H), 7.28-7.23 (m, 2H), 7.21-7.15 (m, 1H), 4.07 (dd, J=10.2, 3.6 Hz, 1H), 3.71-3.61 (m, 4H), 2.62-2.52 (m, 2H), 2.42-2.30 (m, 4H).

Example 5

Prepared from intermediate 5B following the general procedure described for the synthesis of example 2. LCMS Anal. Calc'd for $C_{33}H_{29}ClN_4O_4$ 580.19, found [M+H]580.9; $^1$H NMR (500 MHz, DMSO-$d_6$) δ 9.29 (d, J=8.5 Hz, 1H), 8.38 (s, 1H), 8.07 (d, J=8.0 Hz, 1H), 7.96 (s, 1H), 7.90 (d, J=8.5 Hz, 1H), 7.73 (dd, J=8.3, 1.7 Hz, 1H), 7.54-7.46 (m, 4H), 7.46-7.39 (m, 4H), 7.39-7.29 (m, 2H), 7.28-7.19 (m, 3H), 5.66 (t, J=8.4 Hz, 1H), 4.16-3.16 (m, 1H), 2.90 (s, 4H), 2.74 (s, 4H).

Examples 77 and 1.56 may be synthesized by one skilled in the art by appropriate application of the procedures described for Examples 5.

Example 6. (R)-2'-(1H-benzo[d]imidazol-2-yl)-5'-chloro-N2-cyano-N4-(1-phenylbutyl)-[1,1'-biphenyl]-2,4-dicarboxamide

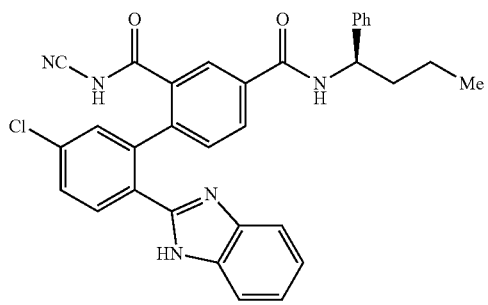 [SMILES: CCC[C@@H](NC(=O)c1ccc(-c2cc(Cl)ccc2-c2nc3ccccc3[nH]2)c(C(=O)NC#N)c1)c1ccccc1]

Into the reaction vessel containing example 2 (5 mg, 10 μmol) was added DCM (1 mL), cyanamide (2.006 mg, 0.04800 mmol), DIEA (8.33 μl, 0.0480 mmol), and HATU (7.26 mg, 0.0190 mmol). The reaction mixture was stirred at rt for 12 h, concentrated under reduced pressure, and subjected to preparative HPLC purification to produce example 6 (2.7 mg, 3.9 μmol, 41% yield). LCMS Anal. Calc'd for $C_{32}H_{26}ClN_5O_2$ 547.18, found [M+H] 547.9; $^1$H NMR (500 MHz, DMSO-$d_6$) δ 8.90 (d, J=8.5 Hz, 1H), 8.11 (s, 1H), 7.88 (d, J=8.3 Hz, 1H), 7.83 (d, J=7.7 Hz, 1H), 7.74 (dd, J=8.4, 1.8 Hz, 1H), 7.56 (dd, J=6.1, 3.3 Hz, 2H), 7.40-7.34 (m, 3H), 7.31 (t, J=7.6 Hz, 2H), 7.26 (dd, J=6.1, 3.0 Hz, 2H), 7.22 (t, J=6.7 Hz, 1H), 7.15 (d, J=7.7 Hz, 1H), 5.06-4.97 (m, 1H), 1.91-1.81 (m, 1H), 1.75-1.67 (m, 1H), 1.43-1.32 (m, 1H), 1.30-1.21 (m, 1H), 0.90 (t, J=7.3 Hz, 3H).

Examples 41-46, 127, and 206 may be synthesized by one skilled in the art by appropriate application of the procedures described for Examples 6.

Example 7. (R)-2'-(1H-benzo[d]imidazol-2-yl)-5'-chloro-2-(hydroxymethyl)-N-(1-phenylbutyl)-[1,1'-biphenyl]-4-carboxamide

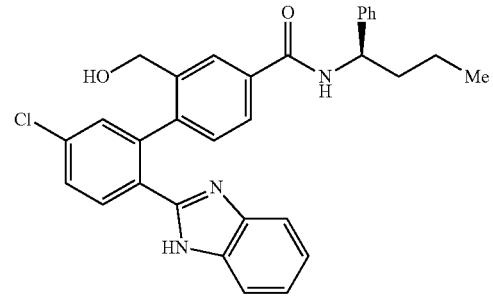 [SMILES: CCC[C@@H](NC(=O)c1ccc(-c2cc(Cl)ccc2-c2nc3ccccc3[nH]2)c(CO)c1)c1ccccc1]

Into the reaction vessel was added example 2 (16 mg, 0.025 mmol) and THF (0.5 mL). The reaction mixture was cooled to 0° C. and $BH_3$-THF (0.251 mL, 0.251 mmol) was added dropwise. After stirring at 0° C. for 10 min, the reaction mixture was allowed to warm to rt and stirred at rt for 1 h. The reaction mixture was diluted with EtOAc (10 mL) and washed with sat $NH_4Cl$ (20 mL). The aqueous phase was extracted with additional EtOAc (10 mL×2). The combined organic phase was dried over $Na_2SO_4$, concentrated under reduced pressure, and subjected to preparative HPLC purification to produce example 7 (5.9 mg, 8.8 μmol, 35% yield). LCMS Anal. Calc'd for $C_{31}H_{28}ClN_3O_2$ 509.19, found [M+H] 509.9; $^1$H NMR (500 MHz, DMSO-$d_6$) δ 8.78 (d, J=8.3 Hz, 1H), 7.98 (s, 1H), 7.90 (d, J=8.3 Hz, 1H), 7.75 (dd, J=8.4, 2.1 Hz, 1H), 7.69 (d, J=8.0 Hz, 1H), 7.55-7.50 (m, 3H), 7.39-7.35 (m, 2H), 7.31 (t, J=7.6 Hz, 2H), 7.26-7.20 (m, 3H), 7.14 (d, J=7.7 Hz, 1H), 5.05-4.97 (m, 1H), 4.36-4.22 (m, 2H), 1.89-1.81 (m, 1H), 1.76-1.66 (m, 1H), 1.43-1.33 (m, 1H), 1.30-1.22 (m, 1H), 0.89 (t, J=7.4 Hz, 3H).

Examples 131 and 205 may be synthesized by one skilled in the art by appropriate application of the procedures described for Examples 7.

Example 8. (R)-5'-chloro-2'-(5-methoxy-1H-benzo[d]imidazol-2-yl)-2-(5-oxo-2,5-dihydro-1,2,4-oxadiazol-3-yl)-N-(1-phenylbutyl)-[1,1'-biphenyl]-4-carboxamide

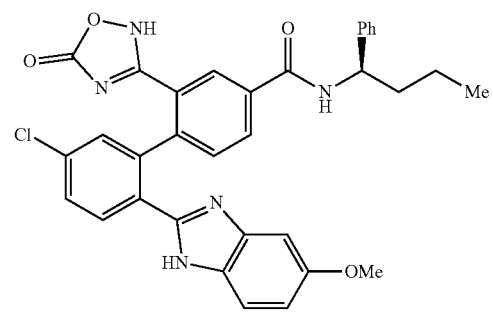 [SMILES: CCC[C@@H](NC(=O)c1ccc(-c2cc(Cl)ccc2-c2nc3cc(OC)ccc3[nH]2)c(-c2nc(=O)o[nH]2)c1)c1ccccc1]

Intermediate 8A. methyl 3-cyano-4-(((trifluoromethyl)sulfonyl)oxy)benzoate

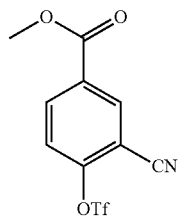 [SMILES: COC(=O)c1ccc(OS(=O)(=O)C(F)(F)F)c(C#N)c1]

Into the reaction vessel was added methyl 3-cyano-4-hydroxybenzoate (426 mg, 2.41 mmol), DCM (6.586 mL), and pyridine (0.972 mL, 12.0 mmol). The reaction mixture was cooled to 0° C. and Tf$_2$O (0.609 mL, 3.61 mmol) was added. The reaction mixture was allowed to warm to rt, stirred at rt for 30 min, cooled to 0° C., and 30 mL DCM and 50 mL water were added. The organic phase was collected, dried over Na$_2$SO$_4$, concentrated under reduced pressure, and subjected to silica gel chromatography purification to produce 8A (682 mg, 2.21 mmol, 92.0% yield). LCMS Anal. Calc'd for C$_{10}$H$_6$F$_3$NO$_5$S, 308.99, found [M+H] 309.7; $^1$H NMR (500 MHz, methanol-d$_4$) δ 8.45 (d, J=1.9 Hz, 1H), 8.38 (dd, J=8.7, 2.1 Hz, 1H), 7.60 (d, J=8.8 Hz, 1H), 4.00 (s, 3H).

Intermediate 8B. 4'-methyl 2-(2,2,2-trichloroethyl) 5-chloro-2'-cyano-[1,1'-biphenyl]-2,4'-dicarboxylate

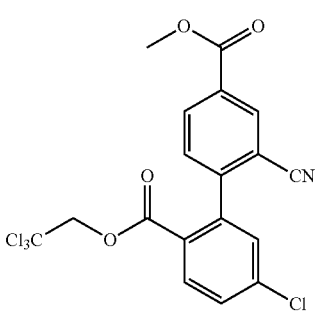

To a degassed solution of 8A (532 mg, 1.72 mmol) in dioxane (10.8 mL) was added 4,4,4',4',5,5,5',5'-octamethyl-2,2'-bi(1,3,2-dioxaborolane) (437 mg, 1.72 mmol) and PdCl$_2$(dppf)-CH$_2$Cl$_2$ adduct (70.2 mg, 0.0860 mmol), followed by potassium acetate (422 mg, 4.30 mmol). The reaction mixture was degassed for 10 min, then sealed and heated to 65° C. for 18 h. After reaction mixture was allowed to cool to rt, the solvent was removed in vacuo and the residue was redissolved in toluene (10.80 mL) then degassed. 2,2,2-trichloroethyl 2-bromo-4-chlorobenzoate (631 mg, 1.72 mmol), Na$_2$CO$_3$ (3.44 mL, 6.88 mmol), and PdCl$_2$(dppf)-CH$_2$Cl2 adduct (70.2 mg, 0.0860 mmol) were added, the reaction mixture was degassed for 10 min, then sealed and heated to 65° C. for 18 h. The reaction mixture was partitioned between 10 mL water, and extracted with EtOAc (3×25 mL). The combined organics were dried over Na$_2$SO$_4$ and concentrated under reduced pressure. Silica gel chromatography purification produced 8B (343 mg, 0.767 mmol, 44.6% yield). $^1$H-NMR (500 MHz, chloroform-d) δ8.40 (d, J=1.7 Hz, 1H), 8.30 (dd, J=8.1, 1.8 Hz, 1H), 8.23 (d, J=8.5 Hz, 1H), 7.61 (dd, J=8.5, 2.2 Hz, 1H), 7.48 (d, J=8.0 Hz, 1H), 7.35 (d, J=2.2 Hz, 1H), 4.90-4.71 (m, 2H), 3.99 (s, 3H).

Intermediate 8C. methyl 2'-((2-((tert-butoxycarbonyl)amino)-5-methoxyphenyl)carbamoyl)-5'-chloro-2-cyano-[1,1'-biphenyl]-4-carboxylate

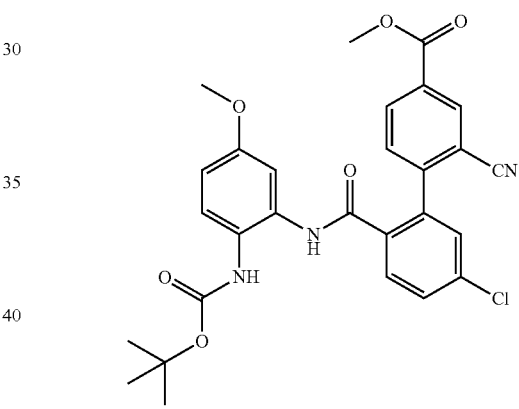

To a vial containing 8B (273 mg, 0.611 mmol) was added THF (3053 μl), sat NH$_4$Cl (aq) (3053 μl), and zinc (200 mg, 3.05 mmol). The reaction mixture was stirred at rt for 18 h, partitioned between water (2 mL), and extracted with EtOAc (3×2 mL). Combined organics were dried over Na$_2$SO$_4$, concentrated under reduced pressure, then redissolved in DCM (1.6 mL). To this solution was added tert-butyl (2-amino-4-methoxyphenyl)carbamate (337 mg, 2.44 mmol), HATU (464 mg, 1.22 mmol), and DIEA (533 μl, 3.05 mmol), and the reaction mixture was stirred at rt for 36 h. Concentration under reduced pressure and subsequent silica gel chromatography purification produced 8C (144 mg, 0.269 mmol, 44.0% yield). $^1$H-NMR (500 MHz, chloroform-d) δ 8.37-8.24 (m, 3H), 7.78 (d, J=8.5 Hz, 1H), 7.59-7.54 (m, 2H), 7.41 (d, J=1.9 Hz, 1H), 7.31 (d, J=8.8 Hz, 1H), 7.04 (d, J=3.0 Hz, 1H), 6.82 (s, 1H), 6.67 (dd, J=8.8, 2.8 Hz, 1H), 3.95 (s, 3H), 3.77 (s, 3H), 1.50 (s, 9H).

Intermediate 8D. tert-butyl (R)-(2-(5-chloro-2'-cyano-4'-((1-phenylbutyl)carbamoyl)-[1,1'-biphenyl]-2-carboxamido)-4-methoxyphenyl)carbamate

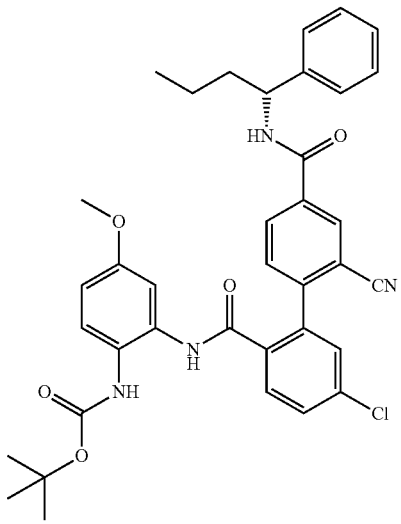

To a solution of 8C in tetrahydrofuran (1866 μl) was added LiOH (187 μl, 0.187 mmol, 1M solution in H₂O). The reaction mixture was stirred at rt for 18 h and 5 mL of sat NH₄Cl was added and the resulting mixture was extracted with DCM (3×5 mL). The combined organics were concentrated under reduced pressure and the residue was redissolved in 2 mL DCM. To this solution was added (R)-1-phenylbutan-1-amine (27.8 mg, 0.187 mmol), HATU (70.9 mg, 0.187 mmol), and DIEA (163 μl, 0.933 mmol). After stirring at rt for 18 h, the reaction mixture was concentrated under reduced pressure and subjected to silica gel chromatography purification to afford 8D (41.3 mg, 0.0630 mmol, 67.8% yield) as a purple foam. LCMS Anal. Calc'd for $C_{37}H_{37}ClN_4O_5$ 652.25, found [M+H-Boc] 552.9.

Example 8

To a solution of intermediate 8D (10 mg, 0.015 mmol) in MeOH (1 mL) was added hydroxylamine hydrochloride (6.38 mg, 0.0920 mmol) and DIEA (0.017 mL, 0.10 mmol). The resulting purple suspension was heated at 50° C. for 36 h. The reaction mixture was allowed to cool to rt and concentrated under reduced pressure. The residue was redissolved in 1,4-Dioxane (0.5 mL) and CDI (7.45 mg, 0.0460 mmol) was added. The reaction mixture was heated to 70° C. for 18 h, concentrated, and redissolved in 2 mL AcOH/H₂O (10:1). After heating at 85° C. for 12 h, the reaction mixture was allowed to cool, concentrated under reduced pressure and subjected to preparative HPLC purification to provide example 8 (2.3 mg, 3.3 μmol, 21% yield). LCMS Anal. Calc'd for $C_{33}H_{28}ClN_5O_4$ 593.18, found [M+H] 594.0; 1H NMR (500 MHz, methanol-d₄) δ 8.92 (d, J=8.0 Hz, 1H), 8.20 (td, J=8.4, 1.7 Hz, 1H), 7.93 (dd, J=9.9, 1.7 Hz, 1H), 7.81-7.77 (m, 3H), 7.72 (d, J=1.4 Hz, 1H), 7.49 (d, J=8.8 Hz, 1H), 7.39-7.36 (m, 2H), 7.33 (dt, J=7.6, 3.9 Hz, 2H), 7.27-7.20 (m, 1H), 7.14 (dd, J=8.9, 2.3 Hz, 1H), 7.05 (d, J=2.2 Hz, 1H), 5.13-5.06 (m, 1H), 3.86 (s, 3H), 1.97-1.89 (m, 1H), 1.87-1.77 (m, 1H), 1.50-1.40 (m, 1H), 1.39-1.31 (m, 1H), 0.97 (td, J=7.4, 2.3 Hz, 3H

Example 9. (R)-2'-(1H-benzo[d]imidazol-2-yl)-5'-chloro-2-(3-oxo-2,3-dihydro-1,2,4-oxadiazol-5-yl)-N-(1-phenylbutyl)-[1,1'-biphenyl]-4-carboxamide

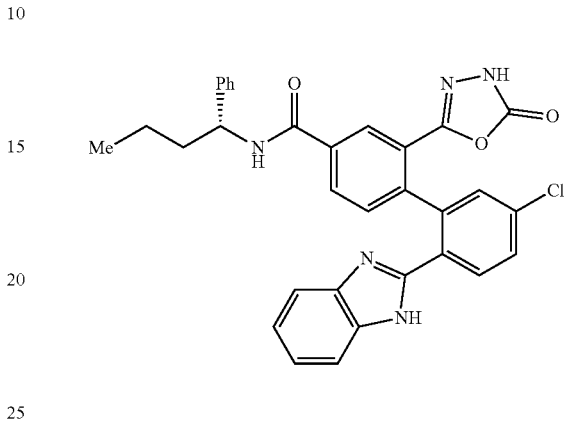

To a solution of example 2 (15 mg, 0.029 mmol) in tetrahydrofuran (286 μl), was added CDI (5.11 mg, 0.0310 mmol). The reaction mixture was stirred at rt for 1 h, then hydrazine (3.14 μl, 0.100 mmol) was added. After stirring at rt for 2 h, the reaction mixture was concentrated under reduced pressure, redissolved in tetrahydrofuran (286 μl), and additional CDI (5.11 mg, 0.0310 mmol) was added. After stirred at rt for 18 hrs, preparative HPLC purification afforded example 9 (13 mg, 0.023 mmol, 79%). LCMS Anal. Calc'd for $C_{32}H_{26}ClN_5O_3$ 563.17, found [M+H] 564.2; ¹H NMR (500 MHz, DMSO-d₆) δ 9.02 (d, J=7.6 Hz, 1H), 8.17 (s, 1H), 8.07-8.00 (m, 1H), 7.84 (d, J=8.5 Hz, 1H), 7.70 (dd, J=8.2, 2.1 Hz, 1H), 7.53 (s, 1H), 7.44 (d, J=7.0 Hz, 1H), 7.42-7.36 (m, J=5.2 Hz, 4H), 7.35-7.28 (m, 2H), 7.21 (d, J=8.2 Hz, 1H), 7.17-7.08 (m, 2H), 5.07-4.99 (m, 1H), 1.94-1.80 (m, J=8.5 Hz, 1H), 1.77-1.65 (m, 1H), 1.44-1.33 (m, 1H), 1.31-1.24 (m, J=7.3 Hz, 1H), 0.95-0.83 (m, J=2.4 Hz, 3H).

Examples 129-130 may be synthesized by one skilled in the art by appropriate application of the procedures described for Examples 9.

Example 10. (R)-5'-chloro-2'-(5-methoxy-1H-benzo[d]imidazol-2-yl)-N-(1-phenylbutyl)-2-(5-thioxo-2,5-dihydro-1,2,4-oxadiazol-3-yl)-[1,1'-biphenyl]-4-carboxamide

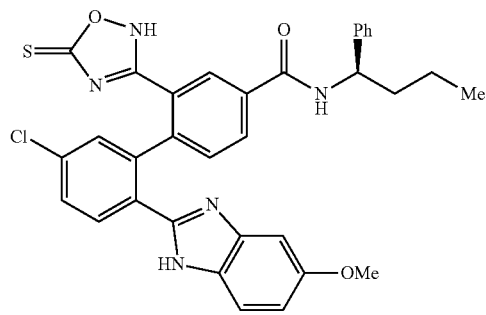 [SMILES: CCC[C@@H](NC(=O)c1ccc(-c2cc(Cl)ccc2-c2nc3cc(OC)ccc3[nH]2)c(-c2nc(=S)o[nH]2)c1)c1ccccc1]

To a solution of example 8D (8 mg, 0.01 mmol) in MeOH (500 μL) was added hydroxylamine hydrochloride (5.11 mg, 0.0730 mmol) and Hunig's Base (12.83 μL, 0.07300 mmol). The resulting purple suspension was heated at 50° C. for 18 h, cooled to rt, partitioned between 1 mL water, and extracted with EtOAc (2 mL×3). The combined organic layer was dried over Na$_2$SO$_4$, concentrated under reduced pressure, and redissolved in 500 uL 1,4-dioxane. After addition of 1,1'-thiocarbonyldiimidazole (4.37 mg, 0.0240 mmol), the reaction mixture was heated at 70° C. for 18 h, cooled to rt, concentrated under reduced pressure, redissolved in 1.5 mL AcOH/H$_2$O (10:1) and heated to 70° C. for 48 h. The reaction mixture was allowed to cool, concentrated under reduced pressure and the residue purified by preparative HPLC to generate example 10 (0.7 mg, 1 μmol, 8% yield). LCMS Anal. Calc'd for C$_{33}$H$_{28}$ClN$_5$O$_3$S 609.16, found [M+H] 610.1; $^1$H NMR (400 MHz, methanol-d$_4$) δ 8.16-8.09 (m, J=5.7 Hz, 1H), 7.93 (d, J=2.4 Hz, 1H), 7.80-7.72 (m, J=1.8 Hz, 2H), 7.72-7.66 (m, 2H), 7.49 (d, J=9.0 Hz, 1H), 7.40-7.36 (m, 2H), 7.32 (t, J=7.6 Hz, 2H), 7.27-7.20 (m, 1H), 7.12 (dd, J=9.0, 2.0 Hz, 1H), 7.05 (s, 1H), 5.14-5.04 (m, 1H), 3.86 (s, 3H), 1.99-1.76 (m, 2H), 1.51-1.27 (m, 2H), 0.97 (t, J=7.4 Hz, 3H).

Example 11. (R)-2'-(1H-benzo[d]imidazol-2-yl)-5'-chloro-5-methyl-4-((1-phenylbutyl)carbamoyl)-[1,1'-biphenyl]-2-carboxylic acid

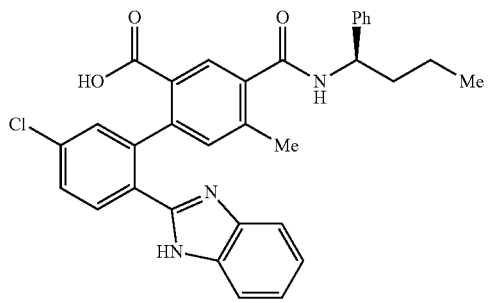 [SMILES: CCC[C@@H](NC(=O)c1cc(C(=O)O)c(-c2cc(Cl)ccc2-c2nc3ccccc3[nH]2)cc1C)c1ccccc1]

Intermediate 11A. 2-(tert-butyl) 2'-methyl 4-(2-(trimethylsilyl)ethyl) 5'-chloro-[1,1'-biphenyl]-2,2',4-tricarboxylate

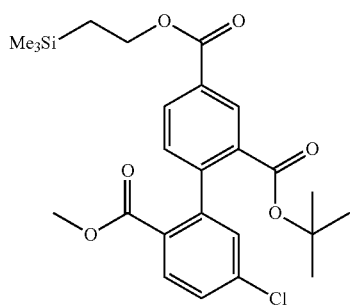 [SMILES: COC(=O)c1ccc(Cl)cc1-c1ccc(C(=O)OCC[Si](C)(C)C)cc1C(=O)OC(C)(C)C]

Into the reaction vessel containing 1D (2000 mg, 4.46 mmol) was added methyl 2-bromo-4-chlorobenzoate (1335 mg, 5.350 mmol), THF (17 mL), water (17 mL), K$_2$CO$_3$ (1849 mg, 13.38 mmol), and Pd(Ph$_3$P)$_4$ (515 mg, 0.446 mmol). The reaction mixture was degassed by bubbling N2 for 10 min, sealed, and stirred at 65° C. for 12 h. The reaction mixture was allowed to cool to rt, was concentrated under reduced pressure and subjected to silica gel chromatography purification to produce 11A (1860 mg, 3.79 mmol, 85.0% yield). LCMS Anal. Calc'd for C$_{25}$H$_{31}$ClO$_6$Si 490.16, found [M+H] 490.8 $^1$H NMR (500 MHz, chloroform-d) δ 8.60 (d, J=1.7 Hz, 1H), 8.64-8.56 (m, 1H), 8.15 (dd, J=8.0, 1.7 Hz, 1H), 7.99 (d, J=8.5 Hz, 1H), 7.43 (dd, J=8.5, 2.2 Hz, 1H), 7.24-7.21 (m, 2H), 4.49-4.43 (m, 2H), 3.60 (s, 3H), 1.25 (s, 9H), 1.20-1.14 (m, 2H), 0.10 (s, 9H).

Intermediate 11B. 2-(tert-butoxycarbonyl)-5'-chloro-2'-(methoxycarbonyl)-5-methyl-[1,1'-biphenyl]-4-carboxylic acid

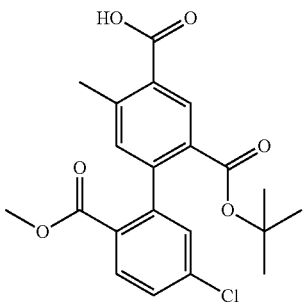 [SMILES: COC(=O)c1ccc(Cl)cc1-c1cc(C)c(C(=O)O)cc1C(=O)OC(C)(C)C]

Into the reaction vessel was added 11A (130 mg, 0.265 mmol), THF (2 mL), and TBAF (0.529 mL, 0.529 mmol). The reaction mixture was stirred at rt for 60 min, diluted with EtOAc (20 mL), and washed with sat NH$_4$Cl (20 mL). The organic phase was collected, dried over Na$_2$SO$_4$, and concentrated under reduced pressure to produce the intermediate acid which was dissolved directly in tBuOH (1.5 mL). 1,4-benzoquinone (0.595 mg, 5.50 μmol), palladium (II) acetate (2.470 mg, 0.01100 mmol), N-(tert-Butoxycarbonyl)-L-phenylalanine (5.84 mg, 0.022 mmol), potassium methyltrifluoroborate (40.2 mg, 0.330 mmol), lithium carbonate (16.26 mg, 0.2200 mmol) and silver carbonate (60.7 mg, 0.220 mmol) were subsequently added. The reaction mixture was degassed by applying vacuum on the reaction vessel followed by charging with N2. After degassing, the reaction mixture was stirred vigorously at rt for 5 min and at 90° C. for 12 h. Upon cooling to rt, the mixture was diluted with EtOAc (20 mL) and washed with sat NH$_4$Cl (10 mL) containing 0.88 mmol HCl. The organic phase was collected and concentrated under reduced pressure. Silica gel chromatography purification produced 11B (24.7 mg, 0.0610 mmol, 55.5% yield). $^1$H NMR (500 MHz, chloroform-d) δ 8.69 (s, 1H), 8.00 (d, J=8.5 Hz, 1H), 7.43 (dd, J=8.5, 2.2 Hz, 1H), 7.23 (d, J=2.2 Hz, 1H), 7.08 (s, 1H), 3.64 (s, 3H), 2.71 (s, 3H).

Intermediate 11C. 2-(tert-butyl) 2'-methyl (R)-5'-chloro-5-methyl-4-((1-phenylbutyl)carbamoyl)-[1,1'-biphenyl]-2,2'-dicarboxylate

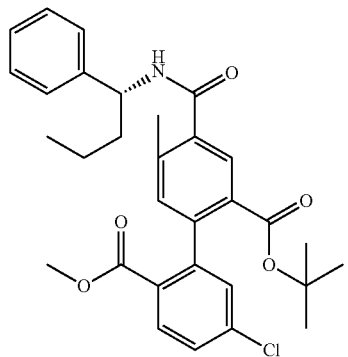 [SMILES: CCC[C@@H](NC(=O)c1cc(C(=O)OC(C)(C)C)c(-c2cc(Cl)ccc2C(=O)OC)cc1C)c1ccccc1]

Into the reaction vessel was added 11B (24.7 mg, 0.0610 mmol), (R)-1-phenylbutan-1-amine (12.29 mg, 0.08200 mmol), DCM (3 mL), DIEA (0.053 mL, 0.31 mmol), and HATU (30.2 mg, 0.0790 mmol). The reaction mixture was stirred at rt for 12 h, concentrated under reduced pressure, and subjected to silica gel chromatography purification to produce 11C (29 mg, 0.054 mmol, 89% yield). LCMS Anal. Calc'd for $C_{31}H_{34}ClNO_5$ 535.21, found [M+H] 535.9 $^1$H NMR (400 MHz, chloroform-d) δ 8.02-7.93 (m, 2H), 7.40 (dd, J=8.5, 2.1 Hz, 1H), 7.37 (dd, J=4.1, 1.7 Hz, 3H), 7.32-7.27 (m, 1H), 7.17 (dd, J=3.4, 2.1 Hz, 1H), 6.99 (d, J=5.1 Hz, 1H), 6.16 (d, J=8.1 Hz, 1H), 5.18 (q, J=7.7 Hz, 1H), 3.65 (d, J=7.0 Hz, 3H), 2.50-2.40 (m, 3H), 1.99-1.80 (m, 2H), 1.52-1.33 (m, 2H), 1.19 (d, J=3.5 Hz, 9H), 0.98 (td, J=7.4, 1.5 Hz, 3H).

Example 11

Into the reaction vessel was added 11C (29 mg, 0.054 mmol), THF (2 mL), water (1 mL), and lithium hydroxide monohydrate (22.70 mg, 0.5410 mmol). The reaction mixture was stirred at rt for 2d, diluted with EtOAc (20 mL), and washed with 10 mL sat NH$_4$Cl containing 0.54 mmol HCl. The organic phased was dried over Na$_2$SO$_4$ and concentrated under reduced pressure to produce the intermediate carboxylic acid (29 mg, 0.056 mmol, 100% yield), which was used for next step without further purification. Into the reaction vessel was added the intermediate carboxylic acid (8 mg, 0.015 mmol), benzene-1,2-diamine (3.31 mg, 0.0310 mmol), DIEA (0.013 mL, 0.077 mmol), DCM (1 mL), and HATU (7.87 mg, 0.0210 mmol). The reaction mixture was stirred at rt for 12 h, concentrated under reduced pressure, and dissolved in AcOH (0.9 mL)/Water (0.1 mL). After stirring at 85° C. for 12 h, the reaction mixture was allowed to cool to rt, concentrated under reduced pressure, and subjected to preparative HPLC purification to produce example 11 (6.1 mg, 9.3.mol, 60% yield). LCMS Anal. Calc'd for $C_{32}H_{28}ClN_3O_3$ 537.18, found [M+H] 537.9; $^1$H NMR (500 MHz, DMSO-d$_6$) δ 8.86 (d, J=8.5 Hz, 1H), 7.87 (d, J=8.3 Hz, 1H), 7.75-7.67 (m, 2H), 7.54 (br. s., 2H), 7.43-7.32 (m, 5H), 7.30-7.17 (m, 4H), 5.05-4.94 (m, 1H), 2.40-2.22 (m, 3H), 1.86-1.76 (m, 1H), 1.73-1.64 (m, 1H), 1.47-1.25 (m, 2H), 0.92 (t, J=7.3 Hz, 3H)

Examples 67-68 may be synthesized by one skilled in the art by appropriate application of the procedures described for Examples 11.

TABLE 2

| Ex # | Structure | IUPAC Name | NMR | RT (min) [M + H] Method | APJ cAMP Human EC50 (nM) |
|---|---|---|---|---|---|
| 1 | 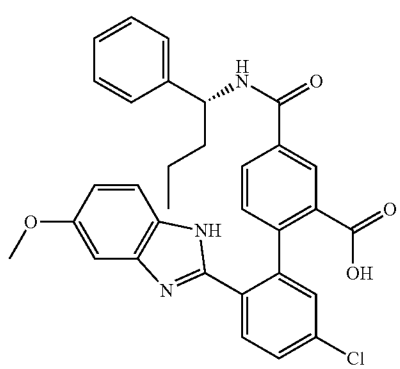 [SMILES: CCC[C@@H](NC(=O)c1ccc(-c2cc(Cl)ccc2-c2nc3cc(OC)ccc3[nH]2)c(C(=O)O)c1)c1ccccc1] | 5'-chloro-2'-(5-methoxy-1H-1,3-benzodiazol-2-yl)-4-{[(1R)-1-phenylbutyl]carbamoyl}-[1,1'-biphenyl]-2-carboxylic acid | $^1$H NMR (500 MHz, methanol-d4) δ 8.98 (d, J = 8.0 Hz, 1H), 8.39 (dd, J = 5.8, 1.7 Hz, 1H), 8.11-8.02 (m, 1H), 7.87 (d, J = 8.3 Hz, 1H), 7.77 (dd, J = 8.4, 2.1 Hz, 1H), 7.61 (d, J = 1.7 Hz, 1H), 7.55 (d, J = 9.1 Hz, 1H), 7.51 (dd, J = 8.0, 4.4 Hz, 1H), 7.41-7.38 (m, 2H), 7.37-7.32 (m, 2H), 7.28-7.23 (m, 1H), 7.19 (dd, J = 9.1, 2.2 Hz, 1H), 7.10 (d, J = 2.2 Hz, 1H), 5.19-5.04 (m, 1H), 2.05-1.76 (m, 2H), 1.56-1.32 (m, 2H), 0.99 (t, J = 7.4 Hz, 3H) | 0.95 553.9 A | A |

TABLE 2-continued

| Ex # | Structure | IUPAC Name | NMR | RT (min), [M + H] Method | APJ cAMP Human EC50 (nM) |
|---|---|---|---|---|---|
| 2 | 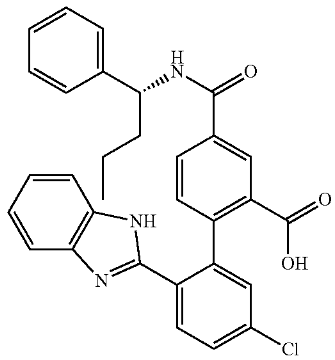 [SMILES: CCC[C@@H](NC(=O)c1ccc(-c2cc(Cl)ccc2-c2nc3ccccc3[nH]2)c(C(=O)O)c1)c1ccccc1] | 2'-(1H-1,3-benzodiazol-2-yl)-5'-chloro-4-{[(1R)-1-phenylbutyl]carbamoyl}-[1,1'-biphenyl]-2-carboxylic acid | 1H NMR (500 MHz, methanol-d4) δ 8.98 (d, J = 8.3 Hz, 1H), 8.34 (d, J = 1.9 Hz, 1H), 8.02 (dd, J = 8.0, 1.7 Hz, 1H), 7.90 (d, J = 8.5 Hz, 1H), 7.72 (dd, J = 8.4, 2.1 Hz, 1H), 7.49 (dd, J = 5.8, 3.3 Hz, 2H), 7.44 (d, J = 1.7 Hz, 1H), 7.42-7.37 (m, 2H), 7.36-7.31 (m, 3H), 7.26-7.20 (m, 3H), 5.08-5.00 (m, 1H), 1.94-1.83 (m, 1H), 1.78-1.68 (m, 1H), 1.44-1.35 (m, 1H), 1.33-1.25 (m, 1H), 0.91 (t, J = 7.4 Hz, 3H). | 0.93 524.0 A | A |
| 3 | 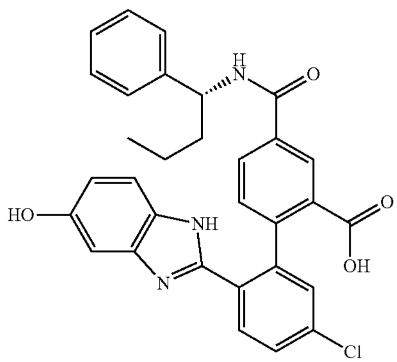 [SMILES: CCC[C@@H](NC(=O)c1ccc(-c2cc(Cl)ccc2-c2nc3cc(O)ccc3[nH]2)c(C(=O)O)c1)c1ccccc1] | 5'-chloro-2'-(5-hydroxy-1H-1,3-benzodiazol-2-yl)-4-{[(1R)-1-phenylbutyl]carbamoyl}-[1,1'-biphenyl]-2-carboxylic acid | $^1$H NMR (500 MHz, methanol-d4) δ 8.98 (d, J = 8.3 Hz, 1H), 8.43-8.29 (m, 1H), 8.03 (t, J = 7.2 Hz, 1H), 7.83 (d, J = 8.3 Hz, 1H), 7.73 (dd, J = 8.4, 2.1 Hz, 1H), 7.58 (s, 1H), 7.52-7.42 (m, 2H), 7.41-7.35 (m, 2H), 7.34-7.28 (m, 2H), 7.26-7.18 (m, 1H), 7.03 (dd, J = 8.9, 2.1 Hz, 1H), 6.93 (d, J = 1.9 Hz, 1H), 5.15-5.05 (m, 1H), 1.98-1.78 (m, 2H), 1.50-1.27 (m, 2H), 0.96 (t, J = 7.4 Hz, 3H) | 0.84 539.8 A | A |
| 4 | 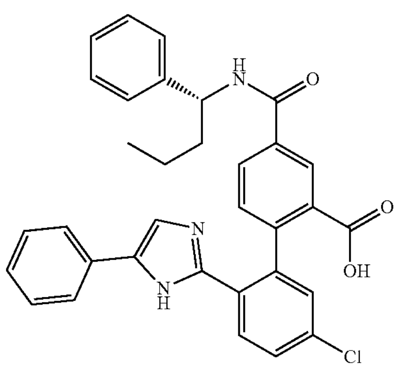 [SMILES: CCC[C@@H](NC(=O)c1ccc(-c2cc(Cl)ccc2-c2ncc(-c3ccccc3)[nH]2)c(C(=O)O)c1)c1ccccc1] | 5'-chloro-2-(5-phenyl-1H-imidazol-2-yl)-4-{[(1R)-1-phenylbutyl]carbamoyl}-[1,1'-biphenyl]-2-carboxylic acid | $^1$H NMR (500 MHz, methanol-d$_4$) δ 8.98 (d, J = 8.3 Hz, 1H), 8.41 (br. s., 1H), 8.11 (t, J = 7.3 Hz, 1H), 7.84-7.79 (m, 1H), 7.76-7.71 (m, 2H), 7.64-7.56 (m, 3H), 7.54-7.44 (m, 4H), 7.43-7.39 (m, 2H), 7.34 (t, J = 7.6 Hz, 2H), 7.29-7.24 (m, 1H), 5.18-5.08 (m, 1H), 2.03-1.81 (m, 2H), 1.54-1.32 (m, 2H), 1.00 (t, J = 7.3 Hz, 3H) | 0.94 550.0 A | A |
| 5 | 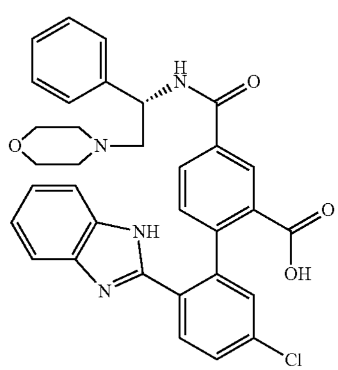 | 2'-(1H-1,3-benzodiazol-2-yl)-5'-chloro-4-{[(1S)-2-(morpholin-4-yl)-1-phenylethyl]carbamoyl}-[1,1'-biphenyl]-2-carboxylic acid | 1H NMR (500 MHz, DMSO-d6) δ 9.29 (d, J = 8.5 Hz, 1H), 8.28 (s, 1H), 8.07 (d, J = 8.0 Hz, 1H), 7.96 (s, 1H), 7.90 (d, J = 8.5 Hz, 1H), 7.73 (dd, J = 8.3, 1.7 Hz, 1H), 7.54-7.46 (m, 4H), 7.46-7.39 (m, 4H), 7.39-7.29 (m, 2H), 7.28-7.19 (m, 3H), 5.66 (t, J = 8.4 Hz, 1H), 4.16-3.16 (m, 1H), 2.90 (s, 4H), 2.74 (s, 4H) | 0.63 581.2 A | B |

TABLE 2-continued

| Ex # | Structure | IUPAC Name | NMR | RT (min), [M + H] Method | APJ cAMP Human EC50 (nM) |
|---|---|---|---|---|---|
| 6 | 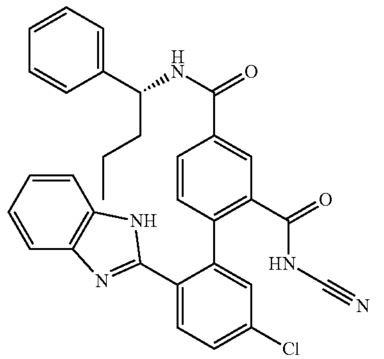 [SMILES: CCC[C@@H](NC(=O)c1ccc(-c2cc(Cl)ccc2-c2nc3ccccc3[nH]2)c(C(=O)NC#N)c1)c1ccccc1] | 2'-(1H-1,3-benzodiazol-2-yl)-5'-chloro-N2-cyano-N4-[(1R)-1-phenylbutyl]-[1,1'-biphenyl]-2,4-dicarboxamide | 1H NMR (500 MHz, DMSO-d6) δ 8.90 (d, J = 8.5 Hz, 1H), 8.1: (s, 1H), 7.88 (d, J = 8.3 Hz, 1H), 7.83 (d, J = 7.7 Hz, 1H), 7.74 (dd, J = 8.4, 1.8 Hz, 1H), 7.56 (dd, J = 6.1, 3.3 Hz, 2H), 7.40-7.34 (m, 3H), 7.31 (t, J = 7.6 Hz, 2H), 7.26 (dd, J = 6.1, 3.0 Hz, 2H), 7.22 (t, J = 6.7 Hz, 1H), 7.15 (d, J = 7.7 Hz, 1H), 5.06-4.97 (m, 1H), 1.91-1.81 (m, 1H), 1.75-1.67 (m, 1H), 1.43-1.32 (m, 1H), 1.30-1.21 (m, 1H), 0.90 (t, J = 7.3 Hz, 3H) | 0.94 547.9 A | C |
| 7 | 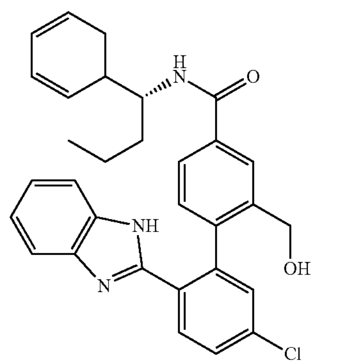 [SMILES: CCC[C@@H](NC(=O)c1ccc(-c2cc(Cl)ccc2-c2nc3ccccc3[nH]2)c(CO)c1)C1C=CC=CC1] | 2'-(1H-1,3-benzodiazol-2-yl)-5'-chloro-2-(hydroxymethyl)-N-[(1R)-1-phenylbutyl]-[1,1'-biphenyl]-4-carboxamide | 1H NMR (500MHz, DMSO-d6) δ 8.78 (d, J = 8.3 Hz, 1H), 7.98 (s, 1H), 7.90 (d, J = 8.3 Hz, 1H), 7.75 (dd, J = 8.4, 2.1 Hz, 1H), 7.69 (d, J = 8.0 Hz, 1H), 7.55-7.50 (m, 3H), 7.39-7.35 (m, 2H), 7.31 (t, J = 7.6 Hz, 2H), 7.26-7.20 (m, 3H), 7.14 (d, J = 7.7 Hz, 1H), 5.05-4.97 (m, 1H), 4.36-4.22 (m, 2H), 1.89-1.81 (m, 1H), 1.76-1.66 (m, 1H), 1.43-1.33 (m, 1H), 1.30-1.22 (m, 1H), 0.89 (t, J = 7.4 Hz, 3H) | 0.91 509.9 A | B |
| 8 | 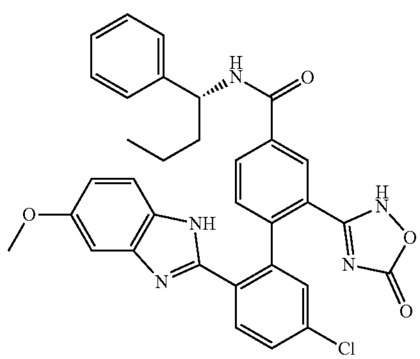 [SMILES: CCC[C@@H](NC(=O)c1ccc(-c2cc(Cl)ccc2-c2nc3cc(OC)ccc3[nH]2)c(-c2nc(=O)o[nH]2)c1)c1ccccc1] | 5'-chloro-2'-(5-methoxy-1H-1,3-benzodiazol-2-yl)-2-(5-oxo-2,5-dihydro-1,2,4-oxadiazol-3-yl)-N-[(1R)-1-phenylbutyl]-[1,1'-biphenyl]-4-carboxamide | 1H NMR (500 MHz, METHANOL-d4) δ 8.92 (d, J = 8.0 Hz, 1H), 8.20 (td, J = 8.4, 1.7 Hz, 1H), 7.93 (dd, J = 9.9, 1.7 Hz, 1H), 7.81-7.77 (m, 3H), 7.72 (d, J = 1.4 Hz, 1H), 7.49 (d, J = 8.8 Hz, 1H), 7.39-7.36 (m, 2H), 7.33 (dt, J = 7.6, 3.9 Hz, 2H), 7.27-7.20 (m, 3H), 7.14 (dd, J = 8.9, 2.3 Hz, 1H), 7.05 (d, J = 2.2 Hz, 1H), 5.13-5.06 (m, 1H), 3.86 (s, 3H), 1.97-1.89 (m, 1H), 1.87-1.77 (m, 1H), 1.50-1.40 (m, 1H), 1.39-1.31 (m, 1H), 0.97 (td, J = 7.4, 2.3 Hz, 3H) | 0.88 594.0 A | B |
| 9 | 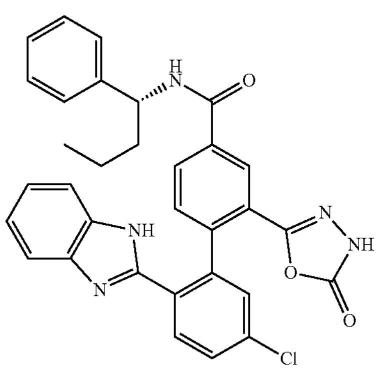 [SMILES: CCC[C@@H](NC(=O)c1ccc(-c2cc(Cl)ccc2-c2nc3ccccc3[nH]2)c(-c2n[nH]c(=O)o2)c1)c1ccccc1] | 2-(1H-1,3-benzodiazol-2-yl)-5'-chloro-2-(5-oxo-4,5-dihydro-1,3,4-oxadiazol-2-yl)-N-[(1R)-1-phenylbutyl]-[1,1'-biphenyl]-4-carboxamide | 1H NMR (500 MHz, DMSO-d6) δ 9.02 (d, J = 7.6 Hz, 1H), 8.17 (s, 1H), 8.07-8.00 (m, 1H), 7.84 (d, J = 8.5 Hz, 1H), 7.70 (dd, J = 8.2, 2.1 Hz, 1H), 7.53 (s, 1H), 7.44 (d, J = 7.0 Hz, 1H), 7.42-7.36 (m, 4H), 7.35-7.28 (m, 2H), 7.21 (d, J = 8.2 Hz, 1H), 7.17-7.08 (m, 2H), 5.07-4.99 (m, 1H), 1.94-1.80 (m, J = 8.5 Hz, 1H), 1.77-1.65 (m, 1H), 1.44-1.33 (m, 1H), 1.31-1.24 (m, J = 7.3 Hz, 1H), 0.95-0.83 (m, J = 2.4 Hz, 3H) | 1.72, 564.2 A | B |

TABLE 2-continued

| Ex # | Structure | IUPAC Name | NMR | RT (min), [M + H] Method | APJ cAMP Human EC50 (nM) |
|---|---|---|---|---|---|
| 10 | 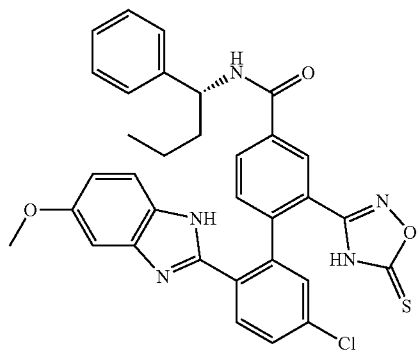 [SMILES: CCC[C@@H](NC(=O)c1ccc(-c2cc(Cl)ccc2-c2nc3cc(OC)ccc3[nH]2)c(-c2noc(=S)[nH]2)c1)c1ccccc1] | 5'-chloro-2'-(5-methoxy-1H-1,3-benzodiazol-2-yl)-N-[(1R)-1-phenylbutyl]-2-(5-sulfanylidene-4,5-dihydro-1,2,4-oxadiazol-3-yl)-[1,1'-biphenyl]-4-carboxamide | 1H NMR (400 MHz, METHANOL-d4) δ 8.16-8.09 (m, J = 5.7 Hz, 1H), 7.93 (d, J = 2.4 Hz, 1H), 7.80-7.72 (m, J = 1.8 Hz, 2H), 7.72-7.66 (m, 2H), 7.49 (d, J = 9.0 Hz, 1H), 7.40-7.36 (m, 2H), 7.32 (t, J = 7.6 Hz, 2H), 7.27-7.20 (m, 1H), 7.12 (dd, J = 9.0, 2.0 Hz, 1H), 7.05 (s, 1H), 5.14-5.04 (m, 1H), 3.86 (5, 3H), 1.99-1.76 (m, 2H), 1.51-1.27 (m, 2H), 0.97 (t, J = 7.4 Hz, 3H) | 0.90, 610.1 A | C |
| 11 | 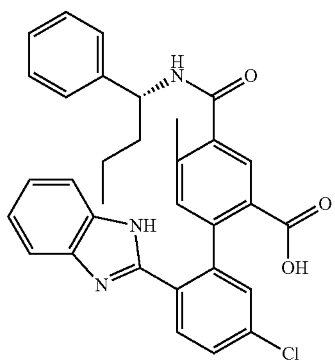 [SMILES: CCC[C@@H](NC(=O)c1cc(C(=O)O)c(-c2cc(Cl)ccc2-c2nc3ccccc3[nH]2)cc1C)c1ccccc1] | 2'-(1H-1,3-benzodiazol-2-yl)-5'-chloro-5-methyl-4-{[(1R)-1-phenylbutyl]carbamoyl}-[1,1'-biphenyl]-2-carboxylic acid | 1H NMR (500 MHz, DMSO-d6) δ 8.86 (d, J = 8.5 Hz, 1H), 7.87 (d, J = 8.3 Hz, 1H), 7.75-7.67 (m, 2H), 7.54 (br. s., 2H), 7.43-7.32 (m, 5H), 7.30-7.17 (m, 4H), 5.05-4.94 (m, 1H), 2.40-2.22 (m, 3H), 1.86-1.76 (m, 1H), 1.73-1.64 (m, 1H), 1.47-1.25 (m, 2H), 0.92 (t, J = 7.3 Hz, 3H) | 0.92 537.9 A | A |
| 12 | 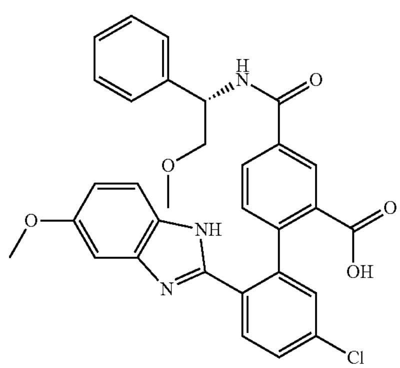 [SMILES: COC[C@@H](NC(=O)c1ccc(-c2cc(Cl)ccc2-c2nc3cc(OC)ccc3[nH]2)c(C(=O)O)c1)c1ccccc1] | 5'-chloro-4-{[(1S)-2-methoxy-1-phenylethyl]carbamoyl}-2'-(5-methoxy-1H-1,3-benzodiazol-2-yl)-[1,1'-biphenyl]-2-carboxylic acid | 1H NMR (500 MHz, methanol-d4) δ 8.43 (d, J = 4.1 Hz, 1H), 8.10 (t, J = 5.8 Hz, 1H), 7.88 (d, J = 8.3 Hz, 1H), 7.77 (dd, J = 8.4, 2.1 Hz, 1H), 7.62 (d, J = 2.2 Hz, 1H), 7.56 (d, J = 9.1 Hz, 1H), 7.53 (d, J = 8.0 Hz, 1H), 7.44-7.39 (m, 2H), 7.36 (t, J = 7.6 Hz, 2H), 7.31-7.26 (m, 1H), 7.19 (dd, J = 9.1, 2.2 Hz, 1H), 7.11 (d, J = 2.2 Hz, 1H), 5.36 (dd, J = 8.8, 5.0 Hz, 1H), 3.88 (s, 3H), 3.79 (dd, J = 10.2, 8.8 Hz, 1H), 3.68 (dd, J = 10.2, 5.0 Hz, 1H), 3.41 (s, 3H) | 0.82 555.8 A | A |
| 13 | 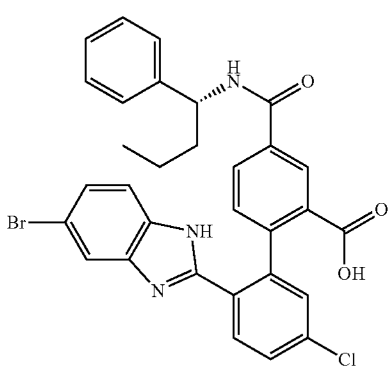 [SMILES: CCC[C@@H](NC(=O)c1ccc(-c2cc(Cl)ccc2-c2nc3cc(Br)ccc3[nH]2)c(C(=O)O)c1)c1ccccc1] | 2'-(5-bromo-1H-1,3-benzodiazol-2-yl)-5'-chloro-4-{[(1R)-1-phenylbutyl]carbamoyl}-[1,1'-biphenyl]-2-carboxylic acid | 1H NMR (500 MHz, DMSO-d6) δ 8.99 (d, J = 7.7 Hz, 1H), 8.33 (s, 1H), 8.01 (d, J = 7.7 Hz, 1H), 7.86 (d, J = 8.3 Hz, 1H), 7.66 (d, J = 8.5 Hz, 1H), 7.58 (s, 1H), 7.42-7.36 (m, 4H), 7.35-7.29 (m, 3H), 7.29-7.19 (m, 2H), 5.09-4.98 (m, J = 7.2 Hz, 1H), 1.93-1.80 (m, J = 6.3 Hz, 1H), 1.77-1.65 (m, J = 5.5 Hz, 1H), 1.45-1.34 (m, J = 6.9 Hz, 1H), 1.33-1.21 (m, 1H), 0.90 (t, J = 6.2 Hz, 3H) | 1.83 604.1 B | A |

TABLE 2-continued

| Ex # | Structure | IUPAC Name | NMR | RT (min), [M + H] Method | APJ cAMP Human EC50 (nM) |
|---|---|---|---|---|---|
| 14 | 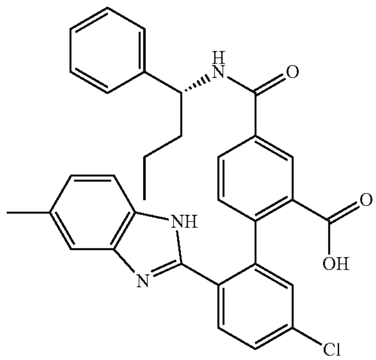 [SMILES: CCC[C@@H](NC(=O)c1ccc(-c2cc(Cl)ccc2-c2nc3cc(C)ccc3[nH]2)c(C(=O)O)c1)c1ccccc1] | 5'-chloro-2'-(5-methyl-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.97 (d, J = 8.3 Hz, 1H), 8.32 (d, J = 1.7 Hz, 1H), 8.02 (dd, J = 8.0, 1.4 Hz, 1H), 7.95 (s, 1H), 7.88 (d, J = 8.5 Hz, 1H), 7.73 (dd, J = 8.4, 1.8 Hz, 1H), 7.46 (s, 1H), 7.42-7.28 (m, 6H), 7.26-7.18 (m, 1H), 7.13-7.05 (m, 1H), 5.11-4.96 (m, 1H), 2.39 (s, 3H), 1.92-1.81 (m, 1H), 1.77-1.66 (m, 1H), 1.37 (dt, J = 14.2, 6.9 Hz, 1H), 1.32-1.21 (m, 1H), 0.90 (t, J = 7.3 Hz, 3H) | 1.70 538.3 B | A |
| 15 | 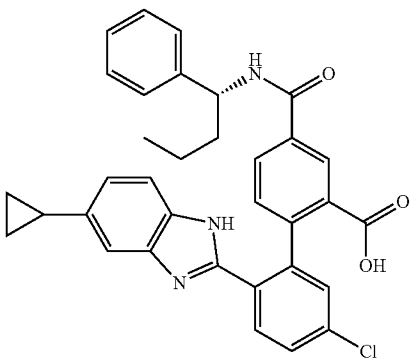 [SMILES: CCC[C@@H](NC(=O)c1ccc(-c2cc(Cl)ccc2-c2nc3cc(C4CC4)ccc3[nH]2)c(C(=O)O)c1)c1ccccc1] | 5'-chloro-2'-(5-cyclopropyl-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 9.00-8.91 (m, 1H), 8.38-8.32 (m, 1H), 8.04-7.98 (m, 1H), 7.85 (d, J = 8.3 Hz, 1H), 7.75 (d, J = 2.2 Hz, 1H), 7.59 (d, J = 1.9 Hz, 1H), 7.52-7.48 (m, 1H), 7.48-7.44 (m, 1H), 7.36 (d, J = 0.8 Hz, 2H), 7.31 (d, J = 12.1 Hz, 5H), 5.14-5.04 (m, 1H), 2.13-2.04 (m, 1H), 1.96-1.87 (m, 1H), 1.87-1.78 (m, 1H), 1.50-1.39 (m, 1H), 1.39-1.32 (m, 1H), 1.06 (d, J = 6.6 Hz, 2H), 0.97 (t, J = 7.4 Hz, 3H), 0.74 (s, 2H) | 0.93 564.0 B | A |
| 16 | 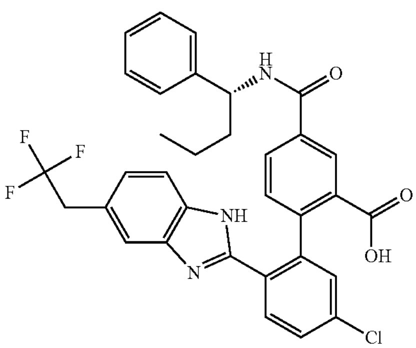 [SMILES: CCC[C@@H](NC(=O)c1ccc(-c2cc(Cl)ccc2-c2nc3cc(CC(F)(F)F)ccc3[nH]2)c(C(=O)O)c1)c1ccccc1] | 5'-chloro-4-{[(1R)-1-phenylbutyl]carbamoyl}-2'-[5-(2,2,2-trifluoroethyl)-1H-1,3-benzodiazol-2-yl]-[1,1'-biphenyl]-2-carboxylic acid | 1H NMR (500 MHz, METHANOL-d4) δ 8.94 (d, J = 8.3 Hz, 1H), 8.33 (d, J = 1.4 Hz, 1H), 7.97 (dd, J = 7.8, 1.0 Hz, 1H), 7.85 (d, J = 8.3 Hz, 1H), 7.70 (dd, J = 8.4, 2.1 Hz, 1H), 7.57 (d, J = 6.6 Hz, 2H), 7.53 (d, J = 2.2 Hz, 1H), 7.41 (d, J = 8.0 Hz, 2H), 7.38-7.34 (m, 2H), 7.34-7.29 (m, 2H), 7.25-7.21 (m, 1H), 5.12-5.04 (m, 1H), 3.63 (q, J = 10.7 Hz, 2H), 1.96-1.87 (m, 1H), 1.86-1.76 (m, 1H), 1.48-1.28 (m, 2H), 0.96 (t, J = 7.3 Hz, 3H) | 0.92 605.8 B | A |
| 17 | 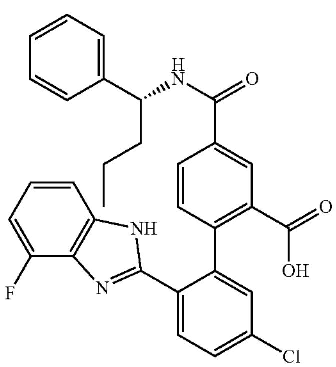 [SMILES: CCC[C@@H](NC(=O)c1ccc(-c2cc(Cl)ccc2-c2nc3c(F)cccc3[nH]2)c(C(=O)O)c1)c1ccccc1] | 5'-chloro-2'-(4-fluoro-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.92 (d, J = 8.3 Hz, 1H), 8.25 (s, 1H), 7.94-7.89 (m, 1H), 7.84 (s, 1H), 7.64 (dd, J = 8.4, 2.1 Hz, 1H), 7.39 (d, J = 7.4 Hz, 2H), 7.35-7.28 (m, 2H), 7.21 (dd, J = 14.3, 7.4 Hz, 3H), 7.07 (d, J = 5.0 Hz, 1H), 6.89 (br. s., 1H), 5.08-4.97 (m, 1H), 1.93-1.81 (m, J = 5.0 Hz, 1H), 1.77-1.66 (m, J = 8.0 Hz, 1H), 1.45-1.33 (m, J = 14.7, 7.5, 7.5 Hz, 1H), 1.32-1.22 (m, J = 6.6 Hz, 1H), 0.90 (t, J = 7.4 Hz, 3H) | 1.80 542.1 B | A |

TABLE 2-continued

| Ex # | Structure | IUPAC Name | NMR | RT (min), [M + H] Method | APJ cAMP Human EC50 (nM) |
|---|---|---|---|---|---|
| 18 | 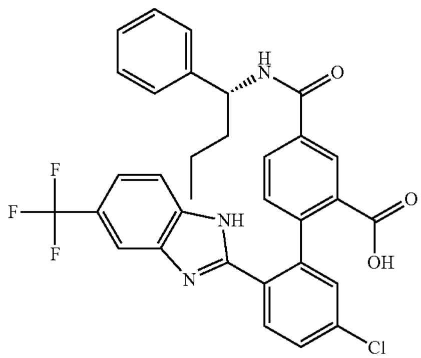 [SMILES: CCC[C@@H](NC(=O)c1ccc(-c2cc(Cl)ccc2-c2nc3cc(C(F)(F)F)ccc3[nH]2)c(C(=O)O)c1)c1ccccc1] | 5'-chloro-4-{[(1R)-1-phenylbutyl]carbamoyl}-2'-[5-(trifluoromethyl)-1H-1,3-benzodiazol-2-yl]-[1,1'-biphenyl]-2-carboxylic acid | 1H NMR (500 MHz, DMSO-d6) δ 8.95 (d, J = 8.3 Hz, 1H), 8.34 (d, J = 1.4 Hz, 1H), 8.01 (dd, J = 8.1,1.5 Hz, 1H), 7.95 (s, 1H), 7.89 (d, J = 8.3 Hz, 1H), 7.72 (s, 1H), 7.67 (dd, J = 8.4, 2.1 Hz, 1H), 7.59 (d, J = 8.3 Hz, 1H), 7.46-7.36 (m, 4H), 7.36-7.29 (m, 3H), 7.26-7.17 (m, 1H), 5.10-4.98 (m, 1H), 1.94-1.82 (m, J = 9.0, 9.0, 4.3 Hz, 1H), 1.79-1.66 (m, 1H), 1.45-1.34 (m, 1H), 1.29 (dt, J = 14.8, 7.3 Hz, 1H), 0.90 (t, J = 7.3 Hz, 3H) | 1.92 592.2 B | A |
| 19 | 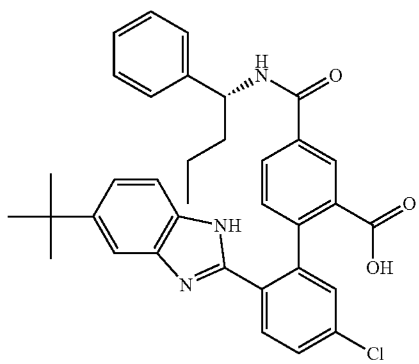 [SMILES: CCC[C@@H](NC(=O)c1ccc(-c2cc(Cl)ccc2-c2nc3cc(C(C)(C)C)ccc3[nH]2)c(C(=O)O)c1)c1ccccc1] | 2'-(5-tert-butyl-1H-1,3-benzodiazol-2-yl)-5'-chloro-4-{[(1R)-1-phenylbutyl]carbamoyl}-[1,1'-biphenyl]-2-carboxylic acid | 1H NMR (500 MHz, DMSO-d6) δ 8.97 (d, J = 8.5 Hz, 1H), 8.35 (d, J = 1.7 Hz, 1H), 8.02 (dd, J = 8.0, 1.4 Hz, 1H), 7.87 (d, J = 8.3 Hz, 1H), 7.72 (dd, J = 8.4, 1.8 Hz, 1H), 7.47-7.41 (m, 3H), 7.40-7.29 (m, 6H), 7.24-7.19 (m, J = 7.4 Hz, 1H), 5.07-4.99 (m, J = 6.3 Hz, 1H), 1.92-1.81 (m, J = 7.2 Hz, 1H), 1.77-1.66 (m, J = 9.1 Hz, 1H), 1.44-1.34 (m, 1H), 1.33-1.22 (m, 10H), 0.90 (t, J = 7.4 Hz, 3H) | 1.90 580.3 B | A |
| 20 | 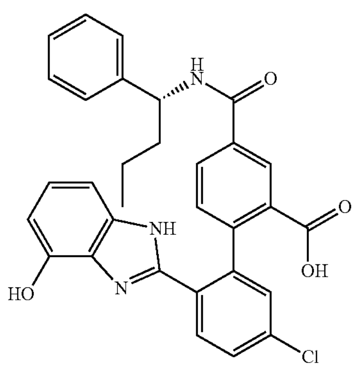 [SMILES: CCC[C@@H](NC(=O)c1ccc(-c2cc(Cl)ccc2-c2nc3c(O)cccc3[nH]2)c(C(=O)O)c1)c1ccccc1] | 5'-chloro-2'-(4-hydroxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.96 (d, J = 8.3 Hz, 1H), 8.29 (s, 1H), 7.98 (d, J = 8.3 Hz, 1H), 7.88 (d, J = 8.5 Hz, 1H), 7.69 (dd, J = 8.3, 1.4 Hz, 1H), 7.43-7.35 (m, 3H), 7.34-7.27 (m, 3H), 7.22 (d, J = 7.4 Hz, 1H), 7.00 (t, J = 7.2 Hz, 1H), 6.88 (d, J = 8.0 Hz, 1H), 6.61 (d, J = 7.2 Hz, 1H), 5.06-4.99 (m, J = 6.3 Hz, 1H), 1.91-1.81 (m, J = 8.8 Hz, 1H), 1.76-1.66 (m, 1H), 1.42-1.31 (m, J = 9.1 Hz, 1H), 1.31-1.22 (m, 1H), 0.89 (t, J = 7.4 Hz, 3H) | 1.42 540.3 B | A |
| 21 | 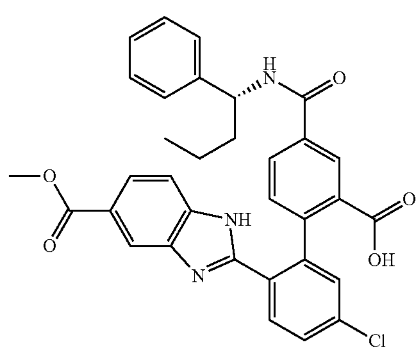 [SMILES: CCC[C@@H](NC(=O)c1ccc(-c2cc(Cl)ccc2-c2nc3cc(C(=O)OC)ccc3[nH]2)c(C(=O)O)c1)c1ccccc1] | 5'-chloro-2'-[5-(methoxycarbonyl)-1H-1,3-benzodiazol-2-yl]-4-{[(1R)-1-phenylbutyl]carbamoyl}-[1,1'-biphenyl]-2-carboxylic acid | 1H NMR (500 MHz, DMSO-d6) δ 8.95 (d, J = 8.3 Hz, 1H), 8.31 (s, 1H), 8.01-7.96 (m, 2H), 7.89 (d, J = 8.5 Hz, 1H), 7.74 (d, J = 8.3 Hz, 1H), 7.66 (dd, J = 8.5, 2.2 Hz, 1H), 7.48 (d, J = 8.5 Hz, 1H), 7.41-7.35 (m, 3H), 7.35-7.27 (m, 3H), 7.22 (s, 1H), 5.08-4.99 (m, 1H), 3.83 (s, 3H), 1.93-1.82 (m, 1H), 1.72 (ddt, J = 13.2, 9.0, 6.4 Hz, 1H), 1.43-1.34 (m, 1H), 1.33-1.22 (m, 1H), 0.91 (t, J = 7.4 Hz, 3H) | 1.76 582.3 B | A |

TABLE 2-continued

| Ex # | Structure | IUPAC Name | NMR | RT (min), [M + H] Method | APJ cAMP Human EC50 (nM) |
|---|---|---|---|---|---|
| 22 | 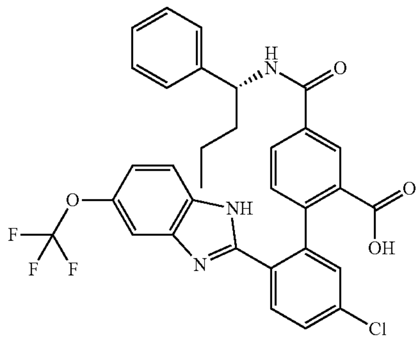 [SMILES: CCC[C@@H](NC(=O)c1ccc(-c2cc(Cl)ccc2-c2nc3cc(OC(F)(F)F)ccc3[nH]2)c(C(=O)O)c1)c1ccccc1] | 5'-chloro-4-{[(1R)-1-phenylbutyl]carbamoyl}-2'-[5-(trifluoromethoxy)-1H-1,3-benzodiazol-2-yl]-[1,1'-biphenyl]-2-carboxylic acid | 1H NMR (500 MHz, DMSO-d6) δ 8.95 (d, J = 8.0 Hz, 1H), 8.35 (br. s., 1H), 8.01 (d, J = 7.7 Hz, 1H), 7.87 (d, J = 7.4 Hz, 1H), 7.66 (d, J = 7.4 Hz, 1H), 7.49 (d, J = 8.5 Hz, 1H), 7.42-7.35 (m, 4H), 7.34-7.28 (m, 3H), 7.26-7.19 (m, 1H), 7.09 (d, J = 8.0 Hz, 1H), 5.12-4.96 (m, J = 7.2 Hz, 1H), 1.94-1.81 (m, J = 6.1 Hz, 1H), 1.77-1.67 (m, J = 6.6 Hz, 1H), 1.44-1.34 (m, J = 5.5 Hz, 1H), 1.33-1.22 (m, 1H), 0.90 (t, J = 6.9 Hz, 3H) | 1.94 608.2 B | B |
| 23 | 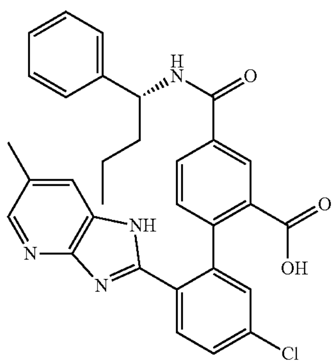 [SMILES: CCC[C@@H](NC(=O)c1ccc(-c2cc(Cl)ccc2-c2nc3ncc(C)cc3[nH]2)c(C(=O)O)c1)c1ccccc1] | 5'-chloro-2'-{6-methyl-1H-imidazo[4,5-b]pyridin-2-yl}-4-{[(1R)-1-phenylbutyl]carbamoyl}-[1,1'-biphenyl]-2-carboxylic acid | 1H NMR (500 MHz, DMSO-d6) δ 8.95-8.85 (m, 1H), 8.17 (br. s., 1H), 8.06 (s, 1H), 7.83 (d, J = 8.3 Hz, 2H), 7.62 (d, J = 8.3 Hz, 1H), 7.58 (s, 1H), 7.38 (d, J = 7.7 Hz, 2H), 7.31 (t, J = 7.6 Hz, 2H), 7.27 (br. s., 1H), 7.24-7.18 (m, J = 7.2 Hz, 1H), 7.17-7.06 (m, 1H), 5.07-4.96 (m, 1H), 2.33 (s, 3H), 1.92-1.81 (m, J = 3.3 Hz, 1H), 1.76-1.63 (m, 1H), 1.42-1.34 (m, 1H), 1.33-1.24 (m, 1H), 0.90 (s, 3H) | 1.49 539.3 B | B |
| 24 | 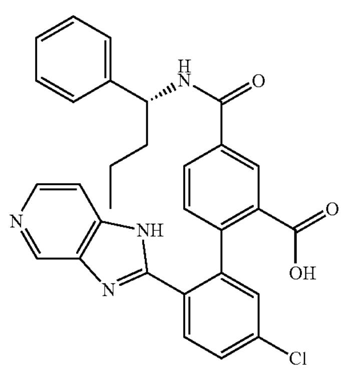 [SMILES: CCC[C@@H](NC(=O)c1ccc(-c2cc(Cl)ccc2-c2nc3cnccc3[nH]2)c(C(=O)O)c1)c1ccccc1] | 5'-chloro-2'-{1H-imidazo[4,5-c]pyridin-2-yl}-4-{[(1R)-1-phenylbutyl]carbamoyl}-[1,1'-biphenyl]-2-carboxylic acid | 1H NMR (500 MHz, DMSO-d6) δ 9.20 (s, 1H), 8.97 (d, J = 8.5 Hz, 1H), 8.46 (d, J = 6.3 Hz, 1H), 8.33 (s, 1H), 8.07 (d, J = 7.1 Hz, 1H), 7.96 (d, J = 6.1 Hz, 2H), 7.75 (dd, J = 8.4, 2.1 Hz, 1H), 7.48 (d, J = 1.9 Hz, 1H), 7.40 (d, J = 7.7 Hz, 3H), 7.33 (t, J = 7.6 Hz, 2H), 7.27-7.19 (m, 1H), 5.04 (d, J = 6.3 Hz, 1H), 1.94-1.83 (m, J = 9.1, 4.7 Hz, 1H), 1.77-1.69 (m, 1H), 1.44-1.34 (m, 1H), 1.33-1.23 (m, 1H), 0.91 (t, J = 7.3 Hz, 3H) | 1.41 525.3 B | B |
| 25 | 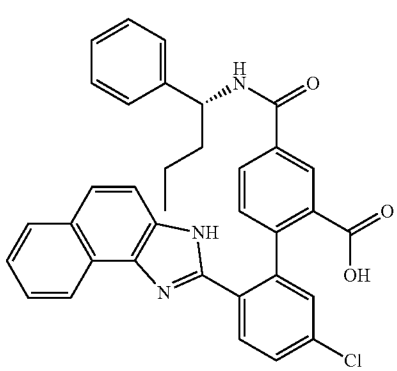 [SMILES: CCC[C@@H](NC(=O)c1ccc(-c2cc(Cl)ccc2-c2nc3c(ccc4ccccc43)[nH]2)c(C(=O)O)c1)c1ccccc1] | 5'-chloro-2'-{3H-naphtho[1,2-d]imidazol-2-yl}-4-{[(1R)-1-phenylbutyl]carbamoyl}-[1,1'-biphenyl]-2-carboxylic acid | 1H NMR (500 MHz, DMSO-d6) δ 8.95 (d, J = 8.3 Hz, 1H), 8.38 (s, 1H), 8.03 (dd, J = 8.0, 1.4 Hz, 1H), 7.98-7.95 (m, 2H), 7.71 (dd, J = 8.3, 1.9 Hz, 1H), 7.66 (d, J = 8.8 Hz, 1H), 7.57 (d, J = 8.8 Hz, 1H), 7.50 (d, J = 7.2 Hz, 1H), 7.48-7.44 (m, 1H), 7.43 (d, J = 1.7 Hz, 1H), 7.41-7.34 (m, 3H), 7.31 (t, J = 7.6 Hz, 2H), 7.26-7.18 (m, 1H), 5.10-4.98 (m, J = 6.3 Hz, 1H), 1.92-1.81 (m, J = 8.8, 4.7 Hz, 1H), 1.76-1.66 (m, 1H), 1.44-1.34 (m, J = 6.1 Hz, 1H), 1.33-1.22 (m, J = 14.6, 14.6, 7.3 Hz, 1H), 0.90 (t, J = 7.3 Hz, 3H) | 1.68 574.3 B | B |

TABLE 2-continued

| Ex # | Structure | IUPAC Name | NMR | RT (min), [M + H] Method | APJ cAMP Human EC50 (nM) |
|---|---|---|---|---|---|
| 26 | 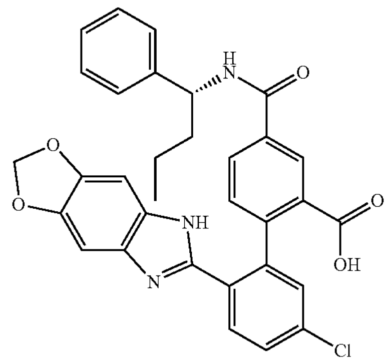 [SMILES: CCC[C@@H](NC(=O)c1ccc(-c2cc(Cl)ccc2-c2nc3cc4c(cc3[nH]2)OCO4)c(C(=O)O)c1)c1ccccc1] | 5'-chloro-2'-{4,6-dioxa-10,12-diazatricyclo[7.3.0.0³,⁷]dodeca-1(9),2,7,10-tetraen-11-yl}-4-{[(1R)-1-phenylbutyl]carbamoyl}-[1,1'-biphenyl]-2-carboxylic acid | 1H NMR (500 MHz, DMSO-d6) δ 8.96 (d, J = 8.3 Hz, 1H), 8.33 (d, J = 1.4 Hz, 1H), 8.01 (dd, J = 8.0, 1.7 Hz, 1H), 7.83 (d, J = 8.5 Hz, 1H), 7.67 (dd, J = 8.3, 1.9 Hz, 1H), 7.43-7.36 (m, 3H), 7.36-7.28 (m, 3H), 7.26-7.19 (m, 1H), 6.98 (s, 2H), 6.00 (s, 2H), 5.08-4.99 (m, 1H), 1.93-1.82 (m, J = 13.7, 9.2, 9.2, 5.1 Hz, 1H), 1.78-1.67 (m, 1H), 1.44-1.34 (m, 1H), 1.33-1.22 (m, 1H), 0.91 (t, J = 7.4 Hz, 3H) | 1.65 568.2 B | B |
| 27 | 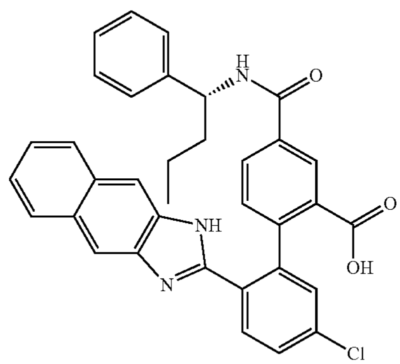 [SMILES: CCC[C@@H](NC(=O)c1ccc(-c2cc(Cl)ccc2-c2nc3cc4ccccc4cc3[nH]2)c(C(=O)O)c1)c1ccccc1] | 5'-chloro-2'-{1H-naphtho[2,3-d]imidazol-2-yl}-4-{[(1R)-1-phenylbutyl]carbamoyl}-[1,1'-biphenyl]-2-carboxylic acid | 1H NMR (500 MHz, DMSO-d6) δ 8.96 (d, J = 8.3 Hz, 1H), 8.34(d, J = 1.4 Hz, 1H), 8.03 (dd, J = 8.1, 1.8 Hz, 1H), 7.98 (d, J = 8.3 Hz, 1H), 7.96-7.93 (m, 4H), 7.72 (dd, J = 8.4, 2.1 Hz, 1H), 7.43 (d, J = 1.7 Hz, 1H), 7.41-7.28 (m, 7H), 7.25-7.18 (m, 1H), 5.08-4.99 (m, 1H), 1.93-1.81 (m, J = 9.1, 4.7 Hz, 1H), 1.77-1.65 (m, 1H), 1.44-1.33 (m, 1H), 1.27 (td, J = 14.9, 7.6 Hz, 1H), 0.90 (t, J = 7.3 Hz, 3H) | 1.68 574.3 B | B |
| 28 | 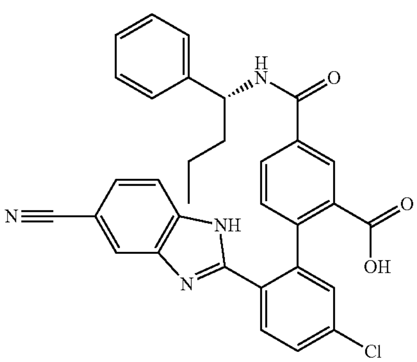 [SMILES: CCC[C@@H](NC(=O)c1ccc(-c2cc(Cl)ccc2-c2nc3cc(C#N)ccc3[nH]2)c(C(=O)O)c1)c1ccccc1] | 5'-chloro-2'-(5-cyano-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.96 (d, J = 8.3 Hz, 1H), 8.33 (s, 1H), 8.02 (d, J = 8.0 Hz, 1H), 7.93-7.86 (m, 2H), 7.67 (dd, J = 8.3, 1.4 Hz, 1H), 7.58-7.53 (m, 1H), 7.51-7.46 (m, 1H), 7.43-7.37 (m, 3H), 7.36-7.29 (m, 3H), 7.26-7.20 (m, 1H), 5.08-5.00 (m, 1H), 1.94-1.82 (m, 1H), 1.78-1.67 (m, 1H), 1.46-1.34 (m, 1H), 1.33-1.22 (m, 1H), 0.91 (t, J = 7.3 Hz, 3H) | 1.73 549.3 B | B |
| 29 | 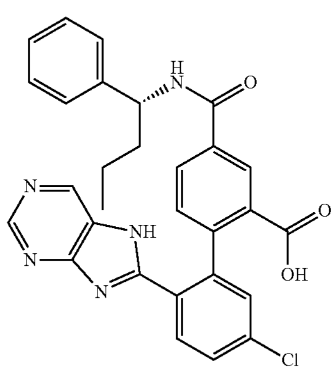 | 5'-chloro-4-{[(1R)-1-phenylbutyl]carbamoyl}-2'-(7H-purin-8-yl)-[1,1'-biphenyl]-2-carboxylic acid | 1H MMR (500 MHz, DMSO-d6) δ 8.97 (d, J = 8.3 Hz, 1H),8.81 (s, 1H), 8.34-8.25 (m, 1H), 8.06 (d, J = 1.7 Hz, 1H), 7.97-7.87 (m, J = 16.0 Hz, 1H), 7.69 (dd, J = 8.4, 1.2 Hz, 1H), 7.45-7.36 (m, 4H), 7.35-7.30 (m, J = 7.6, 7.6 Hz, 1H), 7.26-7.20 (m, 1H), 5.09-5.00 (m, 1H), 1.93-1.82 (m, 1H), 1.78-1.67 (m, 1H), 1.46-1.35 (m, 1H), 1.34-1.22 (m, 1H), 0.91 (s, 3H) | 1.61 526.2 B | B |

TABLE 2-continued

| Ex # | Structure | IUPAC Name | NMR | RT (min), [M + H] Method | APJ cAMP Human EC50 (nM) |
|---|---|---|---|---|---|
| 30 | 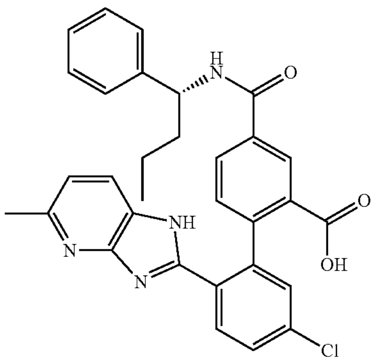 [SMILES: CCC[C@@H](NC(=O)c1ccc(-c2cc(Cl)ccc2-c2nc3nc(C)ccc3[nH]2)c(C(=O)O)c1)c1ccccc1] | 5'-chloro-2'-{5-methyl-1H-imidazo[4,5-b]pyridin-2-yl}-4-{[(1R)-1-phenylbutyl]carbamoyl}-[1,1'-biphenyl]-2-carboxylic acid | 1H NMR (500 MHz, DMSO-d6) δ 8.97 (d, J = 8.5 Hz, 1H), 8.39-8.30 (m, 1H), 8.03 (d, J = 8.0 Hz, 1H), 7.88 (d, J = 8.5 Hz, 1H), 7.70-7.60 (m, 1H), 7.43-7.37 (m, 3H), 7.36-7.29 (m, 3H), 7.26-7.18 (m, 1H), 5.12-4.96 (m, J = 6.3 Hz, 1H), 2.52 (s, 3H), 1.94-1.82 (m, J = 8.9, 4.8 Hz, 1H), 1.78-1.67 (m, 1H), 1.45-1.34 (m, 1H), 1.33-1.22 (m, 1H), 0.91 (t, J = 7.3 Hz, 3H) | 1.49 539.3 B | B |
| 31 | 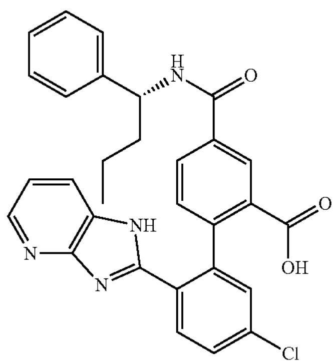 [SMILES: CCC[C@@H](NC(=O)c1ccc(-c2cc(Cl)ccc2-c2nc3ncccc3[nH]2)c(C(=O)O)c1)c1ccccc1] | 5'-chloro-2'-{1H-imidazo[4,5-b]pyridin-2-yl}-4-{[(1R)-1-phenylbutyl]carbamoyl}-[1,1'-biphenyl]-2-carboxylic acid | 1H MMR (500 MHz, DMSO-d6) δ 8.93 (d, J = 8.3 Hz, 1H), 8.26-8.19 (m, 2H), 7.86 (d, J = 8.3 Hz, 1H), 7.81-7.75 (m, 1H), 7.64 (dd, J = 8.4, 2.1 Hz, 1H), 7.38 (d, J = 7.4 Hz, 2H), 7.34-7.27 (m, 3H), 7.21 (t, J = 7.3 Hz, 2H), 7.11 (dd, J = 8.0, 4.7 Hz, 1H), 5.07-4.98 (m, 1H), 1.93-1.80 (m, 1H), 1.77-1.65 (m, 1H), 1.43-1.33 (m, 1H), 1.32-1.21 (m, 1H), 0.90 (t, J = 7.3 Hz, 3H) | 1.44 525.3 B | B |
| 32 | 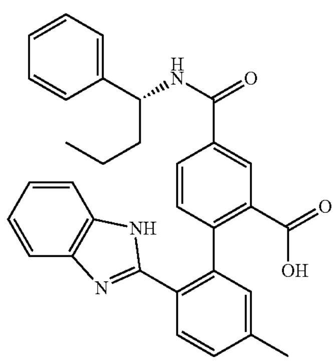 [SMILES: CCC[C@@H](NC(=O)c1ccc(-c2cc(C)ccc2-c2nc3ccccc3[nH]2)c(C(=O)O)c1)c1ccccc1] | 2'-(1H-1,3-benzodiazol-2-yl)-5'-methyl-4-{[(1R)-1-phenylbutyl]carbamoyl}-[1,1'-biphenyl]-2-carboxylic acid | 1H NMR (500 MHz, DMSO-d6) δ 8.95 (d, J = 8.3 Hz, 1H), 8.27 (d, J = 1.9 Hz, 1H), 8.00 (dd, J = 8.0, 1.4 Hz, 1H), 7.78 (d, J = 7.7 Hz, 1H), 7.55 (dd, J = 6.1, 3.0 Hz, 2H), 7.48 (d, J = 7.7 Hz, 1H), 7.41-7.36 (m, 2H), 7.35-7.27 (m, 5H), 7.25- 7.19 (m, 2H), 5.03 (d, J = 6.1 Hz, 1H), 2.45 (s, 3H), 1.92-1.82 (m, J = 9.1, 4.7 Hz, 1H), 1.76-1.66 (m, J = 9.2, 6.5 Hz, 1H), 1.43-1.32 (m, 1H), 1.32-1.22 (m, 1H), 0.90 (t, J = 7.3 Hz, 3H) | 1.57 504.3 B | A |
| 33 | 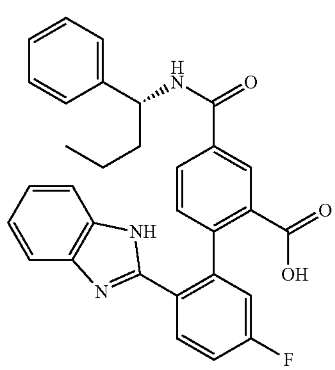 [SMILES: CCC[C@@H](NC(=O)c1ccc(-c2cc(F)ccc2-c2nc3ccccc3[nH]2)c(C(=O)O)c1)c1ccccc1] | 2'-(1H-1,3-benzodiazol-2-yl)-5'-fluoro-4-{[(1R)-1-phenylbutyl]carbamoyl}-[1,1'-biphenyl]-2-carboxylic acid | 1H NMR (500 MHz, DMSO-d6) δ 8.99 (d, J = 8.5 Hz, 1H), 8.32 (s, 1H), 8.01 (d, J = 8.0 Hz, 1H), 7.92 (dd, J = 8.5, 5.8 Hz, 1H), 7.57-7.46 (m, 3H), 7.41-7.19 (m, 9H), 5.06-4.98 (m, 1H), 1.91-1.80 (m, J = 13.6, 9.1, 4.6, 4.6 Hz, 1H), 1.75-1.66 (m, 1H), 1.42-1.33 (m, 1H), 1.31-1.21 (m, J = 15.5, 7.0 Hz, 1H), 0.89 (t, J = 7.3 Hz, 3H) | 1.63 580.2 B | A |

TABLE 2-continued

| Ex # | Structure | IUPAC Name | NMR | RT (min), [M + H] Method | APJ cAMP Human EC50 (nM) |
|---|---|---|---|---|---|
| 34 | 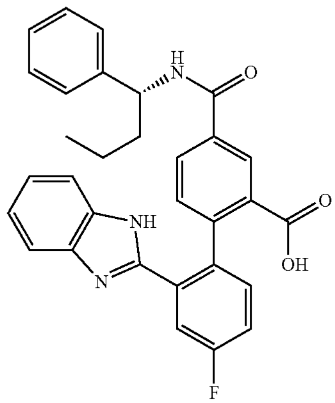 [SMILES: CCC[C@@H](NC(=O)c1ccc(-c2ccc(F)cc2-c2nc3ccccc3[nH]2)c(C(=O)O)c1)c1ccccc1] | 2'-(1H-1,3-benzodiazol-2-yl)-4'-fluoro-4-{[(1R)-1-phenylbutyl]carbamoyl}-[1,1'-biphenyl]-2-carboxylic acid | 1H NMR (500 MHz, DMSO-d6) δ 8.98 (d, J = 8.3 Hz, 1H), 8.31 (d, J = 1.7 Hz, 1H), 7.98 (dd, J = 8.0, 1.7 Hz, 1H), 7.76-7.71 (m, J = 8.0 Hz, 1H), 7.51-7.44 (m, 3H), 7.41-7.35 (m, 3H), 7.35-7.27 (m, 3H), 7.25-7.18 (m, 3H), 5.06-4.98 (m, 1H), 1.91-1.81 (m, J = 9.0, 9.0, 4.5 Hz, 1H), 1.76-1.65 (m, 1H), 1.43-1.33 (m, 1H), 1.32-1.21 (m, J = 15.5, 7.0 Hz, 1H), 0.90 (t, J = 7.4 Hz, 3H) | 1.54 508.3 B | A |
| 35 | 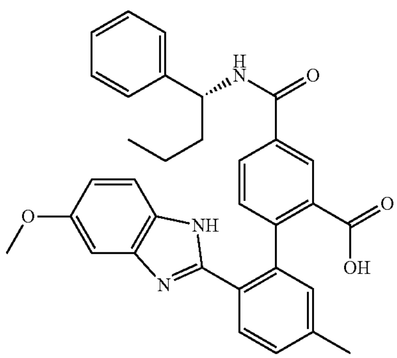 [SMILES: CCC[C@@H](NC(=O)c1ccc(-c2cc(C)ccc2-c2nc3cc(OC)ccc3[nH]2)c(C(=O)O)c1)c1ccccc1] | 2'-(5-methoxy-1H-1,3-benzodiazol-2-yl)-5'-methyl-4-{[(1R)-1-phenylbutyl]carbamoyl}-[1,1'-biphenyl]-2-carboxylic acid | 1H NMR (500 MHz, DMSO-d6) δ 8.96 (d, J = 8.3 Hz, 1H), 8.28 (d, J = 1.7 Hz, 1H), 8.01 (dd, J = 7.8, 1.2 Hz, 1H), 7.76 (d, J = 8.0 Hz, 1H), 7.50-7.44 (m, 2H), 7.41-7.36 (m, 2H), 7.32 (t, J = 7.6 Hz, 3H), 7.25-7.18 (m, 2H), 7.03-6.99 (m, 1H), 6.95 (d, J = 8.8 Hz, 1H), 5.07-4.99 (m, J = 6.1 Hz, 1H), 3.78 (s, 3H), 2.44 (s, 3H), 1.92-1.82 (m, 1H), 1.76-1.67 (m, 1H), 1.42-1.32 (m, 1H), 1.24 (d, J = 6.3 Hz, 1H), 0.90 (t, J = 7.3 Hz, 3H) | 1.61 534.3 B | A |
| 36 | 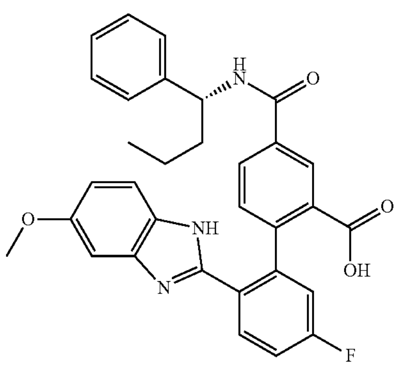 [SMILES: CCC[C@@H](NC(=O)c1ccc(-c2cc(F)ccc2-c2nc3cc(OC)ccc3[nH]2)c(C(=O)O)c1)c1ccccc1] | 5'-fluoro-2'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 9.00 (d, J = 8.3 Hz, 1H), 8.33 (s, 1H), 8.01 (d, J = 7.7 Hz, 1H), 7.90 (dd, J = 8.5, 5.8 Hz, 1H), 7.54-7.48 (m, J = 7.7, 7.7 Hz, 1H), 7.43-7.36 (m, 3H), 7.35-7.29 (m, 3H), 7.27 (d, J = 9.1 Hz, 1H), 7.24-7.20 (m, 1H), 6.96 (s, 1H), 6.88 (d, J = 8.3 Hz, 1H), 5.09-4.96 (m, 1H), 3.76 (s, 3H), 1.92-1.81 (m, 1H), 1.75-1.66 (m, J = 14.4, 8.1 Hz, 1H), 1.43-1.33 (m, 1H), 1.31-1.22 (m, J = 15.1, 7.2 Hz, 1H), 0.90 (t, J = 7.4 Hz, 3H) | 1.67 640.3 B | A |
| 37 | 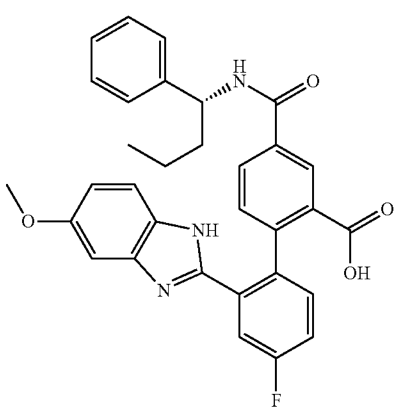 [SMILES: CCC[C@@H](NC(=O)c1ccc(-c2ccc(F)cc2-c2nc3cc(OC)ccc3[nH]2)c(C(=O)O)c1)c1ccccc1] | 4'-fluoro-2'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.99 (d, J = 8.3 Hz, 1H), 8.32 (d, J = 1.4 Hz, 1H), 8.03-7.98 (m, 1H), 7.73 (d, J = 8.5 Hz, 1H), 7.52-7.46 (m, 1H), 7.45-7.36 (m, 4H), 7.35-7.28 (m, 3H), 7.26-7.18 (m, 1H), 6.97 (s, 1H), 6.88 (d, J = 8.3 Hz, 1H), 5.07-4.96 (m, 1H), 3.76 (s, 3H), 1.92-1.81 (m, 1H), 1.76-1.65 (m, 1H), 1.45-1.33 (m, 1H), 1.32-1.21 (m, 1H), 0.90 (t, J = 7.3 Hz, 3H) | 1.58 538.3 B | A |

TABLE 2-continued

| Ex # | Structure | IUPAC Name | NMR | RT (min), [M + H] Method | APJ cAMP Human EC50 (nM) |
|---|---|---|---|---|---|
| 38 | 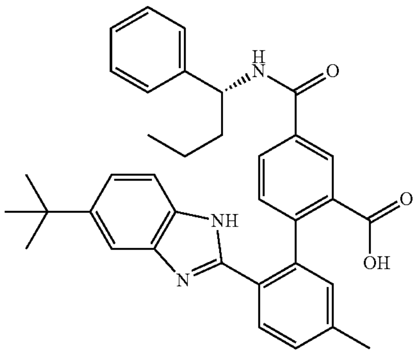 [SMILES: CCC[C@@H](NC(=O)c1ccc(-c2cc(C)ccc2-c2nc3cc(C(C)(C)C)ccc3[nH]2)c(C(=O)O)c1)c1ccccc1] | 2'-(5-tert-butyl-1H-1,3-benzodiazol-2-yl)-5'-methyl-4-{[(1R)-1-phenylbutyl]carbamoyl}-[1,1-biphenyl]-2-carboxylic acid | 1 HNMR (500 MHz, DMSO-d6) δ 8.95 (d, J = 8.3 Hz, 1H), 8.28 (d, J = 1.7 Hz, 1H), 7.99 (s, 1H), 7.75 (d, J = 7.7 Hz, 1H), 7.50-7.44 (m, 3H), 7.43-7.36 (m, J = 7.4 Hz, 3H), 7.34-7.26 (m, J = 7.7, 7.7 Hz, 3H), 7.24-7.18 (m, 2H), 5.07-4.98 (m, J = 6.3 Hz, 1H), 2.44 (s, 3H), 1.92-1.82 (m, J = 5.2 Hz, 1H), 1.76-1.67 (m, 1H), 1.45-1.33 (m, 1H), 1.32-1.22 (m, 10H), 0.90 (t, J = 7.4 Hz, 3H) | 1.85 560.4 B | A |
| 39 | 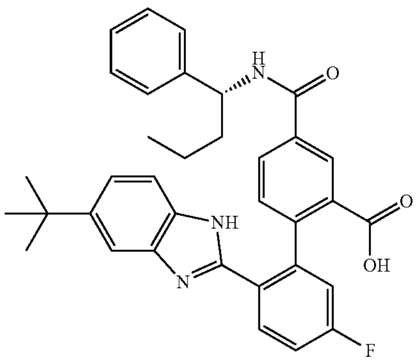 [SMILES: CCC[C@@H](NC(=O)c1ccc(-c2cc(F)ccc2-c2nc3cc(C(C)(C)C)ccc3[nH]2)c(C(=O)O)c1)c1ccccc1] | 2'-(5-tert-butyl-1H-1,3-benzodiazol-2-yl)-5'-fluoro-4-{[(1R)-1-phenylbutyl]carbamoyl}-[1,1'-biphenyl]-2-carboxylic acid | 1H NMR (500 MHz, DMSO-d6) δ 9.00 (d, J = 8.3 Hz, 1H), 8.34 (s, 1H), 8.02 (d, J = 8.3 Hz, 1H), 7.91 (dd, J = 8.5, 5.8 Hz, 1H), 7.54 (t, J = 7.4 Hz, 1H), 7.49-7.43 (m, 2H), 7.42-7.27 (m, 7H), 7.25-7.21 (m, 1H), 5.06-4.98 (m, 1H), 1.92-1.80 (m, 1H), 1.76-1.66 (m, 1H), 1.44-1.33 (m, 1H), 1.32-1.23 (m, 10H), 0.89 (t, J = 7.3 Hz, 3H) | 1.91 564.3 B | B |
| 40 | 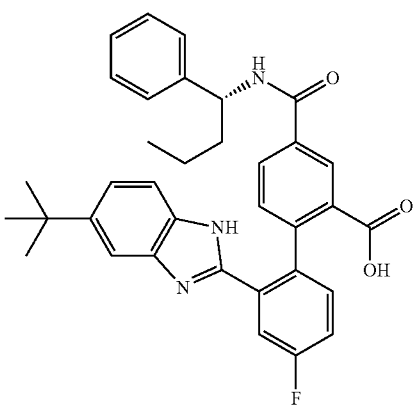 [SMILES: CCC[C@@H](NC(=O)c1ccc(-c2ccc(F)cc2-c2nc3cc(C(C)(C)C)ccc3[nH]2)c(C(=O)O)c1)c1ccccc1] | 2'-(5-tert-butyl-1H-1,3-benzodiazol-2-yl)-4'-fluoro-4-{[(1R)-1-phenylbutyl]carbamoyl}-[1,1'-biphenyl]-2-carboxylic acid | 1H NMR (500 MHz, DMSO-d6) δ 8.98 (d, J = 8.3 Hz, 1H), 8.32 (s, 1H), 8.00 (d, J = 8.3 Hz, 1H), 7.73 (dd, J = 9.4, 2.2 Hz, 1H), 7.55-7.36 (m, 7H), 7.34-7.28 (m, 3H), 7.25-7.19 (m, 1H), 5.07-4.97 (m, J = 6.3 Hz, 1H), 1.91-1.81 (m, J = 5.8 Hz, 1H), 1.76-1.65 (m, 1H), 1.44-1.33 (m, J = 14.9 Hz, 1H), 1.33-1.21 (m, 10H), 0.89 (t, J = 7.3 Hz, 3H) | 1.91 564.3 B | B |
| 41 | 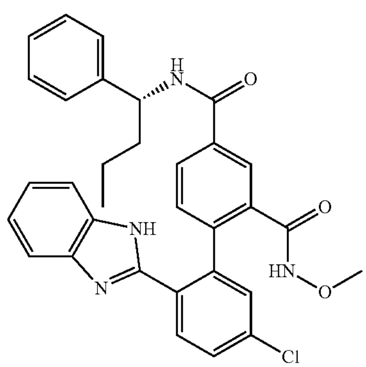 [SMILES: CCC[C@@H](NC(=O)c1ccc(-c2cc(Cl)ccc2-c2nc3ccccc3[nH]2)c(C(=O)NOC)c1)c1ccccc1] | 2'-(1H-1,3-benzodiazol-2-yl)-5'-chloro-N2-methoxy-N4-[(1R)-1-phenylbutyl]-[1,1'-biphenyl]-2,4-dicarboxamide | 1H NMR (500 MHz, DMSO-d6) δ 8.89 (d, J = 8.3 Hz, 1H), 8.03 (d, J = 1.4 Hz, 1H), 7.86 (d, J = 8.3 Hz, 1H), 7.82 (d, J = 8.0 Hz, 1H), 7.71 (dd, J = 8.3, 1.9 Hz, 1H), 7.50-7.44 (m, 2H), 7.41-7.37 (m, 2H), 7.35-7.29 (m, 3H), 7.27-7.21 (m, 1H), 7.13 (d, J = 8.3 Hz, 3H), 5.07-4.95 (m, 1H), 3.37 (s, 3H), 1.92-1.81 (m, 1H), 1.77-1.66 (m, 1H), 1.44-1.33 (m, 1H), 1.31-1.21 (m, 1H), 0.91 (t, J = 7.3 Hz, 3H) | 0.90 553.0 A | B |

TABLE 2-continued

| Ex # | Structure | IUPAC Name | NMR | RT (min), [M + H] Method | APJ cAMP Human EC50 (nM) |
|---|---|---|---|---|---|
| 42 | 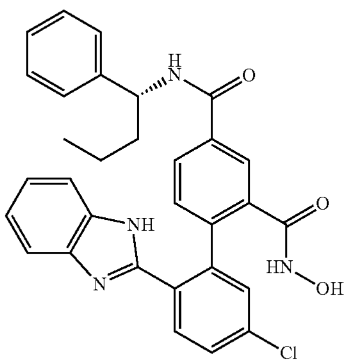 [SMILES: CCC[C@@H](NC(=O)c1ccc(-c2cc(Cl)ccc2-c2nc3ccccc3[nH]2)c(C(=O)NO)c1)c1ccccc1] | 2'-(1H-1,3-benzodiazol-2-yl)-5'-chloro-N2-hydroxy-N4-[(1R)-1-phenylbutyl]-[1,1'-biphenyl]-2,4-dicarboxamide | 1H NMR (500 MHz, DMSO-d6) δ 9.20 (br. s., 1H), 8.92(d, J = 8.3 Hz, 1H), 8.04 (s, 1H), 7.86 (d, J = 8.0 Hz, 1H), 7.76 (d, J = 8.0 Hz, 1H), 7.69 (d, J = 8.3 Hz, 1H), 7.46 (d, J = 3.3 Hz, 2H), 7.41-7.36 (m, 2H), 7.32 (t, J = 7.3 Hz, 2H), 7.27-7.20 (m, 2H), 7.17-7.13 (m, 2H), 7.03 (d, J = 8.0 Hz, 1H), 5.00 (q, J = 7.7 Hz, 1H), 1.89-1.78 (m, 1H), 1.73-1.62 (m, 1H), 1.44-1.33 (m, 1H), 1.32-1.17 (m, 1H), 0.90 (t, J = 7.2 Hz, 3H) | 0.87 538.9 A | B |
| 43 | 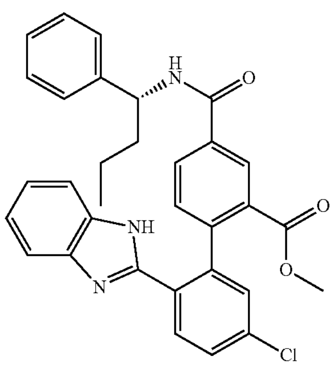 [SMILES: CCC[C@@H](NC(=O)c1ccc(-c2cc(Cl)ccc2-c2nc3ccccc3[nH]2)c(C(=O)OC)c1)c1ccccc1] | methyl 2'-(1H-1,3-benzodiazol-2-yl)-5'-chloro-4-{[(1R)-1-phenylbutyl]carbamoyl}-[1,1'-biphenyl]-2-carboxylate | 1H NMR (500 MHz, DMSO-d6) δ 12.28 (br. s., 1H), 8.97 (d, J = 8.3 Hz, 1H), 8.22 (d, J = 1.1 Hz, 1H), 8.10 (d, J = 8.0 Hz, 1H), 7.82 (d, J = 8.5 Hz, 1H), 7.67 (dd, J = 8.4, 2.1 Hz, 1H), 7.46 (d, J = 8.0 Hz, 1H), 7.43-7.37 (m, 5H), 7.33 (t, J = 7.6 Hz, 2H), 7.26-7.21 (m, 1H), 7.14 (t, J = 7.4 Hz, 1H), 7.10-7.05 (m, 1H), 5.09-5.00 (m, 1H), 3.45 (s, 3H), 1.95-1.81 (m, 1H), 1.78-1.68 (m, 1H), 1.46-1.36 (m, 1H), 1.32-1.23 (m, 1H), 0.92 (t, J = 7.3 Hz, 3H) | 0.94 538.0 A | C |
| 44 | 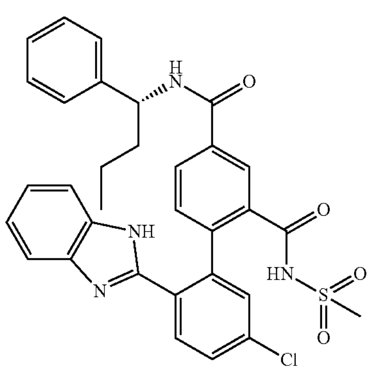 [SMILES: CCC[C@@H](NC(=O)c1ccc(-c2cc(Cl)ccc2-c2nc3ccccc3[nH]2)c(C(=O)NS(C)(=O)=O)c1)c1ccccc1] | 2'-(1H-1,3-benzodiazol-2-yl)-5'-chloro-N2-methanesulfonyl-N4-[(1R)-1-phenylbutyl]-[1,1'-biphenyl]-2,4-dicarboxamide | 1H NMR (500 MHz, METHANOL-d4) δ 8.07 (s, 1H), 7.87 (d, J = 8.0 Hz, 1H), 7.80 (d, J = 8.5 Hz, 1H), 7.68 (d, J = 8.3 Hz, 1H), 7.61 (s, 1H), 7.60-7.56 (m, 2H), 7.48 (s, 1H), 7.44-7.40 (m, 2H), 7.39-7.36 (m, 2H), 7.32 (t, J = 7.4 Hz, 2H), 7.27-7.21 (m, 2H), 5.09 (t, J = 7.4 Hz, 1H), 3.06 (s, 3H), 1.98-1.90 (m, 1H), 1.88-1.80 (m, 1H), 1.50-1.41 (m, 1H), 1.39-1.30 (m, 1H), 0.97 (t, J = 7.3 Hz, 3H) | 0.92 600.9 A | B |
| 45 | 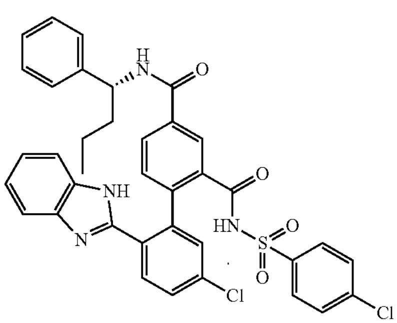 [SMILES: CCC[C@@H](NC(=O)c1ccc(-c2cc(Cl)ccc2-c2nc3ccccc3[nH]2)c(C(=O)NS(=O)(=O)c2ccc(Cl)cc2)c1)c1ccccc1] | 2'-(1H-1,3-benzodiazol-2-yl)-5'-chloro-N2-(4-chlorobenzenesulfonyl)-N4-[(1R)-1-phenylbutyl]-[1,1'-biphenyl]-2,4-dicarboxamide | 1H NMR (500 MHz, METHANOL-d4) δ 8.03 (dd, J = 3.9, 1.7 Hz, 1H), 7.74 (d, J = 8.3 Hz, 1H), 7.72-7.68 (m, 1H), 7.64-7.54 (m, 6H), 7.43-7.28 (m, 8H), 7.26-7.19 (m, 1H), 7.09 (dd, J = 4.0, 2.1 Hz, 1H), 6.97 (d, J = 8.0 Hz, 1H), 5.12-5.01 (m, 1H), 1.98-1.88 (m, 1H), 1.84-1.78 (m, 1H), 1.49-1.41 (m, 1H), 1.37-1.30 (m, 1H), 0.96 (td, J = 7.3, 4.7 Hz, 3H) | 1.06 697.0 a | C |

TABLE 2-continued

| Ex # | Structure | IUPAC Name | NMR | RT (min), [M + H] Method | APJ cAMP Human EC50 (nM) |
|---|---|---|---|---|---|
| 46 | 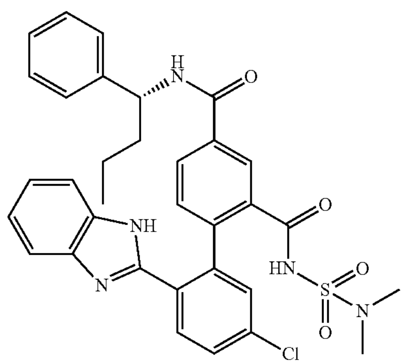 [SMILES: CCC[C@@H](NC(=O)c1ccc(-c2cc(Cl)ccc2-c2nc3ccccc3[nH]2)c(C(=O)NS(=O)(=O)N(C)C)c1)c1ccccc1] | 2'-(1H-1,3-benzodiazol-2-yl)-5-chloro-N2-(dimethylsulfamoyl)-N4-[(1R)-1-phenylbutyl]-[1,1'-biphenyl]-2,4-dicarboxamide | 1H NMR (500 MHz, DMSO-d6) δ 8.99 (d, J = 8.3 Hz, 1H), 8.16 (s, 1H), 7.95 (d, J = 8.3 Hz, 1H), 7.86 (d, J = 7.7 Hz, 1H), 7.81 (d, J = 9.1 Hz, 1H), 7.51 (br. s., 2H), 7.41-7.31 (m, 5H), 7.24 (d, J = 6.6 Hz, 3H), 7.14 (d, J = 8.0 Hz, 1H), 5.07-4.99 (m, 1H), 2.55 (s, 6H), 1.92-1.82 (m, 1H), 1.77-1.67 (m, 1H), 1.44-1.35 (m, 1H), 1.29 (dt, J = 14.9, 7.2 Hz, 1H), 0.91 (t, J = 7.3 Hz, 3H) | 0.90 629.8 A | C |
| 47 | 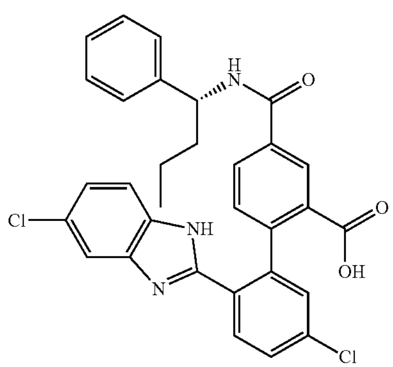 | 5'-chloro-2'-(5-chloro-1H-1,3-benzodiazol-2-yl)-4-{[(1R)-1-phenylbutyl]carbamoyl}-[1,1'-biphenyl]-2-carboxylicacid | 1H NMR (500 MHz, methanol-d4) δ 8.35 (d, J = 2.5 Hz, 1H), 8.02 (t, J = 6.7 Hz, 1H), 7.86 (d, J = 8.5 Hz, 1H), 7.73 (dd, J = 8.4, 2.1 Hz, 1H), 7.65 (s, 1H), 7.62-7.56 (m, 2H), 7.48 (dd, J = 11.0, 9.4 Hz, 2H), 7.40-7.35 (m, 2H), 7.34-7.29 (m, 2H), 7.26-7.19 (m, 1H), 5.08 (dd, J = 8.8, 6.6 Hz, 1H), 1.97-1.89 (m, 1H), 1.86-1.75 (m, 1H), 1.52-1.30 (m, 2H), 0.97 (t, J = 7.4 Hz, 3H) | 1.00 557.9 A | A |
| 48 | 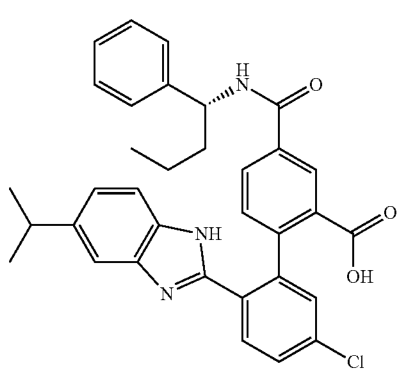 [SMILES: CCC[C@@H](NC(=O)c1ccc(-c2cc(Cl)ccc2-c2nc3cc(C(C)C)ccc3[nH]2)c(C(=O)O)c1)c1ccccc1] | 5'-chloro-4-{[(1R)-1-phenylbutyl]carbamoyl}-2'-[5-(propan-2-yl)-1H-1,3-benzodiazol-2-yl]-[1,1'-biphenyl]-2-carboxylic acid | 1H NMR (500 MHz, methanol-d4) δ 8.39 (d, J = 2.8 Hz, 1H), 8.06 (td, J = 7.7, 1.7 Hz, 1H), 7.89 (d, J = 8.3 Hz, 1H), 7.77 (dd, J = 8.4, 2.1 Hz, 2H), 7.62 (s, 1H), 7.58 (d, J = 9.4 Hz, 1H), 7.54-7.47 (m, 3H), 7.43-7.38 (m, 2H), 7.36-7.32 (m, 2H), 7.28-7.22 (m, 1H), 5.17-5.05 (m, 1H), 3.10 (dt, J = 13.8, 6.9 Hz, 1H), 1.99-1.79 (m, 2H), 1.51-1.34 (m, 2H), 1.32 (d, J = 6.9 Hz, 6H), 0.99 (t, J = 7.4 Hz, 3H) | 1.02 566.0 A | A |
| 49 | 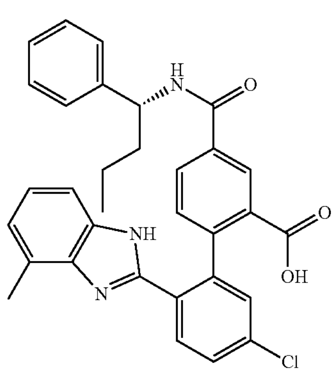 [SMILES: CCC[C@@H](NC(=O)c1ccc(-c2cc(Cl)ccc2-c2nc3c(C)cccc3[nH]2)c(C(=O)O)c1)c1ccccc1] | 5'-chloro-2,-(4-methyl-1H-1,3-benzodiazol-2-yl)-4-{[(1R)-1-phenylbutyl]carbamoyl}-[1,1'-biphenyl]-2-carboxylic acid | 1H NMR (500 MHz, 1:1 CDCl3:methanol-d4) δ 8.17 (d, J = 10.7 Hz, 1H), 7.98 (s, 1H), 7.83-7.74 (m, 1H), 7.65 (dd, J = 8.3, 2.2 Hz, 1H), 7.47 (s, 1H), 7.41-7.35 (m, 3H), 7.35-7.28 (m, 3H), 7.27-7.20 (m, 2H), 7.17 (dd, J = 8.0, 5.5 Hz, 1H), 5.12-5.05 (m, 1H), 2.50 (d, J = 5.5 Hz, 3H), 1.97-1.82 (m, 2H), 1.51-1.31 (m, 2H), 0.96 (td, J = 7.3, 4.7 Hz, 3H) | 0.92 538.0 A | B |

TABLE 2-continued

| Ex # | Structure | IUPAC Name | NMR | RT (min), [M + H] Method | APJ cAMP Human EC50 (nM) |
|---|---|---|---|---|---|
| 50 | 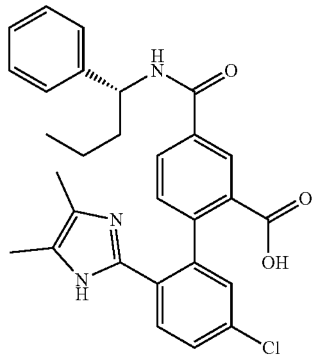 [SMILES: CCC[C@@H](NC(=O)c1ccc(-c2cc(Cl)ccc2-c2nc(C)c(C)[nH]2)c(C(=O)O)c1)c1ccccc1] | 5'-chloro-2'-(4,5-dimethyl-1H-imidazol-2-yl)-4-{[(1R)-1-phenylbutyl]carbamoyl}-[1,1'-biphenyl]-2-carboxylic acid | 1H NMR (500 MHz, DMSO-d6) δ 9.02 (d, J = 8.3 Hz, 1H), 8.35 (br. s., 1H), 8.10 (d, J = 8.0 Hz, 1H), 7.96 (s, 1H), 7.77-7.72 (m, 1H), 7.71-7.66 (m, 1H), 7.53 (s, 1H), 7.46-7.38 (m, 2H), 7.34 (t, J = 7.6 Hz, 1H), 7.27-7.20 (m, 1H), 5.12-5.00 (m, 1H), 2.07 (s, 6H), 1.97-1.86 (m, 1H), 1.81-1.71 (m, 1H), 1.46-1.21 (m, 2H), 0.92 (t, J = 7.3 Hz, 3H) | 0.88 501.9 A | B |
| 51 | 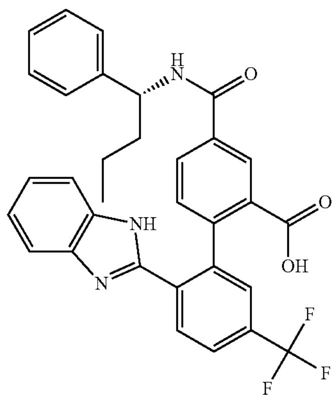 [SMILES: CCC[C@@H](NC(=O)c1ccc(-c2cc(C(F)(F)F)ccc2-c2nc3ccccc3[nH]2)c(C(=O)O)c1)c1ccccc1] | 2'-(1H-1,3-benzodiazol-2-yl)-4-{[(1R)-1-phenylbutyl]carbamoyl}-5'-(trifluoromethyl)-[1,1'-biphenyl]-2-carboxylic acid | 1H NMR (500 MHz, DMSO-d6) δ 9.00 (d, J = 8.3 Hz, 1H), 8.38 (d, J = 1.7 Hz, 1H), 8.11 (d, J = 8.0 Hz, 1H), 8.04 (dd, J = 8.0, 1.7 Hz, 1H), 8.00 (d, J = 8.3 Hz, 1H), 7.67 (s, 1H), 7.52-7.48 (m, 2H), 7.43-7.39 (m, 2H), 7.38-7.31 (m, 3H), 7.26-7.21 (m, 3H), 5.08-5.02 (m, 1H), 1.93-1.84 (m, 1H), 1.78-1.69 (m, 1H), 1.44-1.35 (m, 1H), 1.35-1.25 (m, 1H), 0.92 (t, J = 7.3 Hz, 3H) | 0.90 557.9 A | A |
| 52 | 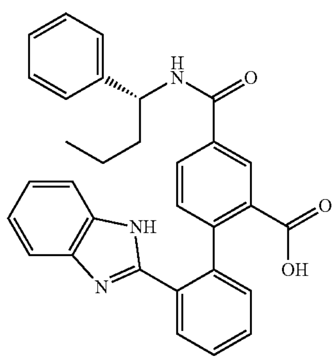 [SMILES: CCC[C@@H](NC(=O)c1ccc(-c2ccccc2-c2nc3ccccc3[nH]2)c(C(=O)O)c1)c1ccccc1] | 2'-(1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.93 (d, J = 8.5 Hz, 1H), 8.26 (d, J = 1.7 Hz, 1H), 7.91 (dd, J = 8.0, 1.7 Hz, 1H), 7.86 (dd, J = 7.4, 1.7 Hz, 1H), 7.58 (quind, J = 7.4, 1.5 Hz, 2H), 7.46-7.39 (m, 4H), 7.33 (t, J = 7.6 Hz, 2H), 7.28 (dd, J = 7.3, 1.5 Hz, 1H), 7.26-7.21 (m, 1H), 7.19 (d, J = 8.0 Hz, 1H), 7.13 (dd, J = 5.8, 3.0 Hz, 2H), 5.08-4.99 (m, 1H), 1.93-1.82 (m, 1H), 1.78-1.68 (m, 1H), 1.46-1.35 (m, 1H), 1.34-1.24 (m, 1H), 0.92 (t, J = 7.4 Hz, 3H) | 0.82 490.3 A | A |
| 53 | 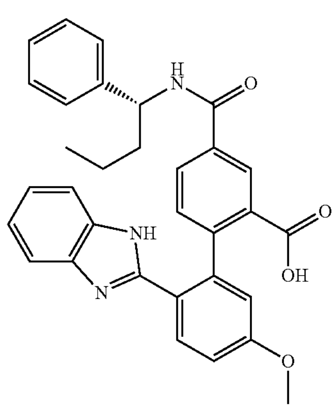 [SMILES: CCC[C@@H](NC(=O)c1ccc(-c2cc(OC)ccc2-c2nc3ccccc3[nH]2)c(C(=O)O)c1)c1ccccc1] | 2'-(1H-1,3-benzodiazol-2-yl)-5'-methoxy-4-{[(1R)-1-phenylbutyl]carbamoyl}-[1,1'-biphenyl]-2-carboxylic acid | 1H NMR (500 MHz, DMSO-d6) δ 9.00 (d, J = 8.0 Hz, 1H), 8.29 (br. s., 1H), 8.04 (d, J = 7.7 Hz, 1H), 7.86 (d, J = 8.3 Hz, 1H), 7.58 (br. s., 2H), 7.44-7.30 (m, 7H), 7.29-7.21 (m, 2H), 6.95 (br. s., 1H), 5.04 (d, J = 7.4 Hz, 1H), 3.90 (s, 3H), 1.88 (d, J = 7.4 Hz, 1H), 1.78-1.67 (m, 1H), 1.39 (d, J = 6.3 Hz, 1H), 1.33-1.22 (m, 1H), 0.91 (t, J = 6.9 Hz, 3H) | 0.84 520.0 A | A |

TABLE 2-continued

| Ex # | Structure | IUPAC Name | NMR | RT (min), [M + H] Method | APJ cAMP Human EC50 (nM) |
|---|---|---|---|---|---|
| 54 | 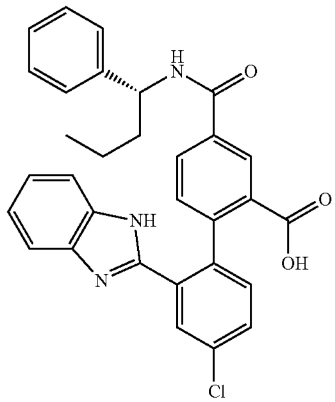 [SMILES: CCC[C@@H](NC(=O)c1ccc(-c2ccc(Cl)cc2-c2nc3ccccc3[nH]2)c(C(=O)O)c1)c1ccccc1] | 2'-(1H-1,3-benzodiazol-2-yl)-4'-chloro-4-{[(1R)-1-phenylbutyl]carbamoyl}-[1,1'-biphenyl]-2-carboxylic acid | 1H NMR (500 MHz, DMSO-d6) δ 9.04-8.96 (m, 1H), 8.34 (d, J = 1.7 Hz, 1H), 8.02 (dd, J = 8.0, 1.9 Hz, 1H), 7.99-7.95 (m, 1H), 7.70 (dd, J = 8.3, 1.9 Hz, 1H), 7.51 (dd, J = 5.9, 32 Hz, 2H), 7.40 (t, J = 7.3 Hz, 3H), 7.36-7.31 (m, 3H), 7.28-7.22 (m, 3H), 5.10-5.00 (m, 1H), 1.94-1.82 (m, 1H), 1.78-1.67 (m, 1H), 1.45-1.34 (m, 1H), 1.34-1.23 (m, 1H), 0.92 (t, J = 7.4 Hz, 3H) | 0.85 523.9 A | B |
| 55 | 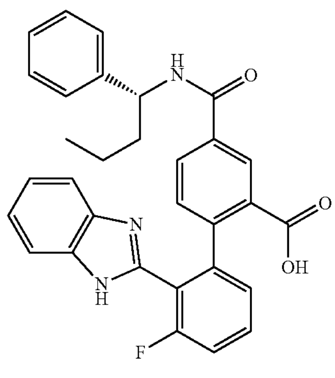 [SMILES: CCC[C@@H](NC(=O)c1ccc(-c2cccc(F)c2-c2nc3ccccc3[nH]2)c(C(=O)O)c1)c1ccccc1] | 2'-(1H-1,3-benzodiazol-2-yl)-3'-fluoro-4-{[(1R)-1-phenylbutyl]carbamoyl}-[1,1'-biphenyl]-2-carboxylic acid | 1H NMR (500 MHz, METHANOL-d4) δ 8.12 (d, J = 1.7 Hz, 1H), 7.70 (d, J = 8.0 Hz, 1H), 7.65 (td, J = 8.0, 5.6 Hz, 1H), 7.51 (dd, J = 5.9, 3.2 Hz, 2H), 7.40 (t, J = 8.8 Hz, 1H), 7.37-7.30 (m, 4H), 7.29-7.21 (m, 4H), 7.18 (d, J = 8.0 Hz, 1H), 5.04 (dd, J = 8.8, 6.3 Hz, 1H), 1.94-1.85 (m, 1H), 1.84-1.76 (m, 1H), 1.47-1.39 (m, 1H), 1.38-1.29 (m, 1H), 0.97 (t, J = 7.4 Hz, 3H) | 0.88 507.9 A | C |
| 56 | 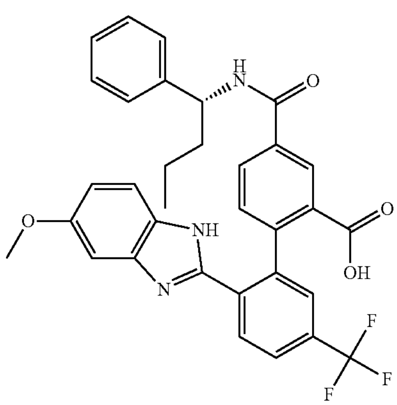 [SMILES: CCC[C@@H](NC(=O)c1ccc(-c2cc(C(F)(F)F)ccc2-c2nc3cc(OC)ccc3[nH]2)c(C(=O)O)c1)c1ccccc1] | 2'-(5-methoxy-1H-1,3-benzodiazol-2-yl)-4-{[(1R)-1-phenylbutyl]carbamoyl}-5'-(trifluoromethyl)-[1,1'-biphenyl]-2-carboxylic acid | 1H NMR (500 MHz, DMSO-d6) δ 9.00 (d, J = 8.3 Hz, 1H), 8.40 (d, J = 1.4 Hz, 1H), 8.09 (d, J = 8.3 Hz, 1H), 8.05 (dd, J = 8.0, 1.7 Hz, 1H), 7.99-7.97 (m, 1H), 7.64 (s, 1H), 7.45-7.32 (m, 6H), 7.27-7.21 (m, 1H), 6.96 (d, J = 1.9 Hz, 1H), 6.84 (d, J = 8.8 Hz, 1H), 5.10-5.02 (m, 1H), 1.95-1.84 (m, 1H), 1.79-1.70 (m, 1H), 1.46-1.36 (m, 1H), 1.35-1.23 (m, 1H), 0.94-0.90 (m, 3H) | 0.88 587.9 A | A |

TABLE 2-continued

| Ex # | Structure | IUPAC Name | NMR | RT (min), [M + H] Method | APJ cAMP Human EC50 (nM) |
|---|---|---|---|---|---|
| 57 | 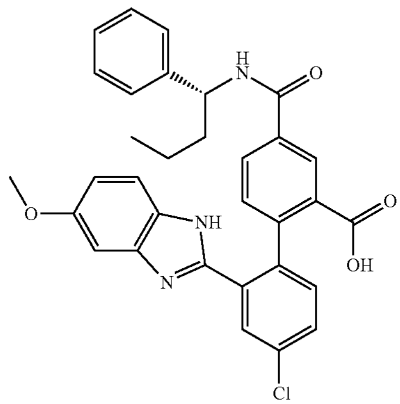 [SMILES: CCC[C@@H](NC(=O)c1ccc(-c2ccc(Cl)cc2-c2nc3cc(OC)ccc3[nH]2)c(C(=O)O)c1)c1ccccc1] | 4'-chloro-2'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 9.01 (d, J = 8.3 Hz, 1H), 8.35 (d, J = 1.9 Hz, 1H), 8.03 (dd, J = 8.0, 1.9 Hz, 1H), 7.96 (d, J = 2.2 Hz, 1H), 7.69 (dd, J = 8.4, 1.8 Hz, 1H), 7.44-7.30 (m, 7H), 7.26-7.21 (m, 1H), 6.97 (d, J = 2.2 Hz, 1H), 6.89 (d, J = 8.8 Hz, 1H), 5.09-5.00 (m, 1H), 1.94-1.84 (m, 1H), 1.79-1.68 (m, 1H), 1.46-1.35 (m, 1H), 1.34-1.23 (m, 1H), 0.92 (t, J = 7.4 Hz, 3H) | 0.86 553.9 A | A |
| 58 | 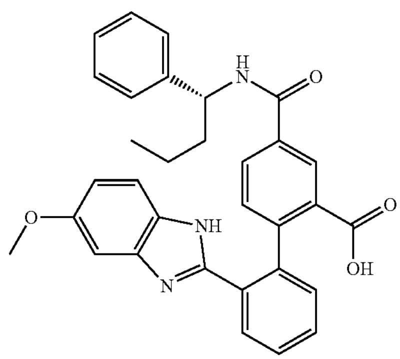 | 2'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.97 (d, J = 8.5 Hz, 1H), 8.31 (d, J = 1.4 Hz, 1H), 8.00 (d, J = 7.7 Hz, 1H), 7.89-7.85 (m, 1H), 7.68-7.64 (m, 2H), 7.46 (d, J = 8.8 Hz, 1H), 7.42-7.28 (m, 6H), 7.26-7.21 (m, 1H), 7.03-6.99 (m, 1H), 6.93 (d, J = 6.9 Hz, 1H), 5.09-5.01 (m, 1H), 1.95-1.82 (m, 1H), 1.78-1.69 (m, 1H), 1.45-1.36 (m, 1H), 1.34-1.23 (m, 1H), 0.92 (t, J = 7.4 Hz, 2H) | 0.83 519.8 A | A |
| 59 | 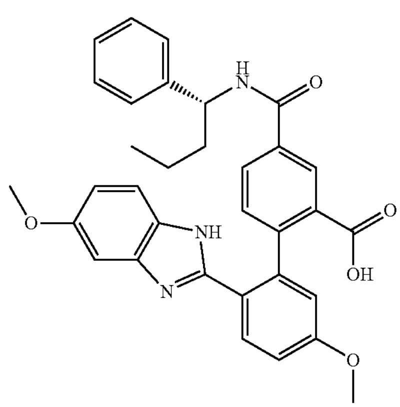 [SMILES: CCC[C@@H](NC(=O)c1ccc(-c2cc(OC)ccc2-c2nc3cc(OC)ccc3[nH]2)c(C(=O)O)c1)c1ccccc1] | 5'-methoxy-2'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 9.00 (d, J = 8.0 Hz, 1H), 8.31 (br. s., 1H), 8.07-8.01 (m, 1H), 7.84 (br. s., 1H), 7.54-7.45 (m, 1H), 7.43-7.31 (m, 5H), 7.29-7.21 (m, 2H), 7.08-6.96 (m, 2H), 6.93 (br. s., 1H), 5.10-4.97 (m, 1H), 1.95-1.83 (m, 1H), 1.79-1.68 (m, 1H), 1.46-1.35 (m, 1H), 1.35-1.21 (m, 1H), 0.91 (t, J = 7.0 Hz, 2H) | 0.85 550.0 A | A |

TABLE 2-continued

| Ex # | Structure | IUPAC Name | NMR | RT (min), [M + H] Method | APJ cAMP Human EC50 (nM) |
|---|---|---|---|---|---|
| 60 | 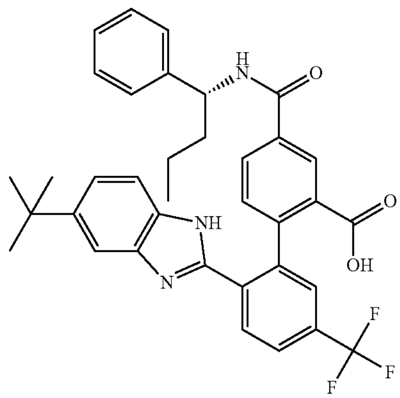 [SMILES: CCC[C@@H](NC(=O)c1ccc(-c2cc(C(F)(F)F)ccc2-c2nc3cc(C(C)(C)C)ccc3[nH]2)c(C(=O)O)c1)c1ccccc1] | 2'-(5-tert-butyl-1H-1,3-benzodiazol-2-yl)-4-{[(1R)-1-phenylbutyl]carbamoyl}-5'-(trifluoromethyl)-[1,1'-biphenyl]-2-carboxylic acid | 1H NMR (500 MHz, DMSO-d6) δ 9.00 (d, J = 8.5 Hz, 1H), 8.40 (d, J = 1.1 Hz, 1H), 8.08 (s, 1H), 8.06-8.03 (m, 1H), 8.02 (s, 1H), 7.68 (s, 1H), 7.49-7.43 (m, 2H), 7.42-7.39 (m, 2H), 7.39-7.30 (m, 4H), 7.27-7.21 (m, 1H), 5.09-5.00 (m, 1H), 1.96-1.84 (m, 1H), 1.79-1.69 (m, 1H), 1.47-135 (m, 1H), 1.33-1.24 (m, 10H), 0.92 (t, J = 7.3 Hz, 3H) | 0.98 614.0 A | A |
| 61 | 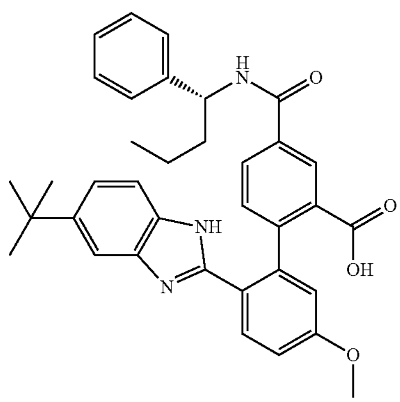 [SMILES: CCC[C@@H](NC(=O)c1ccc(-c2cc(OC)ccc2-c2nc3cc(C(C)(C)C)ccc3[nH]2)c(C(=O)O)c1)c1ccccc1] | 2'-(5-tert-butyl-1H-1,3-benzodiazol-2-yl)-5'-methoxy-4-{[(1R)-1-phenylbutyl]carbamoyl}-[1,1'-biphenyl]-2-carboxylic acid | 1H NMR (500 MHz, DMSO-d6) δ 9.01 (d, J = 8.3 Hz, 1H), 8.33 (br. s., 1H), 8.05 (d, J = 7.7 Hz, 1H), 7.85 (d, J = 8.3 Hz, 1H), 7.57-7.47 (m, 3H), 7.40 (d, J = 7.4 Hz, 3H), 7.37-7.21 (m, 4H), 6.96 (br. s., 1H), 5.08-4.99 (m, 1H), 3.90 (s, 3H), 1.95-1.82 (m, 1H), 1.78-1.68 (m, 1H), 1.44-1.37 (m, 1H), 1.34-1.26 (m, 10H), 0.91 (t, J = 7.0 Hz, 3H) | 0.94 576.0 A | A |
| 62 | 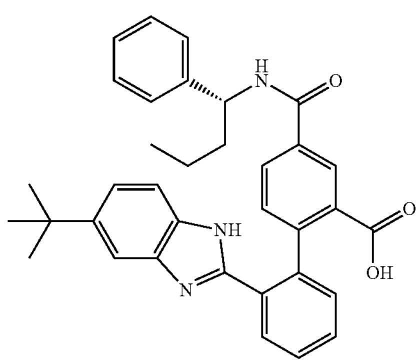 [SMILES: CCC[C@@H](NC(=O)c1ccc(-c2ccccc2-c2nc3cc(C(C)(C)C)ccc3[nH]2)c(C(=O)O)c1)c1ccccc1] | 2'-(5-tert-butyl-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.97 (d, J = 8.5 Hz, 1H), 8.34-8.31 (m, 1H), 8.01 (dd, J = 8.0, 1.7 Hz, 1H), 7.89 (dd, J = 7.4, 1.7 Hz, 1H), 7.73-7.66 (m, 2H), 7.55-7.45 (m, 3H), 7.43-7.38 (m, 3H), 7.36-7.30 (m, 3H), 7.26-7.21 (m, 1H), 5.08-5.01 (m, 1H), 1.94-1.84 (m, 1H), 1.78-1.69 (m, 1H), 1.46-1.35 (m, 1H), 1.33 (s, 9H), 1.31-1.24 (m, 1H), 0.91 (t, J = 7.4 Hz, 3H) | 0.93 545.9 A | A |

TABLE 2-continued

| Ex # | Structure | IUPAC Name | NMR | RT (min), [M + H] Method | APJ cAMP Human EC50 (nM) |
|---|---|---|---|---|---|
| 63 | 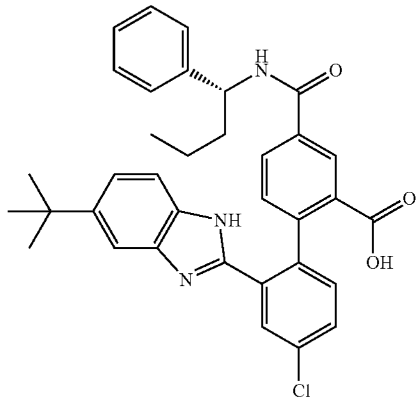 [SMILES: CCC[C@@H](NC(=O)c1ccc(-c2ccc(Cl)cc2-c2nc3cc(C(C)(C)C)ccc3[nH]2)c(C(=O)O)c1)c1ccccc1] | 2'-(5-tert-butyl-1H-1,3-benzodiazol-2-yl)-4'-chloro-4-{[(1R)-1-phenylbutyl]carbamoyl}-[1,1'-biphenyl]-2-carboxylic acid | 1H NMR (500 MHz, DMSO-d6) δ 8.98 (d, J = 8.3 Hz, 1H), 8.36 (d, J = 1.7 Hz, 1H), 8.03 (dd, J = 8.1, 1.8 Hz, 1H), 7.97-7.96 (m, 1H), 7.73 (dd, J = 8.3, 1.9 Hz, 1H), 7.52-7.44 (m, 2H), 7.43-7.37 (m, 4H), 7.33 (dt, J = 7.8, 3.7 Hz, 3H), 7.26-7.21 (m, 1H), 5.08-5.01 (m, 1H), 1.93-1.84 (m, 1H), 1.78-1.68 (m, 1H), 1.46-1.35 (m, 1H), 1.32 (s, 9H), 1.30-1.24 (m, 1H), 0.92 (t, J = 7.4 Hz, 3H) | 0.95 579.9 A | B |
| 64 | 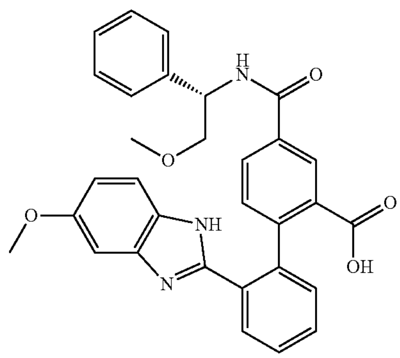 [SMILES: COC[C@@H](NC(=O)c1ccc(-c2ccccc2-c2nc3cc(OC)ccc3[nH]2)c(C(=O)O)c1)c1ccccc1] | 4-{[(1S)-2-methoxy-1-phenylethyl]carbamoyl}-2'-(5-methoxy-1H-1,3-benzodiazol-2-yl)-[1,1'-biphenyl]-2-carboxylic acid | 1H NMR (500 MHz, DMSO-d6) δ 9.08 (d, J = 8.0 Hz, 1H), 8.35 (s, 1H), 8.05 (d, J = 8.0 Hz, 1H), 7.97 (s, 1H), 7.89 (d, J = 7.4 Hz, 1H), 7.70 (quin, J = 7.6 Hz, 1H), 7.51 (d, J = 8.8 Hz, 1H), 7.45-7.39 (m, 2H), 7.39-7.32 (m, 2H), 7.28 (d, J = 7.4 Hz, 1H), 7.07-6.96 (m, 2H), 5.37-5.24 (m, 1H), 3.80 (s, 3H), 3.72 (d, J = 9.4 Hz, 1H), 3.59-3.54 (m, 1H), 3.31 (s, 3H) | 0.69 522.1 A | A |
| 65 | 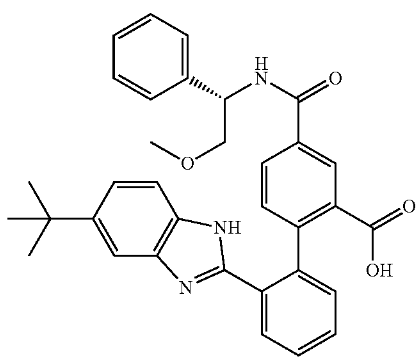 [SMILES: COC[C@@H](NC(=O)c1ccc(-c2ccccc2-c2nc3cc(C(C)(C)C)ccc3[nH]2)c(C(=O)O)c1)c1ccccc1] | 2'-(5-tert-butyl-1H-1,3-benzodiazol-2-yl)-4-{[(1S)-2-methoxy-1-phenylethyl]carbamoyl}-[1,1'-biphenyl]-2-carboxylic acid | 1H NMR (500 MHz, DMSO-d6) δ 9.01 (d, J = 8.3 Hz, 1H), 8.25 (s, 1H), 7.88 (d, J = 8.0 Hz, 1H), 7.82 (d, J = 7.4 Hz, 1H), 7.62-7.52 (m, 2H), 7.43 (d, J = 7.7 Hz, 2H), 7.38-7.31 (m, 4H), 7.29-7.20 (m, 3H), 7.14 (d, J = 8.0 Hz, 1H), 5.35-5.23 (m, 1H), 3.71 (t, J = 9.5 Hz, 1H), 3.56 (dd, J = 10.0, 5.4 Hz, 1H), 3.30 (s, 3H), 1.31 (s, 9H) | 0.78 548.2 A | A |
| 66 | 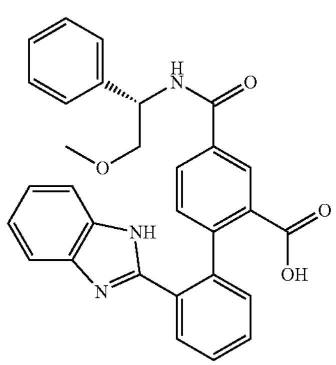 [SMILES: COC[C@@H](NC(=O)c1ccc(-c2ccccc2-c2nc3ccccc3[nH]2)c(C(=O)O)c1)c1ccccc1] | 2'-(1H-1,3-benzodiazol-2-yl)-4-{[(1S)-2-methoxy-1-phenylethyl]carbamoyl}-[1,1'-biphenyl]-2-carboxylic acid | 1H NMR (500 MHz, DMSO-d6) δ 9.03 (d, J = 8.3 Hz, 1H), 8.28 (s, 1H), 7.99-7.83 (m, 2H), 7.61-7.55 (m, 1H), 7.46-7.41 (m, 3H), 7.35 (t, J = 7.6 Hz, 2H), 7.31-7.25 (m, 2H), 7.19 (d, J = 8.0 Hz, 1H), 7.13 (dd, J = 5.8, 3.0 Hz, 2H), 5.37-5.23 (m, 1H), 3.72 (t, J = 9.5 Hz, 1H), 3.56 (dd, J = 10.0, 5.4 Hz, 1H), 3.30 (s, 3H) | 0.68 492.1 A | B |

TABLE 2-continued

| Ex # | Structure | IUPAC Name | NMR | RT (min), [M + H] Method | APJ cAMP Human EC50 (nM) |
|---|---|---|---|---|---|
| 67 | 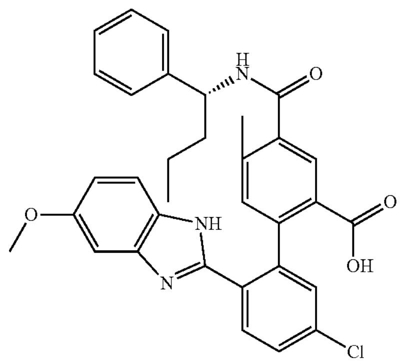 [SMILES: CCC[C@@H](NC(=O)c1cc(C(=O)O)c(-c2cc(Cl)ccc2-c2nc3cc(OC)ccc3[nH]2)cc1C)c1ccccc1] | 5'-chloro-2'-(5-methoxy-1H-1,3-benzodiazol-2-yl)-5-methyl-4-{[(1R)-1-phenylbutyl]carbamoyl}-[1,1'-biphenyl]-2-carboxylic acid | 1H NMR (500 MHz, DMSO-d6) δ 8.87 (d, J = 8.5 Hz, 1H), 7.85 (d, J = 8.3 Hz, 1H), 7.78-7.67 (m, 2H), 7.45 (d, J = 6.6 Hz. 1H), 7.42-7.31 (m, 5H), 7.28-7.18 (m, 2H), 7.00 (br. s., 1H), 6.92 (br. s., 1H), 5.05-4.94 (m, 1H), 3.82-3.76 (m, 4H), 2.40-2.24 (m, 3H), 1.86-1.76 (m, 1H), 1.73-1.61 (m, 1H), 1.47-1.23 (m, 2H), 0.92 (t, J = 7.4 Hz, 3H) | 0.94 567.9 A | A |
| 68 | 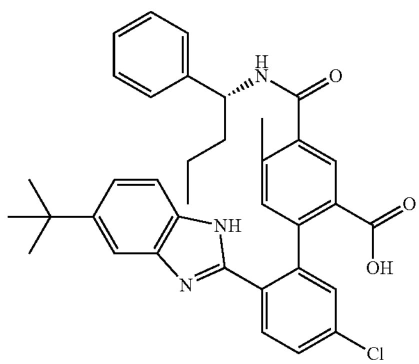 [SMILES: CCC[C@@H](NC(=O)c1cc(C(=O)O)c(-c2cc(Cl)ccc2-c2nc3cc(C(C)(C)C)ccc3[nH]2)cc1C)c1ccccc1] | 2,-(5-tert-butyl-1H-1,3-benzodiazol-2-yl)-5'-chloro-5-methyl-4-{[(1R)-1-phenylbutyl]carbamoyl}-[1,1'-biphenyl]-2-carboxylic acid | 1H NMR (500 MHz, DMSO-d6) δ 8.86 (d, J = 8.3 Hz, 1H), 7.85 (d, J = 8.3 Hz, 1H), 7.78-7.67 (m, 2H), 7.47 (br. s., 2H), 7.43-7.31 (m, 6H), 7.28-7.18 (m, 2H), 5.07-4.94 (m, 1H), 2.39-2.25 (m, 3H), 1.86-1.75 (m, 1H), 1.73-1.63 (m, 1H), 1.46-1.37 (m, 1H), 1.33 (br. s., 9H), 1.30-1.23 (m, 1H), 0.92 (t, J = 7.3 Hz, 3H) | 1.01 594.0 A | A |
| 69 | 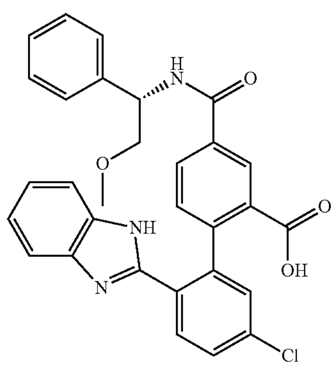 | 2'-(1H-1,3-benzodiazol-2-yl)-5'-chloro-4-{[(1S)-2-methoxy-1-phenylethyl]carbamoyl}-[1,1'-biphenyl]-2-carboxylic acid | 1H NMR (500 MHz, methanol-d4:CDCl3 1:1) δ 8.30 (d, J = 9.6 Hz, 1H), 7.90 (t, J = 6.1 Hz, 1H), 7.77 (d, J = 8.3 Hz, 1H), 7.65 (dd, J = 8.3, 2.2 Hz, 1H), 7.57 (dd, J = 5.4, 2.9 Hz, 2H), 7.47-7.41 (m, 3H), 7.41-7.36 (m, 2H), 7.33 (td, J = 7.6, 3.3 Hz, 2H), 7.27 (dd, J = 7.7, 4.4 Hz, 2H), 5.34 (dd, J = 7.7, 5.0 Hz, 1H), 3.81-3.75 (m, 1H), 3.71-3.66 (m, 1H), 3.39 (d, J = 3.6 Hz, 3H) | 0.80 526.0 A | A |
| 70 | 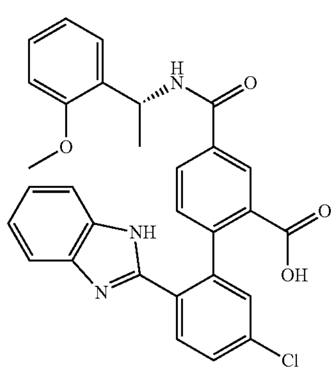 [SMILES: COc1ccccc1[C@@H](C)NC(=O)c1ccc(-c2cc(Cl)ccc2-c2nc3ccccc3[nH]2)c(C(=O)O)c1] | 2'-(1H-1,3-benzodiazol-2-yl)-5'-chloro-4-{[(1R)-1-(2-methoxyphenyl)ethyl]carbamoyl}-[1,1'-biphenyl]-2-carboxylic acid | 1H NMR (500 MHz, DMSO-d6) δ 8.96 (d, J = 7.2 Hz, 1H), 8.36 (br. s., 1H), 8.04 (d, J = 7.7 Hz, 1H), 7.90 (d, J = 8.3 Hz, 1H), 7.71 (d, J = 8.5 Hz, 1H), 7.48 (br. s., 2H), 7.34 (t, J = 8.5 Hz, 2H), 7.21 (br. s., 3H), 6.99 (d, J = 7.7 Hz, 1H), 6.92 (t, J = 7.2 Hz, 1H), 5.48 (t, J = 6.7 Hz, 1H), 3.85 (br. s., 4H), 1.40 (d, J = 6.6 Hz, 3H) | 0.84 525.9 A | A |

TABLE 2-continued

| Ex # | Structure | IUPAC Name | NMR | RT (min), [M + H] Method | APJ cAMP Human EC50 (nM) |
|---|---|---|---|---|---|
| 71 | 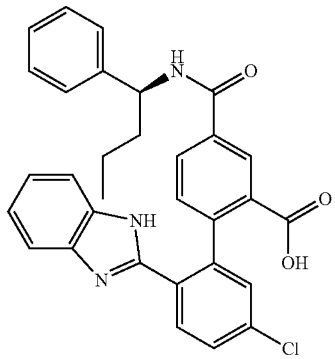 [SMILES: CCC[C@H](NC(=O)c1ccc(-c2cc(Cl)ccc2-c2nc3ccccc3[nH]2)c(C(=O)O)c1)c1ccccc1] | 2'-(1H-1,3-benzodiazol-2-yl)-5'-chloro-4-{[(1S)-1-phenylbutyl]carbamoyl}-[1,1'-biphenyl]-2-carboxylic acid | 1H NMR (500 MHz, methanol-d4:1 CDCl3) δ 6.82 (d, J = 9.9 Hz, 1H), 6.44 (t, J = 8.5 Hz, 1H), 6.34 (d, J = 8.3 Hz, 1H), 6.21 (dd, J = 8.3, 1.7 Hz, 1H), 6.14 (d, J = 3.0 Hz, 2H), 6.02 (d, J = 6.1 Hz, 3H), 5.94 (br. s., 2H), 5.91-5.85 (m, 2H), 5.85-5.77 (m, 2H), 3.65 (t, J = 7.3 Hz, 1H), 0.53-0.37 (m, 1H), 0.27-0.16 (m, 2H), 0.06--0.02 (m, 1H), -0.39 (t, J = 7.4 Hz, 1H), -0.47 (t, J = 7.3 Hz, 3H) | 0.89 524.1 A | B |
| 72 | 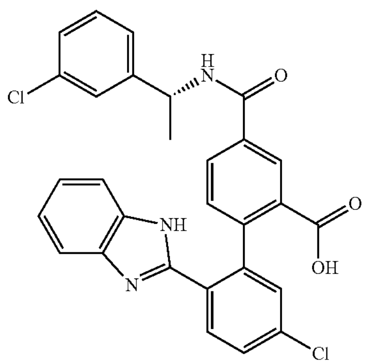 [SMILES: C[C@@H](NC(=O)c1ccc(-c2cc(Cl)ccc2-c2nc3ccccc3[nH]2)c(C(=O)O)c1)c1cccc(Cl)c1] | 2'-(1H-1,3-benzodiazol-2-yl)-5'-chloro-4-{[(1R)-1-(3-chlorophenyl)ethyl]carbamoyl}-[1,1'-biphenyl]-2-carboxylic acid | 1H NMR (500 MHz, DMSO-d6) δ 9.03 (d, J = 7.2 Hz, 1H), 8.29 (br. s., 1H), 8.00-7.77 (m, 3H), 7.65 (d, J = 8.3 Hz, 1H), 7.49-7.27 (m, 5H), 7.21 (d, J = 7.4 Hz, 1H), 7.11 (d, J = 3.3 Hz, 2H), 5.18 (t, J = 6.9 Hz, 1H), 1.49 (d, J = 6.3 Hz, 3H) | 0.90 530.1 A | B |
| 73 | 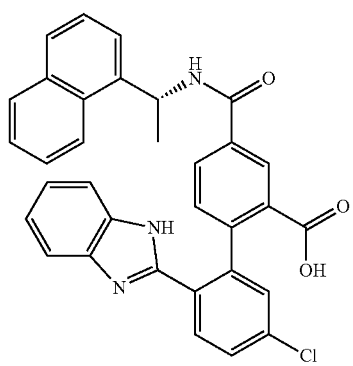 [SMILES: C[C@@H](NC(=O)c1ccc(-c2cc(Cl)ccc2-c2nc3ccccc3[nH]2)c(C(=O)O)c1)c1cccc2ccccc12] | 2'-(1H-1,3-benzodiazol-2-yl)-5'-chloro-4-{[(1R)-1-(naphthalen-1-yl)ethyl]carbamoyl}-[1,1'-biphenyl]-2-carboxylic acid | 1H NMR (500 MHz, DMSO-d6) δ 9.17-9.06 (m, 1H), 8.33 (br. s., 1H), 7.97 (br. s., 1H), 7.92-7.81 (m, 3H), 7.70-7.58 (m, 2H), 7.50 (br. s., 2H), 7.40 (br. s., 1H), 7.34 (br. s., 1H), 7.28-7.19 (m, 2H), 7.11 (br. s., 2H), 5.44-5.30 (m, 1H), 1.59 (d, J = 6.6 Hz, 3H) | 1.75 546.2 C | B |
| 74 | 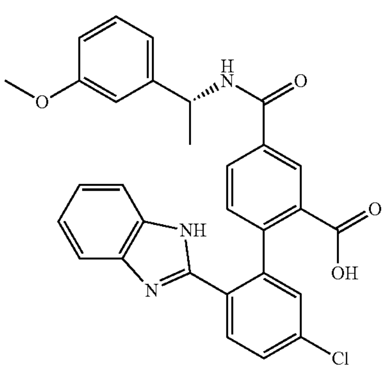 [SMILES: COc1cccc([C@@H](C)NC(=O)c2ccc(-c3cc(Cl)ccc3-c3nc4ccccc4[nH]3)c(C(=O)O)c2)c1] | 2'-(1H-1,3-benzodiazol-2-yl)-5'-chloro-4-{[(1R)-1-(3-methoxyphenyl)ethyl]carbamoyl}-[1,1'-biphenyl]-2-carboxylic acid | 1H NMR (500 MHz, DMSO-d6) δ 8.96 (d, J = 6.6 Hz, 1H), 8.25 (br. s., 1H), 7.85 (d, J = 7.7 Hz, 2H), 7.64 (d, J = 8.5 Hz, 1H), 7.40 (d, J = 3.6 Hz, 2H), 7.30 (br. s., 1H), 7.25 (t, J = 7.3 Hz, 1H), 7.10 (d, J = 3.6 Hz, 2H), 6.97 (br. s., 2H), 6.81 (d, J = 8.0 Hz, 1H), 5.15 (t, J = 7.0 Hz, 1H), 3.75 (br. s., 3H), 1.47 (d, J = 6.3 Hz, 3H) | 0.86 525.9 A | B |

TABLE 2-continued

| Ex # | Structure | IUPAC Name | NMR | RT (min), [M + H] Method | APJ cAMP Human EC50 (nM) |
|---|---|---|---|---|---|
| 75 | 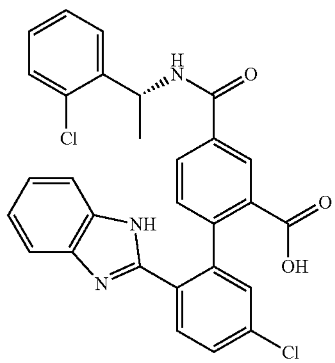 [SMILES: C[C@@H](NC(=O)c1ccc(-c2cc(Cl)ccc2-c2nc3ccccc3[nH]2)c(C(=O)O)c1)c1ccccc1Cl] | 2'-(1H-1,3-benzodiazol-2-yl)-5'-chloro-4-{[(1R)-1-(2-chlorophenyl)ethyl]carbamoyl}-[1,1'-biphenyl]-2-carboxylic acid | 1H NMR (500 MHz, DMSO-d6) δ 9.17 (d, J = 5.2 Hz, 1H), 8.37 (br. s., 1H), 8.04 (d, J = 7.7 Hz, 1H), 7.90 (d, J = 8.3 Hz, 1H), 7.71 (d, J = 8.3 Hz, 1H), 7.55 (d, J = 7.4 Hz, 1H), 7.48 (br. s., 2H), 7.43 (br. s., 2H), 7.35 (br. s., 2H), 7.28 (br. s., 1H), 7.22 (br. s., 1H), 5.48 (t, J = 6.9 Hz, 1H), 1.47 (d, J = 6.6 Hz, 3H) | 0.87 530.1 A | B |
| 76 | 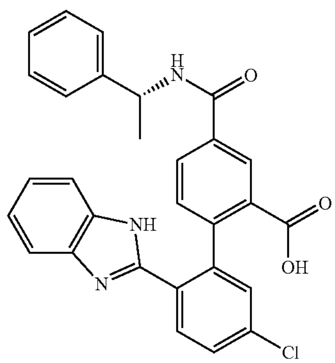 [SMILES: C[C@@H](NC(=O)c1ccc(-c2cc(Cl)ccc2-c2nc3ccccc3[nH]2)c(C(=O)O)c1)c1ccccc1] | 2'-(1H-1,3-benzodiazol-2-yl)-5'-chloro-4-{[(1R)-1-phenylethyl]carbamoyl}-[1,1'-biphenyl]-2-carboxylic acid | 1H NMR (500 MHz, DMSO-d6) δ 9.01 (br. s., 1H), 8.24 (br. s., 1 H), 7.84 (d, J = 7.7 Hz, 2H), 7.64 (d, J = 8.3 Hz, 1H), 7.40 (d, J = 5.5 Hz, 3H), 7.32 (d, J = 18.4 Hz, 2H), 7.23 (br. s., 1H), 7.18-7.06 (m, 3H), 5.18 (br. s., 1H), 1.48 (br. s., 3H) | 0.79 495.8 A | B |
| 77 | 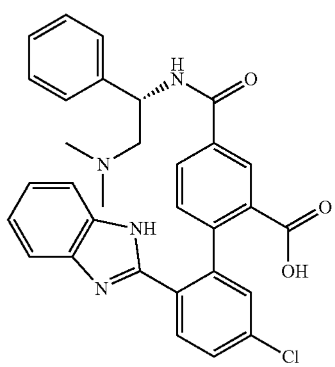 [SMILES: CN(C)C[C@@H](NC(=O)c1ccc(-c2cc(Cl)ccc2-c2nc3ccccc3[nH]2)c(C(=O)O)c1)c1ccccc1] | 2'-(1H-1,3-benzodiazol-2-yl)-5'-chloro-4-{[(1S)-2-(dimethylamino)-1-phenylethyl]carbamoyl}-[1,1'-biphenyl]-2-carboxylic acid | 1H NMR (500 MHz, DMSO-d6) δ 9.26 (d, J = 8.9 Hz, 1H), 8.33 (s, 1H), 8.03 (d, J = 7.6 Hz, 1H), 7.86 (d, J = 8.5 Hz, 1H), 7.70 (d, J = 8.2 Hz, 1H), 7.47 (br. s., 4H), 7.44-7.31 (m, 5H), 7.22 (br. s., 2H), 5.65-5.52 (m, 1H), 3.68-3.57 (m, 1H), 3.45 (d, J = 11.9 Hz, 1H), 2.88 (br. s., 6H) | 0.63 539.2 A | B |
| 78 | 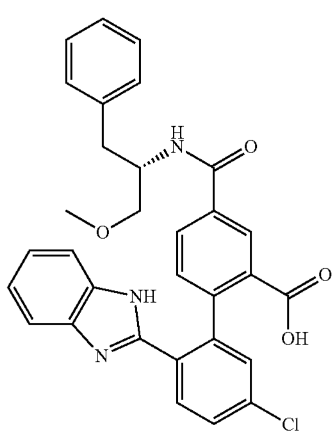 [SMILES: COC[C@H](Cc1ccccc1)NC(=O)c1ccc(-c2cc(Cl)ccc2-c2nc3ccccc3[nH]2)c(C(=O)O)c1] | 2'-(1H-1,3-benzodiazol-2-yl)-5'-chloro-4-{[(2S)-1-methoxy-3-phenylpropan-2-yl]carbamoyl}-[1,1'-biphenyl]-2-carboxylic acid | $^1$H NMR (500 MHz, DMSO-d$_6$) δ 8.57 (d, J = 6.3 Hz, 1H), 8.27 (d, J = 1.7 Hz, 1H), 7.98-7.87 (m, 2H), 7.71 (dd, J = 8.5, 1.9 Hz, 1H), 7.48 (dd, J = 5.5, 3.3 Hz, 2H), 7.43 (s, 1H), 7.36-7.20 (m, 7H), 4.41-4.30 (m, 1H), 3.47-3.37 (m, 2H), 3.29 (s, 3H), 2.95-2.80 (m, 2H) | 0.84 539.8 A | C |

TABLE 2-continued

| Ex # | Structure | IUPAC Name | NMR | RT (min), [M + H] Method | APJ cAMP Human EC50 (nM) |
|---|---|---|---|---|---|
| 79 | 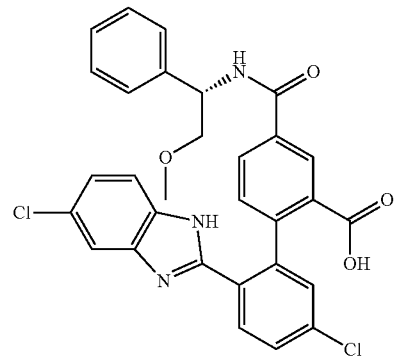 [SMILES: COC[C@@H](NC(=O)c1ccc(-c2cc(Cl)ccc2-c2nc3cc(Cl)ccc3[nH]2)c(C(=O)O)c1)c1ccccc1] | 5'-chloro-2'-(5-chloro-1H-1,3-benzodiazol-2-yl)-4-{[(1S)-2-methoxy-1-phenylethyl]carbamoyl}-[1,1'-biphenyl]-2-carboxylic acid | 1H NMR (500 MHz, DMSO-d6) δ 8.57 (d, J = 6.3 Hz, 1H), 8.27 (d, J = 1.7 Hz, 1H), 7.98-7.87 (m, 2H), 7.71 (dd, J = 8.5, 1.9 Hz, 1H), 7.48 (dd, J = 5.5, 3.3 Hz, 2H), 7.43 (s, 1H), 7.36-7.20 (m, 7H), 4.41-4.30 (m, 1H), 3.47-3.37 (m, 2H), 2.95-2.80 (m, 2H) | 0.87 559.9 A | A |
| 80 | 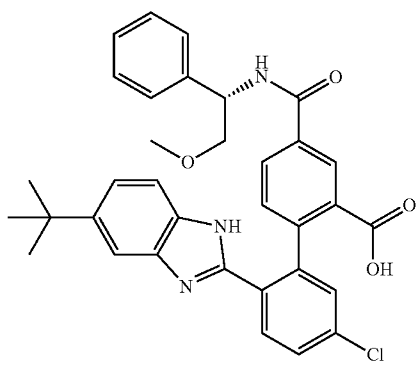 [SMILES: COC[C@@H](NC(=O)c1ccc(-c2cc(Cl)ccc2-c2nc3cc(C(C)(C)C)ccc3[nH]2)c(C(=O)O)c1)c1ccccc1] | 2'-(5-tert-butyl-1H-1,3-benzodiazol-2-yl)-5'-chloro-4-{[(1S)-2-methoxy-1-phenylethyl]carbamoyl}-[1,1'-biphenyl]-2-carboxylic acid | 1H NMR (500 MHz, DMSO-d6) δ 9.05 (d, J = 7.7 Hz, 1H), 8.34 (br. s., 1H), 7.95 (br. s., 1H), 7.88-7.83 (m, 1H), 7.66 (br. s., 1H), 7.46-7.41 (m, 2H), 7.38-7.31 (m, 5H), 7.29-7.18 (m, 3H), 5.35-5.26 (m, 1H), 3.72 (t, J = 9.2 Hz, 1H), 3.56 (m, J = 5.2 Hz, 1H), 3.31 (br. s., 3H), 1.30 (s, 9H) | 0.93 581.9 A | A |

Example 81. (S)-2'-(1H-benzo[d]imidazol-2-yl)-6'-chloro-4-(((R)-1-phenylbutyl)carbamoyl)-[1,1'-biphenyl]-2-carboxylic acid

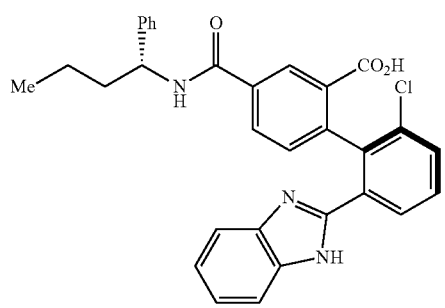

Intermediate 81A. 2-(tert-butyl) 2'-methyl 4-(2-(trimethylsilyl)ethyl) (S)-6'-chloro-[1,1'-biphenyl]-2,2',4-tricarboxylate

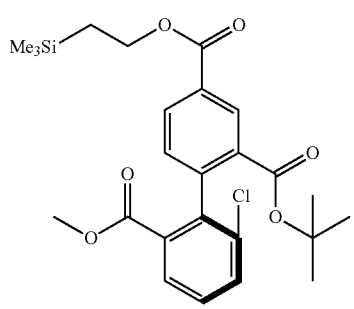

Into the reaction vessel containing 1C (1200 mg, 2.68 mmol) was added methyl 2-bromo-3-chlorobenzoate (868 mg, 3.48 mmol), THF (11 mL), Water (11 mL), K$_2$CO$_3$ (1110 mg, 8.03 mmol), and Pd(Ph$_3$P)$_4$ (773 mg, 0.669 mmol). The reaction mixture was degassed by bubbling N$_2$ for 10 min, sealed, and stirred at 70° C. for 36 h. After cooled to rt, the mixture was concentrated and subjected to silica gel chromatography purification and subsequently SFC separation (PIC Solution 200 SFC; Column: Whelko-1(R,R), 21×250 mm, 5 micron; Mobile Phase: 10% Methanol/90% CO$_2$; Flow Conditions: 45 mL/min, 150 Bar, 40° C.; Detector Wavelength: 220 nm) to provide 81A (282 mg, 0.574 mmol, 21.46% yield) (1 st eluent, RT=5.90 min) and enantiomer of 81A (300 mg, 0.611 mmol, 22.83% yield) (2nd eluent, RT=6.77 min). The absolute stereochemistry of 81A was confirmed by x-ray crystallography analysis of example 81. LCMS Anal. Calc'd for C25H31ClO6Si 490.16, found [M+H] 490.8; $^1$H NMR (500 MHz, chloroform-d) δ 8.60 (d, J=1.7 Hz, 1H), 8.07 (dd, J=8.0, 1.9 Hz, 1H), 7.82 (dd, J=7.8, 1.2 Hz, 1H), 7.52 (dd, J=8.1, 1.2 Hz, 1H), 7.29 (t, J=8.0 Hz, 1H), 7.05 (d, J=8.0 Hz, 1H), 4.39-4.31 (m, 2H), 3.47 (s, 3H), 1.13 (s, 9H), 1.09-1.03 (m, 2H), 0.00 (s, 9H).

Intermediate 81B. 2-(tert-butyl) 2'-methyl (S)-6'-chloro-4-(((R)-1-phenylbutyl)carbamoyl)-[1,1'-biphenyl]-2,2'-dicarboxylate

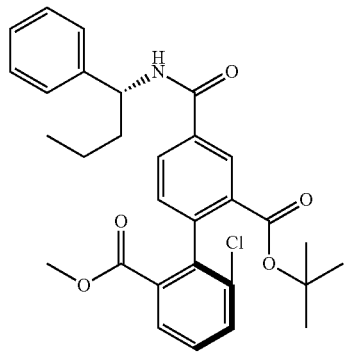

Into the reaction vessel was added 81A (282 mg, 0.574 mmol), THF (5 mL), and TBAF (1.149 mL, 1.149 mmol). The reaction was stirred at rt for 60 min, diluted with EtOAc (20 mL), and washed with sat NH$_4$Cl (20 mL) containing 1.15 mmol HCl. The organic phase was collected, dried over Na$_2$SO$_4$, and concentrated to produce the crude acid which was dissolved in DCM (6 mL). (R)-1-phenylbutan-1-amine (104 mg, 0.700 mmol), DIEA (0.306 mL, 1.750 mmol), and HATU (288 mg, 0.758 mmol) were subsequently added. The reaction was stirred at rt for 5 h, concentrated, and subjected to silica gel chromatography purification to produce 81B (281.6 mg, 0.539 mmol, 9/1% yield). LCMS Anal. Calc'd for C30H32ClNOs 521.20, found [M+H] 522.4; $^1$H NMR (500 MHz, chloroform-d) δ 8.39 (s, 1H), 8.06 (d, J=8.0 Hz, 1H), 7.94 (d, J=8.0 Hz, 1H), 7.64 (d, J=8.0 Hz, 1H), 7.44-7.35 (m, 5H), 7.33-7.29 (m, 1H), 7.18 (d, J=8.0 Hz, 1H), 6.47 (d, J=7.7 Hz, 1H), 5.24 (q, J=7.5 Hz, 1H), 3.62 (s, 3H), 2.04-1.83 (m, 2H), 1.52-1.33 (m, 2H), 1.00 (t, J=7.3 Hz, 3H).

Example 81

Into the reaction vessel was added 81B (281 mg, 0.538 mmol), THF (8 mL), Water (4 mL), and lithium hydroxide monohydrate (113 mg, 2.69 mmol). The reaction was stirred at rt for 36 h, diluted with EtOAc (30 mL), and washed with 20 mL sat NH$_4$Cl containing 2.69 mmol HCl. The organic phased was dried over Na$_2$SO$_4$ and concentrated to produce the crude carboxylic acid (280 mg, 0.551 mmol, 102% yield), which was dissolved in DCM (5 mL), benzene-1,2-diamine (106 mg, 0.984 mmol), DIEA (0.258 mL, 1.476 mmol), and HATU (243 mg, 0.640 mmol) were subsequently added. The reaction was stirred at rt for 12 h, concentrated, and dissolved in AcOH (4.5 mL)/Water (0.5 mL). After stirring at 85° C. for 12 h, the reaction was cooled to rt, concentrated, and subjected to preparative HPLC purification to produce example 81 (258 mg, 0.404 mmol, 75% yield). LCMS Anal. Calc'd for C$_{31}$H$_{26}$ClN$_3$O$_3$ 523.17, found [M+H] 524.2; 1H NMR (500 MHz, methanol-d$_4$) δ 8.95 (d, J=8.3 Hz, 1H), 8.43 (d, J=1.7 Hz, 1H), 7.92 (dd, J=8.0, 1.9 Hz, 1H), 7.84 (ddd, J=12.0, 7.9, 1.0 Hz, 2H), 7.71-7.65 (m, 1H), 7.61 (dd, J=6.2, 3.2 Hz, 2H), 7.48 (dd, J=6.2, 3.2 Hz, 2H), 7.38-7.33 (m, 2H), 7.32-7.27 (m, 3H), 7.25-7.19 (m, 1H), 5.11-5.01 (m, 1H), 1.95-1.85 (m, 1H), 1.84-1.75 (m, 1H), 1.49-1.38 (m, 1H), 1.38-1.29 (m, 1H), 0.95 (t, J=7.4 Hz, 3H).

Example 82. (S)-2'-(1H-benzo[d]imidazol-2-yl)-6'-chloro-4-(((S)-2-methoxy-1-phenylethyl)carbamoyl)-[1,1'-biphenyl]-2-carboxylic acid

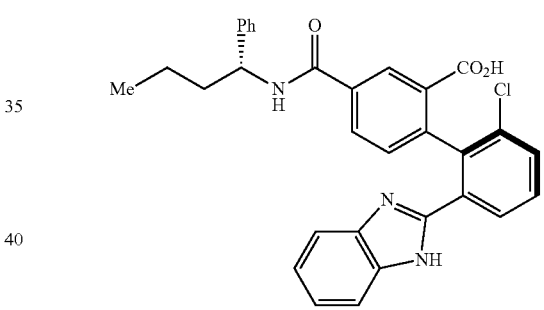

Intermediate 82A. benzyl 2-bromo-3-chlorobenzoate

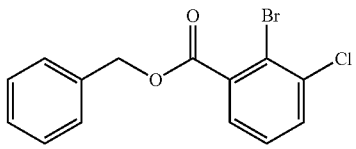 [SMILES: O=C(OCc1ccccc1)c1cccc(Cl)c1Br]

Into the reaction vessel was added 2-bromo-3-chlorobenzoic acid (5200 mg, 22.08 mmol), K$_2$CO$_3$ (4578 mg, 33.1 mmol), MeCN (100 mL), and benzyl bromide (2.63 mL, 22.08 mmol). The mixture was stirred at 45° C. for 12 h, cooled to rt, filtered, and concentrated. Silica gel chromatography purification produced 82A (7060 mg, 21.68 mmol, 98% yield). $^1$H NMR (500 MHz, chloroform-d) δ 7.59 (ddd, J=7.8, 6.0, 1.7 Hz, 2H), 7.52-7.46 (m, 2H), 7.45-7.37 (m, 3H), 7.32 (t, J=7.8 Hz, 1H), 5.41 (s, 2H).

Intermediate 82B. 2'-benzyl 2-(tert-butyl) 4-(2-(trimethylsilyl)ethyl) (S)-6'-chloro-2U [1,1'-biphenyl]-2,2',4-tricarboxylate

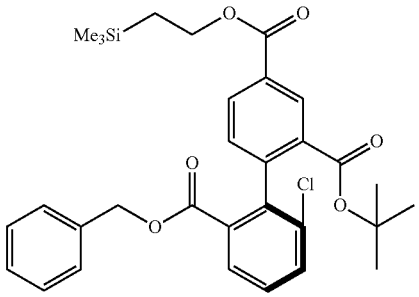

To a solution of 82A (5 g, 11.15 mmol), benzyl 2-bromo-3-chlorobenzoate (3.99 g, 12.26 mmol), 4,5-bis(diphenylphosphino)-9,9-dimethyxanthene (1.290 g, 2.230 mmol) in toluene (90 mL) was added $PdOAc_2$ (0.250 g, 1.115 mmol) and potassium phosphate tribasic (1M, 22.30 mL, 22.30 mmol). The resulting mixture was bubbled $N_2$ for 3-5 min and then heated at 70° C. under $N_2$ for 72 h. After the reaction was cooled down to rt, the mixture was diluted with EtOAc and washed with saturated $NH_4Cl$. Organic layer was separated, dried over $Na_2SO_4$ and evaporated to give a brown residue which was subjected to silica gel chromatography purification to provide 4.65 g of racemic product. Subsequent SFC purification (PIC Solution 200 SFC; Column: Lux 5u Cellulose-4, 30×250 mm, 5 micron; Mobile Phase: 10% $MeOH$/90% $CO_2$; Flow Conditions: 100 mL/min, 150 Bar, 40° C.; Detector Wavelength: 220 nm) produced enantiomer of 82B (2.12 g, 3.74 mmol, 33.5% yield, $1^{st}$ eluent, RT=4.67 min) and 82B (2.10 g, 3.70 mmol, 33.2% yield, $2^{nd}$ eluent, RT=6.26 min). LCMS Anal. Calc'd for $C_{31}H_{35}ClO_6Si$ 566.19, found [M+H] 567.1; $^1H$ NMR (500 MHz, chloroform-d) δ 8.42 (d, J=1.7 Hz, 1H), 7.92 (dd, J=8.0, 1.7 Hz, 1H), 7.84 (dd, J=7.8, 1.2 Hz, 1H), 7.48 (dd, J=8.0, 1.4 Hz, 1H), 7.27 (t, J=8.0 Hz, 1H), 7.14-7.10 (m, 3H), 6.96 (d, J=8.0 Hz, 1H), 6.94-6.91 (m, 2H), 4.84 (s, 2H), 4.38-4.30 (m, 2H), 1.07 (s, 9H), 1.06-1.03 (m, 2H), 0.00 (s, 9H).

Intermediate 82C. 2-(tert-butyl) 4-(2-(trimethylsilyl)ethyl) (S)-2'-((2-((tert-butoxycarbonyl)amino)phenyl)carbamoyl)-6'-chloro-[1,1'-biphenyl]-2,4-dicarboxylate

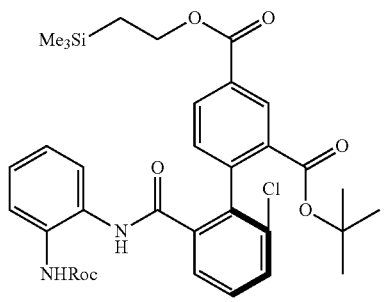

Intermediate 82B (710 mg, 1.252 mmol) was dissolved in EtOAc (15 mL). After the addition of platinum(iv) oxide (28.4 mg, 0.125 mmol), the reaction was stirred at rt under 1 atm $H_2$. After stirring for 2 h, the reaction mixture was filtered through Celite. Concentration produced crude carboxylic acid (601 mg, 1.260 mmol, 101% yield), which was dissolved in 10 mL of DCM (400 mg, 0.839 mmol). tert-butyl (2-amino-4-fluoro-5-methoxyphenyl)carbamate (258 mg, 1.006 mmol), DCM (10 mL), DIEA (0.439 mL, 2.52 mmol), and HATU (478 mg, 1.258 mmol) were subsequently added. The reaction was stirred at rt for 12 h, concentrated, and subjected to silica gel chromatography purification to produce 82C (504 mg, 0.705 mmol, 84% yield). LCMS Anal. Calc'd for $C_{35}H_{43}ClN_2O_7Si$ 666.25, found [M+H] 667.3, $^1H$ NMR (500 MHz, chloroform-d) δ 8.51 (s, 1H), 8.40 (d, J=1.7 Hz, 1H), 8.11 (dd, J=7.8, 1.8 Hz 1H), 7.64-7.57 (m, 2H), 7.46 (dd, J=8.1, 1.2 Hz, 1H), 7.40-7.33 (m, 1H), 7.23 (d, J=8.0 Hz 1H), 7.08-7.01 (m, 1H), 6.82 (td, J=7.6, 1.5 Hz, 1H), 6.75 (br. s., 1H), 6.49 (dd, J=8.0, 1.1 Hz, 1H), 4.38-4.31 (m, 2H), 1.34 (s, 9H), 1.08-1.02 (m, 2H), 0.03 (s, 9H).

Example 82

Into the reaction vessel was added 82C (28 mg, 0.042 mmol), THF (0.6 mL), water (0.3 mL), and lithium hydroxide monohydrate (17.61 mg, 0.420 mmol). The reaction was stirred at 40° C. for 48 h, diluted with EtOAc (30 mL), and washed with 20 mL sat $NH_4Cl$ containing 0.42 mmol HCl. The organic phased was dried over $Na_2SO_4$ and concentrated to produce the corresponding crude carboxylic acid (25 mg, 0.044 mmol, 105% yield), which was used for next step without further purification. Into the reaction vessel was added crude carboxylic acid (9 mg, 0.016 mmol), (S)-2-methoxy-1-phenylethanamine-HCl (3.87 mg, 0.021 mmol), DIEA (0.014 mL, 0.079 mmol), DCM (1 mL), and HATU (8.15 mg, 0.021 mmol). The reaction was stirred at rt for 12 h, concentrated, and dissolved in AcOH (1 mL)/Water (0.1 mL). After stirring at 85° C. for 12 h, the reaction was cooled to rt, concentrated, and subjected to preparative HPLC purification to produce example 82 (8.5 mg, 0.013 mmol, 84% yield). LCMS Anal. Calc'd for $C30H_{24}ClN_3O_4$ 525.15, found [M+H] 526.0; 1H NMR (500 MHz, methanol-$d_4$) δ 8.37 (d, J=1.9 Hz, 1H), 7.85 (dd, J=8.0, 1.9 Hz, 1H), 7.78 (dd, J=7.7, 1.1 Hz, 1H), 7.73 (dd, J=8.0, 1.1 Hz, 1H), 7.63-7.57 (m, 1H), 7.53-7.47 (m, 2H), 7.41-7.37 (m, 2H), 7.34 (t, J=7.6 Hz, 2H), 7.29-7.25 (m, 3H), 7.16 (d, J=8.0 Hz, 1H), 5.32 (dd, J=8.5, 5.0 Hz, 1H), 3.77-3.72 (m, 1H), 3.65 (dd, J=10.2, 5.0 Hz, 1H), 3.39 (s, 3H).

Examples 84-85, 87-101, 108-126, and 132-157 may be made by one skilled in the art by appropriate application of the procedures described for Examples 81-82.

Example 83. methyl (S)-2'-chloro-6'-(6-fluoro-5-methoxy-1H-benzo[d]imidazol-2-yl)-4-(((R)-1-phenylbutyl)carbamoyl)-[1,1'-biphenyl]-2-carboxylate

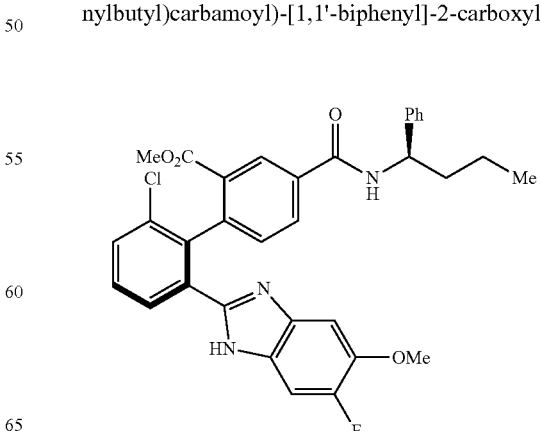

A solution of example 84 (38 mg, 0.055 mmol) in 2N HCl/MeOH (4 mL) solution was stirred at 50° C. for 25 h. After cooled to rt, solvent was evaporated and residue was taking up in MeOH and purified by preparative HPLC to produce example 83 (28.6 mg, 72% yield). LCMS Anal. Calc'd for $C_{33}H_{29}ClFN_3O_4$ 585.18, found [M+H] 586.2; $^1$H NMR (500 MHz, methanol-$d_4$) δ 8.95 (d, J=8.0 Hz, 1H), 8.42 (d, J=1.9 Hz, 1H), 7.95 (dd, J=8.0, 1.7 Hz, 1H), 7.80 (ddd, J=11.1, 7.8, 1.1 Hz, 2H), 7.68-7.63 (m, 1H), 7.37-7.28 (m, 6H), 7.25-7.20 (m, 1H), 7.16 (d, J=7.2 Hz, 1H), 5.10-5.03 (m, 1H), 3.89 (s, 3H), 3.75 (s, 3H), 1.97-1.75 (m, 2H), 1.49-1.28 (m, 2H), 0.96 (t, J=7.4 Hz, 3H).

Examples 86, 128, and 203-204 may be made by one skilled in the art by appropriate application of the procedures described for Examples 83.

TABLE 3

| Ex # | Structure | IUPAC Name | NMR | RT (min), [M + H] Method | APJ cAMP Human EC50 (nM) |
|---|---|---|---|---|---|
| 81 | 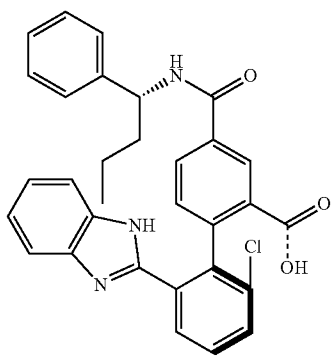 | (S)-2'-(1H-1,3-benzodiazol-2-yl)-6'-chloro-4-{[(1R)-1-phenylbutyl]carbamoyl}[1,1'-biphenyl]-2-carboxylic acid | 1H NMR (500 MHz, METHANOL-d4) δ 8.95 (d, J = 8.3 Hz, 1H), 8.43 (d, J = 1.7 Hz, 1H), 7.92 (dd, J = 8.0, 1.9 Hz, 1H), 7.84 (ddd, J = 12.0, 7.9, 1.0 Hz, 2H), 7.71-7.65 (m, 1H), 7.61 (dd, J = 6.2, 3.2 Hz, 2H), 7.48 (dd, J = 6.2, 3.2 Hz, 2H), 7.38-7.33 (m, 2H), 7.32-7.27 (m, 3H), 7.25-7.19 (m, 1H), 5.11-5.01 (m, 1H), 1.95-1.85 (m, 1H), 1.84-1.75 (m, 1H), 1.49-1.38 (m, 1H), 1.38-1.29 (m, 1 H), 0.95 (t, J = 7.4 Hz, 3H) | 0.83 524.2 A | A |
| 82 | 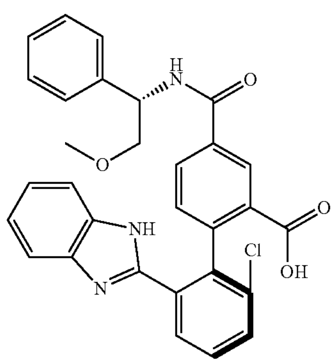 | (S)-2'-(1H-1,3-benzodiazol-2-yl)-6'-chloro-4-{[(1S)-2-methoxy-1-phenylethyl]carbamoyl}-[1,1'-biphenyl]-2-carboxylic acid | 1H NMR (500 MHz, METHANOL-d4) δ 9.03 (d, J = 7.7 Hz, 1H), 8.49 (d, J = 1.7 Hz, 1H), 8.01 (dd, J = 8.0, 1.9 Hz, 1H), 7.90 (dd, J = 8.1, 1.2 Hz, 1H), 7.86 (dd, J = 7.7, 1.1 Hz, 1H), 7.74-7.68 (m, 1H), 7.68-7.62 (m, 2H), 7.57-7.52 (m, 2H), 7.40-7.30 (m, 5H), 7.28-7.23 (m, 1H), 5.37-5.26 (m, 1H), 3.73 (dd, J = 10.2, 8.8 Hz, 1H), 3.67-3.61 (m, 1H), 3.38-3.37 (s, 3H) | 0.67 526.1 A | B |
| 83 | 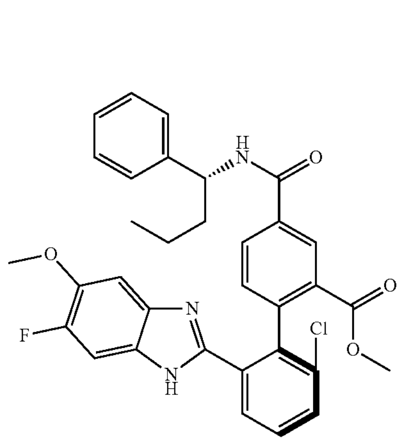 | (S)-methyl 2'-chloro-6'-(6-fluoro-5-methoxy-1H-1,3-benzodiazol-2-yl)-4-{[(1R)-1-phenylbutyl]carbamoyl}-[1,1'-biphenyl]-2-carboxylate | 1H NMR (500 MHz, METHANOL-d4) δ 8.95 (d, J = 8.0 Hz, 1H), 8.42 (d, J = 1.9 Hz, 1H), 7.95 (dd, J = 8.0, 1.7 Hz, 1H), 7.80 (ddd, J = 11.1, 7.8, 1.1 Hz, 2H), 7.68-7.63 (m, 1H), 7.37-7.28 (m, 6H), 7.25-7.20 (m, 1H), 7.16 (d, J = 7.2 Hz, 1H), 5.10-5.03 (m, 1H), 3.89 (s, 3H), 3.75 (s, 3H), 1.97-1.75 (m, 2H), 1.49-1.28 (m, 2H), 0.96 (t, J = 7.4 Hz, 3H) | 1.19 586.2 A | B |

TABLE 3-continued

| Ex # | Structure | IUPAC Name | NMR | RT (min), [M + H] Method | APJ cAMP Human EC50 (nM) |
|---|---|---|---|---|---|
| 84 | 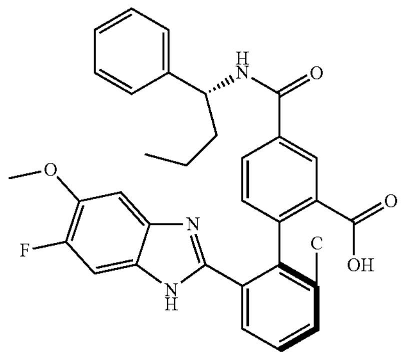 | (S)-2'-chloro-6'-(6-fluoro-5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.95 (d, J = 8.3 Hz, 1H), 8.44 (d, J = 1.9 Hz, 1H), 7.92 (d, J = 1.9 Hz, 1H), 7.80 (ddd, J = 13.6, 7.8, 1.1 Hz, 2H), 7.67- 7.62 (m, 1H), 7.38-7.34 (m, 3H), 7.33-7.28 (m, 2H), 7.27-7.18 (m, 3H), 5.09-5.02 (m, J = 2.2 Hz, 1H), 1.97-1.74 (m, 2H), 1.49-1.26 (m, 2H), 0.96 (t, J = 7.4 Hz, 3H) | 3.46 572.2 C | A |
| 85 | 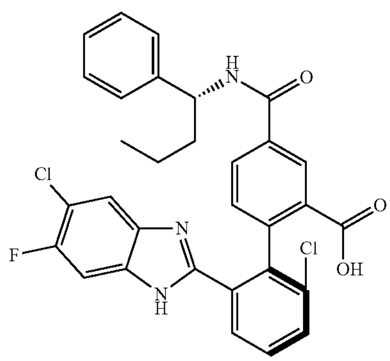 | (S)-2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.43 (d, J = 1.4 Hz, 1H), 7.88 (dd, J = 7.8, 1.8 Hz, 1H), 7.75 (t, J = 8.5 Hz, 2H), 7.62-7.57 (m, 2H), 7.39-7.33 (m, 3H), 7.33-7.28 (m, 2H), 7.24-7.19 (m, 2H), 5.09-5.02 (m, J = 15.1 Hz, 1H), 1.95-1.86 (m, J = 5.5 Hz, 1H), 1.85-1.75 (m, 1H), 1.51-1.40 (m, 1H), 1.39-1.25 (m, 1H), 0.96 (t, J = 7.4 Hz, 3H) | 1.01 576.1 A | A |
| 86 | 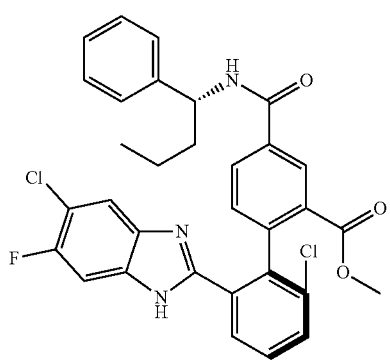 | (S)-methyl 2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylate | 1H NMR (500 MHz, METHANOL-d4) δ 8.93 (d, J = 8.3 Hz, 1H), 8.39 (s, 1H), 7.94-7.89 (m, J = 1.9 Hz, 1H), 7.75 (td, J = 7.6, 1.2 Hz, 2H), 7.60 (d, J = 16.0 Hz, 1H), 7.55 (d, J = 6.3 Hz, 1H), 7.38-7.29 (m, 5H), 7.26 (d, J = 8.0 Hz, 1H), 7.24-7.20 (m, 1H), 5.10-5.02 (m, 1H), 3.72 (s, 3H), 1.96-1.75 (m, 2H), 1.49-1.28 (m, 2H), 0.96 (t, J = 7.4 Hz, 3H) | 1.32 590.2 A | C |
| 87 | 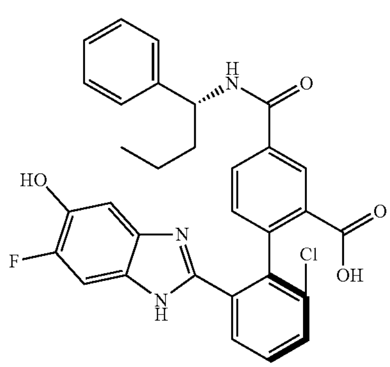 | (S)-2'-chloro-6'-(6-fluoro-5-hydroxy-1H-1,3-benzodiazol-2-yl)-4-{[(1R)-1-phenylbutyl]carbamoyl}-[1,1'-biphenyl]-2-carboxylic acid | $^1$H NMR (500 MHz, METHANOL-d$_4$) δ 8.45 (d, J = 1.9 Hz, 1H), 7.93 (dd, J = 8.0, 1.9 Hz, 1H), 7.84 (dd, J = 8.3, 1.1 Hz, 1H), 7.79 (dd, J = 7.8, 1.2 Hz, 1H), 7.69-7.63 (m, 1H), 7.38-7.33 (m, 3H), 7.33-7.26 (m, 3H), 7.25-7.20 (m, 1H), 7.08 (d, J = 7.4 Hz, 1H), 5.06 (dd, J = 8.8, 6.6 Hz, 1H), 1.97-1.86 (m, 1H), 1.81 (dd, J = 9.4, 6.6 Hz, 1H), 1.50-1.26 (m, J = 9.4, 7.2 Hz, 2H), 0.96 (t, J = 7.3 Hz, 3H) | 0.78 558.2 A | A |

TABLE 3-continued

| Ex # | Structure | IUPAC Name | NMR | RT (min), [M + H] Method | APJ cAMP Human EC50 (nM) |
|---|---|---|---|---|---|
| 88 | 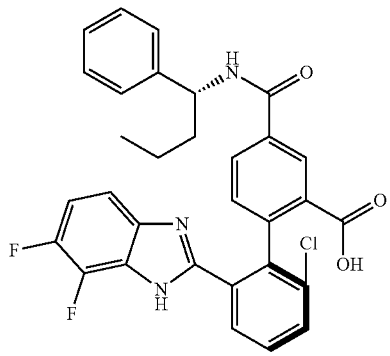 | (S)-2'-chloro-6'-(6,7-difluoro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.40 (d, J = 1.7 Hz, 1H), 7.87 (dd, J = 8.0, 1.9 Hz, 1H), 7.74 (dd, J = 7.7, 1.4 Hz, 1H), 7.69 (dd, J = 8.3, 1.1 Hz, 1H), 7.59-7.53 (m, J = 15.7 Hz, 1H), 7.38-7.27 (m, 2H), 7.25-7.19 (m, 1H), 7.16-7.06 (m, 2H), 5.09-5.02 (m, J = 8.5 Hz, 1H), 5.17-4.98 (m, 1H), 1.94-1.85 (m, J = 9.1, 9.1, 5.0 Hz, 1H), 1.84-1.74 (m, J = 9.4 Hz, 1H), 1.48-1.39 (m, 1H), 1.39-1.28 (m, 1H), 0.96 (t, J = 7.4 Hz, 3H) | 0.99 560.1 | A |
| 89 | 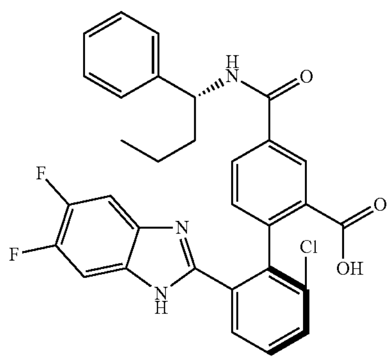 | (S)-2'-chloro-6'-(5,6-difluoro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.43 (d, J = 1.9 Hz, 1H), 7.88 (dd, J = 8.0, 1.7 Hz, 1H), 7.78-7.73 (m, 2H), 7.63-7.57 (m, 1H), 7.42 (t, J = 8.5 Hz, 2H), 7.37-7.33 (m, 2H), 7.33-7.28 (m, 2H), 7.24-7.19 (m, 2H), 5.05 (dd, J = 8.8, 6.6 Hz, 1H), 1.95-1.85 (m, 1H), 1.85-1.76 (m, J = 9.2, 6.5 Hz, 1H), 1.50-1.39 (m, J = 3.9 Hz, 1H), 1.39-1.27 (m, 1H), 0.96 (t, J = 7.4 Hz, 3H) | 0.94 560.1 | A |
| 90 | 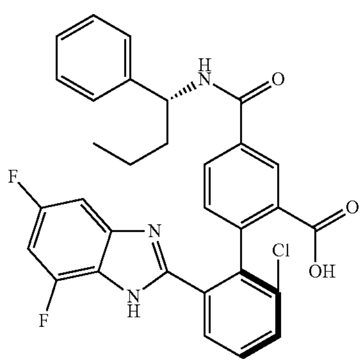 | (S)-2'-chloro-6'-(5,7-difluoro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.41 (s, 1H), 7.87 (d, J = 8.0 Hz, 1H), 7.73 (d, J = 7.7 Hz, 1H), 7.70 (d, J = 8.3 Hz, 1H), 7.59-7.52 (m, 1H), 7.56 (t, J = 1.0 Hz, 1H), 7.39-7.26 (m, 4H), 7.25-7.19 (m, 2H), 6.96 (d, J = 8.5 Hz, 1H), 6.85 (t, J = 9.8 Hz, 1H), 5.09-5.02 (m, J = 6.6 Hz, 1H), 1.95-1.84 (m, 1H), 1.84-1.75 (m, 1H), 1.50-1.39 (m, 1H), 1.39-1.27 (m, 1H), 0.96 (t, J = 7.4 Hz, 3H) | 0.99 560.2 A | A |
| 91 | 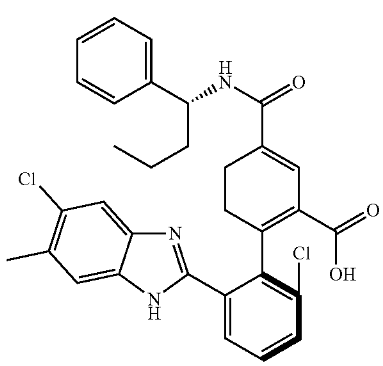 | (S)-2'-chloro-6'-(5-chloro-6-methyl-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.43 (s, 1H), 7.91 (d, J = 8.0 Hz, 1H), 7.81 (t, J = 8.1 Hz, 2H), 7.67-7.62 (m, 1H), 7.60 (s, 1H), 7.49 (s, 1H), 7.37-7.33 (m, 2H), 7.33-7.28 (m, 2H), 7.26 (d, J = 8.0 Hz, 1H), 7.24-7.19 (m, J = 7.2 Hz, 1H), 5.08-5.02 (m, 2H), 3.31 (s, 10H), 1.95-1.85 (m, 1H), 1.85-1.75 (m, 1H), 1.50-1.50 (m, 1H), 1.49-1.27 (m, 2H), 0.96 (t, J = 7.4 Hz, 3H) | 0.95 572.1 A | A |

TABLE 3-continued

| Ex # | Structure | IUPAC Name | NMR | RT (min), [M + H] Method | APJ cAMP Human EC50 (nM) |
|---|---|---|---|---|---|
| 92 | 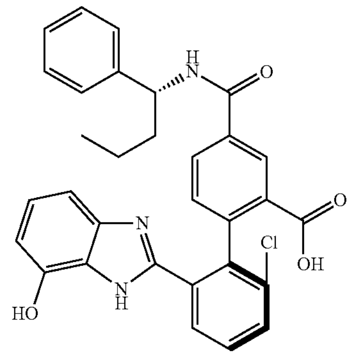 | (S)-2'-chloro-6'-(7-hydroxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.36 (d, J = 1.7 Hz, 1H), 7.88 (dd, J = 8.0, 1.9 Hz, 1H), 7.81 (dd, J = 16.4, 7.3 Hz, 2H), 7.68-7.61 (m, 1H), 7.38-7.19 (m, 7H), 6.98 (d, J = 8.3 Hz, 1H), 6.79 (d, J = 7.7 Hz, 1H), 5.09-5.01 (m, 1H), 1.94-1.74 (m, 2H), 1.47-1.26 (m, 3H), 0.95 (t, J = 7.4 Hz, 3H) | 3.37 540.0 C | A |
| 93 | 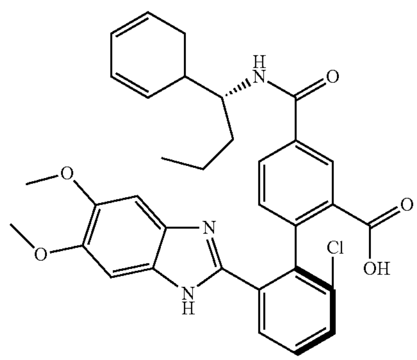 | (S)-2'-chloro-6'-(5,6-dimethoxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.46 (s, 1H), 7.94 (d, J = 8.0 Hz, 1H), 7.88-7.77 (m, J = 7.4 Hz, 2H), 7.71-7.65 (m, 1H), 7.39-7.28 (m, J = 8.0, 8.0 Hz, 5H), 7.26-7.20 (m, 1H), 7.12-7.06 (m, 2H), 3.86 (s, 6H), 1.96-1.76 (m, 2H), 1.49-1.26 (m, 2H), 0.96 (t, J = 7.3 Hz, 3H) | 0.81 584.2 A | A |
| 94 | 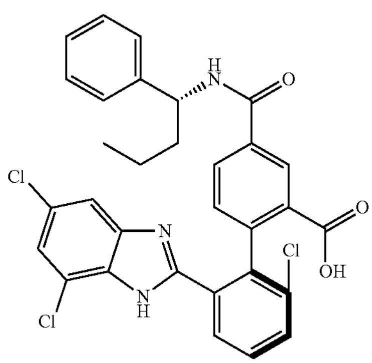 | (S)-2'-chloro-6'-(5,7-dichloro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.40 (d, J = 1.9 Hz, 1H), 7.88 (dd, J = 8.0, 1.9 Hz, 1H), 7.76 (dd, J = 7.7, 1.1 Hz, 1H), 7.71 (dd, J = 8.1, 1.0 Hz, 1H), 7.60-7.54 (m, J = 8.0 Hz, 1H), 7.37-7.33 (m, 3H), 7.33-7.27 (m, 3H), 7.24-7.19 (m, 2H), 7.20 (br. s., 1H), 5.05 (dd, J = 8.8, 6.3 Hz, 1H), 1.94-1.84 (m, 1H), 1.84-1.75 (m, 1H), 1.49-1.39 (m, 1H), 1.39-1.28 (m, 1H), 0.96 (t, J = 7.4 Hz, 3H) | 1.07 592.2 A | A |
| 95 | 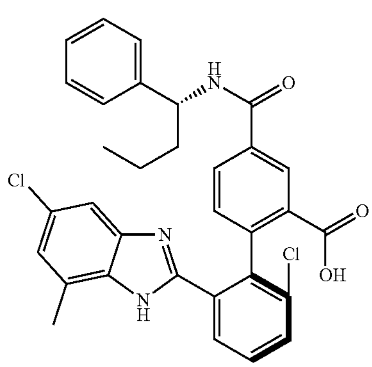 | (S)-2'-chloro-6'-(5-chloro-7-methyl-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.36 (d, J = 1.4 Hz, 1H), 7.87 (dd, J = 8.0, 1.7 Hz, 1H), 7.76 (t, J = 7.8 Hz, 2H), 7.64-7.57 (m, 1H), 7.37-7.33 (m, 2H), 7.33-7.27 (m, 3H), 7.23 (d, J = 8.0 Hz, 2H), 7.11 (s, 1H), 5.09-5.02 (m, J = 8.5 Hz, 1H), 2.44 (s, 3H), 1.95-1.84 (m, 1H), 1.84-1.75 (m, J = 9.4 Hz, 1H), 1.50-1.39 (m, 1H), 1.39-1.25 (m, 1H), 0.96 (t, J = 7.3 Hz, 3H) | 0.97 572.1 A | A |

TABLE 3-continued

| Ex # | Structure | IUPAC Name | NMR | RT (min), [M + H] Method | APJ cAMP Human EC50 (nM) |
|---|---|---|---|---|---|
| 96 | 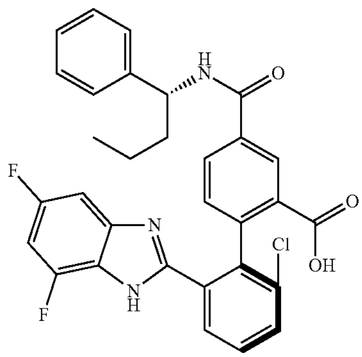 | (S)-2'-chloro-6'-(5,7-difluoro-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.92 (d, J = 8.3 Hz, 1H), 8.40 (d, J = 1.9 Hz, 1H), 7.87 (dd, J = 8.0, 1.9 Hz, 1H), 7.69 (dd, J = 8.3, 1.1 Hz, 1H), 7.58-7.53 (m, 1H), 7.38-7.34 (m, 2H), 7.33-7.29 (m, 2H), 7.25-7.19 (m, 2H), 6.95 (dd, J = 8.5, 1.9 Hz, 1H), 6.83 (td, J = 10.3, 2.2 Hz, 1H), 5.10-5.03 (m, 1H), 1.94-1.85 (m, 1H), 1.84-1.75 (m, 1H), 1.48-1.28 (m, 2H), 0.95 (t, J = 7.4 Hz, 3H) | 0.99 560.1 A | A |
| 97 | 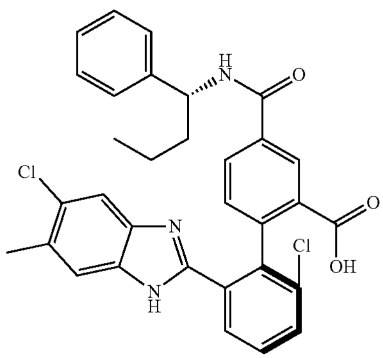 | (S)-2'-chloro-6'-(5-chloro-6-methyl-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.42 (d, J = 1.7 Hz, 1H), 7.91 (dd, J = 7.8, 1.8 Hz, 1H), 7.82-7.77 (m, 2H), 7.66-7.60 (m, 1H), 7.58 (s, 1H), 7.47 (s, 1H), 7.37-7.34 (m, 2H), 7.34-7.29 (m, 2H), 7.27-7.19 (m, 2H), 5.10-5.02 (m, 1H), 2.44 (s, 3H), 1.94-1.85 (m, 1H), 1.84-1.75 (m, 1H), 1.47-1.27 (m, 2H), 0.95 (t, J = 7.3 Hz, 3H) | 0.92 572.1 A | B |
| 98 | 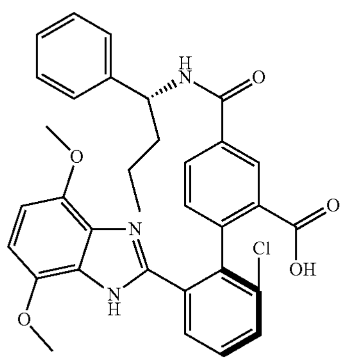 | (S)-2'-chloro-6'-(4,7-dimethoxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.37 (d, J = 1.9 Hz, 1H), 7.98 (dd, J = 8.0, 1.9 Hz, 1H), 7.86 (dd, J = 8.1, 1.0 Hz, 1H), 7.76 (dd, J = 7.7, 1.1 Hz, 1H), 7.69-7.62 (m, 1H), 7.43 (d, J = 8.0 Hz, 1H), 7.37-7.33 (m, 2H), 7.33-7.28 (m, 2H), 7.25-7.18 (m, J = 7.2 Hz, 1H), 6.87 (s, 2H), 5.05 (dd, J = 8.8, 6.6 Hz, 1H), 3.89 (s, 6H), 1.95-1.73 (m, 2H), 1.47-1.24 (m, 2H), 0.95 (t, J = 7.4 Hz, 3H) | 0.87 584.3 A | B |
| 99 | 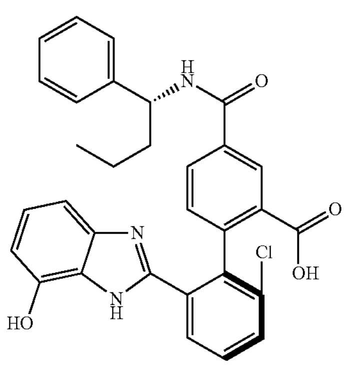 | (S)-2'-chloro-6'-(7-hydroxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.96 (d, J = 8.3 Hz, 1H), 8.38 (s, 1H), 7.93 (d, J = 8.0 Hz, 1H), 7.84 (d, J = 8.0 Hz, 1H), 7.80 (d, J = 7 7 Hz, 1H), 7.69-7.63 (m, 1H), 7.69-7.63 (m, 1H), 7.66 (t, J = 1.0 Hz, 1H), 7.37-7.33 (m, 2H), 7.33-7.28 (m, 2H), 7.28-7.19 (m, 2H), 6.99 (d, J = 8.3 Hz, 1H), 6.82 (d, J = 8.0 Hz, 1H), 5.09-5.01 (m, 1H), 1.95-1.84 (m, 1H), 1.84-1.74 (m, 1H), 1.48-1.26 (m, 2H), 0.95 (t, J = 7.4 Hz, 3H) | 0.86 540.0 A | B |

TABLE 3-continued

| Ex # | Structure | IUPAC Name | NMR | RT (min), [M + H] Method | APJ cAMP Human EC50 (nM) |
|---|---|---|---|---|---|
| 100 | 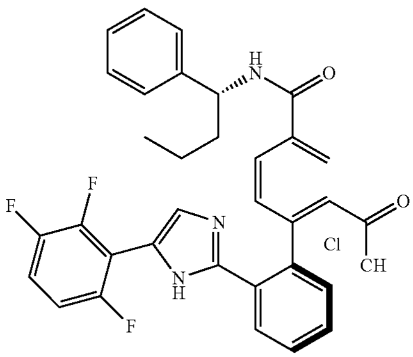 | (S)-2'-chloro-4-{[(1R)-1-phenylbutyl]carbamoyl}-6'-[5-(2,3,6-trifluorophenyl)-1H-imidazol-2-yl]-[1,1'-biphenyl]-2-carboxylic acid | 1H NMR (500 MHz, METHANOL-d4) δ 8.45 (d, J = 1.9 Hz, 171H), 8.41-8.36 (m, 1H), 8.00 (dd, J = 8.0, 1.9 Hz, 1H), 7.77 (dd, J = 8.1, 1.2 Hz, 1H), 7.74 (dd, J = 7.7, 1.1 Hz, 1H), 7.64-7.59 (m, 2H), 7.40-7.34 (m, 3H), 7.34-7.29 (m, 2H), 7.28 (d, J = 8.0 Hz, 1H), 7.23 (t, J = 6.7 Hz, 1H), 7.09-7.01 (m, 1H), 5.15-5.05 (m, 1H), 2.00-1.78 (m, 2H), 1.52-1.31 (m, 2H), 0.97 (t, J = 7.4 Hz, 3H) | 0.86 604.5 A | A |
| 101 | 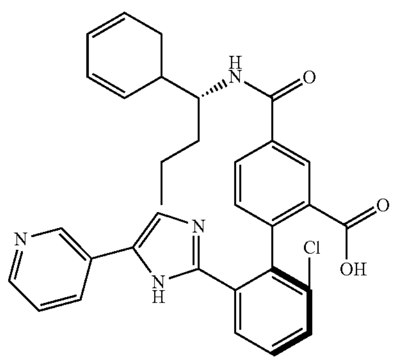 | (S)-2'-chloro-4-{[(1R)-1-phenylbutyl]carbamoyl}-6'-[5-(pyridin-3-yl)-1H-imidazol-2-yl]-[1,1'-biphenyl]-2-carboxylic acid | 1H NMR (500 MHz, METHANOL-d4) δ 8.84 (s, 1H), 8.54 (d, J = 5.2 Hz, 1H), 8.49 (d, J = 1.9 Hz, 1H), 8.47-8.43 (m, J = 3.3 Hz, 1H), 7.94 (dd, J = 3.0, 1.9 Hz, 1H), 7.79-7.73 (m, 2H), 7.70 (dd, J = 7.7, 1.4 Hz, 1H), 7.67 (dd, J = 8.1, 1.2 Hz, 1H), 7.57-7.51 (m, J = 8.0 Hz, 1H), 7.39-7.35 (m, J = 1.4 Hz, 2H), 7.34-7.28 (m, 2H), 7.26-7.21 (m, 2H), 5.09 (dd, J = 8.8, 6.3 Hz, 1H), 1.98-1.88 (m, 1H), 1.87-1.78 (m, 1H), 1.52-1.29 (m, 2H), 0.97 (t, J = 7.4 Hz, 3H) | 0.86 551.3 A | A |
| 102 | 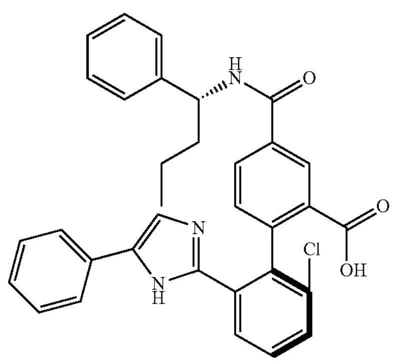 | (S)-2'-chloro-6'-(5-phenyl-1H-imidazol-2-yl)-4-{[(1R)-1-phenylbutyl]carbamoyl}-[1,1'-biphenyl]-2-carboxylic acid | 1H NMR (500 MHz, METHANOL-d4) δ 8.97 (d, J = 8.3 Hz, 1H), 8.43 (d, J = 1.7 Hz, 1H), 8.00 (dd, J = 8.0, 1.9 Hz, 1H), 7.83 (dd, J = 8.0, 1.1 Hz, 1H), 7.76 (dd, J = 7.7, 1.1 Hz, 1H), 7.68-7.62 (m, 2H), 7.57-7.52 (m, 2H), 7.47-7.40 (m, 3H), 7.37 (d, J = 8.0 Hz, 2H), 7.35-7.29 (m, 2H), 7.25-7.20 (m, J = 7.4 Hz, 1H), 5.13-5.04 (m, 1H), 1.96-1.76 (m, 2H), 1.49-1.28 (m, 2H), 0.96 (t, J = 7.3 Hz, 3H) | 0.93 550.2 A | A |
| 103 | 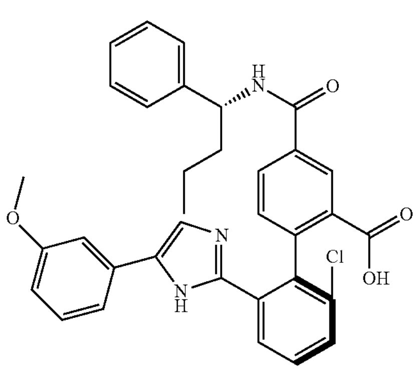 | (S)-2'-chloro-6'-[5-(3-methoxyphenyl)-1H-imidazol-2-yl]-4-{[(1R)-1-phenylbutyl]carbamoyl}-[1,1'-biphenyl]-2-carboxylic acid | 1H NMR (500 MHz, METHANOL-d4) δ 8.99 (d, J = 8.3 Hz, 1H), 8.47 (d, J = 1.9 Hz, 1H), 8.04 (dd, J = 8.0, 1.9 Hz, 1H), 7.85 (dd, J = 8.1, 1.2 Hz, 1H), 7.77 (dd, J = 7.7, 1.1 Hz, 1H), 7.69-7.63 (m, 2H), 7.41-7.29 (m, 6H), 7.26-7.20 (m, J = 1.2, 1.2 Hz, 1H), 7.15-7.08 (m, 2H), 7.02-6.97 (m, 1H), 5.13-5.04 (m, J = 8.8 Hz, 1H), 3.80 (s, 3H), 1.96-1.87 (m, J = 13.2 Hz, 1H), 1.86-1.77 (m, J = 9.4 Hz, 1H), 1.49-1.29 (m, 2H), 0.96 (t, J = 7.4 Hz, 3H) | 0.98 580 A | A |

TABLE 3-continued

| Ex # | Structure | IUPAC Name | NMR | RT (min), [M + H] Method | APJ cAMP Human EC50 (nM) |
|---|---|---|---|---|---|
| 104 | 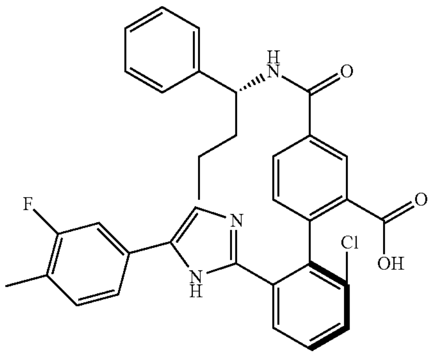 | (S)-2'-chloro-6'-[5-(3-fluoro-4-methylphenyl)-1H-imidazol-2-yl]-4-{[(1R)-1-phenylbutyl]carbamoyl}-[1,1'-biphenyl]-2-carboxylic acid | 1H NMR (500 MHz, METHANOL-d4) δ 8.97 (d, J = 8.0 Hz, 1H), 8.44 (d, J = 1.9 Hz, 1H), 8.01 (dd, J = 7.8, 1.8 Hz, 1H), 7.83 (dd, J = 8.1, 1.2 Hz, 1H), 7.76 (dd, J = 7.7, 1.1 Hz, 1H), 7.67-7.62 (m, 2H), 7.40-7.19 (m, 9H), 5.12-5.05 (m, J = 8.8 Hz, 1H), 2.29 (d, J = 1.4 Hz, 3H), 1.96-1.77 (m, 2H), 1.49-1.29 (m, 2H), 0.96 (t, J = 7.4 Hz, 3H) | 0.98 582.2 A | A |
| 105 | 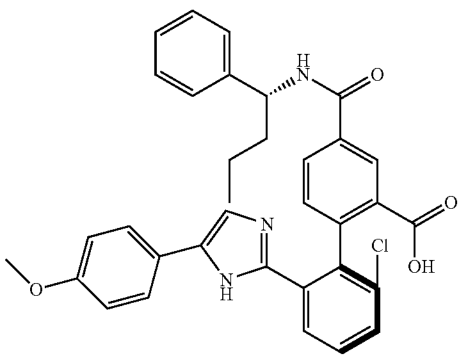 | (S)-2'-chloro-6'-[5-(4-methoxyphenyl)-1H-imidazol-2-yl]-4-{[(1R)-1-phenylbutyl]carbamoyl}-[1,1'-biphenyl]-2-carboxylic acid | 1H NMR (500 MHz, METHANOL-d4) δ 8.99 (d, J = 8.3 Hz, 1H), 8.47 (d, J = 1.9 Hz, 1H), 8.03 (dd, J = 8.0, 1.9 Hz, 1H), 7.84 (dd, J = 8.0, 1.1 Hz, 1H), 7.76 (dd, J = 7.7, 1.1 Hz, 1H), 7.68-7.63 (m, 1H), 7.52 (s, 1H), 7.49-7.45 (m, 2H), 7.40-7.35 (m, 3H), 7.34-7.29 (m, 2H), 7.26-7.20 (m, 1H), 7.04-6.96 (m, 2H), 5.13-5.05 (m, 1H), 3.83 (s, 3H), 1.97-1.76 (m, 2H), 1.49-1.29 (m, 2H), 0.96 (t, J = 7.4 Hz, 3H) | 0.98 580 A | A |
| 106 | 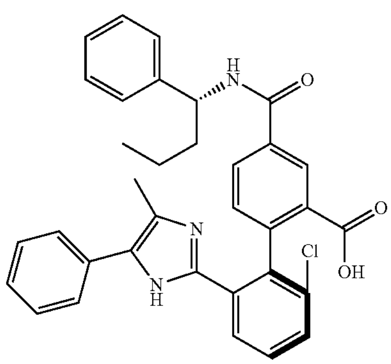 | (S)-2'-chloro-6'-(4-methyl-5-phenyl-1H-imidazol-2-yl)-4-{[(1R)-1-phenylbutyl]carbamoyl}-[1,1'-biphenyl]-2-carboxylic acid | 1H NMR (500 MHz, METHANOL-d4) δ 9.01 (d, J = 8.3 Hz, 1H), 8.46 (d, J = 1.9 Hz, 1H), 8.06 (dd, J = 8.0, 1.9 Hz, 1H), 7.83 (dd, J = 8.1, 1.2 Hz, 1H), 7.74-7.70 (m, 1H), 7.67-7.62 (m, 1H), 7.45-7.36 (m, 6H), 7.30-7.26 (m, 2H), 7.26-7.21 (m, 1H), 5.15-5.07 (m, 1H), 2.30 (s, 3H), 1.99-1.89 (m, 1H), 1.88-1.76 (m, 1H), 1.51-1.30 (m, 2H), 0.97 (t, J = 7.4 Hz, 3H) | 0.83 564.2 A | B |
| 107 | 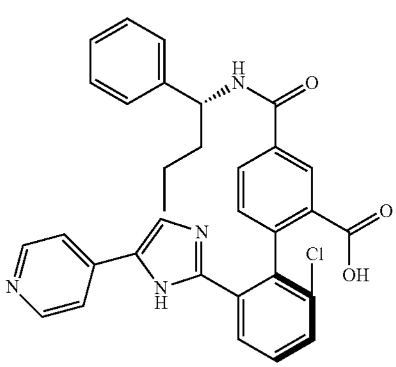 | (S)-2'-chloro-4-{[(1R)-1-phenylbutyl]carbamoyl}-6'-[5-(pyridin-4-yl)-1H-imidazol-2-yl]-[1,1'-biphenyl]-2-carboxylic acid | 1H NMR (500 MHz, METHANOL-d4) δ 8.93 (d, J = 8.3 Hz, 1H), 8.51 (d, J = 1.7 Hz, 1H), 8.43 (d, J = 6.9 Hz, 2H), 8.03 (s, 1H), 7.97 (d, J = 6.9 Hz, 2H), 7.94 (dd, J = 8.0, 1.9 Hz, 1H), 7.70 (dd, J = 7.7, 1.1 Hz, 1H), 7.62 (dd, J = 8.0, 1.1 Hz, 1H), 7.54-7.48 (m, 1H), 7.41-7.36 (m, 2H), 7.32 (t, J = 7.7 Hz, 2H), 7.26-7.20 (m, 2H), 5.14-5.07 (m, 1H), 1.99-1.89 (m, 1H), 1.88-1.79 (m, 1H), 1.53-1.31 (m, 2H), 0.98 (t, J = 7.3 Hz, 3H) | 0.86 551.2 A | B |

TABLE 3-continued

| Ex # | Structure | IUPAC Name | NMR | RT (min), [M + H] Method | APJ cAMP Human EC50 (nM) |
|---|---|---|---|---|---|
| 108 | 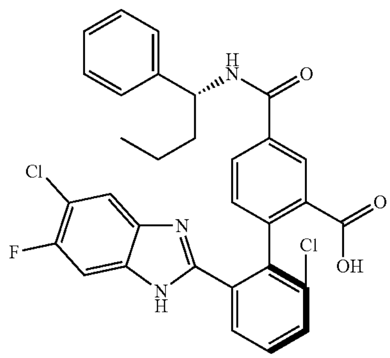 | (S)-2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylic acid | 1H NMR (400 MHz, METHANOL-d4) δ 8.42 (s, 1H), 7.90 (dd, J = 8.0, 1.9 Hz, 1H), 7.79-7.72 (m, J = 4.6, 4.6 Hz, 2H), 7.65-7.55 (m, 2H), 7.43-7.28 (m, 4H), 7.26-7.19 (m, 2H), 5.06 (dd, J = 8.7, 6.5 Hz, 1H), 1.96-1.72 (m, 2H), 1.50-1.24 (m, 2H), 0.96 (t, J = 7.4 Hz, 3H) | 0.98 576.1 A | A |
| 109 | 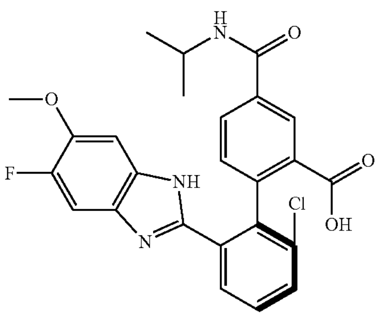 | (S)-2'-chloro-6'-(5-fluoro-6-methoxy-1H-1,3-benzodiazol-2-yl)-4-[(propan-2-yl)carbamoyl]-[1,1'-biphenyl]-2-carboxylic acid | 1H NMR (500 MHz, DMSO-d6) δ 8.40 (d, J = 7.6 Hz, 1H), 8.37 (s, 1H), 7.87 (d, J = 7.9 Hz, 1H), 7.74 (d, J = 7.6 Hz, 1H), 7.63 (d, J = 7.9 Hz, 1H), 7.55-7.50 (m, 1H), 7.23 (d, J = 11.3 Hz, 1H), 7.09-7.03 (m, 2H), 4.14-3.99 (m, 1H), 3.77 (s, 3H), 1.19-1.06 (m, 6H) | 2.27 482.1 B | B |
| 110 | 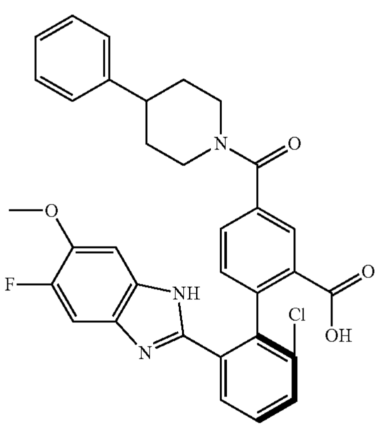 | (S)-2'-chloro-6'-(5-fluoro-6-methoxy-1H-1,3-benzodiazol-2-yl)-4-(4-phenylpiperidine-1-carbonyl)-[1,1'-biphenyl]-2-carboxylic acid | 1H NMR (500 MHz, DMSO-d6) δ 7.98-7.87 (m, 1H), 7.82 (d, J = 7.6 Hz, 1H), 7.71 (d, J = 8.2 Hz, 1H), 7.63-7.56 (m, 1H), 7.50 (s, 1H), 7.35-7.18 (m, 6H), 7.09 (d, J = 7.6 Hz, 1H), 7.05 (d, J = 7.6 Hz, 1H), 4.72-4.58 (m, J = 4.3 Hz, 1H), 3.28-3.09 (m, 2H), 2.97-2.75 (m, 2H), 1.95-1.77 (m, 1H), 1.61 (d, J = 10.1 Hz, 3H) | 1.63 584.2 B | A |
| 111 | 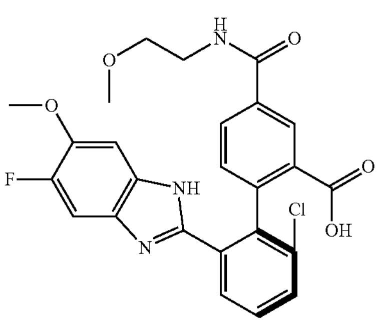 | (S)-2'-chloro-6'-(5-fluoro-6-methoxy-1H-1,3-benzodiazol-2-yl)-4-[(2-methoxyethyl)carbamoyl]-[1,1'-biphenyl]-2-carboxylic acid | 1H NMR (500 MHz, DMSO-d6) δ 8.72 (t, J = 5.2 Hz, 1H), 8.40 (d, J = 1.5 Hz, 1H), 7.90 (dd, J = 7.9, 1.8 Hz, 1H), 7.77 (d, J = 7.6 Hz, 1H), 7.67 (d, J = 7.9 Hz, 1H), 7.58-7.54 (m, 1H), 7.26 (d, J = 5.2 Hz, 1H), 7.12 (d, J = 7.9 Hz, 1H), 7.08 (d, J = 7.6 Hz, 1H), 3.80 (s, 3H), 3.63-3.50 (m, J = 4.6 Hz, 1H), 3.48-3.38 (m, 3H), 3.25 (s, 3H) | 1.13 498.1 B | A |

TABLE 3-continued

| Ex # | Structure | IUPAC Name | NMR | RT (min), [M + H] Method | APJ cAMP Human EC50 (nM) |
|---|---|---|---|---|---|
| 112 | 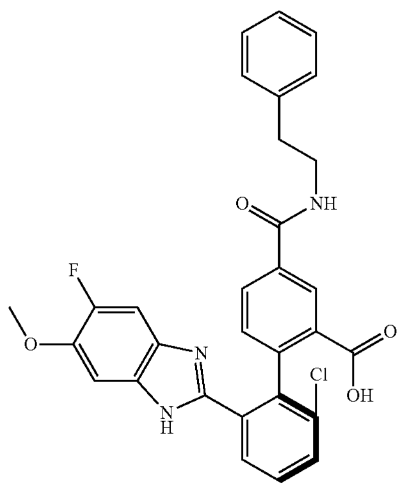 | (S)-2'-chloro-6'-(5-fluoro-6-methoxy-1H-1,3-benzodiazol-2-yl)-4-[(2-phenylethyl)carbamoyl]-[1,1'-biphenyl]-2-carboxylic acid | 1H NMR (500 MHz, DMSO-d6) δ 8.80-8.70 (m, 1H), 8.38 (s, 1H), 7.90-7.85 (m, 1H), 7.77 (d, J = 7.6 Hz, 1H), 7.67 (d, J = 7.9 Hz, 1H), 7.59-7.54 (m, 1H), 7.30-7.26 (m, 2H), 7.25-7.21 (m, 3H), 7.19 (d, J = 7.3 Hz, 1H), 7.12 (d, J = 7.9 Hz, 1H), 7.08 (d, J = 7.9 Hz, 1H), 3.59-3.40 (m, 2H), 2.84 (t, J = 7.5 Hz, 2H) | 1.50 544.1 B | A |
| 113 | 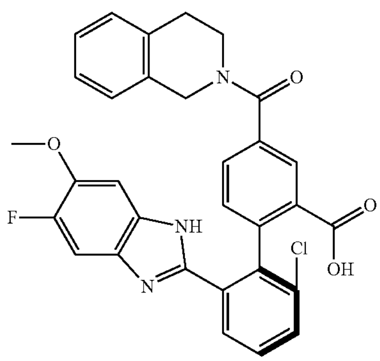 | (S)-2'-chloro-6'-(5-fluoro-6-methoxy-1H-1,3-benzodiazol-2-yl)-4-(1,2,3,4-tetrahydroisoquinoline-2-carbonyl)-[1,1'-biphenyl]-2-carboxylic acid | 1H NMR (500 MHz, DMSO-d6) δ 7.91 (br. s., 1H), 7.79 (d, J = 7.6 Hz, 1H), 7.68 (d, J = 7.9 Hz, 1H), 7.60-7.53 (m, 1H), 7.53-7.44 (m, 1H), 7.24 (br. s., 2H), 7.16 (d, J = 16.2 Hz, 3H), 7.08 (d, J = 7.6 Hz, 2H), 4.87-4.65 (m, 1H), 4.54-4.35 (m, 1H), 3.80 (s, 3H), 3.62-3.42 (m, 2H), 2.93-2.69 (m, J = 4.9 Hz, 2H) | 1.52 556.1 B | A |
| 114 | 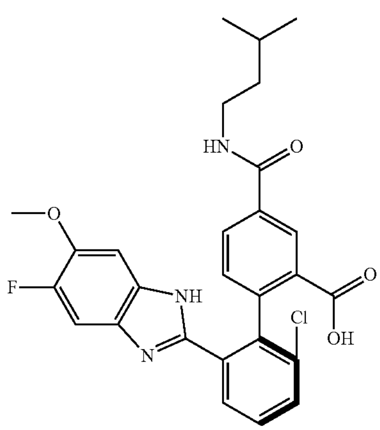 | (S)-2'-chloro-6'-(5-fluoro-6-methoxy-1H-1,3-benzodiazol-2-yl)-4-[(3-methylbutyl)carbamoyl]-[1,1'-biphenyl]-2-carboxylic acid | 1H NMR (500 MHz, DMSO-d6) δ 8.61 (t, J = 5.3 Hz, 1H), 8.38 (s, 1H), 7.88 (dd, J = 8.1, 1.4 Hz, 1H), 7.76 (d, J = 7.6 Hz, 1H), 7.66 (d, J = 7.6 Hz, 1H), 7.58-7.52 (m, 1H), 7.25 (s, 1H), 7.10 (d, J = 7.9 Hz, 1H), 7.07 (d, J = 7.9 Hz, 1H), 3.79 (s, 3H), 3.58-3.41 (m, 1H), 3.27 (q, J = 6.4 Hz, 2H), 1.69-1.52 (m, J = 13.3, 6.5, 6.5 Hz, 1H), 1.41 (q, J = 7.0 Hz, 2H), 0.89 (d, J = 6.4 Hz, 6H) | 1.51 510.2 B | A |

TABLE 3-continued

| Ex # | Structure | IUPAC Name | NMR | RT (min), [M + H] Method | APJ cAMP Human EC50 (nM) |
|---|---|---|---|---|---|
| 115 | 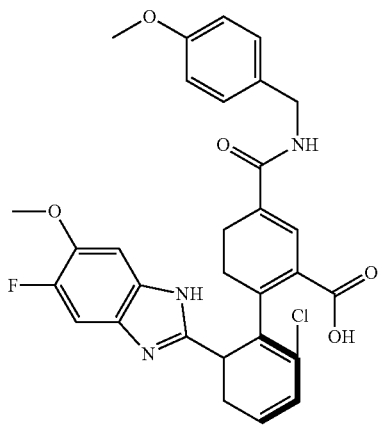 | (S)-2'-chloro-6'-(5-fluoro-6-methoxy-1H-1,3-benzodiazol-2-yl)-4-{[(4-methoxyphenyl)methyl]carbamoyl}-[1,1'-biphenyl]-2-carboxylic acid | 1H NMR (500 MHz, DMSO-d6) δ 9.17 (s, 1H), 8.41 (d, J = 1.2 Hz, 1H), 7.92 (dd, J = 8.1, 1.7 Hz, 1H), 7.75 (d, J = 7.6 Hz, 1H), 7.65 (d, J = 7.6 Hz, 1H), 7.59-7.51 (m, 1H), 7.27-7.20 (m, 4H), 7.15 (s, 1H), 7.11 (d, J = 7.9 Hz, 1H), 7.08-7.03 (m, 1H), 6.87 (d, J = 8.5 Hz, 2H), 4.39 (d, J = 5.8 Hz, 2H), 3.78 (s, 3H), 3.71 (s, 3H) | 1.41 560.1 B | B |
| 116 | 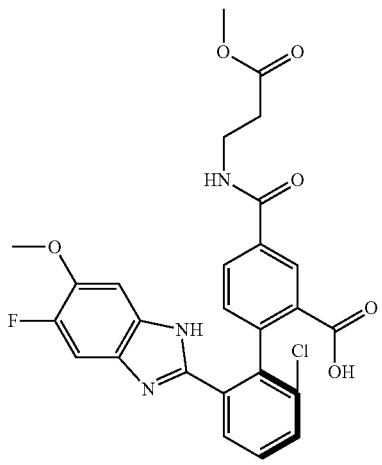 | (S)-2'-chloro-6'-(5-fluoro-6-methoxy-1H-1,3-benzodiazol-2-yl)-4-[(3-methoxy-3-oxopropyl)carbamoyl]-[1,1'-biphenyl]-2-carboxylic acid | 1H NMR (500 MHz, DMSO-d6) δ 8.77-8.72 (m, 1H), 8.38 (d, J = 1.5 Hz, 1H), 7.87 (dd, J = 7.9, 1.5 Hz, 1H), 7.76 (d, J = 7.6 Hz, 1H), 7.66 (d, J = 7.9 Hz, 1H), 7.55 (t, J = 7.9 Hz, 1H), 7.22 (s, 1H), 7.11 (d, J = 8.2 Hz, 1H), 7.06 (d, J = 7.9 Hz, 1H), 3.79 (s, 3H), 3.59 (s, 3H), 3.55-3.43 (m, J = 11.0 Hz, 2H), 2.59 (t, J = 6.9 Hz, 2H) | 1.17 526.1 B | B |
| 117 | 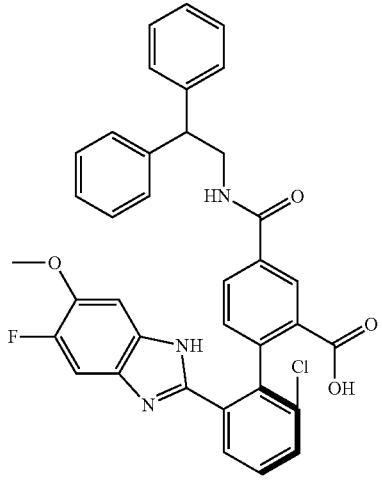 | (S)-2'-chloro-4-[(2,2-diphenylethyl)carbamoyl]-6'-(5-fluoro-6-methoxy-1H-1,3-2-benzodiazol-2-yl)-[1,1'-biphenyl]-2-carboxylic acid | 1H NMR (500 MHz, DMSO-d6) δ 8.72 (t, J = 5.2 Hz, 1H), 8.30 (s, 1H), 7.79-7.74 (m, 2H), 7.64 (d, J = 7.9 Hz, 1H), 7.56 (s, 1H), 7.34-7.26 (m, 9H), 7.22-7.15 (m, 3H), 7.08-7.04 (m, 2H), 4.43 (t, J = 7.9 Hz, 1H), 3.95-3.86 (m, 2H), 3.80 (s, 3H) | 1.76 620.2 B | B |

TABLE 3-continued

| Ex # | Structure | IUPAC Name | NMR | RT (min), [M + H] Method | APJ cAMP Human EC50 (nM) |
|---|---|---|---|---|---|
| 118 | 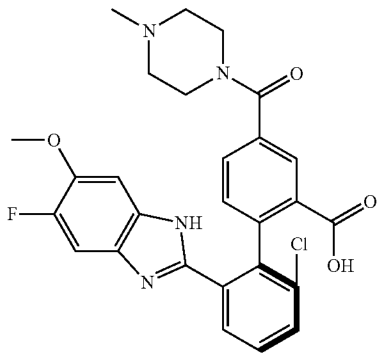 | (S)-2'-chloro-6'-(5-fluoro-6-methoxy-1H-1,3-benzodiazol-2-yl)-4-(4-methylpiperazine-1-carbonyl)-[1,1'-biphenyl]-2-carboxylic acid | 1H NMR (500 MHz, DMSO-d6) δ 7.98 (s, 1H), 7.81 (d, J = 7.6 Hz, 1H), 7.67 (d, J = 7.9 Hz, 1H), 7.59-7.54 (m, 1H), 7.51 (d, J = 7.6 Hz, 1H), 7.19 (d, J = 11.3 Hz, 1H), 7.10 (d, J = 7.9 Hz, 1H), 7.05 (s, 1H), 3.80 (s, 3H), 2.83 (s, 3H), 2.54 (s, 8H) | 0.94 523.2 B | B |
| 119 | 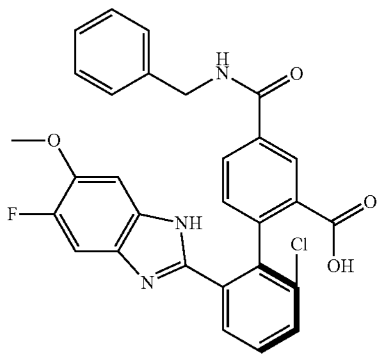 | (S)-4-(benzylcarbamoyl)-2'-chloro-6'-(5-fluoro-6-methoxy-1H-1,3-benzodiazol-2-yl)-[1,1'-biphenyl]-2-carboxylic acid | 1H NMR (500 MHz, DMSO-d6) δ 9.28-9.21 (m, 1H), 8.45 (s, 1H), 7.95 (dd, J = 7.9, 1.2 Hz, 1H), 7.76 (d, J = 7.6 Hz, 1H), 7.65 (d, J = 7.9 Hz, 1H), 7.58-7.52 (m, 1H), 7.32 (d, J = 4.3 Hz, 5H), 7.26-7.19 (m, 3H), 7.12 (d, J = 8.2 Hz, 2H), 7.08-7.01 (m, 2H), 4.47 (d, J = 6.1 Hz, 2H), 3.79 (s, 3H) | 1.43 530.1 B | B |
| 120 | 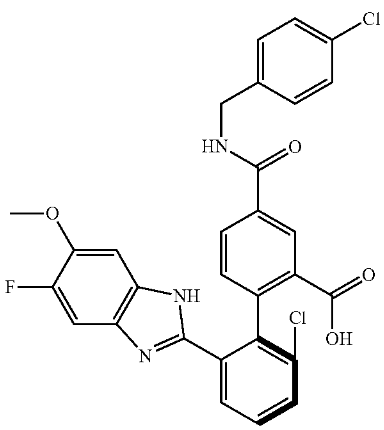 | (S)-2'-chloro-4-{[(4-chlorophenyl)methyl]carbamoyl}-6'-(5-fluoro-6-methoxy-1H-1,3-benzodiazol-2-yl)-[1,1'-biphenyl]-2-carboxylic acid | 1H NMR (500 MHz, DMSO-d6) δ 9.27 (br. s., 1H), 8.42 (s, 1H), 7.93 (d, J = 7.6 Hz, 1H), 7.75 (d, J = 7.6 Hz, 1H), 7.66 (d, J = 7.9 Hz, 1H), 7.55 (t, J = 7.8 Hz, 1H), 7.40-7.30 (m, 4H), 7.23 (d, J = 11.3 Hz, 1H), 7.13 (d, J = 7.6 Hz, 1H), 7.07 (d, J = 7.6 Hz, 1H), 4.44 (d, J = 5.8 Hz, 2H), 3.79 (s, 3H) | 1.59 564.1 B | B |
| 121 | 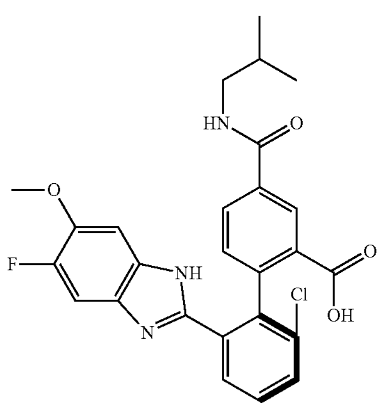 | (S)-2'-chloro-6'-(5-fluoro-6-methoxy-1H-1,3-benzodiazol-2-yl)-4-[(2-methylpropyl)carbamoyl [1,1'-biphenyl]-2-carboxylic acid | 1H NMR (500 MHz, DMSO-d6) δ 8.65 (t, J = 5.5 Hz, 1H), 8.41 (s, 1H), 7.91 (dd, J = 7.9, 1.2 Hz, 1H), 7.78 (d, J = 7.6 Hz, 1H), 7.66 (d, J = 7.9 Hz, 1H), 7.59-7.52 (m, 1H), 7.22 (s, 1H), 7.12-7.09 (m, 1H), 7.06 (d, J = 7.9 Hz, 1H), 3.80 (s, 3H), 3.13-3.04 (m, 2H), 1.85 (dt, J = 13.4, 6.7 Hz, 1H), 0.89 (d, J = 6.7 Hz, 6H) | 1.39 496.1 B | B |

TABLE 3-continued

| Ex # | Structure | IUPAC Name | NMR | RT (min), [M + H] Method | APJ cAMP Human EC50 (nM) |
|---|---|---|---|---|---|
| 122 | 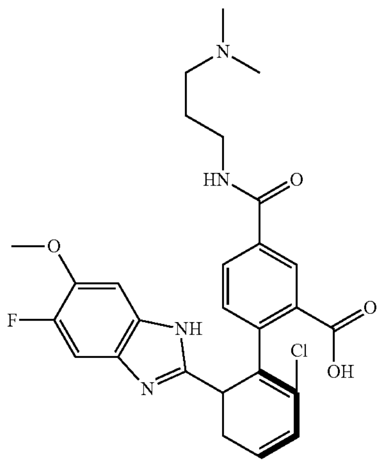 | (S)-2'-chloro-4-{[3-(dimethylamino) propyl] carbamoyl}-6'-(5-fluoro-6-methoxy-1H-1,3-benzodiazol-2-yl)-[1,1'-biphenyl]-2-carboxylic acid | 1H NMR (500 MHz, DMSO-d6) δ 8.80 (t, J = 5.5 Hz, 1H), 8.40 (s, 1H), 7.90 (d, J = 7.9 Hz, 1H), 7.76 (d, J = 7.6 Hz, 1H), 7.66 (d, J = 7.9 Hz, 1H), 7.59-7.53 (m, 1H), 7.23 (d, J = 11.3 Hz, 1H), 7.13 (d, J = 7.9 Hz. 1H), 7.08 (s, 1H), 3.80 (s, 3H), 3.58-3.43 (m, 1H), 3.33 (q, J = 6.4 Hz, 2H), 3.14-3.03 (m, 2H), 2.77 (br. s., 6H), 1.94-1.80 (m, 2H) | 0.95 525.2 B | B |
| 123 | 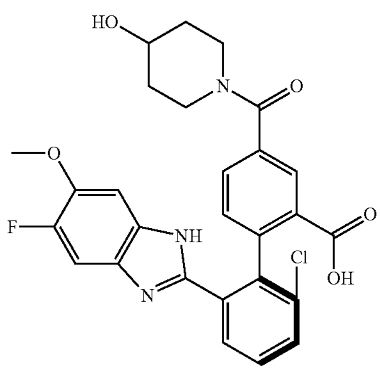 | (S)-2'-chloro-6'-(5-fluoro-6-methoxy-1H-1,3-benzodiazol-2-yl)-4-(4-hydroxypiperidine-1-carbonyl)-[1,1'-biphenyl]-2-carboxylic acid | 1H NMR (500 MHz, DMSO-d6) δ 7.81 (d, J = 1.2 Hz, 1H), 7.77 (d, J = 7.6 Hz, 1H), 7.65 (d, J = 7.9 Hz, 1H), 7.56-7.50 (m, 1H), 7.39 (dd, J = 7.8, 1.4 Hz, 1H), 7.18-7.15 (m, 1H), 7.05-6.99 (m, 1H), 3.70 (dt, J = 7.6, 4.1 Hz, 1H), 3.26-2.98 (m, 4H), 1.84-1.50 (m, 2H), 1.45-1.12 (m, 2H) | 1.01 524.1 B | B |
| 124 | 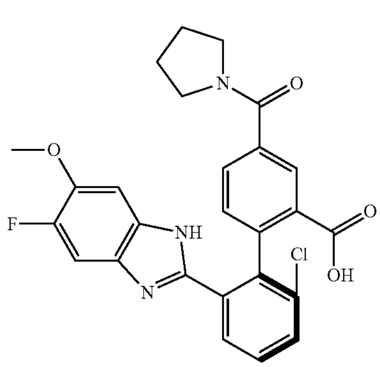 | (S)-2'-chloro-6'-(5-fluoro-6-methoxy-2-yl)-4-(pyrrolidine-1-carbonyl)-[1,1'-biphenyl]-2-carboxylic acid | 1H NMR (500 MHz, DMSO-d6) δ 7.94 (d, J = 0.9 Hz, 1H), 7.75 (d, J = 7.6 Hz, 1H), 7.62 (d, J = 7.9 Hz, 1H), 7.54-7.49 (m, 2H), 7.17 (s, 1H), 7.00 (t, J = 7.6 Hz, 2H), 3.76 (s, 3H), 3.42 (t, J = 6.7 Hz, 4H), 1.87-1.80 (m, 2H), 1.80-1.73 (m, 2H) | 1.22 494.1 B | B |

TABLE 3-continued

| Ex # | Structure | IUPAC Name | NMR | RT (min), [M + H] Method | APJ cAMP Human EC50 (nM) |
|---|---|---|---|---|---|
| 125 | 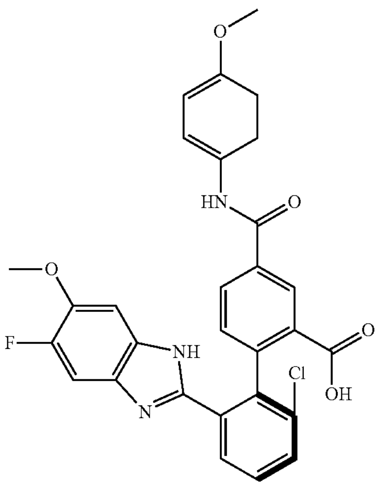 | (S)-2'-chloro-6'-(5-fluoro-6-methoxy-1H-1,3-benzodiazol-2-yl)-4-[(4-methoxyphenyl)carbamoyl]-[1,1'-biphenyl]-2-carboxylic acid | 1H NMR (500 MHz, DMSO-d6) δ 10.30 (s, 1H), 8.47 (s, 1H), 7.99 (d, J = 7.9 Hz, 1H), 7.78 (d, J = 7.6 Hz, 1H), 7.66 (d, J = 8.8 Hz, 3H), 7.59-7.53 (m, 1H), 7.24 (d, J = 11.3 Hz, 1H), 7.14 (d, J = 7.9 Hz, 1H), 7.06 (d, J = 7.9 Hz, 1H), 6.93 (d, J = 8.9 Hz, 2H), 3.80 (s, 3H), 3.74 (s, 3H) | 1.43 546.1 B | B |
| 126 | 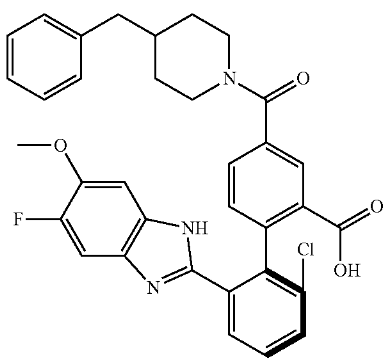 | (S)-4-(4-benzylpiperidine-1-carbonyl)-2'-chloro-6'-(5-fluoro-6-methoxy-1H-1,3-benzodiazol-2-yl)-[1,1'-biphenyl]-2-carboxylic acid | 1H NMR (500 MHz, DMSO-d6) δ 7.83 (s, 1H), 7.80 (d, J = 7.9 Hz, 1H), 7.67 (d, J = 7.9 Hz, 1H), 7.59-7.53 (m, 1H), 7.40 (s, 1H), 7.31-7.26 (m, 2H), 7.21-7.15 (m, 5H), 6.97 (d, J = 7.6 Hz, 1H), 3.71 (s, 2H), 3.08-2.90 (m, 1H), 1.85-1.40 (m, 4H), 1.32-0.82 (m, 4H) | 1.73 598.2 B | C |
| 127 | 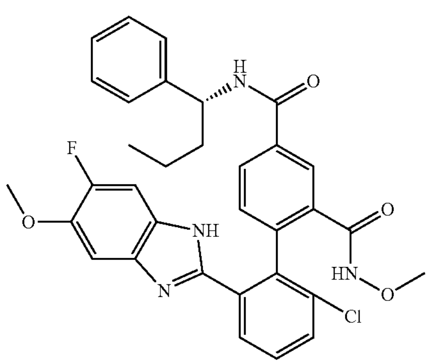 | 2'-chloro-6'-(6-fluoro-5-methoxy-1H-1,3-benzodiazol-2-yl)-N2-methoxy-N4-[(1R)-1-phenylbutyl]-[1,1'-biphenyl]-2,4-dicarboxamide | 1H NMR (500 MHz, METHANOL-d4) δ 8.83 (dd, J = 8.0, 4.1 Hz, 1H), 8.02 (t, J = 1.7 Hz, 1H), 7.90 (ddd, J = 8.0, 3.7, 1.8 Hz, 1H), 7.86 (d, J = 8.0 Hz, 1H), 7.82 (d, J = 7.7 Hz, 1H), 7.73-7.68 (m, 1H), 7.45 (dd, J = 10.2, 4.7 Hz, 1H), 7.38-7.32 (m, 2H), 7.32-7.27 (m, 3H), 7.26-7.19 (m, 2H), 5.11-5.00 (m, 1H), 3.91 (d, J = 4.4 Hz, 3H), 3.70 (s, 3H), 1.93-1.84 (m, 1H), 1.84-1.76 (m, 1H), 1.48-1.38 (m, 1H), 1.38-1.29 (m, 1H), 0.99-0.92 (m, 3H) | 1.18 601.3 A | A |

TABLE 3-continued

| Ex # | Structure | IUPAC Name | NMR | RT (min), [M + H] Method | APJ cAMP Human EC50 (nM) |
|---|---|---|---|---|---|
| 128 | Diastereomer Mixture | (S)-methyl 2'-chloro-6'-(5-hydroxy-1H-1,3-benzodiazol-2-yl)-4-{[(1R)-1-phenylbutyl]carbamoyl}-[1,1'-biphenyl]-2-carboxylate | 1H NMR (500 MHz, METHANOL-d4) δ 8.98 (d, J = 8.3 Hz, 1H), 8.43 (s, 1H), 8.01-7.97 (m, 1H), 7.89 (d, J = 8.0 Hz, 1H), 7.83 (d, J = 7.4 Hz, 1H), 7.73-7.68 (m, 1H), 7.43 (d, J = 9.1 Hz, 1H), 7.38-7.33 (m, 3H), 7.32-7.28 (m, 2H), 7.26-7.20 (m, 1H), 7.02 (dd, J = 8.9, 2.1 Hz, 1H), 6.91 (d, J = 1.7 Hz, 1H), 5.11-5.03 (m, 1H), 3.75 (s, 3H), 1.93-1.86 (m, 1H), 1 84-1.76 (m, 1H), 1.48-1.38 (m, 1H), 1.37-1.29 (m, 1H), 0.96 (t, J = 7.4 Hz, 3H) | 0.82 554.4 A | B |
| 129 | 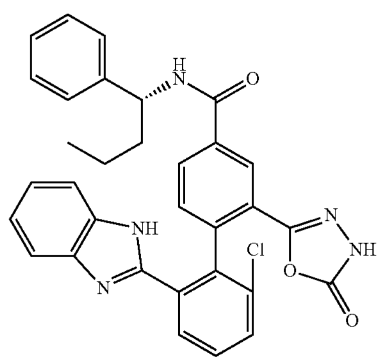 [SMILES: CCC[C@@H](NC(=O)c1ccc(-c2c(Cl)cccc2-c2nc3ccccc3[nH]2)c(-c2n[nH]c(=O)o2)c1)c1ccccc1] | 2'-(1H-1,3-benzodiazol-2-yl)-6'-chloro-2-(5-oxo-4,5-dihydro-1,3,4-oxadiazol-2-yl)-N-[(1R)-1-phenylbutyl]-[1,1'-biphenyl]-4-carboxamide | 1H NMR (500 MHz, METHANOL-d4) δ 8.99 (d, J = 8.3 Hz, 1H), 8.32 (d, J = 8.5 Hz, 1H), 7.95-7.88 (m, 3H), 7.79-7.72 (m, 1H), 7.66-7.59 (m, 2H), 7.52 (dd, J = 6.1, 3.0 Hz, 2H), 7.39 (dd, J = 8.0, 3.6 Hz, 1H), 7.36-7.28 (m, 5H), 7.25-7.20 (m, 1H), 5.13-5.00 (m, 1H), 1.89 (qd, J = 8.8, 4.8 Hz, 1H), 1.84-1.76 (m, 1H), 1.46-1.38 (m, 1H), 1.33 (dd, J = 14.4, 7.8 Hz, 1H), 0.95 (td, J = 7.4, 4.0 Hz, 3H) | 0.89 564.2 A | B |
| 130 | Diastereomer Mixture | 2'-chloro-6'-(6-fluoro-5-methoxy-1H-1,3-benzodiazol-2-yl)-2-(5-oxo-4,5-dihydro-1,3,4-oxadiazol-2-yl)-N-[(1R)-1-phenylbutyl]-[1,1'-biphenyl]-4-carboxamide | 1H NMR (500 MHz, METHANOL-d4) δ 8.98 (d, J = 8.3 Hz, 1H), 8.32 (dd, J = 8.8, 1.7 Hz, 1H), 7.91 (ddd, J = 10.1, 8.0, 1.9 Hz, 1H), 7.85 (dd, J = 8.3, 1.1 Hz, 1H), 7.81 (d, J = 7.7 Hz, 1H), 7.72-7.68 (m, 1H), 7.38-7.29 (m, 6H), 7.26-7.20 (m, 1H), 7.16 (d, J = 7.4 Hz, 1H), 5.10-5.03 (m, 1H), 3.89 (s, 3H), 1.96-1.86 (m, 1H), 1.85-1.77 (m, 1H), 1.49-1.39 (m, 1H), 1.38-1.29 (m, 1H), 0.96 (td, J = 7.4, 3.4 Hz, 3H) | 1.14 612.2 A | A |

TABLE 3-continued

| Ex # | Structure | IUPAC Name | NMR | RT (min), [M + H] Method | APJ cAMP Human EC50 (nM) |
|---|---|---|---|---|---|
| | | Diastereomer Mixture | | | |
| 131 | 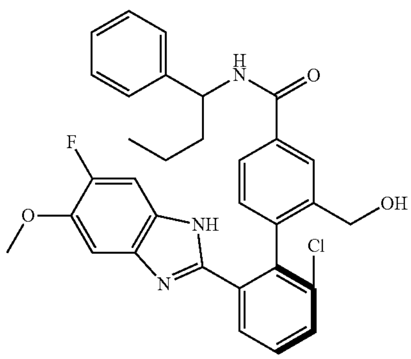 | (S)-2'-chloro-6'-(6-fluoro-5-methoxy-1H-1,3-benzodiazol-2-yl)-2-(hydroxymethyl)-N-(1-phenylbutyl)-[1,1'-biphenyl]-4-carboxamide | 1H NMR (500 MHz, METHANOL-d4) δ 8.79 (d, J = 8.3 Hz, 1H), 7.97 (d, J = 1.9 Hz, 1H), 7.90 (dd, J = 8.3, 1.1 Hz, 1H), 7.84 (dd, J = 7.7, 1.1 Hz, 1H), 7.75-7.71 (m, 1H), 7.68 (dd, J = 7.8, 1.8 Hz, 1H), 7.38 (d, J = 10.2 Hz, 1H), 7.36-7.28 (m, 4H), 7.21 (d, J = 7.4 Hz, 1H), 7.08 (d, J = 7.7 Hz, 1H), 5.08-5.03 (m, 1H), 4.65-4.54 (m, 2H), 1.94-1.86 (m, 1H), 1.83-1.76 (m, 1H), 1.50-1.41 (m, 1H), 1.38-1.30 (m, 1H), 0.96 (t, J = 7.3 Hz, 3H) | 1.18 558.2 A | B |
| 132 | 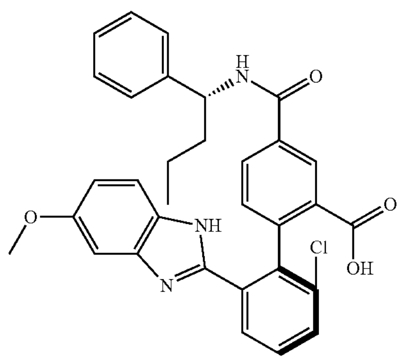 | (S)-2'-chloro-6'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, METHANOL-d4) δ 8.96 (d, J = 8.0 Hz, 1H), 8.47 (d, J = 1.9 Hz, 1H), 7.95 (dd, J = 8.0. 1.9 Hz, 1H), 7.87 (dd, J = 8.3, 1.1 Hz, 1H), 7.82 (dd, J = 7.7, 1.1 Hz, 1H), 7.71-7.67 (m, 1H), 7.53-7.50 (m, 1H), 7.37-7.28 (m, 5H), 7.24-7.20 (m, 1H), 7.14 (dd, J = 9.1, 2.5 Hz, 1H), 7.07 (d, J = 2.2 Hz, 1H), 5.09-5.02 (m, 1H), 3.84 (s, 3H), 1.95-1.86 (m, 1H), 1.80 (ddt, J = 13.4, 9.5, 6.6 Hz, 1H), 1.48-1.38 (m, 1H), 1.37-1.28 (m, 1H), 0.96 (t, J = 7.3 Hz, 3H) | 0.83 554.0 A | A |
| 133 | 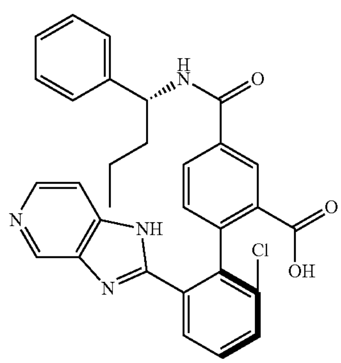 | (S)-2'-chloro-6'-{1H-imidazo[4,5-c]pyridin-2-yl}-4-{[(1R)-1-phenylbutyl]carbamoyl}-[1,1'-biphenyl]-2-carboxylic acid | 1H NMR (500 MHz, METHANOL-d4) δ 9.02 (s, 1H), 8.94 (d, J = 8.3 Hz, 1H), 8.47 (dd, J = 13.8, 1.9 Hz, 1H), 8.42 (d, J = 6.6 Hz, 1H), 7.96 (d, J = 6.6 Hz, 1H), 7.91 (ddd, J = 13.7, 7.9, 2.1 Hz, 1H), 7.87 (dd, J = 7.7, 1.1 Hz, 1H), 7.78-7.73 (m, 1H), 7.62 (t, J = 8.0 Hz, 1H), 7.41-7.36 (m, 2H), 7.35-7.29 (m, 2H), 7.27-7.20 (m, 2H), 5.14-5.04 (m, 1H), 1.97-1.89 (m, 1H), 1.87-1.77 (m, 1H), 1.50-1.41 (m, 1H), 1.41-1.31 (m, 1H), 0.98 (td, J = 7.4, 4.1 Hz, 3H) | 0.77 525.1 A | A |
| 134 | 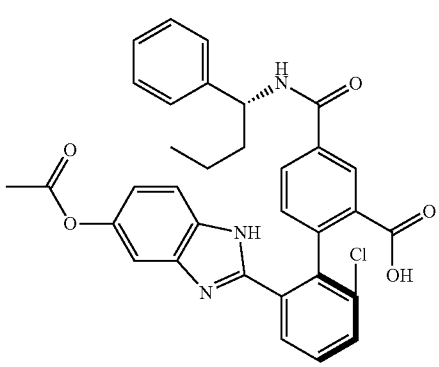 | (S)-2'-[5-(acetyloxy)-1H-1,3-benzodiazol-2-yl]-6'-chloro-4-{[(1R)-1-phenylbutyl]carbamoyl}-[1,1'-biphenyl]-2-carboxylic acid | 1H NMR (500 MHz, METHANOL-d4) δ 8.96 (d, J = 8.0 Hz, 1H), 8.45 (s, 1H), 7.92 (d, J = 7.7 Hz, 1H), 7.87-7.79 (m, 2H), 7.70-7.63 (m, 1H), 7.60 (d, J = 9.1 Hz, 1H), 7.41-7.25 (m, 6H), 7.25-7.17 (m, 2H), 5.12-4.98 (m, 1H), 2.30 (s, 3H), 1.93-1.85 (m, 1H), 1.83-1.74 (m, 1H), 1.49-1.39 (m, 1H), 1.34 (dt, J = 14.4, 7.1 Hz, 2H), 0.96 (t, J = 7.3 Hz, 3H) | 0.90 582.1 A | A |

TABLE 3-continued

| Ex # | Structure | IUPAC Name | NMR | RT (min), [M + H] Method | APJ cAMP Human EC50 (nM) |
|---|---|---|---|---|---|
| 135 | 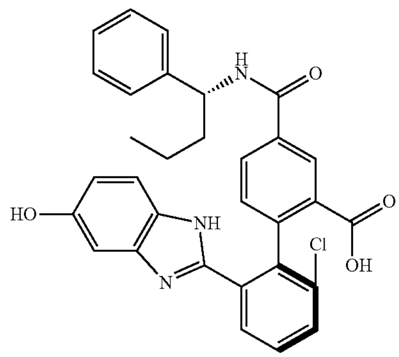 | (S)-2'-chloro-6'-(5-hydroxy-1H-1,3-benzodiazol-2-yl)-4-{[(1R)-1-phenylbutyl]carbamoyl}-[1,1'-biphenyl]-2-carboxylic acid | 1H NMR (400 MHz, METHANOL-d4) δ 8.90 (d, J = 7.9 Hz, 1H), 8.23 (d, J = 1 8 Hz, 1H), 7.79-7.69 (m, 3H), 7.62-7.54 (m, 1H), 7.39-7.27 (m, 5H), 7.25-7.18 (m, 1H), 7.07 (d, J = 7.9 Hz, 1H), 6.86-6.79 (m, 2H), 5.11-5.00 (m, 1H), 1.95-1.72 (m, 2H), 1.49-1.26 (m, 2H), 0.95 (t, J = 7.4 Hz, 3H) | 0.82 540.1 A | B |
| 136 | 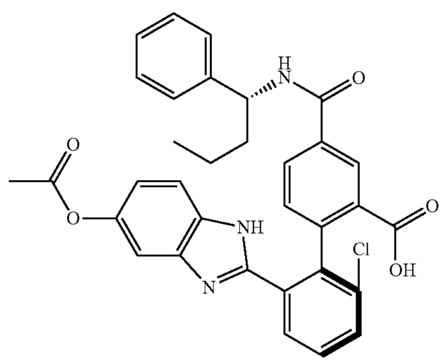 | (S)-2'-[5-(acetyloxy)-1H-1,3-benzodiazol-2-yl]-6'-chloro-4-{[(1R)-1-phenylbutyl]carbamoyl}-[1,1'-biphenyl]-2-carboxylic acid | 1H NMR (500 MHz, METHANOL-d4) δ 8.96 (d, J = 8.3 Hz, 1H), 8.48-8.40 (m, 1H), 7.97-7.91 (m, 1H), 7.83 (t, J = 7.4 Hz, 2H), 7.70-7.63 (m, 1H), 7.59 (d, J = 8.8 Hz, 1H), 7.41-7.27 (m, 6H), 7.25-7.18 (m, 1H), 5.10-5.02 (m, 1H), 1.93-1.74 (m, 2H), 1.47-1.26 (m, 2H), 1.00-0.90 (m, 3H) | 0.91 582.1 A | C |
| 137 | Diastereomer Mixture | 2'-methyl-6'-(1-methyl-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 8.95 (d, J = 8.3 Hz, 1H), 8.23 (br. s., 1H), 8.01-7.90 (m, 2H), 7.74 (d, J = 7.2 Hz, 1H), 7.68-7.56 (m, 4H), 7.48-7.28 (m, 7H), 7.26-7.18 (m, 1H), 3.71 (s, 3H), 2.04 (s, 3H). 1.89-1.77 (m, 1H), 1.73-1.64 (m, 1H), 1.40-1.31 (m, 1H), 1 23 (dq, J = 14.1. 7.2 Hz, 1H), 0.88 (t, J = 7.3 Hz, 3H) | 0.85 517.9 A | B |
| 138 | 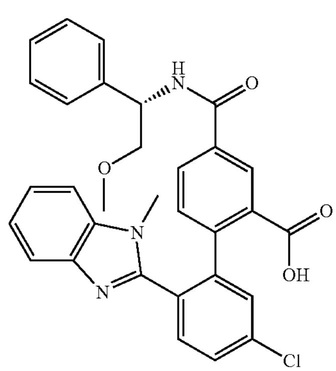 [SMILES: COC[C@@H](NC(=O)c1ccc(-c2cc(Cl)ccc2-c2nc3ccccc3n2C)c(C(=O)O)c1)c1ccccc1] | 5'-chloro-4-{[(1S)-2-methoxy-1-phenylethyl]carbamoyl}-2'-(1-methyl-1H-1,3-benzodiazol-2-yl)-[1,1'-biphenyl]-2-carboxylic acid | 1H NMR (500 MHz, methanol-d4) δ 8.34 (s, 1H), 8.00-7.93 (m, 1H), 7.74-7.69 (m, 2H), 7.67-7.62 (m, 2H), 7.57-7.49 (m, 3H), 7.41-7.36 (m, 2H), 7.34-7.29 (m, 2H), 7.29-7.22 (m, 1H), 5.32 (dd, J = 8.3, 5.0 Hz, 1H), 3.79-3.72 (m, 1H), 3.70 (s, 3H). 3.67-3.63 (m, 1H), 3.38 (s, 3H) | 0.81 540.0 A | C |

TABLE 3-continued

| Ex # | Structure | IUPAC Name | NMR | RT (min), [M + H] Method | APJ cAMP Human EC50 (nM) |
|---|---|---|---|---|---|
| 139 | Diastereomer Mixture | 2'-(1H-1,3-benzodiazol-2-yl)-6'-methyl-4-{[(1R)-1-phenylbutyl]carbamoyl}-[1,1'-biphenyl]-2-carboxylic acid | 1H NMR (500 MHz, DMSO-d6) δ 8.98 (d, J = 8.5 Hz, 1H), 8.30 (d, J = 2.5 Hz, 1H), 7.95 (d, J = 8.0 Hz, 1H), 7.71 (dd, J = 6.9, 1.7 Hz, 1H), 7.60-7.53 (m, 4H), 7.41-7.36 (m, 2H), 7.35-7.29 (m, 4H), 7.25-7.17 (m, 2H), 5.07-4.97 (m, 1H), 1.98 (s, 3H), 1.90-1.81 (m, 1H), 1.76-1.67 (m, 1H), 1.42-1.32 (m, 1H), 1.31-1.21 (m, 1H), 0.92-0.87 (m, 3H) | 0.84 503.9 A | A |
| 140 | Diastereomer Mixture | 2'-(1H-1,3-benzodiazol-2-yl)-6'-fluoro-4-{[(1R)-1-phenylbutyl]carbamoyl}-[1,1'-biphenyl]-2-carboxylic acid | 1H NMR (500 MHz, DMSO-d6) δ 9.02 (d, J = 8.3 Hz, 1H), 8.47 (br. s., 1H), 8.04-7.92 (m, 2H), 7.77 (d, J = 7.7 Hz, 1H), 7.70 (q, J = 7.0 Hz, 1H), 7.55 (br. s., 3H), 7.39 (d, J = 3.9 Hz, 2H), 7.36-7.27 (m, 4H), 7.24 (d, J = 7.7 Hz, 2H), 5.06-4.99 (m, 1H), 1.87 (d, J = 6.3 Hz, 1H), 1.76-1.66 (m, 1H), 1.44-1.22 (m, 2H), 0.90 (d, J = 1.9 Hz, 3H) | 0.87 507.9 A | A |
| 141 | Diastereomer Mixture | (R)-2'-(1H-1,3-benzodiazol-2-yl)-6'-chloro-4-{[(1R)-1-phenylbutyl]carbamoyl}-[1,1'-biphenyl]-2-carboxylic acid | 1H NMR (500 MHz, METHANOL-d4) δ 8.89 (d, J = 8.3 Hz, 1H), 8.29 (d, J = 1.9 Hz, 1H), 7.76 (ddd, J = 12.7, 7.8, 1.5 Hz, 2H), 7.69 (dd, J = 8.3, 1.1 Hz, 1H), 7.59-7.54 (m, 1H), 7.46 (dd, J = 6.1, 3.3 Hz, 2H), 7.38-7.33 (m, 2H), 7.32-7.28 (m, 2H), 7.25-7.19 (m, 3H), 7.11 (d, J = 8.0 Hz, 1H), 5.08-5.01 (m, 1H), 1.93-1.83 (m, 1H), 1.82-1.73 (m, 1H), 1.47-1.38 (m, 1H), 1.37-1.26 (m, 1H), 0.94 (t, J = 7.3 Hz, 3H) | 0.83 524.2 A | B |

TABLE 3-continued

| Ex # | Structure | IUPAC Name | NMR | RT (min), [M + H] Method | APJ cAMP Human EC50 (nM) |
|---|---|---|---|---|---|
| 142 | Diastereomer Mixture | 2'-(5-methoxy-1H-1,3-benzodiazol-2-yl)-6'-methyl-4-{[(1R)-1-phenylbutyl]carbamoyl}-[1,1'-biphenyl]-2-carboxylic acid | 1H NMR (500 MHz,, DMSO-d6) δ 9.01-8.97 (m, 1H), 8.32-8.29 (m, 1H), 7.97 (s, 1H), 7.69 (dd, J = 6.7, 2.1 Hz, 1H), 7.60-7.53 (m, 2H), 7.45 (d, J = 8.8 Hz, 1H), 7.41-7.37 (m, 2H), 7.33 (td, J = 7.6, 1.8 Hz, 2H), 7.26-7.21 (m, 1H), 7.18 (d, J = 7.7 Hz, 1H), 7.01 (d, J = 1.9 Hz, 1H), 6.94 (d, J = 8.5 Hz, 1H), 5.06-4.97 (m, 1H), 1.92-1.82 (m, 1H), 1.76-1.67 (m, 1H), 1.43-1.34 (m, 1H), 1.32-1.23 (m, 1H), 0.90 (td, J = 7.3, 2.2 Hz, 3H) | 0.85 533.9 A | A |
| 143 | Diastereomer Mixture | 2'-fluoro-6'-(5-methoxy-1H-1,3-benzodiazol-2-yl)-4-{[(1R)-1-phenylbutyl]carbamoyl}-[1,1'-biphenyl]-2-carboxylic acid | 1H NMR (500 MHz, DMSO-d6) δ 9.00 (d, J = 8.0 Hz, 1H), 8.43 (br. s., 1H), 7.92 (d, J = 7.4 Hz, 1H), 7.70 (d, J = 7.7 Hz, 1H), 7.60 (d, J = 6.6 Hz, 1H), 7.40 (br. s., 3H), 7.37-7.27 (m, 3H), 7.23 (br. s., 1H), 7.16 (d, J = 8.0 Hz, 1H), 6.89 (br. s., 1H), 6.74 (d, J = 7.2 Hz, 1H), 3.04 (br. s., 1H), 1.87 (br. s., 1H) 1.73 (br. s., 1H), 1.40 (br. s., 1H), 1.35-1.22 (m, 1H), 0.91 (br. s., 3H) | 0.90 537.8 A | A |
| 144 | 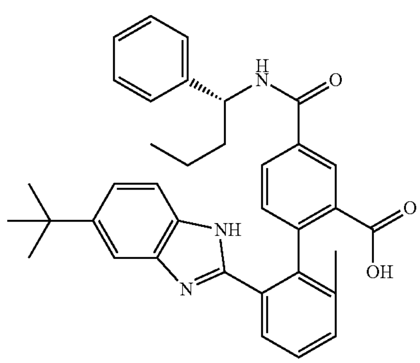 [SMILES: CCC[C@@H](NC(=O)c1ccc(-c2c(F)cccc2-c2nc3cc(C(C)(C)C)ccc3[nH]2)c(C(=O)O)c1)c1ccccc1] | 2'-(5-tert-butyl-1H-1,3-benzodiazol-2-yl)-6'-methyl-4-{[(1R)-1-phenylbutyl]carbamoyl}-[1,1'-biphenyl]-2-carboxylic acid | 1H NMR (500 MHz, DMSO-d6) δ 8.99 (d, J = 8.3 Hz, 1H), 8.37-8.32 (m, 1H), 8.01-7.97 (m, 1H), 7.74-7.69 (m, 1H), 7.65-7.57 (m, 2H), 7.56-7.47 (m, 3H), 7.41-7.36 (m, 2H), 7.32 (t, Hz, 2H), 7.27-7.20 (m, 2H), 5.05-4.97 (m, 1H), 1.92-1.80 (m, 1H), 1.76-1.67 (m, 1H), 1.42-1.34 (m, 1H), 1.32 (s, 9H), 1.29-1.22 (m, 2H), 0.92-0.87 (m, 3H) | 0.94 560.0 A | A |

TABLE 3-continued

| Ex # | Structure | IUPAC Name | NMR | RT (min), [M + H] Method | APJ cAMP Human EC50 (nM) |
|---|---|---|---|---|---|
| 145 | Diastereomer Mixture | 2'-(5-tert-butyl-1H-1,3-benzodiazol-2-yl)-6'-fluoro-4-{[(1R)-1-phenylbutyl]carbamoyl}-[1,1'-biphenyl]-2-carboxylic acid | 1H NMR (500 MHz, DMSO-d6) δ 9.02 (d, J = 8.0 Hz, 1H), 8.49-8.44 (m, 1H), 7.96-7.92 (m, 1H), 7.76-7.64 (m, 2H), 7.58-7.29 (m, 8H), 7.27-7.18 (m, 2H), 5.07-4.96 (m, 1H), 1.94-1.81 (m, 1H), 1.79-1.66 (m, 1H), 1.44-1.35 (m, 1H), 1.31 (br. s., 10H), 0.94-0.86 (m, 3H) | 0.97 563.9 A | A |
| 146 | Diastereomer Mixture | (S)-2'-methyl-4-{[(1R)-1-phenylbutyl]carbamoyl}-6'-[5-(trifluoromethyl)-1H-1,3-benzodiazol-2-yl]-[1,1'-biphenyl]-2-carboxylic acid | 1H NMR (400 MHz, METHANOL-d4) δ 8.88 (d, J = 8.6 Hz, 1H), 8.19-8.04 (m, 1H), 7.79-7.54 (m, 5H), 7.51-7.39 (m, 3H), 7.31 (d, J = 14.7 Hz, 4H), 7.25-7.16 (m, 1H), 7.04-6.96 (m, 1H), 5.03 (m. 1H), 1.93-1.83 (m, 1H), 1.82-1.72 (m, 1H), 1.43 (d, J = 7.5 Hz, 1H), 1.38-1.32 (m, 1H), 0.95 (t, J = 7.4 Hz, 3H) | 0.94 572.2 A | A |
| 147 | 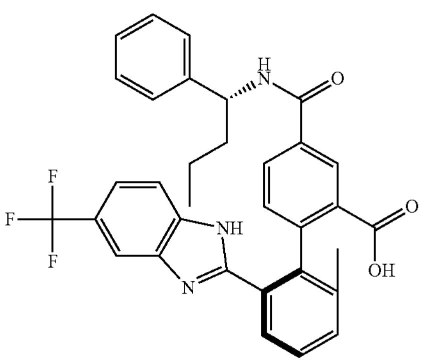 | (R)-2'-methyl-4-{[(1R)-1-phenylbutyl]carbamoyl}-6'-[5-(trifluoromethyl)-1H-1,3-benzodiazol-2-yl]-[1,1'-biphenyl]-2-carboxylic acid | 1H NMR (500 MHz, METHANOL-d4) δ 8.88 (d, J = 8.3 Hz, 1H), 8.25 (s, 1H), 7.84-7.72 (m, 2H), 7.67-7.56 (m, 2H), 7.52-7.44 (m, 3H), 7.38-7.28 (m, 4H), 7.25-7.18 (m, 1H), 7.13 (d, J = 8.0 Hz, 1H), 5.10-5.00 (m, 1H), 1.87 (dd, J = 9.1, 5.0 Hz, 1H), 1.79 (dd, J = 9.4, 6.3 Hz, 1H), 1.46-1.38 (m, 1H), 1.37-1.27 (m, 1H), 0.95 (t, J = 7.4 Hz, 3H) | 0.94 572.2 A | C |
| 148 | 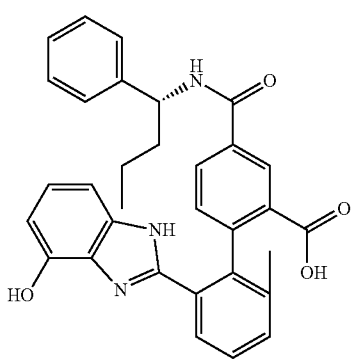 [SMILES: CCC[C@@H](NC(=O)c1ccc(-c2c(C)cccc2-c2nc3c(O)cccc3[nH]2)c(C(=O)O)c1)c1ccccc1] | 2'-(4-hydroxy-1H-1,3-benzodiazol-2-yl)-6'-methyl-4-{[(1R)-1-phenylbutyl]carbamoyl}-[1,1'-biphenyl]-2-carboxylic acid | 1H NMR (500 MHz, DMSO-d6) δ 10.11 (br. s., 1H), 9.02-8.88 (m, 1H), 8.17 (br. s., 1H), 7.97 (br. s., 1H), 7.87 (br. s., 1H), 7.65 (br. s., 1H), 7.53 (br. s., 2H), 7.43-7.29 (m, 4H), 7.23 (br. s., 1H), 7.15-6.98 (m, 3H), 6.92 (br. s., 1H), 6.64 (br. s., 1H), 5.08-4.95 (m, 1H), 1.94 (br. s., 3H), 1.90-1.79 (m, 1H), 1.76-1.66 (m, 1H), 1.46-1.33 (m, 1H), 1.31-1.21 (m, 1H), 0.90 (br. s., 3H) | 0.82 520.0 A | A |

TABLE 3-continued

| Ex # | Structure | IUPAC Name | NMR | RT (min), [M + H] Method | APJ cAMP Human EC50 (nM) |
|---|---|---|---|---|---|
| 149 | Diastereomer Mixture | 2'-{1H-imidazo[4,5-c]pyridin-2-yl}-6'-methyl-4-{[(1R)-1-phenylbutyl]carbamoyl}-[1,1'-biphenyl]-2-carboxylic acid | 1H NMR (500 MHz, DMSO-d6) δ 9.04 (br. s., 1H), 8.98-8.91 (m, 1H), 8.38 (br. s., 2H), 8.03-7.94 (m, 1H), 7.84-7.78 (m, 1H), 7.76-7.70 (m, 1H), 7.54 (br. s., 2H), 7.41 (br. s., 2H), 7.34 (br. s., 2H), 7.24 (br. s., 1H), 7.18 (d, J = 6.6 Hz, 1H), 5.10-4.97 (m, 1H), 1.99 (br. s., 3H), 1.94-1.81 (m, 1H), 1.79-1.66 (m, 1H), 1.46-1.35 (m, 1H), 1.34-1.21 (m, 1H), 0.92 (br. s., 3H) | 0.81 505.0 A | A |
| 150 | Diastereomer Mixture | (S)-2'-(1H-1,3-benzodiazol-2-yl)-6'-chloro-4-{[(1S)-2-methoxy-1-phenylethyl]carbamoyl}-[1,1'-biphenyl]-2-carboxylic acid | 1H NMR (500 MHz, METHANOL-d4) δ 8.37 (d, J = 1.9 Hz, 1H), 7.85 (dd, J = 8.0, 1.9 Hz, 1H), 7.78 (dd, J = 7.7, 1.1 Hz, 1H), 7.73 (dd, J = 8.0, 1.1 Hz, 1H), 7.63-7.57 (m, 1H), 7.53-7.47 (m, 2H), 7.41-7.37 (m, 2H), 7.34 (t, J = 7.6 Hz, 2H), 7.29-7.25 (m, 3H), 7.16 (d, J = 8.0 Hz, 1H), 5.32 (dd, J = 8.5, 5.0 Hz, 1H), 3.77-3.72 (m, 1H), 3.65 (dd, J = 10.2, 5.0 Hz, 1H), 3.39 (s, 3H) | 0.73 526.0 A | A |
| 151 | 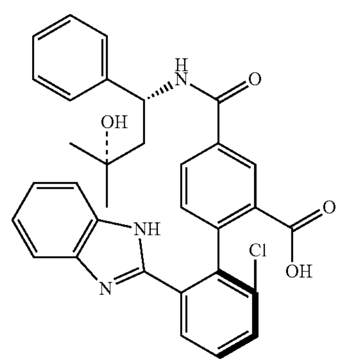 | (S)-2'-(1H-1,3-benzodiazol-2-yl)-6'-chloro-4-{[(1R)-3-hydroxy-3-methyl-1-phenylbutyl]carbamoyl}-[1,1'-biphenyl]-2-carboxylic acid | 1H NMR (500 MHz, METHANOL-d4) δ 9.01 (d, J = 7.2 Hz, 1H), 8.46 (d, J = 1.9 Hz, 1H), 7.94 (dd, J = 7.8. 1.8 Hz, 1H), 7.88 (dd, J = 8.1, 1.2 Hz, 1H), 7.84 (dd, J = 7.8, 1.2 Hz, 1H), 7.73-7.67 (m, 1H), 7.66-7.61 (m, 2H), 7.55-7.50 (m, 2H), 7.38-7.27 (m, 5H), 7.24-7.18 (m, 1H), 5.31-5.24 (m, 1H), 2.13 (dd, J = 14.9, 9.9 Hz, 1H), 1.95-1.88 (m, 1H), 1.25 (s, 3H), 1.24 (s, 3H) | 0.87 554.2 A | A |
| 152 | 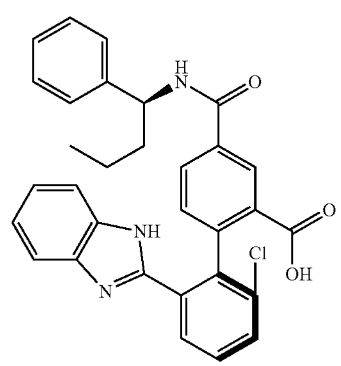 | (S)-2'-(1H-1,3-benzodiazol-2-yl)-6'-chloro-4-{[(1S)-1-phenylbutyl]carbamoyl}-[1,1'-biphenyl]-2-carboxylic acid | 1H NMR (500 MHz, DMSO-d6) δ 9.00 (d, J = 8.4 Hz, 1H), 8.38 (s, 1H), 7.93 (d, J = 8.1 Hz, 1H), 7.80 (d, J = 7.4 Hz, 1H), 7.70 (d, J = 7.7 Hz, 1H), 7.62-7.56 (m, 1H), 7.44-7.36 (m, 4H), 7.32 (t, J = 7.4 Hz, 2H), 7.26-7.20 (m, 1H), 7.13 (t, J = 7.6 Hz, 3H), 5.07-4.96 (m, 1H), 1.96-1.79 (m, 1H), 1.76-1.63 (m, 1H), 1.44-1.31 (m, 1H), 1.29-1.18 (m, 1H), 0.89 (t, J = 7.4 Hz, 3H) | 0.84 524.2 A | B |

TABLE 3-continued

| Ex # | Structure | IUPAC Name | NMR | RT (min), [M + H] Method | APJ cAMP Human EC50 (nM) |
|---|---|---|---|---|---|
| 153 | 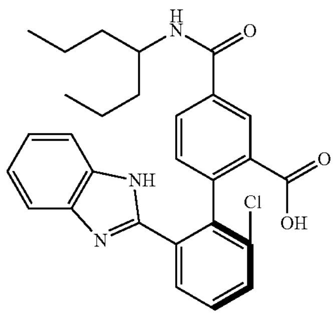 | (S)-2'-(1H-1,3-benzodiazol-2-yl)-6'-chloro-4-[(heptan-4-yl)carbamoyl]-[1,1'-biphenyl]-2-carboxylic acid | 1H NMR (500 MHz, METHANOL-d4) δ 8.34 (d, J = 1.9 Hz, 1H), 8.28 (d, J = 8.8 Hz, 1H), 7.81 (dd, J = 7.8, 1.8 Hz, 1H), 7.79 (dd, J = 7.7, 1.1 Hz, 1H), 7.76-7.73 (m, 1H), 7.64-7.59 (m, 1H), 7.55-7.50 (m, 2H), 7.30 (dd, J = 6.2, 3.2 Hz, 2H), 7.18 (d, J = 8.0 Hz, 1H), 4.15-3.99 (m, 1H), 1.61-1.48 (m, 4H), 1.45-1.31 (m, 4H), 0.94 (td, J = 7.4, 2.6 Hz, 6H) | 0.86 490.2 A | B |
| 154 | 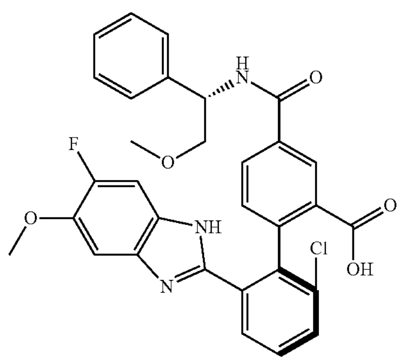 | (S)-2'-chloro-6'-(6-fluoro-5-methoxy-1H-1,3-benzodiazol-2-yl)-4-{[(1S)-2-methoxy-1-phenylethyl]carbamoyl}-[1,1'-biphenyl]-2-carboxylic acid | 1H NMR (500 MHz, DMSO-d6) δ 9.05 (br. s., 1H), 8.43 (br. s., 1H), 8.07-7.53 (m, 4H), 7.41 (d, J = 6.7 Hz, 2H), 7.33 (t, J = 7.3 Hz, 3H), 7.28-7.18 (m, 2H), 5.27 (br. s., 1H), 3.71 (t, J = 9.3 Hz, 1H), 3.55 (br. s., 1H), 3.40 (br. s., 3H) | 1.02 574.2 A | A |
| 155 | 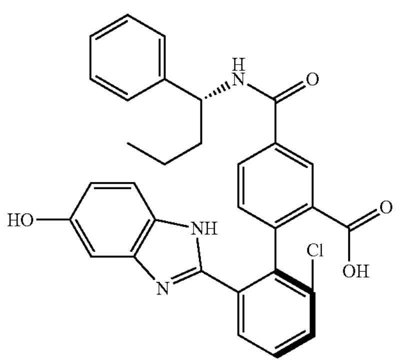 | (S)-2'-chloro-6'-(5-hydroxy-1H-1,3-benzodiazol-2-yl)-4-{[(1R)-1-phenylbutyl]carbamoyl}-[1,1'-biphenyl]-2-carboxylic acid | 1H NMR (400 MHz, METHANOL-d4) δ 8.96 (d, J = 8.6 Hz, 1H), 8.43 (d, J = 1.5 Hz, 2H), 7.91 (dd, J = 7.9, 2.0 Hz, 86H), 7.84 (dd, J = 8.1, 1.3 Hz, 84H), 7.79 (dd, J = 7.8, 1.2 Hz, 82H), 7.70-7.63 (m, 86H), 7.41 (dd, J = 9.0, 0.4 Hz, 88H), 7.37-7.19 (m, 1H), 6.98 (dd, J = 8.9, 2.3 Hz, 1H), 6.90 (d, J = 1.8 Hz, 1H), 5.18-4.99 (m, 1H), 1.97-1.74 (m, 2H), 1.50-1.27 (m, 2H), 0.96 (t, J = 7.4 Hz, 3H) | 0.82 540.1 A | A |
| 156 | 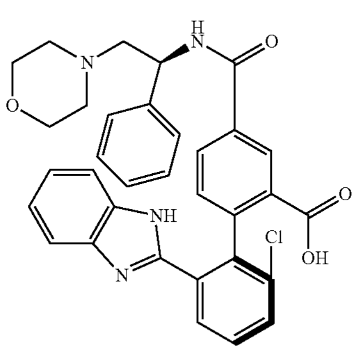 | (S)-2'-(1H-1,3-benzodiazol-2-yl)-6'-chloro-4-{[(1S)-2-(morpholin-4-yl)-1-phenylethyl]carbamoyl}-[1,1'-biphenyl]-2-carboxylic acid | 1H NMR (500 MHz, METHANOL-d4) δ 8.54 (d, J = 1.7 Hz, 1H), 8.06 (dd, J = 8.0, 1.7 Hz, 1H), 7.88 (dd, J = 8.0, 1.1 Hz, 1H), 7.84 (dd, J = 7.8, 1.0 Hz, 1H), 7.72-7.67 (m, 1H), 7.59 (dd, J = 6.1, 3.0 Hz, 2H), 7.52-7.46 (m, 4H), 7.45-7.39 (m, 2H), 7.38-7.34 (m, 2H), 5.79-5.70 (m, 1H), 3.89 (br. s., 4H), 3.79 (dd, J = 13.3, 11.1 Hz, 1H), 3.64-3.57 (m, 1H), 3.45-3.32 (m, 4H) | 0.60 581.2 A | A |

TABLE 3-continued

| Ex # | Structure | IUPAC Name | NMR | RT (min), [M + H] Method | APJ cAMP Human EC50 (nM) |
|---|---|---|---|---|---|
| 157 | 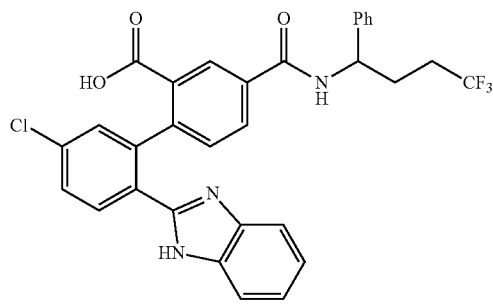 [SMILES: O=C(NC(CCC(F)(F)F)c1ccccc1)c1ccc(-c2cc(Cl)ccc2-c2nc3ccccc3[nH]2)c(C(=O)O)c1] | (S)-2'-(1H-1,3-benzodiazol-2-yl)-6'-chloro-4-{[(1S)-2-ethoxy-1-phenylethyl]carbamoyl}-[1,1'-biphenyl]-2-carboxylic acid | 1H NMR (400 MHz, METHANOL-d4) δ 8.33 (d, J = 1.8 Hz, 1H), 7.80 (dd, J = 7.9, 2.0 Hz, 1H), 7.77 (d, J = 6.4 Hz, 1H), 7.73-7.69 (m, 1H), 7.61-7.56 (m, 1H), 7.48 (dd, J = 6.2, 3.1 Hz, 2H), 7.42-7.38 (m, 2H), 7.37-7.31 (m, 2H), 7.28 (d, J = 7.0 Hz, 1H), 7.25-7.21 (m, 2H), 7.12 (d, J = 7.7 Hz, 1H), 5.34-5.26 (m, 1H), 3.83-3.68 (m, 2H), 3.64-3.50 (m, 2H), 1.18 (t, J = 7.0 Hz, 3H) | 0.77 540.2 A | A |

Example 158. 2'-(1H-Benzo[d]imidazol-2-yl)-5'-chloro-4-((4,4,4-trifluoro-1-phenylbutyl)carbamoyl)-[1,1'-biphenyl]-2-carboxylic acid

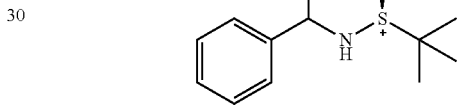

Intermediate 158A. (S,E)-N-Benzylidene-2-methylpropane-2-sulfinamide

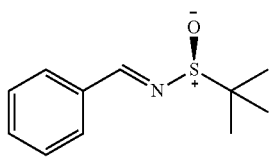

Into the reaction vessel was added benzaldehyde (478 mg, 4.50 mmol), 2-methylpropane-2-sulfinamide (182 mg, 1.5 mmol), DCM (1 mL), MgSO₄ (903 mg, 7.50 mmol), and PPTS (18.85 mg, 0.075 mmol). The reaction was stirred at rt for 24 h, loaded to silica cartridge, and subjected to silica gel chromatography purification to produce 158A (301 mg, 1.438 mmol, 96% yield) as a colorless oil. ¹H NMR (500 MHz, chloroform-d) δ 8.60 (s, 1H), 7.89-7.84 (m, 2H), 7.56-7.44 (m, 3H), 1.27 (s, 9H).

Intermediate 158B. (S)-2-Methyl-N-(4,4,4-trifluoro-1-phenylbutyl)propane-2-sulfinamide Into the reaction vessel was added magnesium (116 mg, 4.78 mmol). The vessel was charged with N₂. THF (2 mL) and 3-bromo-1,1,1-trifluoropropane (1.27 mg, 0.717 mmol) were subsequently added. The reaction was sonicated for 2 min and allowed to stir at rt for 4 h. The resulting pale brown solution was added to a solution of 158A (50 mg, 0.239 mmol) in THF (2 mL), which was pre-cooled to −50° C. This mixture was stirred at −50° C. for 2 h and was allowed to warm to rt over 4 h. After quenching the reaction with sat NH₄Cl (10 mL), the mixture was extracted with EtOAc (15 mL×3). The combined organic phased was dried over Na₂SO₄, concentrated, and subjected to silica gel chromatography purification (0-70% EtOAc/hexanes) to produce 158B (40 mg, 0.130 mmol, 54.5% yield) as 1.6:1 mixture of diastereomers (white solid). LCMS Anal. Calc'd for C₁₄H₂₀F₃NOS 307.12, found [M+H] 308.1; ¹H NMR (500 MHz, chloroform-d) δ 7.44-7.27 (m, 5H), 4.45-4.36 (m, 1H), 3.46-3.34 (m, 1H), 2.17-1.99 (m, 3H), 1.98-1.85 (m, 1H), 1.24 (s, 3.5H), 1.18 (s, 5.5H).

Intermediate 158C. 4,4,4-Trifluoro-1-phenylbutan-1-amine hydrochloride

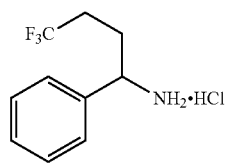

Into the reaction vessel was added MeOH (2 mL) and AcCl (0.028 mL, 0.390 mmol). The mixture was stirred at rt for 15 min and 158B (40 mg, 0.130 mmol) was added. After stirring at rt for 30 min, the reaction mixture was concentrated to produce 158C (30 mg, 0.125 mmol, 96% yield) as a white solid, which was used for next step without further purification. LCMS Anal. Calc'd for $C_{10}H_{12}F_3N$, 203.09, found [M+H]204.1; $^1$H NMR (500 MHz, methanol-$d_4$) δ 7.53-7.33 (m, 5H), 4.16 (dd, J=8.8, 5.5 Hz, 1H), 2.23-1.99 (m, 3H), 1.96-1.82 (m, 1H).

Example 158

Into the reaction vessel was added 2C (15 mg, 0.026 mmol), DCM (1 mL), 158C (10.14 mg, 0.042 mmol), DIEA (0.023 mL, 0.132 mmol), and HATU (14.08 mg, 0.037 mmol). The reaction was stirred at rt for 12 h, concentrated, and dissolved in AcOH (1 mL)/water (0.1 mL). After stirring at 85° C. for 12 h, the reaction was cooled to rt, concentrated, and subjected to preparative HPLC purification to produce 158 (4.9 mg, 6.66 μmol, 25.2%). LCMS Anal. Calc'd for $C_{31}H_{23}C_1F_3N_3O_3$ 577.14, found [M+H]578.1; $^1$H NMR (500 MHz, DMSO-$d_6$) δ 9.10 (d, J=8.3 Hz, 1H), 8.02 (dd, J=8.0, 1.7 Hz, 1H), 7.97 (s, 1H), 7.90 (d, J=8.5 Hz, 1H), 7.70 (dd, J=8.4, 2.1 Hz, 1H), 7.48-7.32 (m, 8H), 7.30-7.26 (m, 1H), 7.19-7.18 (m, 2H), 5.18-5.11 (m, 1H), 2.37 (qd, J=11.2, 5.2 Hz, 1H), 2.30-2.21 (m, 1H), 2.18-2.10 (m, 1H), 2.05-1.95 (m, 1H).

Examples 159-241 may be made by one skilled in the art by appropriate application of the procedures described for Examples 158.

TABLE 4

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 158 | 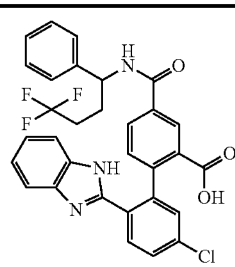 | 2'-(1H-1,3-benzodiazol-2-yl)-5'-chloro-4-[(4,4,4-trifluoro-1-phenylbutyl)carbamoyl]-[1,1'-biphenyl]-2-carboxylic acid | 1.6:1 mixture of diastereomers | $^1$H NMR (500 MHz, DMSO-$d_6$) δ 9.10 (d, J = 8.3 Hz, 1H), 8.02 (dd, J = 8.0, 1.7 Hz, 1H), 7.97 (s, 1H), 7.90 (d, J = 8.5 Hz, 1H), 7.70 (dd, J = 8.4, 2.1 Hz, 1H), 7.48-7.32 (m, 8H), 7.30-7.26 (m, 1H), 7.19-7.18 (m, 2H), 5.18-5.11 (m, 1H), 2.37 (qd, J = 11.2, 5.2 Hz, 1H), 2.30-2.21 (m, 1H), 2.18-2.10 (m, 1H), 2.05-1.95 (m, 1H) | 0.89 578.1 A | B |
| 159 | 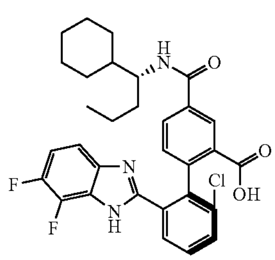 | (S)-2'-chloro-4-{[(1R)-1-cyclohexylbutyl]carbamoyl}-6'-(6,7-difluoro-1H-1,3-benzodiazol-2-yl)-[1,1'-biphenyl]-2-carboxylic acid | 2.19 C Single diastereomer | 1H NMR (500 MHz, METHANOL-d4) δ 8.38 (d, J = 1.9 Hz, 1H), 8.23 (d, J = 9.4 Hz, 1H), 7.86 (dd, J = 8.0, 1.9 Hz, 1H), 7.77-7.70 (m, 2H), 7.60-7.54 (m, J = 8.0 Hz, 1H), 7.24 (d, J = 8.0 Hz, 1H), 7.20-7.08 (m, 2H), 3.95-3.82 (m, 1H), 1.84-1.71 (m, 4H), 1.71-1.54 (m, 2H), 1.54-1.35 (m, 3H), 1.35-1.11 (m, 4H), 1.09-0.98 (m, 2H), 0.92 (t, J = 7.4 Hz, 3H) | 4.13 565.0 C | A |
| 160 | 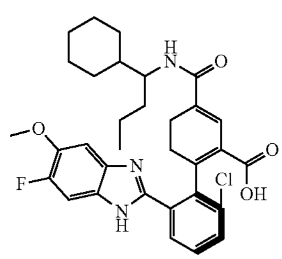 | (S)-2'-chloro-4-{[(1R)-1-cyclohexylbutyl]carbamoyl}-6'-(6-fluoro-5-methoxy-1H-1,3-benzodiazol-2-yl)-[1,1'-biphenyl]-2-carboxylic acid | 2.19 C Single diastereomer | 1H NMR (500 MHz, METHANOL-d4) δ 8.42 (d, J = 1.7 Hz, 1H), 8.31-8.23 (m, 1H), 7.92 (dd, J = 8.0, 1.7 Hz, 1H), 7.82 (dd, J = 18.6, 7.8 Hz, 2H), 7.70-7.62 (m, J = 8.0 Hz, 1H), 7.39 (d, J = 10.2 Hz, 1H), 7.30 (d, J = 8.0 Hz, 1H), 7.24 (d, J = 7.2 Hz, 1H), 3.89 (br. s., 1H), 1.85-1.71 (m, J = 13.2 Hz, 4H), 1.69-1.54 (m, 2H), 1.54-1.36 (m, J = 9.4, 4.7 Hz, 4H), 1.35-1.11 (m, 5H), 1.10-0.99 (m, J = 11.8 Hz, 2H), 0.92 (t, J = 7.3 Hz, 3H) | 1.00 578.2 A | A |
| 161 | 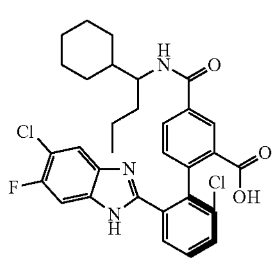 | (S)-2'-chloro-6'-(5-chloro-6-fluoro-1H-1,3-benzodiazol-2-yl)-4-{[(1R)-1-cyclohexylbutyl]carbamoyl}-[1,1'-biphenyl]-2-carboxylic acid | 2.19 C Single diastereomer | 1H NMR (500 MHz, METHANOL-d4) δ 8.40 (d, J = 1.9 Hz, 1H), 7.86 (dd, J = 8.0, 1.9 Hz, 1H), 7.75 (td, J = 7.6, 1.2 Hz, 2H), 7.64-7.57 (m, 2H), 7.39 (d, J = 8.8 Hz, 1H), 7.22 (d, J = 8.0 Hz, 1H), 3.95-3.84 (m, 1H), 1.82-1.70 (m, 4H), 1.70-1.53 (m, 2H), 1.53-1.35 (m, 3H), 1.35-1.12 (m, 4H), 1.10-1.00 (m, 2H), 0.93 (t, J = 7.3 Hz, 3H) | 1.20 582.2 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 162 | 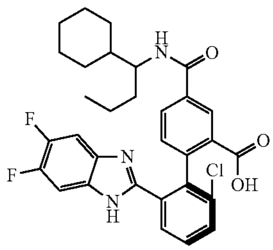 | (S)-2'-chloro-4-{[(1R)-1-cyclohexylbutyl]carbamoyl}-6'-(5,6-difluoro-1H-1,3-benzodiazol-2-yl)-[1,1'-biphenyl]-2-carboxylic acid | 2.19 C Single diastereomer | 1H NMR (500 MHz, METHANOL-d4) δ 8.40 (d, J = 1.7 Hz, 1H), 8.23 (d, J = 9.1 Hz, 1H), 7.86 (dd, J = 8.0, 1.9 Hz, 1H), 7.74 (td, J = 7.8, 1.1 Hz, 2H), 7.62-7.56 (m, 1H), 7.40 (t, J = 8.5 Hz, 2H), 7.21 (d, J = 8.0 Hz, 1H), 3.97-3.82 (m, 1H), 1.83-1.71 (m, J = 12.4 Hz, 4H), 1.70-1.54 (m, 2H), 1.54-1.36 (m, 3H), 1.35-1.13 (m, 4H), 1.10-1.00 (m, 2H), 0.93 (t, J = 7.4 Hz, 3H) | 4.03 556.1 C | A |
| 163 | 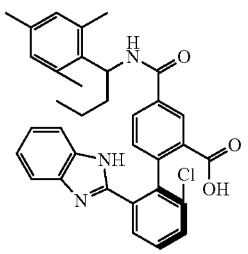 | (S)-2'-(1H-1,3-benzodiazol-2-yl)-6'-chloro-4-{[1-(2,4,6-trimethylphenyl)butyl]carbamoyl}-[1,1'-biphenyl]-2-carboxylic acid | 2.36 C Single Diastereomer | 1H NMR (500 MHz, METHANOL-d4) δ 8.81 (d, J = 6.3 Hz, 1H), 8.42 (d, J = 1.7 Hz, 1H), 7.91 (dd, J = 8.0, 1.9 Hz, 1H), 7.89 (dd, J = 8.1, 1.0 Hz, 1H), 7.85 (dd, J = 7.7, 1.1 Hz, 1H), 7.72-7.67 (m, 1H), 7.61 (dd, J = 6.2, 3.2 Hz, 2H), 7.50 (dd, J = 6.2, 3.2 Hz, 2H), 7.29 (d, J = 8.0 Hz, 1H), 6.75 (s, 2H), 5.38 (dt, J = 9.3, 6.4 Hz, 1H), 2.41 (s, 6H), 2.19 (s, 3H), 2.13-2.02 (m, J = 14.1, 9.5, 9.5, 5.0 Hz, 1H), 1.77-1.65 (m, 1H), 1.56-1.43 (m, J = 5.0 Hz, 1H), 1.37-1.23 (m, 1H), 0.95 (t, J = 7.3 Hz, 3H) | 0.90 566.2 A | A |
| 164 | 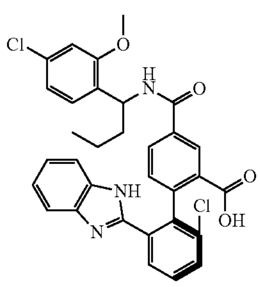 | (S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid | 2.29 C fast eluent from silica gel chromatography purification | 1H NMR (500 MHz, METHANOL-d4) δ 8.81 (d, J = 8.0 Hz, 1H), 8.43 (d, J = 1.9 Hz, 1H), 7.93 (dd, J = 8.0, 1.9 Hz, 1H), 7.86 (dd, J = 8.3, 1.1 Hz, 1H), 7.84 (dd, J = 8.0, 1.1 Hz, 1H), 7.71-7.66 (m, 1H), 7.64-7.60 (m, J = 6.2, 3.2 Hz, 2H), 7.53-7.46 (m, 2H), 7.31 (d, J = 8.0 Hz, 1H), 7.21 (d, J = 8.3 Hz, 1H), 6.98 (d, J = 1.9 Hz, 1H), 6.90 (dd, J = 8.3, 1.9 Hz, 1H), 5.41-5.31 (m, 1H), 3.86 (s, 3H), 1.83-1.71 (m, 2H), 1.48-1.38 (m, J = 1.4 Hz, 1H), 1.38-1.28 (m, 1H), 0.95 (t, J = 7.4 Hz, 3H) | 0.86 588.5 A | A |
| 165 | 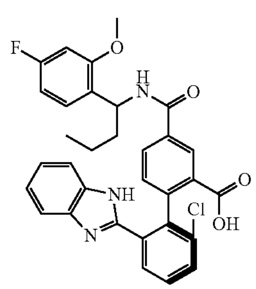 | (S)-2'-(1H-1,3-benzodiazol-2-yl)-6'-chloro-4-{[1-(4-fluoro-2-methoxyphenyl)butyl]carbamoyl}-[1,1'-biphenyl]-2-carboxylic acid | 2.21 C slow eluent from silica gel chromatography purification | 1H NMR (500 MHz, DMSO-d6) δ 8.86 (d, J = 8.2 Hz, 1H), 8.41 (s, 1H), 7.96-7.91 (m, 1H), 7.83 (d, J = 7.6 Hz, 1H), 7.73 (d, J = 7.9 Hz, 1H), 7.65-7.58 (m, 1H), 7.44 (dd, J = 5.8, 3.4 Hz, 2H), 7.34 (t, J = 7.6 Hz, 1H), 7.20-7.15 (m, 3H), 6.86 (dd, J = 11.3, 2.1 Hz, 1H), 6.75-6.67 (m, J = 2.1 Hz, 1H), 5.35 (td, J = 8.8, 5.3 Hz, 1H), 3.83 (s, 3H), 1.72 (dtd, J = 13.7, 9.2, 5.0 Hz, 1H), 1.65-1.54 (m, 1H), 1.45-1.33 (m, 1H), 1.32-1.20 (m, 1H), 0.88 (t, J = 7.3 Hz, 3H) | 1.75 572.2 B | A |
| 166 | 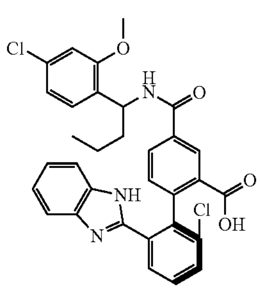 | (S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid | 2.29 C fast eluent from silica gel chromatography purification | 1H NMR (500 MHz, DMSO-d6) δ 8.88 (d, J = 8.5 Hz, 1H), 8.39 (d, J = 1.5 Hz, 1H), 7.92 (dd, J = 7.9, 1.8 Hz, 1H), 7.80 (d, J = 7.6 Hz, 1H), 7.71 (d, J = 7.9 Hz, 1H), 7.63-7.56 (m, 1H), 7.42 (dd, J = 6.0, 3.2 Hz, 2H), 7.32 (d, J = 8.2 Hz, 1H), 7.15 (d, J = 8.5 Hz, 3H), 7.05-7.01 (m, 1H), 6.95 (dd, J = 8.2, 1.8 Hz, 1H), 5.32 (td, J = 8.7, 5.2 Hz, 1H), 3.83 (s, 3H), 1.77-1.65 (m, J = 13.6, 9.1, 4.8, 4.8 Hz, 1H), 1.59 (td, J = 13.9, 6.4 Hz, 1H), 1.44-1.32 (m, 1H), 1.30-1.21 (m, 1H), 0.87 (t, J = 7.5 Hz, 3H) | 1.84 588.2 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 167 | 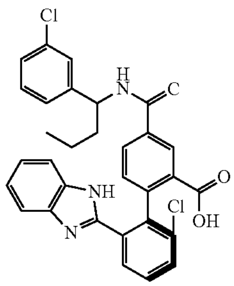 | (S)-2'-(1H-1,3-benzodiazol-2-yl)-6'-chloro-4-{[1-(3-chlorophenyl)butyl]carbamoyl}-[1,1'-biphenyl]-2-carboxylic acid | 2.32 C slow eluent from silica gel chromatography purification | 1H NMR (500 MHz, DMSO-d6) δ 8.95 (d, J = 7.6 Hz, 1H), 8.36 (s, 1H), 7.89 (d, J = 7.6 Hz, 1H), 7.79 (d, J = 7.6 Hz, 1H), 7.68 (d, J = 7.6 Hz, 1H), 7.60-7.52 (m, 1H), 7.44-7.35 (m, 3H), 7.30 (s, 2H), 7.25 (s, 1H), 7.13 (d, J = 5.5 Hz, 3H), 5.01-4.90 (m, J = 7.3 Hz, 1H), 1.87-1.75 (m, J = 8.9 Hz, 1H), 1.66 (dd, J = 12.5, 5.8 Hz, 1H), 1.41-1.28 (m, 1H), 1.28-1.16 (m, 1H), 0.85 (t, J = 6.4 Hz, 3H) | 1.78 558.1 B | A |
| 168 | 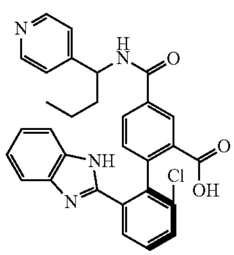 | (S)-2'-(1H-1,3-benzodiazol-2-yl)-6'-chloro-4-{[1-(pyridin-4-yl)butyl]carbamoyl}-[1,1'-biphenyl]-2-carboxylic acid | 1.61 C fast eluent from silica gel chromatography purification | 1H NMR (500 MHz, DMSO-d6) δ 9.17 (d, J = 7.3 Hz, 1H), 8.65 (d, J = 4.3 Hz, 2H), 8.42-8.38 (m, 1H), 7.97-7.92 (m, J = 8.2 Hz, 1H), 7.81 (d, J = 7.6 Hz, 1H), 7.74-7.67 (m, 3H), 7.62-7.57 (m, 1H), 7.43 (dd, J = 5.5, 3.1 Hz, 2H), 7.18-7.14 (m, 3H), 5.12-5.03 (m, 1H), 1.93-1.81 (m, 1H), 1.79-1.68 (m, 1H), 1.48-1.38 (m, 1H), 1.31 (dq, J = 14.2, 7.1 Hz, 1H), 0.90 (t, J = 7.2 Hz, 3H) | 1.08 525.2 B | A |
| 169 | 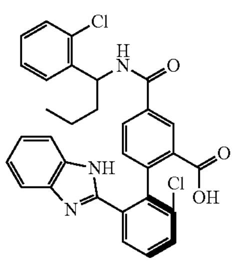 | (S)-2'-(1H-1,3-benzodiazol-2-yl)-6'-chloro-4-{[1-(2-chlorophenyl)butyl]carbamoyl}-[1,1'-biphenyl]-2-carboxylic acid | Chiral SFC separation RT = 8.41 min Chiralpak IC, 4.6 × 250 mm, 5 micron 40% IPA/ 90% CO₂ 2 mL/min, 150 Bar, 40° C. Detector Wavelength: 220 nm | 1H NMR (500 MHz, DMSO-d6) δ 9.08 (d, J = 7.6 Hz, 1H), 8.42 (d, J = 1.5 Hz, 1H), 7.95 (dd, J = 7.9, 1.5 Hz, 1H), 7.83 (d, J = 7.6 Hz, 1H), 7.74 (d, J = 7.9 Hz. 1H), 7.65-7.58 (m, 1H), 7.52 (d, J = 6.7 Hz, 1H), 7.46 (dd, J = 6.0, 3.2 Hz, 2H), 7.40 (d, J = 7.3 Hz, 1H), 7.31 (s, 1H), 7.25 (s, 1H), 7.22-7.18 (m, 2H), 5.45-5.35 (m, 1H), 1.81 (dtd, J = 13.8, 9.3, 4.9 Hz, 1H), 1.71-1.59 (m, J = 13.7, 6.8, 6.8 Hz, 1H), 1.52-1.40 (m, 1H), 1.39-1.26 (m, 1H), 0.91 (t, J = 7.3 Hz, 3H) | 1.79 558.1 B | A |
| 170 | 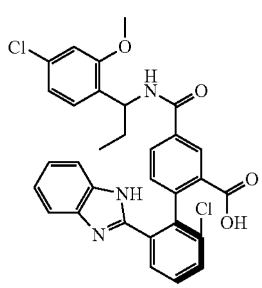 | (S)-2'-(1H-1,3-benzodiazol-2-yl)-6'-chloro-4-{[1-(4-chloro-2-methoxyphenyl)propyl]carbamoyl}-[1,1'-biphenyl]-2-carboxylic acid | 2.24 C slow eluent from silica gel chromatography purification | 1H NMR (500 MHz, METHANOL-d4) δ 8.34 (s, 1H), 7.82 (dd, J = 7.8, 1.5 Hz, 1H), 7.75 (dd, J = 15.0, 7.8 Hz, 2H), 7.63-7.57 (m, J = 8.0 Hz, 1H), 7.54-7.48 (m, J = 3.3 Hz, 2H), 7.30 (dd, J = 6.1, 3.0 Hz, 2H), 7.21 (d, J = 8.0 Hz, 1H), 7.16 (s, 1H), 6.97 (d, J =1.7 Hz, 1H), 6.90 (dd, J = 8.3, 1.9 Hz, 1H), 5.30-5.16 (m, J = 13.8 Hz, 1H), 3.86 (s, 3H), 1.90-1.73 (m, J = 8.8 Hz, 2H), 0.95 (s, 3H) | 1.70 574.1 B | A |

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 171 | 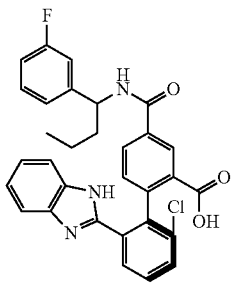 | (S)-2'-(1H-1,3-benzodiazol-2-yl)-6'-chloro-4-{[1-(3-fluorophenyl)butyl]carbamoyl}-[1,1-biphenyl]-2-carboxylic acid | 2.24 C slow eluent from silica gel chromatography purification | 1H NMR (500 MHz, DMSO-d6) δ 8.94 (d, J = 7.9 Hz, 1H), 8.36 (s, 1H), 7.89 (d, J = 7.6 Hz, 1H), 7.79 (d, J = 7.3 Hz, 1H), 7.68 (d, J = 7.6 Hz, 1H), 7.61-7.54 (m, 1H), 7.43-7.37 (m, J = 1.5 Hz, 1H), 7.31 (q, J = 6.7 Hz, 1H), 7.21-7.09 (m, 5H), 7.00 (t, J = 8.4 Hz, 1H), 5.04-4.91 (m, J = 7.3 Hz, 1H), 1.88-1.76 (m, J = 6.1 Hz, 1H), 1.66 (dd, J = 13.0, 6.3 Hz, 1H), 1.41-1.29 (m, J = 6.7 Hz, 1H), 1.28-1.17 (m, 1H), 0.86 (t, J = 6.7 Hz, 3H) | 1.70 542.2 B | A |
| 172 | 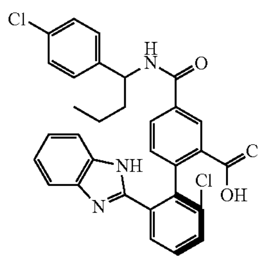 | (S)-2'-(1H-1,3-benzodiazol-2-yl)-6'-chloro-4-{[1-(4-chlorophenyl)butyl]carbamoyl}-[1,1'-biphenyl]-2-carboxylic acid | 1.01 A slow eluent from silica gel chromatography purification | 1H NMR (500 MHz, DMSO-d6) δ 9.00 (d, J = 8.2 Hz, 1H), 8.35 (s, 1H), 7.89 (d, J = 7.3 Hz, 1H), 7.78 (d, J = 7.6 Hz, 1H), 7.70 (d, J = 8.2 Hz, 1H), 7.62-7.55 (m, 1H), 7.42 (dd, J = 6.0, 3.2 Hz, 2H), 7.40-7.33 (m, 4H), 7.19-7.14 (m, 3H), 5.01-4.91 (m, 1H), 1.89-1.77 (m, 1H), 1.72-1.62 (m, 1H), 1.40-1.29 (m, 1H), 1.28-1.18 (m, J = 9.2 Hz, 1H), 0.87 (t, J = 7.3 Hz, 3H) | 1.77 558.1 B | A |
| 173 | 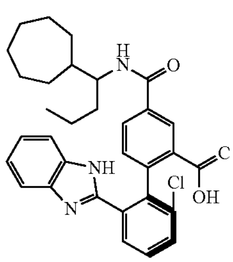 | (S)-2'-(1H-1,3-benzodiazol-2-yl)-6'-chloro-4-[(1-cycloheptylbutyl)carbamoyl]-[1,1'-biphenyl]-2-carboxylic acid | 2.50 C Single Diastereomer | 1H NMR (500 MHz, DMSO-d6) δ 8.33 (s, 1H), 8.18 (d, J = 8.9 Hz, 1H), 7.86 (d, J = 7.9 Hz, 1H), 7.78 (d, J = 7.6 Hz, 1H), 7.69 (d, J = 7.9 Hz, 1H), 7.60-7.53 (m, 1H), 7.40 (d, J = 2.7 Hz, 2H), 7.15-7.10 (m, 3H), 3.89-3.77 (m, 1H), 1.74-1.66 (m, J = 10.7 Hz, 1H), 1.65-1.52 (m, 5H), 1.52-1.35 (m, 7H), 1.35-1.24 (m, 4H), 1.23-1.09 (m, 3H), 0.82 (t, J = 7.0 Hz, 3H) | 1.97 544.2 B | A |
| 174 | 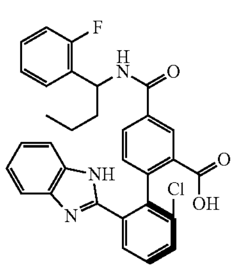 | (S)-2'-(1H-1,3-benzodiazol-2-yl)-6'-chloro-4-{[1-(2-fluorophenyl)butyl]carbamoyl}-[1,1-biphenyl]-2-carboxylic acid | 0.99 A fast eluent from silica gel chromatography purification | 1H NMR (500 MHz, DMSO-d6) δ 9.03 (d, J = 7.9 Hz, 1H), 8.35 (s, 1H), 7.89 (d, J = 7.9 Hz, 1H), 7.76 (d, J = 7.6 Hz, 1H), 7.67 (d, J = 7.9 Hz, 1H), 7.61-7.54 (m, 1H), 7.45 (s, 1H), 7.41-7.35 (m, 2H), 7.30-7.22 (m, 1H), 7.18-7.08 (m, 5H), 5.34-5.21 (m, 1H), 1.90-1.79 (m, 1H), 1.71-1.60 (m, 1H), 1.42-1.32 (m, 1H), 1.30-1.18 (m, J = 14.6, 7.2, 7.2 Hz, 1H), 0.87 (t, J = 7.2 Hz, 3H) | 1.70 542.2 B | A |
| 175 | 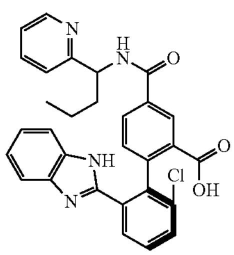 | (S)-2'-(1H-1,3-benzodiazol-2-yl)-6'-chloro-4-{[1-(pyridin-2-yl)butyl]carbamoyl}-[1,1'-biphenyl]-2-carboxylic acid | 1.67 C fast eluent from silica gel chromatography purification | 1H NMR (500 MHz, DMSO-d6) δ 9.11-9.06 (m, J = 7.3 Hz, 1H), 8.56 (d, J = 4.0 Hz, 1H), 8.44-8.38 (m, 1H), 8.01-7.91 (m, 2H), 7.83 (d, J = 7.6 Hz, 1H), 7.78 (d, J = 7.9 Hz, 1H), 7.64 (t, J = 7.8 Hz, 1H), 7.55 (d, J = 7.9 Hz, 1H), 7.50 (dd, J = 5.5, 3.1 Hz, 2H), 7.42 (t, J = 5.8 Hz, 1H), 7.27 (dd, J = 5.6, 2.9 Hz, 2H), 7.24-7.20 (m, 1H), 5.10 (q, J = 7.5 Hz, 1H), 1.93-1.77 (m, 2H), 1.44-1.34 (m, 1H), 1.33-1.22 (m, 1H), 0.88 (t, J = 7.2 Hz, 3H) | 1.09 525.2 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 176 | 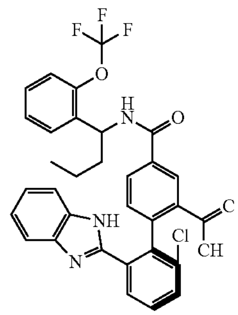 | (S)-2'-(1H-1,3-benzodiazol-2-yl)-6'-chloro-4-({1-[2-(trifluoromethoxy)phenyl]butyl}carbamoyl)-[1,1'-biphenyl]-2-carboxylic acid | 2.24 C fast eluent from silica gel chromatography purification | 1H NMR (500 MHz, DMSO-d6) δ 8.97 (d, J = 7.9 Hz, 1H), 8.36 (d, J = 1.5 Hz, 1H), 7.90 (dd, J = 8.1, 1.7 Hz, 1H), 7.79 (d, J = 7.6 Hz, 1H), 7.68 (d, J = 7.9 Hz, 1H), 7.62-7.54 (m, 2H), 7.39 (dd, J = 5.8, 3.4 Hz, 2H), 7.36-7.31 (m, 2H), 7.30-7.26 (m, 1H), 7.17-7.10 (m, 3H), 5.42-5.31 (m, 1H), 1.91-1.79 (m, 1H), 1.61-1.50 (m, 1H), 1.38 (td, J = 13.2, 7.5 Hz, 1H), 1.26 (td, J = 14.3, 7.3 Hz, 1H), 0.92-0.80 (m, 3H) | 1.88 608.2 B | A |
| 177 | 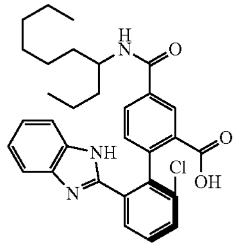 | (S)-2'-(1H-1,3-benzodiazol-2-yl)-6'-chloro-4-[(1-cyclohexylbutyl)carbamoyl]-[1,1'-biphenyl]-2-carboxylic acid | 2.42 C Single diastereomer | 1H NMR (500 MHz, DMSO-d6) δ 8.36 (s, 1H), 8.19 (d, J = 8.9 Hz, 1H), 7.90 (d, J = 7.9 Hz, 1H), 7.82 (d, J = 7.9 Hz, 1H), 7.72 (d, J = 7.9 Hz, 1H), 7.63-7.57 (m, 1H), 7.44 (d, J = 3.7 Hz, 2H), 7.20-7.12 (m, 3H), 3.86-3.75 (m, J = 5.2 Hz, 1H), 1.78-1.64 (m, 4H), 1.59 (d, J = 10.1 Hz, 1H), 1.53-1.36 (m, 3H), 1.36-1.25 (m, 1H), 1.25-1.04 (m, 5H), 1.02-0.90 (m, J = 9.8 Hz, 2H), 0.84 (t, J = 7.0 Hz, 3H) | 1.83 530.2 B | A |
| 178 | 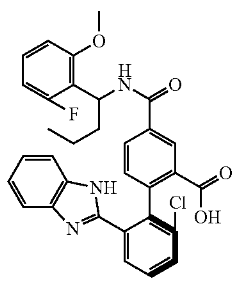 | (S)-2'-(1H-1,3-benzodiazol-2-yl)-6'-chloro-4-{[1-(2-fluoro-6-methoxyphenyl)butyl]carbamoyl}-[1,1'-biphenyl]-2-carboxylic acid | 2.15 C fast eluent from silica gel chromatography purification | 1H NMR (500 MHz, DMSO-d6) δ 8.66 (d, J = 7.6 Hz, 1H), 8.37-8.32 (m, 1H), 7.90 (dd, J = 7.9. 1.8 Hz, 1H), 7.83 (d, J = 7.6 Hz, 1H), 7.73 (d, J = 7.9 Hz, 1H), 7.64-7.56 (m, 1H), 7.45 (dd, J = 5.8, 3.4 Hz, 2H), 7.27-7.12 (m, 4H), 6.84 (d, J = 8.2 Hz, 1H), 6.74 (t, J = 9.2 Hz, 1H), 5.47 (q, J = 7.9 Hz, 1H), 3.88-3.79 (m, 3H), 2.03-1.90 (m, 1H), 1.71 (dt, J = 9.2, 6.7 Hz, 1H), 1.40-1.28 (m, 1H), 1.26-1.14 (m, 1H), 0.87 (t, J = 7.3 Hz, 3H) | 1.75 572.2 B | A |
| 179 | 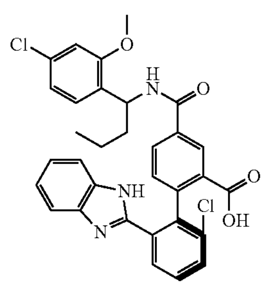 | (S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid | 2.29 C fast eluent from silica gel chromatography purification | 1H NMR (500 MHz, DMSO-d6) δ 8.88 (d, J = 8.2 Hz, 1H), 8.39 (s, 1H), 7.94 (dd, J = 7.9, 1.5 Hz, 1H), 7.82 (d, J = 7.6 Hz, 1H), 7.71 (d, J = 8.2 Hz, 1H), 7.64-7.57 (m, 1H), 7.46-7.39 (m, 2H), 7.35 (d, J = 8.2 Hz, 1H), 7.18-7.12 (m, 3H), 7.04 (d, J = 1.5 Hz, 1H), 6.98 (dd, J = 8.2, 1.5 Hz, 1H), 5.34 (td, J = 8.8, 5.0 Hz, 1H), 3.85 (s, 3H), 1.77-1.66 (m, J = 13.6, 9.1, 4.7, 4.7 Hz, 1H), 1.65-1.55 (m, 1H), 1.44-1.33 (m, 1H), 1.32-1.20 (m, J = 14.8, 7.2, 7.2 Hz, 1H), 0.88 (t, J = 7.3 Hz, 3H) | 1.85 588.2 B | A |
| 180 | 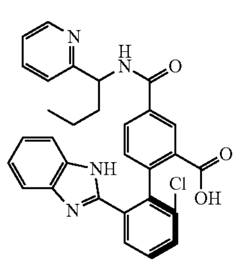 | (S)-2'-(1H-1,3-benzodiazol-2-yl)-6'-chloro-4-{[1-(pyridin-2-yl)butyl]carbamoyl}-[1,1'-biphenyl]-2-carboxylic acid | 1.67 C fast eluent from silica gel chromatography purification | 1H NMR (500 MHz, DMSO-d6) δ 9.12 (d, J = 7.3 Hz, 1H), 8.57 (d, J = 4.3 Hz, 1H), 8.42-8.35 (m, 1H), 8.03-7.92 (m, 2H), 7.81 (dd, J = 15.0, 7.9 Hz, 2H), 7.64 (t, J = 7.9 Hz, 1H), 7.59 (d, J = 7.9 Hz, 1H), 7.52 (dd, J = 5.8, 3.1 Hz, 2H), 7.45 (d, J = 6.4 Hz, 1H), 7.30 (dd, J = 5.8, 3.1 Hz, 2H), 7.23 (d, J = 7.6 Hz, 1H), 5.10 (q, J = 7.6 Hz, 1H), 1.93-1.76 (m, J = 7.6 Hz, 2H), 1.43-1.33 (m, 1H), 1.26 (td, J = 13.8, 7.2 Hz, 1H), 0.87 (t, J = 7.2 Hz, 3H) | 1.06 525.2 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 181 | 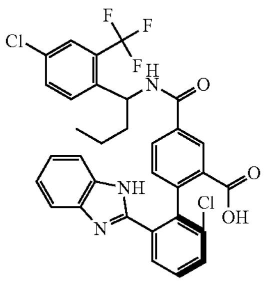 | (S)-2'-(1H-1,3-benzodiazol-2-yl)-6'-chloro-4-({1-[4-chloro-2-(trifluoromethyl)phenyl]butyl}carbamoyl)-[1,1'-biphenyl]-2-carboxylic acid | 1.38 A fast eluent from silica gel chromatography purification | 1H NMR (500 MHz, DMSO-d6) δ 9.10 (d, J = 7.6 Hz, 1H), 8.39 (s, 1H), 7.93 (d, J = 7.6 Hz, 1H), 7.87-7.81 (m, 2H), 7.78 (d, J = 8.5 Hz, 1H), 7.74-7.70 (m, 2H), 7.64-7.55 (m, 1H), 7.42 (d, J = 3.1 Hz, 2H), 7.20-7.13 (m, 3H), 5.43-5.29 (m, 1H), 1.89 (d, J = 10.1 Hz, 1H), 1.63-1.41 (m, 2H), 1.39-1.20 (m, 1H), 0.93-0.82 (m, 3H) | 2.02 626.1 B | A |
| 182 | 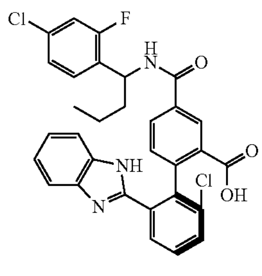 | (S)-2'-(1H-1,3-benzodiazol-2-yl)-6'-chloro-4-{[1-(4-chloro-2-fluorophenyl)butyl]carbamoyl}-[1,1'-biphenyl]-2-carboxylic acid | 1.38 A fast eluent from silica gel chromatography purification | 1H NMR (500 MHz, DMSO-d6) δ 9.06 (d, J = 7.9 Hz, 1H), 8.40 (d, J = 1.5 Hz, 1H), 7.94 (dd, J = 8.1, 1.7 Hz, 1H), 7.83 (d, J = 7.9 Hz, 1H), 7.73 (d, J = 7.9 Hz, 1H), 7.64-7.58 (m, 1H), 7.51 (t, J = 8.2 Hz, 1H), 7.45 (dd, J = 6.0, 3.2 Hz, 2H), 7.38 (dd, J = 10.1, 1.8 Hz, 1H), 7.28 (dd, J = 8.2, 1.8 Hz, 1H), 7.21-7.15 (m, 3H), 5.31-5.20 (m, 1H), 1.93-1.81 (m, 1H), 1.72-1.61 (m, 1H), 1.43-1.33 (m, 1H), 1.32-1.18 (m, 1H), 0.89 (t, J = 7.3 Hz, 3H) | 1.85 576.1 B | A |
| 183 | 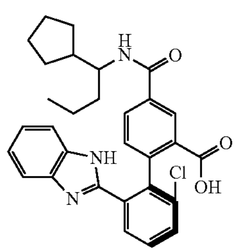 | (S)-2'-(1H-1,3-benzodiazol-2-yl)-6'-chloro-4-[(1-cyclopentylbutyl)carbamoyl]-[1,1'-biphenyl]-2-carboxylic acid | 2.31 Single Diastereomer | 1H NMR (500 MHz, DMSO-d6) δ 8.31 (d, J = 1.5 Hz, 1H), 8.21 (d, J = 9.2 Hz, 1H), 7.66 (d, J = 7.6 Hz, 1H), 7.58-7.50 (m, 1H), 7.40-7.33 (m, 2H), 7.12-7.07 (m, 3H), 3.82 (qd, J = 8.9, 4.3 Hz, 1H), 1.99-1.88 (m, 1H), 1.69-1.61 (m, 1H), 1.60-1.35 (m, 7H), 1.33-1.09 (m, 5H), 0.82 (t, J = 7.3 Hz, 3H) | 1.76 516.2 B | A |
| 184 | 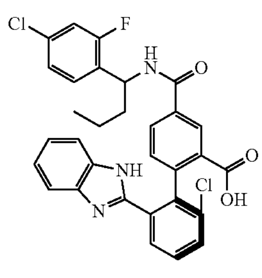 | (S)-2'-(1H-1,3-benzodiazol-2-yl)-6'-chloro-4-{[1-(4-chloro-2-fluorophenyl)butyl]carbamoyl}-[1,1'-biphenyl]-2-carboxylic acid | 1.38 A fast eluent from silica gel chromatography purification | 1H NMR (500 MHz, DMSO-d6) δ 9.06 (d, J = 7.6 Hz, 1H), 8.40 (dd, J = 6.9, 1.7 Hz, 1H), 7.93 (td, J = 7.2, 1.8 Hz, 1H), 7.83 (d, J = 7.9 Hz, 1H), 7.73 (d, J = 7.9 Hz, 1H), 7.65-7.58 (m, 1H), 7.54-7.48 (m, 1H), 7.44 (d, J = 5.8, 3.4 Hz, 2H), 7.37 (d, J = 10.4 Hz, 1H), 7.31-7.25 (m, 1H), 7.18 (d, J = 7.9 Hz, 3H), 5.31-5.19 (m, 1H), 1.92-1.80 (m, 1H), 1.71-1.60 (m, 1H), 1.43-1.33 (m, 1H), 1.32-1.21 (m, 1H), 0.89 (td, J = 7.3, 3.4 Hz, 3H) | 1.85 576.1 B | A |
| 185 | 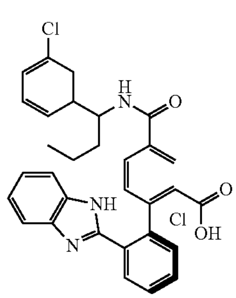 | (S)-2'-(1H-1,3-benzodiazol-2-yl)-6'-chloro-4-{[1-(3-chlorophenyl)butyl]carbamoyl}-[1,1'-biphenyl]-2-carboxylic acid | 2.32 C slow eluent from silica gel chromatography purification | 1H NMR (500 MHz, DMSO-d6) δ 8.95 (d, J = 7.9 Hz, 1H), 8.36 (s, 1H), 7.89 (d, J = 7.9 Hz, 1H), 7.78 (d, J = 7.6 Hz, 1H), 7.67 (d, J = 7.9 Hz, 1H), 7.58-7.53 (m, 2H), 7.42 (s, 1H), 7.40-7.35 (m, 2H), 7.31 (s, 2H), 7.28-7.22 (m, 1H), 7.14-7.07 (m, 3H), 5.01-4.91 (m, J = 7.3 Hz, 1H), 1.88-1.76 (m, J = 6.4 Hz, 1H), 1.72-1.59 (m, J = 6.7 Hz, 1H), 1.38-1.27 (m, J = 6.4 Hz, 1H), 1.22 (dd, J = 13.6, 6.9 Hz, 1H), 0.85 (t, J = 6.7 Hz, 3H) | 1.81 558.1 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 186 | 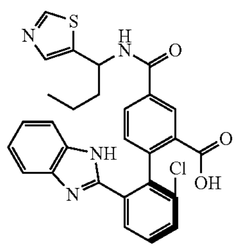 | (S)-2'-(1H-1,3-benzodiazol-2-yl)-6'-chloro-4-{[1-(1,3-thiazol-5-yl)butyl]carbamoyl}-[1,1'-biphenyl]-2-carboxylic acid | 1.62 C fast eluent from silica gel chromatography purification | 1H NMR (500 MHz, DMSO-d6) δ 9.12 (d, J = 8.2 Hz, 1H), 8.94 (s, 1H), 8.37 (s, 1H), 7.90 (dd, J = 7.8, 1.1 Hz, 1H), 7.80 (t, J = 3.2 Hz, 2H), 7.70 (d, J = 7.9 Hz, 1H), 7.60 (d, J = 7.9 Hz, 1H), 7.41 (dd, J = 5.8, 3.1 Hz, 2H), 7.16 (br. s., 1H), 5.42-5.30 (m, 1H), 2.03-1.92 (m, 1H), 1.92-1.82 (m, J = 8.5 Hz, 1H), 1.46-1.25 (m, 2H), 0.90 (t, J = 7.2 Hz, 3H) | 1.28 531.1 B | A |
| 187 | 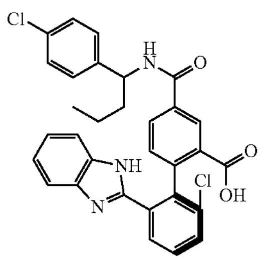 | (S)-2'-(1H-1,3-benzodiazol-2-yl)-6'-chloro-4-{[1-(4-chlorophenyl)butyl]carbamoyl}-[1,1'-biphenyl]-2-carboxylic acid | 1.01 A slow eluent from silica gel chromatography purification | 1H NMR (500 MHz, DMSO-d6) δ 9.00 (d, J = 8.2 Hz, 1H), 8.36 (s, 1H), 7.95-7.89 (m, 1H), 7.80 (d, J = 7.6 Hz, 1H), 7.73 (d, J = 7.9 Hz, 1H), 7.63-7.57 (m, 1H), 7.45 (dd, J = 6.0, 3.2 Hz, 2H), 7.41-7.31 (m, 4H), 7.22-7.15 (m, 3H), 5.02-4.93 (m, 1H), 1.90-1.75 (m, 1H), 1.73-1.61 (m, 1H), 1.39-1.29 (m, 1H), 1.28-1.17 (m, 1H), 0.87 (t, J = 7.3 Hz, 3H) | 1.77 558.1 B | A |
| 188 | 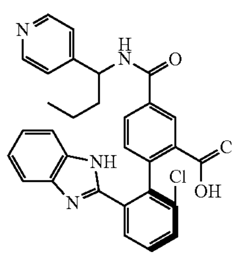 | (S)-2'-(1H-1,3-benzodiazol-2-yl)-6'-chloro-4-{[1-(pyridin-4-yl)butyl]carbamoyl}-[1,1'-biphenyl]-2-carboxylic acid | 1.61 C fast eluent from silica gel chromatography purification | 1H NMR (500 MHz, DMSO-d6) δ 9.23 (d, J = 7.3 Hz, 1H), 8.66 (br. s., 2H), 8.38-8.31 (m, 1H), 7.97-7.89 (m, J = 8.5 Hz, 1H), 7.81-7.76 (m, 3H), 7.74 (d, J = 8.2 Hz, 1H), 7.64-7.57 (m, 1H), 7.49-7.42 (m, 2H), 7.24-7.17 (m, 3H), 5.12-5.02 (m, 1H), 1.90-1.80 (m, 1H), 1.78-1.68 (m, 1H), 1.45-1.35 (m, J = 7.9 Hz, 1H), 1.34-1.23 (m, 1H), 0.87 (t, J = 7.2 Hz, 3H) | 1.09 525.2 B | A |
| 189 | 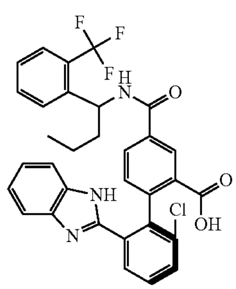 | (S)-2'-(1H-1,3-benzodiazol-2-yl)-6'-chloro-4-({1-[2-(trifluoromethyl)phenyl]butyl}carbamoyl)-[1,1'-biphenyl]-2-carboxylic acid | 2.16 C fast eluent from silica gel chromatography purification | 1H NMR (500 MHz, DMSO-d6) δ 9.06 (d, J = 7.6 Hz, 1H), 8.33 (s, 1H), 7.89 (d, J = 7.9 Hz, 1H), 7.77 (dd, J = 13.4, 7.6 Hz, 2H), 7.70-7.62 (m, 3H), 7.60-7.55 (m, 1H), 7.43 (t, J = 7.6 Hz, 1H), 7.39 (dd, J = 5.8, 3.4 Hz, 2H), 7.17-7.08 (m, 3H), 5.44-5.31 (m, J = 7.0, 7.0 Hz, 1H), 1.92-1.80 (m, 1H), 1.59-1.50 (m, 1H), 1.49-1.39 (m, 1H), 1.35-1.23 (m, 1H), 0.86 (t, J = 7.3 Hz, 3H) | 1.86 592.2 B | B |
| 190 | 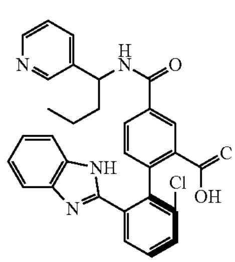 | (S)-2'-(1H-1,3-benzodiazol-2-yl)-6'-chloro-4-{[1-(pyridin-3-yl)butyl]carbamoyl}-[1,1'-biphenyl]-2-carboxylic acid | 1.60 C fast eluent from silica gel chromatography purification | 1H NMR (500 MHz, DMSO-d6) δ 9.08 (d, J = 7.9 Hz, 1H), 8.66 (br. s., 1H), 8.50 (d, J = 4.3 Hz, 1H), 8.37 (s, 1H), 7.94 (dd, J = 19.2, 7.9 Hz, 2H), 7.80 (d, J = 7.6 Hz, 1H), 7.70 (d, J = 7.9 Hz, 1H), 7.63-7.56 (m, 1H), 7.50 (dd, J = 7.6, 5.2 Hz, 1H), 7.41 (dd, J = 6.0, 3.2 Hz, 2H), 7.18-7.10 (m, 3H), 5.12-5.00 (m, 1H), 1.96-1.84 (m, 1H), 1.80-1.67 (m, 1H), 1.44-1.32 (m, 1H), 1.31-1.19 (m, 1H), 0.89 (t, J = 7.3 Hz, 3H) | 1.07 525.4 B | B |

TABLE 4-continued

| Ex # | IUPAC Name | Chiral amine Intermediate RT (min) Method | NMR | RT (min), [M + H] Method | APJ cAMP Human EC50 (nM) |
|---|---|---|---|---|---|
| 191 | (S)-2'-(1H-1,3-benzodiazol-2-yl)-6'-chloro-4-({1-[2-(trifluoromethoxy)phenyl]butyl}carbamoyl)-[1,1-biphenyl]-2-carboxylic acid | 2.24 C fast eluent from silica gel chromatography purification | 1H NMR (500 MHz, DMSO-d6) δ 9.01 (d, J = 8.2 Hz, 1H), 8.41 (d, J = 1.5 Hz, 1H), 7.94 (dd, J = 7.9, 1.5 Hz, 1H), 7.83 (d, J = 7.6 Hz, 1H), 7.73 (d, J = 7.9 Hz, 1H), 7.65-7.58 (m, 2H), 7.44 (dd, J = 5.8, 3.1 Hz, 2H), 7.39-7.35 (m, 2H), 7.34-7.30 (m, 1H), 7.20-7.15 (m, 3H), 5.45-5.34 (m, 1H), 1.95-1.82 (m, 1H), 1.64-1.54 (m, 1H), 1.49-1.37 (m, 1H), 1.31 (td, J = 14.4, 7.5 Hz, 1H), 0.91 (t, J = 7.3 Hz, 3H) | 1.88 608.2 B | B |
| 192 | (S)-2'-(1H-1,3-benzodiazol-2-yl)-6'-chloro-4-{[1-(pyridin-4-yl)butyl]carbamoyl}-[1,1'-biphenyl]-2-carboxylic acid | 1.61 C fast eluent from silica gel chromatography purification | 1H NMR (500 MHz, DMSO-d6) δ 9.22 (d, J = 7.3 Hz, 1H), 8.63 (d, J = 1.5 Hz, 2H), 8.38-8.32 (m, 1H), 7.96-7.88 (m, J = 7.9 Hz, 1H), 7.81-7.70 (m, 4H), 7.64-7.56 (m, 1H), 7.44 (dd, J = 5.3, 2.9 Hz, 2H), 7.19 (d, J = 5.2 Hz, 3H), 5.11-4.99 (m, J = 6.1 Hz, 1H), 1.90-1.79 (m, 1H), 1.78-1.66 (m, 1H), 1.46-1.34 (m, 1H), 1.34-1.23 (m, 1H), 0.88 (t, J = 7.0 Hz, 3H) | 1.08 525.2 B | B |
| 193 | (S)-2'-(1H-1,3-benzodiazol-2-yl)-6'-chloro-4-{[1-(pyridin-3-yl)butyl]carbamoyl}-[1,1'-biphenyl]-2-carboxylic acid | 1.60 C fast eluent from silica gel chromatography purification | 1H NMR (500 MHz, DMSO-d6) δ 9.13 (d, J = 7.6 Hz, 1H), 8.70 (br. s. 1H), 8.56 (d, J = 3.4 Hz, 1H), 8.35 (s, 1H), 8.11 (d, J = 7.6 Hz, 1H), 7.92 (d, J = 8.2 Hz, 1H), 7.80 (d, J = 7.9 Hz, 1H), 7.73 (d, J = 8.2 Hz, 1H), 7.66-7.57 (m, 2H), 7.45 (dd, J = 6.0, 3.2 Hz, 2H), 7.23-7.17 (m, 3H), 5.13-5.02 (m, J = 6.7 Hz, 1H), 1.95-1.85 (m, J = 6.1 Hz, 1H), 1.81-1.69 (m, 1H), 1.42-1.32 (m, 1H), 1.31-1.19 (m, 1H), 0.88 (t, J = 7.2 Hz, 3H) | 1.04 525.2 B | B |
| 194 | (S)-2'-(1H-1,3-benzodiazol-2-yl)-6'-chloro-4-{[1-(1,3-thiazol-5-yl)butyl]carbamoyl}-[1,1'-biphenyl]-2-carboxylic acid | 1.62 C fast eluent from silica gel chromatography purification | 1H NMR (500 MHz, DMSO-d6) δ 9.13 (d, J = 8.2 Hz, 1H), 8.94 (s, 1H), 8.36 (s, 1H), 7.90 (d, J = 8.2 Hz, 1H), 7.80 (d, J = 3.4 Hz, 2H), 7.72 (d, J = 7.9 Hz, 1H), 7.63-7.55 (m, 1H), 7.43 (dd, J = 6.0, 3.2 Hz, 2H), 7.17 (dd, J = 8.5, 3.4 Hz, 3H), 5.43-5.28 (m, J = 6.4 Hz, 1H), 2.02-1.92 (m, 1H), 1.91-1.81 (m, 1H), 1.43-1.24 (m, 2H), 0.89 (t, J = 7.3 Hz, 3H) | 1.26 531.2 B | B |
| 195 | (S)-2'-chloro-4-[(1-cyclopentylbutyl)carbamoyl]-6'-(6-fluoro-5-methoxy-1H-1,3-benzodiazol-2-yl)-[1,1'-biphenyl]-2-carboxylic acid | 2.31 Single Diastereomer | 1H NMR (500 MHz, DMSO-d6) δ 8.38 (d, J = 0.9 Hz, 1H), 8.26 (d, J = 8.9 Hz, 1H), 7.89 (d, J = 7.9 Hz, 1H), 7.77 (d, J = 7.9 Hz, 1H), 7.66 (d, J = 7.9 Hz, 1H), 7.60-7.52 (m, 1H), 7.24 (d, J = 11.3 Hz, 1H), 7.09 (dd. J = 19.8, 7.9 Hz, 2H), 3.87 (qd, J = 8.9, 4.3 Hz, 1H), 3.80 (s, 3H), 2.04-1.92 (m, 1H), 1.75-1.66 (m, 1H), 1.65-1.40 (m, 7H), 1.37-1.14 (m, 5H), 0.90-0.82 (m, 3H) | 1.81 564.2 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 196 | 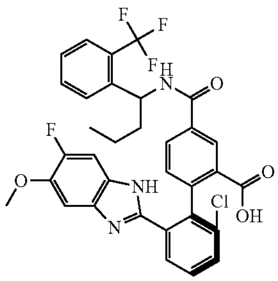 | (S)-2'-chloro-6'-(6-fluoro-5-methoxy-1H-1,3-benzodiazol-2-yl)-4-({1-[2-(trifluoromethyl)phenyl]butyl}carbamoyl)-[1,1'-biphenyl]-2-carboxylic acid | 2.16 C fast eluent from silica gel chromatography purification | 1H NMR (500 MHz, DMSO-d6) δ 9.04 (d, J = 7.6 Hz, 1H), 8.40 (d, J = 1.5 Hz, 1H), 7.91 (dd, J = 7.9, 1.5 Hz, 1H), 7.79 (d, J = 7.9 Hz, 1H), 7.75 (d, J = 7.3 Hz, 1H), 7.67-7.59 (m, 3H), 7.57-7.50 (m, 1H), 7.40 (t, J = 7.6 Hz, 1H), 7.22 (d, J = 11.3 Hz, 1H), 7.11 (d, J = 7.9 Hz, 1H), 7.03 (d, J = 7.9 Hz, 1H), 5.46-5.32 (m, J = 7.5, 7.5 Hz, 1H), 3.76 (s, 3H), 1.94-1.80 (m, 1H), 1.58-1.41 (m, 2H), 1.31 (dt, J = 14.1, 6.8 Hz, 1H), 0.87 (t, J = 7.2 Hz, 3H) | 1.92 640.2 B | A |
| 197 | 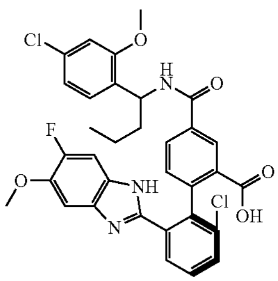 | (S)-2'-chloro-4-{1-(4-chloro-2-methoxyphenyl)butyl]carbamoyl}-6'-(6-fluoro-5-methoxy-1H-1,3-benzodiazol-2-yl)-[1,1'-biphenyl]-2-carboxylic acid | 2.29 C fast eluent from silica gel chromatography purification | 1H NMR (500 MHz, DMSO-d6) δ 8.89 (d, J = 8.2 Hz, 1H), 8.44 (s, 1H), 7.95 (d, J = 7.9 Hz, 1H), 7.78 (d, J = 7.6 Hz, 1H), 7.67 (d, J = 7.9 Hz, 1H), 7.60-7.53 (m, 1H), 7.35 (d, J = 8.2 Hz, 1H), 7.25 (d, J = 11.3 Hz, 1H), 7.13 (d, J = 7.9 Hz, 1H), 7.08-7.02 (m, 2H), 7.01-6.94 (m, 1H), 5.39-5.30 (m, 1H), 3.85 (s, 3H), 3.80 (s, 3H), 1.79-1.68 (m, 1H), 1.61 (td, J = 13.8, 6.0 Hz, 1H), 1.45-1.35 (m, 1H), 1.34-1.21 (m, 1H), 0.89 (t, J = 7.3 Hz, 3H) | 1.91 636.2 B | A |
| 198 | 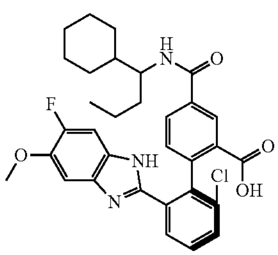 | (S)-2'-chloro-4-cyclohexylbutyl)carbamoyl]-6'-(6-fluoro-5-methoxy-1H-1,3-benzodiazol-2-yl)-[1,1'-biphenyl]-2-carboxylic acid | 2.19 C Single diastereomer | 1H NMR (500 MHz, METHANOL-d4) δ 8.38-8.31 (m, 1H), 8.22 (d, J = 11.8 Hz, 1H), 7.82 (d, J = 10.5 Hz, 1H), 7.71 (dd, J = 16.5, 8.0 Hz, 2H), 7.61-7.53 (m, 1H), 7.23 (d, J = 10.5 Hz, 1H), 7.12 (s, 1H), 3.93-3.87 (m, J = 5.2 Hz, 1H), 3.86 (s, 3H), 1.86-1.71 (m, 2H), 1.70-1.55 (m, J = 16.0 Hz, 2H), 1.54-1.13 (m, J = 14.0 Hz, 7H), 1.11-1.00 (m, 2H), 0.93 (d, J = 14.3 Hz, 3H) | 1.92 578.2 B | A |
| 199 | 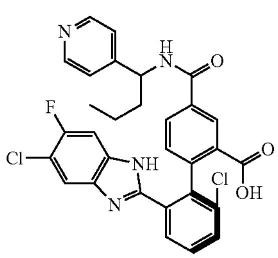 | (S)-2'-chloro-6'-(5-chloro-6-fluoro-1H-1,3-benzodiazol-2-yl)-4-{[1-(pyridin-4-yl)butyl]carbamoyl}-[1,1'-biphenyl]-2-carboxylic acid | 1.61 C fast eluent from silica gel chromatography purification | 1H NMR (500 MHz, DMSO-d6) δ 9.18 (dd, J = 7.5, 4.1 Hz, 1H), 8.65 (d, J = 4.0 Hz, 2H), 8.45-8.36 (m, J = 9.2 Hz, 1H), 7.97-7.90 (m, 1H), 7.77-7.71 (m, 3H), 7.67 (d, J = 7.6 Hz, 1H), 7.58-7.50 (m, 2H), 7.37 (d, J = 9.8 Hz, 1H), 7.14 (br. s., 1H), 5.14-4.98 (m, 1H), 1.92-1.80 (m, J = 7.3 Hz, 1H), 1.78-1.67 (m, J = 6.7 Hz, 1H), 1.47-1.36 (m, 1H), 1.35-1.24 (m, J = 4.3 Hz, 1H), 0.88 (td, J = 7.2, 3.7 Hz, 3H) | 1.32 577.1 B | A |
| 200 | 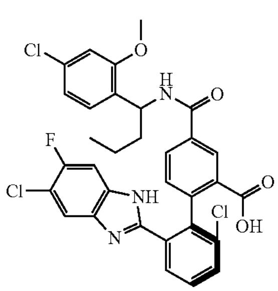 | (S)-2'-chloro-4-{[1-(4-chloro-2-methoxyphenyl)butyl]carbamoyl}-6'-(5-chloro-6-fluoro-1H-1,3-benzodiazol-2-yl)-[1,1'-biphenyl]-2-carboxylic acid | 2.29 C fast eluent from silica gel chromatography purification | 1H NMR (500 MHz, DMSO-d6) δ 8.89 (d, J = 8.2 Hz, 1H), 8.45 (s, 1H), 7.96 (dd, J = 7.9, 1.2 Hz, 1H), 7.81 (d, J = 7.6 Hz, 1H), 7.70 (d, J = 7.9 Hz, 1H), 7.61-7.54 (m, 2H), 7.41 (d, J = 9.5 Hz, 1H), 7.36 (d, J = 7.9 Hz, 1H), 7.16 (d, J = 7.9 Hz, 1H), 7.05 (d, J = 1.5 Hz, 1H), 7.00-6.96 (m, 1H), 5.36 (td, J = 8.9, 4.9 Hz, 1H), 3.86 (s, 3H), 1.74 (dtd, J = 13.7, 9.2, 5.0 Hz, 1H), 1.67-1.57 (m, 1H), 1.41 (dq, J = 13.9, 7.0 Hz, 1H), 1.34-1.23 (m, J = 8.5 Hz, 1H), 0.90 (t, J = 7.2 Hz, 3H) | 2.09 640.1 B | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 201 | 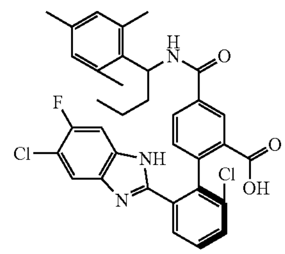 | (S)-2'-chloro-6'-(5-chloro-6-fluoro-1H-1,3-benzodiazol-2-yl)-4-{[1-(2,4,6-trimethylphenyl)butyl]carbamoyl}-[1,1'-biphenyl]-2-carboxylic acid | 2.36 C Single Diastereomer | 1H NMR (500 MHz, DMSO-d6) δ 8.78 (d, J = 6.4 Hz, 1H), 8.40 (d, J = 0.9 Hz, 1H), 7.93 (dd, J = 8.2, 1.2 Hz, 1H), 7.79 (d, J = 7.6 Hz, 1H), 7.69 (d, J = 7.9 Hz, 1H), 7.59-7.55 (m, 1H), 7.53 (d, J = 7.0 Hz, 1H), 7.38 (d, J = 9.5 Hz, 1H), 7.13 (d, J = 7.9 Hz, 1H), 6.74 (s, 2H), 5.24 (dt, J = 9.7, 5.8 Hz, 1H), 2.43-2.35 (m, 6H), 2.16 (s, 3H), 2.08 (dtd, J = 13.7, 9.4, 4.4 Hz, 1H), 1.63-1.43 (m, 2H), 1.30-1.20 (m, 1H), 0.90 (t, J = 7.3 Hz, 3H) | 2.21 618.2 B | A |
| 202 | 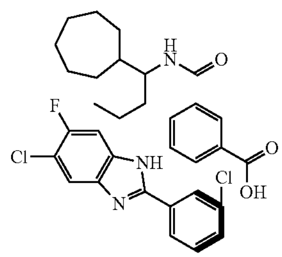 | (S)-2'-chloro-6'-(5-chloro-6-fluoro-1H-1,3-benzodiazol-2-yl)-4-[(1-cycloheptylbutyl)carbamoyl]-[1,1'-biphenyl]-2-carboxylic acid | 2.50 C Single Diastereomer | 1H NMR (500 MHz, DMSO-d6) δ 8.31 (d, J = 1.2 Hz, 1H), 8.12 (d, J = 8.9 Hz, 1H), 7.83 (dd, J = 8.1, 1.7 Hz, 1H), 7.71 (d, J = 7.6 Hz, 1H), 7.61 (d, J = 8.2 Hz, 1H), 7.53-7.44 (m, 2H), 7.32 (d, J = 9.8 Hz, 1H), 7.05 (d, J = 7.9 Hz, 1H), 3.87-3.74 (m, 1H), 1.70-1.62 (m, 1H), 1.54 (dd, J = 10.1, 6.7 Hz, 5H), 1.48-1.32 (m, 7H), 1.31-1.20 (m, 4H), 1.19-1.05 (m, 3H), 0.83-0.74 (m, 3H) | 2.22 596.2 B | A |
| 203 | 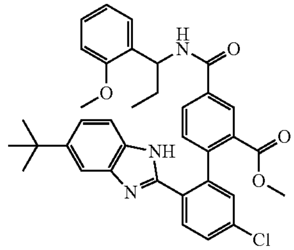 [SMILES: CCC(NC(=O)c1ccc(-c2cc(Cl)ccc2-c2nc3cc(C(C)(C)C)ccc3[nH]2)c(C(=O)OC)c1)c1ccccc1OC] | methyl 2'-(5-tert-butyl-1H-1,3-benzodiazol-2-yl)-5'-chloro-4-{[1-(2-methoxyphenyl)butyl]carbamoyl}-[1,1'-biphenyl]-2-carboxylate | 2 1.00 A fast eluent from prep-HPLC Purification | 1H NMR (500 MHz, METHANOL-d4) δ 8.78 (d, J = 8.3 Hz, 1H), 8.30 (d, J = 1.7 Hz, 1H), 8.08 (d, J = 8.0 Hz, 1H), 7.87 (d, J = 8.5 Hz, 1H), 7.77 (dd, J = 8.3, 2.2 Hz, 1H), 7.68 (dd, J = 8.8, 1.9 Hz, 1H), 7.63-7.55 (m, 4H), 7.28-7.20 (m, 2H), 6.97 (d, J = 7.7 Hz, 1H), 6.89 (t, J = 7.4 Hz, 1H), 5.48-5.38 (m, 1H), 3.87 (s, 3H), 3.64 (s, 3H), 1.85-1.77 (m, 2H), 1.40 (m, 1H), 1.38 (s, 9H), 1.35-1.27 (m, 1H), 0.95 (t, J = 7.4 Hz, 3H) | 0.96 624.6 A | B |
| 204 | 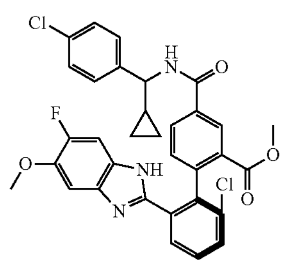 | (S)-methyl 2'-chloro-4-{[(4-chlorophenyl)(cyclopropyl)methyl]carbamoyl}-6'-(6-fluoro-5-methoxy-1H-1,3-benzodiazol-2-yl)-[1,1'-biphenyl]-2-carboxylate | 12 1.13 A slow eluent from silica gel chromatography purification | 1H NMR (500 MHz, METHANOL-d4) δ 9.26-9.21 (m, 1H), 8.45 (dd, J = 5.2, 1.9 Hz, 1H), 8.01 (ddd, J = 8.1, 6.5, 1.9 Hz, 1H), 7.85 (dd, J = 8.3, 1.1 Hz, 1H), 7.82 (dd, J = 7.8, 1.0 Hz, 1H), 7.72-7.66 (m, 1H), 7.43-7.38 (m, 2H), 7.37-7.35 (m, 1H), 7.34-7.31 (m, 2H), 7.20 (d, J = 7.4 Hz, 1H), 4.40-4-.34 (m, 1H), 3.91 (s, 3H), 3.76 (d, J = 1.4 Hz, 3H), 1.37-1.27 (m, 1H), 0.68-0.61 (m, 2H), 0.49-0.38 (m, 2H) | 1.22 618.1 A | C |
| 205 | 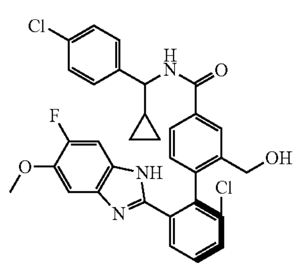 | (S)-2'-chloro-N-[(4-chlorophenyl)(cyclopropyl)methyl]-6'-(6-fluoro-5-methoxy-1H-1,3-benzodiazol-2-yl)-2-(hydroxymethyl)-[1,1'-biphenyl]-4-carboxamide | 12 1.13 A slow eluent from silica gel chromatography purification | 1H NMR (500 MHz, METHANOL-d4) δ 9.07 (d, J = 7.7 Hz, 1H), 8.01 (d, J = 1.7 Hz, 1H), 7.92 (dd, J = 8.3, 1.1 Hz, 1H), 7.85 (dd, J = 7.7, 1.1 Hz, 1H), 7.75 (d, J = 8.0 Hz, 1H), 7.73-7.69 (m, 1H), 7.43-7.38 (m, 3H), 7.32-7.29 (m, 2H), 7.24 (d, J = 7.2 Hz, 1H), 7.10 (d, J = 7.7 Hz, 1H), 4.67-4.55 (m, 2H), 4.40-4.33 (m, 1H), 3.91 (s, 3H), 1.34-1.27 (m, 1H), 0.67-0.62 (m, 2H), 0.48- 0.39 (m, 2H) | 1.17 590.1 A | B |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 206 | 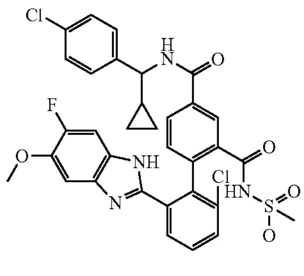 | 2'-chloro-N4-[(4-chlorophenyl)(cyclopropyl)methyl]-6'-(6-fluoro-5-methoxy-1H-1,3-benzodiazol-2-yl)-N2-methanesulfonyl-[1,1'-biphenyl]-2,4-dicarboxamide | 12 1.13 A slow eluent from silica gel chromatography purification | 1H NMR (500 MHz, METHANOL-d4) δ 8.18 (t, J = 2.2 Hz, 1H), 7.87 (dt, J = 8.0, 2.3 Hz, 1H), 7.77 (d, J = 7.7 Hz, 1H), 7.73 (d, J = 8.0 Hz, 1H), 7.67-7.62 (m, 1H), 7.46-7.42 (m, 2H), 7.36-7.32 (m, 2H), 7.25 (d, J = 11.0 Hz, 1H), 7.15 (d, J = 7.4 Hz, 1H), 7.11 (d, J = 8.0 Hz, 1H), 4.39 (dd, J = 9.4, 2.2 Hz, 1H), 3.88 (s, 3H), 3.07 (s, 3H), 1.38-1.30 (m, 1H), 0.66 (dd, J = 8.0, 1.9 Hz, 2H), 0.46 (dd, J =9.2, 4.8 Hz, 2H) | 1.19 681.1 A | B |
| 207 | 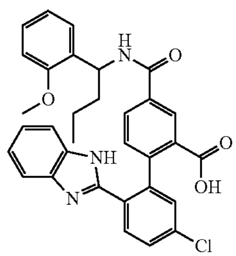 [SMILES: C=C(O)c1cc(C(=O)NC(CCC)c2ccccc2OC)ccc1-c1cc(Cl)ccc1-c1nc2ccccc2[nH]1] | 2'-(1H-1,3-benzodiazol-2-yl)-5'-chloro-4-{[1-(2-methoxyphenyl)butyl]carbamoyl}-[1,1'-biphenyl]-2-carboxylic acid | 2 1.00 A fast eluent from prep-HPLC Purification | 1H NMR (500 MHz, DMSO-d6) δ 8.87 (d, J = 8.5 Hz, 1H), 8.35 (d, J = 1.4 Hz, 1H), 8.04 (dd, J = 8.0, 1.9 Hz, 1H), 7.91 (d, J = 8.5 Hz, 1H), 7.72 (dd, J = 8.3, 1.9 Hz, 1H), 7.56-7.42 (m, 3H), 7.36 (t, J = 7.7 Hz, 2H), 7.28-7.17 (m, 3H), 7.03-6.96 (m, 1H), 6.92 (t, J = 7.3 Hz, 1H), 5.44 (td, J = 8.9. 5.0 Hz, 1H), 3.84 (5, 3H), 1.78-1.54 (m, 4H), 0.95 (t, J = 7.4 Hz, 3H) | 0.89 553.8 A | A |
| 208 | 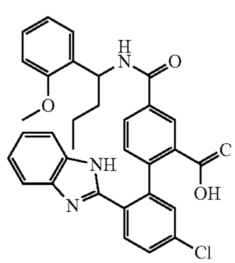 | 2'-(1H-1,3-benzodiazol-2-yl)-5'-chloro-4-{[1-(2-methoxyphenyl)butyl]carbamoyl}-[1,1'-biphenyl]-2-carboxylic acid | 1.03 A slow eluent from prep-HPLC Purification | 1H NMR (500 MHz, METHANOL-d4) δ 8.76 (d, J = 8.5 Hz, 1H), 8.34 (br. s., 1H), 8.01 (d, J = 8.0 Hz, 1H), 7.87 (d, J = 8.3 Hz, 1H), 7.74 (dd, J = 8.4, 2.1 Hz, 1H), 7.67-7.61 (m, 2H), 7.59 (d, J = 1.9 Hz, 1H), 7.55-7.49 (m, 2H), 7.47 (d, J = 8.0 Hz, 1H), 7.28-7.19 (m, 2H), 6.99-6.94 (m, 1H), 6.90 (td, J = 7.5, 1.0 Hz, 1H), 5.46-5.38 (m, 1H), 3.87 (s, 3H), 1.86-1.76 (m, 2H), 1.49-1.40 (m, 1H), 1.38-1.27 (m, 1H), 0.95 (t, J = 7.4 Hz, 3H) | 0.89 553.8 A | A |
| 209 | 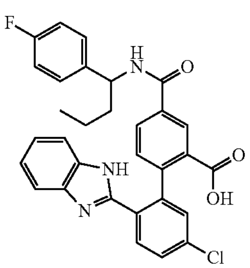 [SMILES: CCCC(NC(=O)c1ccc(-c2cc(Cl)ccc2-c2nc3ccccc3[nH]2)c(C(=O)O)c1)c1ccc(F)cc1] | 2'-(1H-1,3-benzodiazol-2-yl)-5'-chloro-4-{[1-(4-fluorophenyl)butyl]carbamoyl}-[1,1'-biphenyl]-2-carboxylic acid | 0.99 A slow eluent from silica gel chromatography purification | 1H NMR (500 MHz, DMSO-d6) δ 9.00 (d, J = 8.2 Hz, 1H), 8.31 (s, 1H), 8.04-8.00 (m, 1H), 7.90 (d, J = 8.5 Hz, 1H), 7.73 (dd, J = 8.2, 1.8 Hz, 1H), 7.53 (dd, J = 6.0, 3.2 Hz, 2H), 7.48-7.40 (m, 3H), 7.37 (d, J = 7.9 Hz, 1H), 7.28 (dd, J = 5.8, 3.1 Hz, 2H), 7.15 (t, J = 8.9 Hz, 2H), 5.09-4.96 (m, 1H), 1.94-1.81 (m, 1H), 1.76-1.65 (m, 1H), 1.44-1.32 (m, 1H), 1.30-1.19 (m, 1H), 0.90 (t, J = 7.3 Hz, 3H) | 0.85 542.1 A | A |
| 210 | 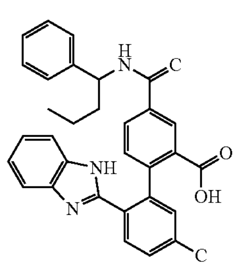 [SMILES: C=C(NC(CCC)c1ccccc1)c1ccc(-c2cc(C)ccc2-c2nc3ccccc3[nH]2)c(C(=O)O)c1] | 2'-(1H-1,3-benzodiazol-2-yl)-5'-chloro-4-[(3-methyl-1-phenylbutyl)carbamoyl]-[1,1'-biphenyl]-2-carboxylic acid | racemic commercially available | 1H NMR (500 MHz, DMSO-d6) δ 8.98 (d, J = 8.5 Hz, 1H), 8.34 (s, 1H), 8.02 (d, J = 8.0 Hz, 1H), 7.96 (s, 1H), 7.90 (d, J = 8.5 Hz, 1H), 7.71 (d, J = 8.3 Hz, 1H), 7.47 (d, J = 3.3 Hz, 2H), 7.44-7.36 (m, 3H), 7.36-7.29 (m, 3H), 7.27-7.15 (m, 3H), 5.18-5.08 (m, 1H), 1.92-1.81 (m, 1H), 1.63-1.49 (m, 1H), 1.32 (d, J = 7.2 Hz, 1H), 0.93 (t, J = 5.9 Hz, 6H) | 0.93 538.0 A | A |

… TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 211 | 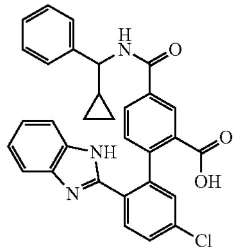 [SMILES: O=C(NC(c1ccccc1)C1CC1)c1ccc(-c2cc(Cl)ccc2-c2nc3ccccc3[nH]2)c(C(=O)O)c1] | 2'-(1H-1,3-benzodiazol-2-yl)-5'-chloro-4-{[cyclopropyl(phenyl)methyl]carbamoyl}-[1,1'-biphenyl]-2-carboxylic acid | Chiral SFC separation RT = 6.70 min Regis (R,R)-Whelk-o1,, 21 × 250 mm, 5 micron 5% MeOH/95% CO2 100 mL/min, 150 Bar, 40 C. or 85 mL/min 150 Bbar Detector Wavelength: 220 nm | 1H NMR (500 MHz, DMSO-d6) δ 9.27 (d, J = 7.9 Hz, 1H), 8.37 (d, J = 1.0 Hz, 1H), 8.03 (dd, J = 7.9, 1.5 Hz, 1H), 7.89 (d, J = 8.4 Hz, 1H), 7.69 (dd, J = 8.4, 2.0 Hz, 1H), 7.51-7.42 (m, 4H), 7.40 (s, 1H), 7.34 (q, J = 7.4 Hz, 3H), 7.28-7.22 (m, 1H), 7.18 (br. s., 2H), 4.38 (t, J = 8.9 Hz, 1H), 1.35 (dt, J = 8.5, 3.9 Hz, 1H), 0.56 (d, J = 7.9 Hz, 2H), 0.45-0.34 (m, 2H) | 0.86 521.9 A | A |
| 212 | 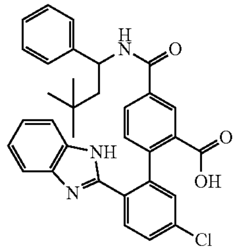 [SMILES: CC(C)(C)CC(NC(=O)c1ccc(-c2cc(Cl)ccc2-c2nc3ccccc3[nH]2)c(C(=O)O)c1)c1ccccc1] | 2'-(1H-1,3-benzodiazol-2-yl)-5'-chloro-4-[(3,3-dimethyl-1-phenylbutyl)carbamoyl]-[1,1'-biphenyl]-2-carboxylic acid | racemic commercially available | 1H NMR (500 MHz, DMSO-d6) δ 8.96 (d, J = 8.3 Hz, 1H), 8.32 (s, 1H), 7.97 (br. s., 1H), 7.88 (d, J = 8.3 Hz, 1H), 7.66 (d, J = 8.3 Hz, 1H), 7.40 (d, J = 6.9 Hz, 4H), 7.38-7.30 (m, 2H), 7.30-7.18 (m, 2H), 7.11 (d, J = 2.5 Hz, 2H), 5.22 (t, J = 8.9 Hz, 1H), 2.09-1.98 (m, 1H), 1.58 (d, J = 14.3 Hz, 1H), 0.96 (s, 9H) | 0.96 551.9 A | B |
| 213 | 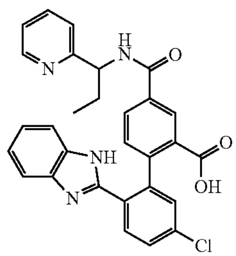 [SMILES: CCC(NC(=O)c1ccc(-c2cc(Cl)ccc2-c2nc3ccccc3[nH]2)c(C(=O)O)c1)c1ccccn1] | 2'-(1H-1,3-benzodiazol-2-yl)-5'-chloro-4-{[1-(pyridin-2-yl)propyl]carbamoyl}-[1,1'-biphenyl]-2-carboxylic acid | racemic commercially available | 1H NMR (500 MHz, DMSO-d6) δ 9.09 (d, J = 6.9 Hz, 1H), 8.59 (d, J = 5.0 Hz, 1H), 8.38 (br. s., 1H), 8.08 (d, J = 6.4 Hz, 1H), 7.94-7.87 (m, 2H), 7.75 (dd, J = 8.4, 1.5 Hz, 1H), 7.58-7.45 (m, 3H), 7.40 (d, J = 5.9 Hz, 2H), 7.29 (br. s., 2H), 5.09-4.99 (m, 1H), 2.01-1.82 (m, 2H), 0.93 (t, J = 7.2 Hz, 3H) | 0.65 510.9 A | B |
| 214 | 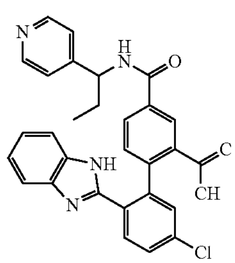 [SMILES: C=C(C)c1cc(C(=O)NC(CC)c2ccncc2)ccc1-c1cc(Cl)ccc1-c1nc2ccccc2[nH]1] | 2'-(1H-1,3-benzodiazol-2-yl)-5'-chloro-4-{[1-(pyridin-4-yl)propyl]carbamoyl}-[1,1'-biphenyl]-2-carboxylic acid | racemic commercially available | 1H NMR (500 MHz, DMSO-d6) δ 9.09 (d, J = 6.9 Hz, 1H), 8.59 (d, J = 5.0 Hz, 1H), 8.38 (br. s., 1H), 8.08 (d, J = 6.4 Hz, 1H), 7.94-7.87 (m, 2H), 7.75 (dd, J = 8.4, 1.5 Hz, 1H), 7.58-7.45 (m, 3H), 7.40 (d, J = 5.9 Hz, 2H), 7.29 (br. s., 2H), 5.09-4.99 (m, 1H), 2.01-1.82 (m, 2H), 0.93 (t, J = 7.2 Hz, 3H) | 0.63 510.7 A | B |
| 215 | 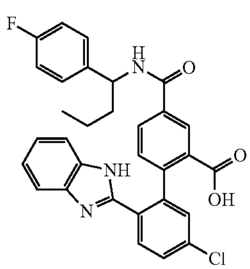 [SMILES: CCCC(NC(=O)c1ccc(-c2cc(Cl)ccc2-c2nc3ccccc3[nH]2)c(C(=O)O)c1)c1ccc(F)cc1] | 2'-(1H-1,3-benzodiazol-2-yl)-5'-chloro-4-{[1-(4-fluorophenyl)butyl]carbamoyl}-[1,1'-biphenyl]-2-carboxylic acid | 0.99 A fast eluent from silica gel chromatography purification | 1H NMR (500 MHz, DMSO-d6) δ 8.99 (d, J = 8.2 Hz, 1H), 8.31 (s, 1H), 8.01 (d, J = 7.9 Hz, 1H), 7.89 (d, J = 8.2 Hz, 1H), 7.72 (d, J = 8.5 Hz, 1H), 7.53-7.39 (m, 5H), 7.35 (d, J = 7.9 Hz, 1H), 7.25 (dd, J = 6.0, 3.2 Hz, 2H), 7.15 (t, J = 8.9 Hz, 2H), 5.10-4.96 (m, 1H), 1.86 (dd, J = 9.2, 4.9 Hz, 1H), 1.76-1.67 (m, 1H), 1.36 (br. s., 1H), 1.27 (dd, J = 15.6, 7.0 Hz, 1H), 0.90 (t, J = 7.3 Hz, 3H) | 0.85 542.1 A | C |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 216 | 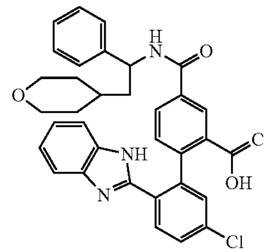 [SMILES: C=C(O)c1cc(C(=O)NC(CC2CCOCC2)c2ccccc2)ccc1-c1cc(Cl)ccc1-c1nc2ccccc2[nH]1] | 2'-(1H-1,3-benzodiazol-2-yl)-5'-chloro-4-{[2-(oxan-4-yl)-1-phenylethyl]carbamoyl}-[1,1'-biphenyl]-2-carboxylic acid | 0.84 A slow eluent from silica gel chromatography purification | 1H NMR (500 MHz, METHANOL-d4) δ 8.98 (d, J = 7.7 Hz, 1H), 8.36 (s, 1H), 8.04 (t, J = 6.2 Hz, 1H), 7.92-7.85 (m, 1H), 7.75 (dd, J = 8.3, 2.2 Hz, 1H), 7.68-7.62 (m, 2H), 7.60 (d, J = 1.9 Hz, 1H), 7.57-7.52 (m, 2H), 7.50 (d, J = 8.0 Hz, 1H), 7.41-7.36 (m, 2H), 7.35-7.30 (m, 2H), 7.26-7.21 (m, 1H), 5.30-5.20 (m, 1H), 3.90 (dd, J = 11.4, 2.6 Hz, 2H), 3.36-3.28 (m, 2H), 1.96-1.86 (m, 1H), 1.79-1.65 (m, 3H), 1.57 (br. s., 1H), 1.41-1.26 (m, 2H) | 0.77 580.2 A | C |
| 217 | 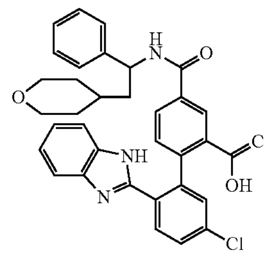 [SMILES: C=C(O)c1cc(C(=O)NC(CC2CCOCC2)c2ccccc2)ccc1-c1cc(Cl)ccc1-c1nc2ccccc2[nH]1] | 2'-(1H-1,3-benzodiazol-2-yl)-5'-chloro-4-{[2-(oxan-4-yl)-1-phenylethyl]carbamoyl}-[1,1'-biphenyl]-2-carboxylic acid | 0.87 A fast eluent from silica gel chromatography purification | 1H NMR (500 MHz, METHANOL-d4) δ 8.98 (d, J = 7.7 Hz, 1H), 8.36 (s, 1H) 8.04 (t, J = 6.1 Hz, 1H), 7.88 (d, J = 8.3 Hz, 1H), 7.75 (dd, J = 8.3, 2.2 Hz, 1H), 7.68-7.62 (m, 2H), 7.60 (d, J = 1.9 Hz, 1H), 7.57-7.52 (m, 2H), 7.50 (d, J = 8.0 Hz, 1H), 7.40-7.36 (m, 2H), 7.35-7.29 (m, 2H), 7.27-7.21 (m, 1H), 5.29-5.19 (m, 1H), 3.90 (dd, J = 11.6, 2.8 Hz, 2H), 3.37-3.28 (m, 2H), 1.96-1.88 (m, 1H), 1.81-1.65 (m, 3H), 1.63-1.52 (m, 1H), 1.29 (s, 2H) | 0.77 580.2 A | C |
| 218 | 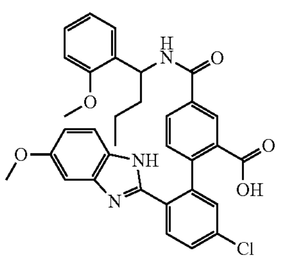 [SMILES: CCCC(NC(=O)c1ccc(-c2cc(Cl)ccc2-c2nc3cc(OC)ccc3[nH]2)c(C(=O)O)c1)c1ccccc1OC] | 5'-chloro-2'-(5-methoxy-1H-1,3-benzodiazol-2-yl)-4-{[1-(2-methoxyphenyl)butyl]carbamoyl}-[1,1'-biphenyl]-2-carboxylic acid | 1.00 A fast eluent from prep-HPLC Purification | 1H NMR (500 MHz, METHANOL-d4) δ 8.78 (d, J = 8.8 Hz, 1H), 8.36 (dd, J = 4.7, 1.7 Hz, 1H), 8.03 (td J = 5.2, 2.3 Hz, 1H), 7.85 (d, J = 8.3 Hz, 1H), 7.74 (dd, J = 8.4, 2.1 Hz, 1H), 7.59 (d, J = 1.7 Hz, 1H), 7.53 (d, J = 9.1 Hz, 1H), 7.49 (d, J = 8.0 Hz, 1H), 7.27 (d, J = 7.4 Hz, 1H), 7.24-7.20 (m, 1H), 7.16 (dd, J = 9.1, 2.2 Hz, 1H), 7.08 (d, J = 2.2 Hz, 1H), 6.97 (d, J = 7.4 Hz, 1H), 6.90 (t, J = 7.4 Hz, 1H), 5.47-5.38 (m, 1H), 3.89-3.86 (m, 3H), 3.85 (s, 3H), 1.86-1.77 (m, 2H), 1.50-1.41 (m, 1H), 1.39-1.29 (m, 1H), 0.96 (t, J = 7.3 Hz, 3H) | 0.98 584.1 A | A |
| 219 | 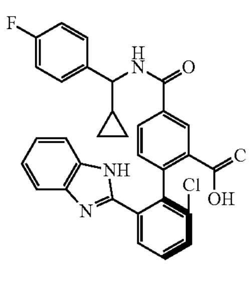 | (S)-2'-(1H-1,3-benzodiazol-2-yl)-6'-chloro-4-{[cyclopropyl(4-fluorophenyl)methyl]carbamoyl}-[1,1'-biphenyl]-2-carboxylic acid | 2.13 C slow eluent from silica gel chromatography purification | 1H NMR (500 MHz, METHANOL-d4) δ 8.43 (d, J = 1.7 Hz, 1H), 7.91 (dd, J = 8.0, 1.7 Hz, 1H), 7.81 (dd, J = 7.2, 6.1 Hz, 2H), 7.68-7.63 (m, 1H), 7.60-7.55 (m, 2H), 7.47-7.43 (m, 2H), 7.41-7.36 (m, 2H), 7.25 (d, J = 8.0 Hz, 1H), 7.09-7.02 (m, 2H), 4.40 (d, J = 9.4 Hz, 1H), 1.39-1.29 (m, 1H), 0.65 (d, J = 8.3 Hz, 2H), 0.50-0.38 (m, 2H) | 1.12 540.2 A | A |
| 220 | 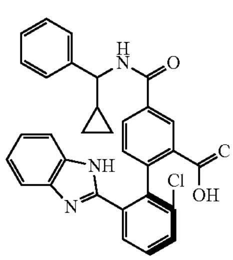 | (S)-2'-(1H-1,3-benzodiazol-2-yl)-6'-chloro-4-{[cyclopropyl(phenyl)methyl]carbamoyl}-[1,1'-biphenyl]-2-carboxylic acid | Chiral SFC separation RT = 6.70 min Regis (R,R)-Whelk-o1,, 21 × | 1H NMR (500 MHz, METHANOL-d4) δ 8.39 (d, J = 1.9 Hz, 1H), 7.87 (dd, J = 8.0, 1.9 Hz, 1H), 7.79 (dd, J = 7.7, 1.1 Hz, 1H), 7.76 (dd, J = 8.0, 1.1 Hz, 1H), 7.65-7.60 (m, 1H), 7.56-7.50 (m, 2H), 7.43 (d, J = 7.4 Hz, 2H), 7.36-7.29 (m, 4H), 7.27-7.22 (m, 1H), 7.19 (d, J = 8.0 Hz, 1H), 4.41 (d, J = 9.4 Hz, 1H), 1.39-1.30 (m, 1H), 0.67-0.59 (m, 2H), 0.49-0.40 (m, 2H) | 0.81 522.1 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| | | | 250 mm, 5 micron 5% MeOH/95% CO2 100 mL/min, 150 Bar, 40° C. or 85 mL/min 150 Bbar Detector Wavelength: 220 nm | | | |
| 221 | 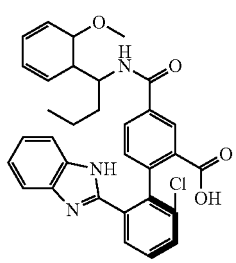 | (S)-2'-(1H-1,3-benzodiazol-2-yl)-6'-chloro-4-{[1-(2-methoxyphenyl)butyl]carbamoyl}-[1,1'-biphenyl]-2-carboxylic acid | 1.00 A fast eluent from prep-HPLC Purification | 1H NMR (400 MHz, METHANOL-d4) δ 8.29 (d, J = 2.0 Hz, 1H), 7.80-7.74 (m, 2H), 7.72-7.69 (m, 1H), 7.61-7.56 (m, 1H), 7.51-7.46 (m, 2H), 7.29-7.20 (m, 4H), 7.11 (d, J = 7.9 Hz, 1H), 7.00-6.96 (m, 1H), 6.94-6.88 (m, 1H), 5.44-5.38 (m, 1H), 3.88 (s, 3H), 1.85-1.76 (m, 2H), 1.51-1.30 (m, 2H), 0.97 (t, J = 7.4 Hz, 3H) | 0.85 554.1 A | A |
| 222 | 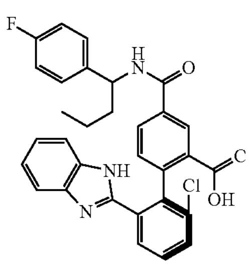 | (S)-2'-(1H-1,3-benzodiazol-2-yl)-6'-chloro-4-{[1-(4-fluorophenyl)butyl]carbamoyl}-[1,1'-biphenyl]-2-carboxylic acid | 0.99 A slow eluent from silica gel chromatography purification | 1H NMR (500 MHz, METHANOL-d4) δ 8.34 (d, J = 1.7 Hz, 1H), 7.81 (dd, J = 8.0, 1.9 Hz, 1H), 7.78 (dd, J = 7.7, 1.1 Hz, 1H), 7.73 (dd, J = 8.1, 1.0 Hz, 1H), 7.63-7.58 (m, 1H), 7.53-7.47 (m, 2H), 7.41-7.36 (m, 2H), 7.30-7.25 (m, 2H), 7.16 (d, J = 8.0 Hz, 1H), 7.08-7.01 (m, 2H), 5.09-5.02 (m, 1H), 1.95-1.86 (m, 1H), 1.83-1.73 (m, 1H), 1.50-1.39 (m, 1H), 1.39-1.28 (m, 1H), 0.97 (t, J = 7.4 Hz, 3H) | 0.84 542.1 A | A |
| 223 | 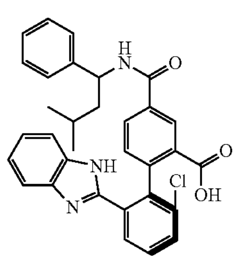 | (S)-2'-(1H-1,3-benzodiazol-2-yl)-6'-chloro-4-[(3-methyl-1-phenylbutyl)carbamoyl]-[1,1'-biphenyl]-2-carboxylic acid | racemic commercially available | 1H NMR (400 MHz, METHANOL-d4) δ 8.31 (d, J = 2.0 Hz, 1H), 7.78 (ddd, J = 7.9, 4.5, 1.5 Hz, 2H), 7.71 (dd, J = 8.1, 1.1 Hz, 1H), 7.62-7.56 (m, 1H), 7.48 (dd, J = 6.1, 3.2 Hz, 2H), 7.40-7.29 (m, 4H), 7.27-7.21 (m, 3H), 7.12 (d, J = 7.9 Hz, 1H), 5.17 (dd, J = 9.2, 5.5 Hz, 1H), 1.93-1.81 (m, 1H), 1.71-1.59 (m, 2H), 0.99 (dd, J = 6.2, 3.7 Hz, 6H) | 0.85 538.1 A | A |
| 224 | 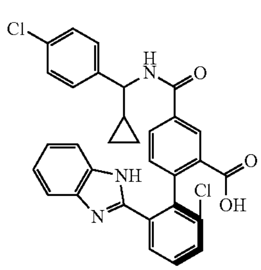 | (S)-2'-(1H-1,3-benzodiazol-2-yl)-6'-chloro-4-{[(4-chlorophenyl)(cyclopropyl)methyl]carbamoyl}-[1,1'-biphenyl]-2-carboxylic acid | 1.13 A slow eluent from silica gel chromatography purification | 1H NMR (500 MHz, METHANOL-d4) δ 8.44 (d, J = 1.9 Hz, 1H), 7.93 (dd, J = 8.0, 1.9 Hz, 1H), 7.84-7.80 (m, 2H), 7.69-7.63 (m, 1H), 7.61-7.56 (m, 2H), 7.45-7.39 (m, 4H), 7.36-7.31 (m, 2H), 7.27 (d, J = 8.0 Hz, 1H), 4.37 (d, J = 9.4 Hz, 1H), 1.40-1.27 (m, 1H), 0.71-0.61 (m, 2H), 0.51-0.38 (m, 2H) | 0.99 556.2 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 225 | 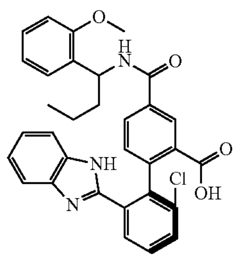 | (S)-2'-(1H-1,3-benzodiazol-2-yl)-6'-chloro-4-{[1-(2-methoxyphenyl)butyl]carbamoyl}-[1,1'-biphenyl]-2-carboxylic acid | 1.00 A fast eluent from prep-HPLC Purification | 1H NMR (400 MHz, METHANOL-d4) δ 8.31-8.27 (m, 1H), 7.80-7.75 (m, 2H), 7.74-7.69 (m, 1H), 7.62-7.56 (m, 1H), 7.51-7.45 (m, 2H), 7.30-7.21 (m, 4H), 7.12 (d, J = 8.1 Hz, 1H), 7.01-6.96 (m, 1H), 6.94-6.89 (m, 1H), 5.44-5.37 (m, 1H), 3.89 (s, 3H), 1.85-1.76 (m, 2H), 1.48-1.29 (m, 2H), 0.96 (t, J = 7.4 Hz, 3H) | 0.86 554.2 A | A |
| 226 | 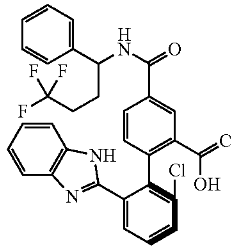 | (S)-2'-(1H-1,3-benzodiazol-2-yl)-6'-chloro-4-[(4,4,4-trifluoro-1-phenylbutyl)carbamoyl]-[1,1'-biphenyl]-2-carboxylic acid | 0.96 A slow eluent from silica gel chromatography purification | 1H NMR (500 MHz, METHANOL-d4) δ 8.32 (s, 1H), 7.80 (d, J = 7.7 Hz, 1H), 7.75 (d, J = 7.4 Hz, 1H), 7.70 (d, J = 7.7 Hz, 1H), 7.61-7.54 (m, 1H), 7.48 (dd, J = 5.8, 3.0 Hz, 2H), 7.42-7.33 (m, 4H) 7.30-7.22 (m, 3H) 7.12 (d, J = 8.0 Hz, 1H), 5.18-5.09 (m, 1H), 2.35-2.23 (m, 1H), 2.21-2.04 (m, 3H) | 0.85 578.1 A | A |
| 227 | 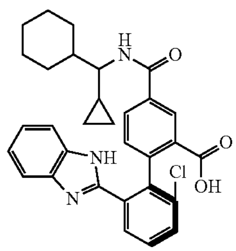 | (S)-2'-(1H-1,3-benzodiazol-2-yl)-6'-chloro-4-{[cyclohexyl(cyclopropyl)methyl]carbamoyl}-[1,1'-biphenyl]-2-carboxylic acid | chiral SFC separation. RT = 7.14 min. Chiralpak AD-H, 21 × 250 mm, 5 micron 10% MeOH/90% CO2 100 mL/min, 150 Bar, 40° C. Detector Wavelength: 220 nm | 1H NMR (500 MHz, METHANOL-d4) δ 8.27 (d, J = 8.8 Hz, 1H), 8.11 (d, J = 1.4 Hz, 1H), 7.60 (dd, J = 8.0, 1.7 Hz, 1H), 7.55 (t, J = 8.3 Hz, 2H), 7.39 (s, 1H), 7.31 (dd, J = 6.1, 3.0 Hz, 2H), 7.14-7.08 (m, 2H), 6.97 (d, J = 8.0 Hz, 1H), 2.93 (s, 1H), 1.82-1.73 (m, 1H), 1.61-1.49 (m, 3H), 1.47-1.36 (m, 2H), 1.10-0.94 (m, 3H), 0.92-0.81 (m, 2H), 0.80-0.70 (m, 1H), 0.43-0.34 (m, 1H), 0.19-0.13 (m, 1H), 0.13-0.06 (m, 1H), 0.04--0.07 (m, 1H) | 0.85 528.2 A | A |
| 228 | 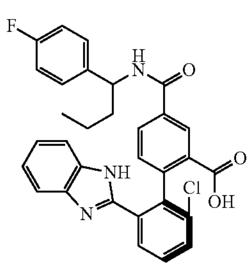 | (S)-2'-(1H-1,3-benzodiazol-2-yl)-6'-chloro-4-{[1-(4-fluorophenyl)butyl]carbamoyl}-[1,1-biphenyl]-2-carboxylic acid | 0.99 A fast eluent from silica gel chromatography purification | 1H NMR (500 MHz, METHANOL-d4) δ 8.96 (d, J = 8.0 Hz, 1H), 8.44 (d, J = 1.9 Hz, 1H), 7.97 (dd, J = 8.0, 1.9 Hz, 1H), 7.89 (dd, J = 8.3, 1.1 Hz, 1H), 7.85 (dd, J = 8.0, 1.1 Hz, 1H), 7.73-7.68 (m, 1H), 7.67-7.62 (m, 2H), 7.57-7.51 (m, 2H), 7.39-7.34 (m, 3H), 7.07-7.01 (m, 2H), 5.10-5.01 (m, 1H), 1.92-1.85 (m, 1H), 1.83-1.74 (m, 1H), 1.70-1.62 (m, 2H), 1.02 (t, J = 7.4 Hz, 3H) | 0.81 542.1 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 229 | 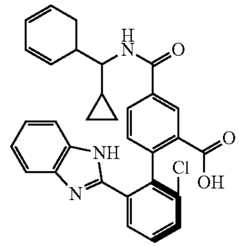 | (S)-2'-(1H-1,3-benzodiazol-2-yl)-6'-chloro-4-{[cyclopropyl(phenyl)methyl]carbamoyl}-[1,1'-biphenyl]-2-carboxylic acid | Chiral SFC separation RT = 4.57 min Regis (R,R)-Whelk-o1,, 21 × 250 mm, 5 micron 5% MeOH/95% CO₂ 100 mL/min, 150 Bar, 40° C. or 85 ml/min 150 Bbar Detector Wavelength: 220 nm | 1H NMR (500 MHz, METHANOL-d4) δ 8.30 (d, J = 1.9 Hz, 1H), 7.78 (dd, J = 8.0, 1.9 Hz, 1H), 7.70 (dd, J = 7.7, 1.1 Hz, 1H), 7.66 (dd, J = 8.0, 1.1 Hz, 1H), 7.56-7.50 (m, 1H), 7.46-7.40 (m, 2H), 7.35 (d, J = 7.4 Hz, 2H), 7.28-7.19 (m, 4H), 7.18-7.13 (m, 1H), 7.10 (d, J = 8.0 Hz, 1H), 4.33 (d, J = 9.4 Hz, 1H), 1.30-1.20 (m, 1H), 0.58-0.51 (m, 2H), 0.35 (m, 2H) | 0.78 522.1 A | B |
| 230 | 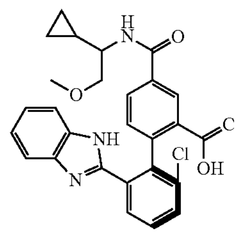 | (S)-2'-(1H-1,3-benzodiazol-2-yl)-6'-chloro-4-[(1-cyclopropyl-2-methoxyethyl)carbamoyl]-[1,1'-biphenyl]-2-carboxylic acid | racemic commercially available | 1H NMR (500 MHz, METHANOL-d4) δ 8.04-8.00 (m, 1H), 7.50 (dt, J = 8.0, 1.8 Hz, 1H), 7.47-7.43 (m, 1H), 7.41 (d, J = 7.4 Hz, 1H), 7.30-7.25 (m, 1H), 7.21-7.16 (m, 2H), 6.99-6.93 (m, 2H), 6.84 (d, J = 8.0 Hz, (H), 3.26 (s, 3H), 3.03 (d, J = 3.6 Hz, 2H), 0.75-0.65 (m, 1H), 0.28-0.20 (m, 1H), 0.18-0.11 (m, 1H), 0.09--0.05 (m, 2H) | 0.68 490.1 A | C |
| 231 | 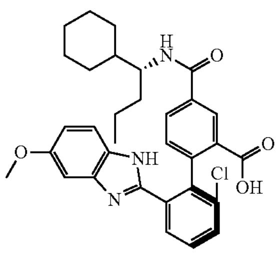 | (S)-2'-chloro-4-{[(1R)-1-cyclohexylbutyl]carbamoyl}-6'-(5-methoxy-1H-1,3-benzodiazol-2-yl)-[1,1'-biphenyl]-2-carboxylic acid | 2.19 C Single diastereomer | 1H NMR (500 MHz, METHANOL-d4) δ 8.42 (d, J = 1.9 Hz, 1H), 8.31-8.24 (m, 1H), 7.93 (dd, J = 8.0, 1.9 Hz, 1H), 7.86 (dd, J = 8.3, 1.1 Hz, 1H), 7.82 (dd, J = 7.8, 1.0 Hz, 1H), 7.70-7.65 (m, 1H), 7.55-7.49 (m, 1H), 7.34-7.29 (m, 1H), 7.13 (dd, J = 9.1, 2.5 Hz, 1H), 7.08 (d, J = 2.2 Hz, 1H), 3.94-3.86 (m, 1H), 3.84 (s, 3H), 1.83-1.71 (m, 3H), 1.66 (d, J = 12.1 Hz, 1H), 1.59 (dtd, J = 13.5, 6.6, 3.3 Hz, 1H) 1.52-1.43 (m, 2H), 1.42-1.36 (m, 1H), 1.34-1.14 (m, 4H), 1.10-0.99 (m, 2H), 0.92 (t, J = 7.3 Hz, 2H) | 0.93 560.2 A | A |
| 232 | 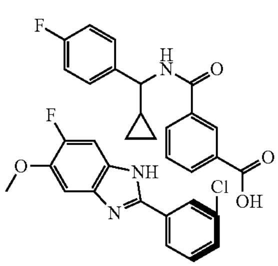 | (S)-2'-chloro-4-{[cyclopropyl(4-fluorophenyl)methyl]carbamoyl}-6'-(6-fluoro-5-methoxy-1H-1,3-benzodiazol-2-yl)-[1,1'-biphenyl]-2-carboxylic acid | 2.13 C slow eluent from silica gel chromatography purification | 1H NMR (500 MHz, METHANOL-d4) δ 8.43 (s, 1H), 7.93-7.87 (m, 1H), 7.74 (dd, J = 14.9, 8.0 Hz, 2H), 7.62-7.56 (m, 1H), 7.46 (dd, J = 8.3, 5.5 Hz, 2H), 7.27 (d, J = 10.7 Hz, 1H), 7.19 (d, J = 8.0 Hz, 1H), 7.14 (d, J = 7.4 Hz, 1H), 7.06 (t, J = 8.8 Hz, 2H), 4.40 (d, J = 9.6 Hz, 1H), 3.88 (s, 3H), 1.43-1.27 (m, 1H), 0.66 (d, J = 8.3 Hz, 2H), 0.45 (dd, J = 16.8, 5.0 Hz, 2H) | 1.15 588.1 A | A |
| 233 | 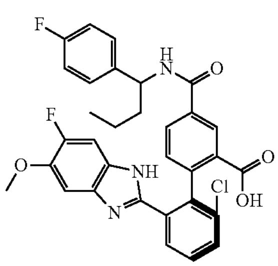 | (S)-2'-chloro-6'-(6-fluoro-5-methoxy-1H-1,3-benzodiazol-2-yl)-4-{1-(4-fluorophenyl)butyl]carbamoyl}-[1,1'-biphenyl]-2-carboxylic acid | 0.99 A slow eluent from silica gel chromatography purification | 1H NMR (500 MHz, METHANOL-d4) δ 8.36 (d, J = 1.2 Hz, 1H), 7.82 (dd, J = 7.9, 1.5 Hz, 1H), 7.73 (d, J = 7.6 Hz, 1H), 7.68 (d, J = 7.9 Hz, 1H), 7.62-7.53 (m, 1H), 7.39 (dd, J = 8.4, 5.3 Hz, 2H), 7.22 (d, J = 11.0 Hz, 1H), 7.12 (dd, J = 14.8, 7.8 Hz, 2H), 7.05 (t, J = 8.7 Hz, 2H), 5.10-5.04 (m, 1H), 3.86 (s, 3H), 1.96-1.87 (m, 1H), 1.85-1.74 (m, 1H), 1.52-1.41 (m, 1H), 1.41-1.29 (m, 1H), 0.98 (t, J = 7.3 Hz, 3H) | 1.15 590.1 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 234 | 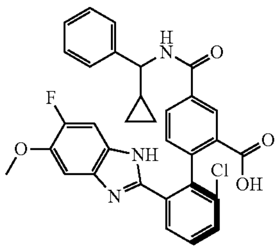 | (S)-2'-chloro-4-{[cyclopropyl(phenyl)methyl]carbamoyl}-6'-(6-fluoro-5-methoxy-1H-1,3-benzodiazol-2-yl)-[1,1'-biphenyl]-2-carboxylic acid | 11 Chiral SFC separation RT = 6.70 min Regis (R,R)-Whelk-o1,, 21 × 250 mm, 5 micron 5% MeOH/95% $CO_2$ 100 mL/min, 150 Bar, 40° C. or 85 ml/min 150 Bbar Detector Wavelength: 220 nm | 1H NMR (500 MHz, METHANOL-d4) δ 8.44 (d, J = 1.9 Hz, 1H), 7.91 (dd, J = 8.0, 1.7 Hz, 1H), 7.79-7.73 (m, 2H), 7.61 (d, J = 7.7 Hz, 1H), 7.44 (d, J = 7.4 Hz, 2H), 7.33 (t, J = 7.7 Hz, 2H), 7.30-7.23 (m, 2H), 7.21 (d, J = 8.0 Hz, 1H), 7.15 (d, J = 7.7 Hz, 1H), 4.42 (d, J = 9.4 Hz, 1H), 3.88 (s, 3H), 1.42-1.31 (m, 1H), 0.71-0.58 (m, 2H), 0.51-0.37 (m, 2H) | 0.97 570.2 A | A |
| 235 | 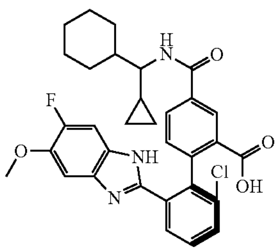 | (S)-2'-chloro-4-{[cyclohexyl(cyclopropyl)methyl]carbamoyl}-6'-(6-fluoro-5-methoxy-1H-1,3-benzodiazol-2-yl)-[1,1'-biphenyl]-2-carboxylic acid | 13 chiral SFC separation. RT = 7.14 min. Chiralpak AD-H, 21 × 250 mm, 5 micron 10% MeOH/90% $CO_2$ 100 mL/min, 150 Bar, 40° C. Detector Wavelength: 220 nm | 1H NMR (500 MHz, METHANOL-d4) δ 8.52 (d, J = 8.8 Hz, 1H), 8.39 (d, J = 1.7 Hz, 1H), 7.87 (dd, J = 8.0, 1.9 Hz, 1H), 7.79-7.72 (m, 2H), 7.62 (d, J = 8.0 Hz, 1H), 7.29 (d, J = 10.7 Hz, 1H), 7.21 (d, J = 8.0 Hz, 1H), 7.17 (d, J = 7.4 Hz, 1H), 3.89 (s, 3H), 3.23-3.15 (m, 1H), 2.08-1.99 (m, 1H), 1.87-1.73 (m, 3H), 1.71-1.59 (m, 2H), 1.39-1.18 (m, 3H), 1.18-1.06 (m, 2H), 1.05-0.97 (m, 1H), 0.70-0.57 (m, 1H), 0.49-0.39 (m, 1H), 0.38-0.31 (m, 1H) 0.30-0.19 (m, 1H) | 0.88 576.2 A | A |
| 236 | 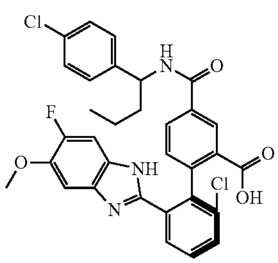 | (S)-2'-chloro-4-{[1-(4-chlorophenyl)butyl]carbamoyl}-6'-(6-fluoro-5-methoxy-1H-1,3-benzodiazol-2-yl)-[1,1'-biphenyl]-2-carboxylic acid | 1.01 A slow eluent from silica gel chromatography purification | 1H NMR (500 MHz, DMSO-d6) δ 9.01 (d, J = 8.2 Hz, 1H), 8.42 (s, 1H), 7.94 (d, J = 7.9 Hz, 1H), 7.78 (d, J = 7.6 Hz, 1H), 7.68 (d, J = 7.9 Hz, 1H), 7.60-7.54 (m, 1H), 7.45-7.35 (m, 4H), 7.28-7.22 (m, 2H), 7.17-7.11 (m, 2H), 7.09-7.02 (m, 2H), 5.06-4.96 (m, 1H), 3.81 (s, 3H), 1.92-1.82 (m, 1H), 1.77-1.67 (m, 1H), 1.44-1.34 (m, 1H), 1.32-1.21 (m, 1H), 0.91 (t, J = 7.2 Hz, 3H) | 0.98 606.2 A | A |
| 237 | 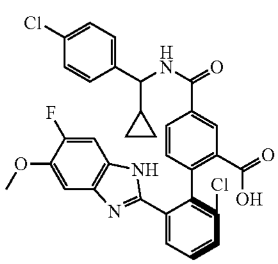 | (S)-2'-chloro-4-{[(4-chlorophenyl)(cyclopropyl)methyl]carbamoyl}-6'-(6-fluoro-5-methoxy-1H-1,3-benzodiazol-2-yl)-[1,1'-biphenyl]-2-carboxylic acid | 1.13 A slow eluent from silica gel chromatography purification | 1H NMR (500 MHz, METHANOL-d4) δ 8.44 (d, J = 1.9 Hz, 1H), 7.91 (dd, J = 8.0, 1.9 Hz, 1H), 7.78-7.72 (m, 2H), 7.63-7.58 (m, 1H), 7.45-7.41 (m, 2H), 7.36-7.32 (m, 2H), 7.28 (d, J = 10.7 Hz, 1H), 7.22-7.19 (m, 1H), 7.15 (d, J = 7.4 Hz, 1H), 4.38 (d, J = 9.4 Hz, 1H), 3.89 (s, 3H), 1.36-1.29 (m, 1H), 0.71-0.62 (m, 2H), 0.51-0.40 (m, 2H) | 1.12 604.1 A | A |
| 238 | 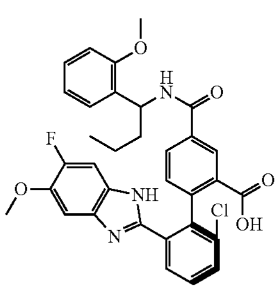 | (S)-2'-chloro-6'-(6-fluoro-5-methoxy-1H-1,3-benzodiazol-2-yl)-4-{[1-(2-methoxyphenyl)butyl]carbamoyl}-[1,1'-biphenyl]-2-carboxylic acid | 2.10 A fast eluent from silica gel chromatography purification | 1H NMR (500 MHz, METHANOL-d4) δ 8.40 (d, J = 1.5 Hz, 1H), 7.89 (dd, J = 7.9, 1.8 Hz, 1H), 7.76 (t, J = 8.4 Hz, 2H), 7.64-7.58 (m, 1H), 7.31-7.27 (m, 2H), 7.26-7.19 (m, 2H), 7.16 (d, J = 7.3 Hz, 1H), 6.99 (d, J = 8.2 Hz, 1H), 6.92 (t, J = 7.3 Hz, 1H), 5.42 (s, 1H), 3.89 (s, 3H), 3.88 (s, 4H), 1.88-1.75 (m, 3H), 1.52-1.42 (m, 1H), 1.40-1.29 (m, 1H), 0.97 (t, J = 7.5 Hz, 3H) | 1.15 602.3 A | A |

TABLE 4-continued

| Ex # | Structure | IUPAC Name | Chiral amine Intermediate RT (min) Method | NMR | RT (min), [M + H] Method | APJ cAMP Human EC50 (nM) |
|---|---|---|---|---|---|---|
| 239 | 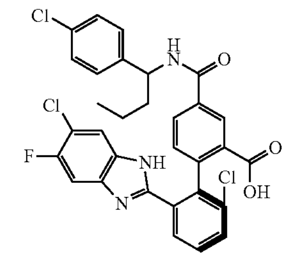 | (S)-2'-chloro-6'-(6-chloro-5-fluoro-1H-1,3-benzodiazol-2-yl)-4-{[1-(4-chlorophenyl)butyl]carbamoyl}-[1,1'-biphenyl]-2-carboxylic acid | 1.01 A slow eluent from silica gel chromatography purification | 1H NMR (500 MHz, METHANOL-d4) δ 8.34 (s, 1H), 7.82-7.77 (m, 1H), 7.73 (d, J = 7.6 Hz, 1H), 7.68 (d, J = 7.9 Hz, 1H), 7.59-7.55 (m, 1H), 7.54-7.51 (m, 1H), 7.35 (q, J = 8.5 Hz, 4H), 7.29 (d, J = 9.2 Hz, 1H), 7.11 (d, J = 7.9 Hz, 1H), 5.05 (dd, J = 8.7, 6.6 Hz, 1H), 1.96-1.86 (m, 1H), 1.85-1.75 (m, 1H), 1.52-1.42 (m, 1H), 1.41-1.32 (m, 1H), 0.98 (t, J = 7.3 Hz, 3H) | 1.14 610.2 A | A |
| 240 | 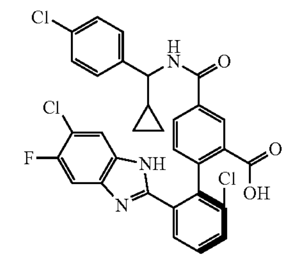 | (S)-2'-chloro-6'-(6-chloro-5-fluoro-1H-1,3-benzodiazol-2-yl)-4-{[(4-chlorophenyl)(cyclopropyl)methyl]carbamoyl}-[1,1'-biphenyl]-2-carboxylic acid | 1.13 A slow eluent from silica gel chromatography purification | 1H NMR (500 MHz, METHANOL-d4) δ 8.43 (d, J = 1.7 Hz, 1H), 7.87 (dd, J = 8.0, 1.7 Hz, 1H), 7.74 (d, J = 7.7 Hz, 1H), 7.69 (d, J = 8.0 Hz, 1H), 7.59-7.56 (m, 1H), 7.55-7.52 (m, 1H), 7.43 (d, J = 8.5 Hz, 2H), 7.34 (d, J = 8.3 Hz, 2H), 7.30 (d, J = 9.4 Hz, 1H), 7.16 (d, J = 8.0 Hz, 1H), 4.39 (d, J = 9.4 Hz, 1H), 1.33 (qd, J = 8.5, 4.5 Hz, 1H), 0.70-0.62 (m, 2H), 0.52-0.41 (m, 2H) | 1.24 608.0 A | A |
| 241 | 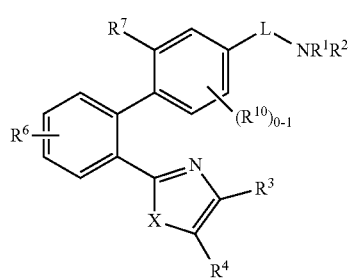 | 2'-(5-tert-butyl-1H-1,3-benzodiazol-2-yl)-5'-chloro-4-{[1-(2-methoxyphenyl)butyl]carbamoyl}-[1,1'-biphenyl]-2-carboxylic acid | 1.00 A fast eluent from prep-HPLC Purification | 1H NMR (500 MHz, METHANOL-d4) δ 8.78 (d, J = 8.3 Hz, 1H), 8.37 (s, 1H), 8.03 (d, J = 8.0 Hz, 1H), 7.87 (d, J = 8.3 Hz, 1H), 7.75 (dd, J = 8.5, 2.2 Hz, 1H), 7.68 (dd, J = 8.8, 1.7 Hz, 1H), 7.63-7.59 (m, 2H), 7.57 (d, J = 0.8 Hz, 1H), 7.49 (dd, J = 7.8, 2.3 Hz, 1H), 7.26 (d, J = 7.4 Hz, 1H), 7.24-7.19 (m, 1H), 6.97 (dd, J = 8.1, 0.7 Hz, 1H), 6.90 (td, J = 7.5, 1.0 Hz, 1H), 5.47-5.16 (m, 1H), 3.87 (s, 3H), 1.86-1.74 (m, 2H), 1.50-1.41 (m, 1H), 1.37 (s, 9H), 1.33 (m, 1H), 0.95 (t, J = 7.4 Hz, 3H) | 1.05 610.0 A | A |

What is claimed is:

1. A compound of Formula (I):

(I)

or a stereoisomer, a tautomer, or a pharmaceutically acceptable salt thereof, wherein:

X is independently selected from: $NR^5$, O, and S;
L is independently selected from: C=O, $CH_2$, and $CHCF_3$;
$R^1$ is independently selected from: H and $C_{1-4}$ alkyl substituted with 0-1 $R^b$;
$R^2$ is independently selected from: $C_{1-4}$ alkyl substituted with 0-1 $R^b$, and $-(CHR^8)_{0-2}-R^9$;
alternatively, $R^1$ and $R^2$, together with the nitrogen atom to which they are attached, combine to form a 5- to 10-membered heterocyclic ring consisting of carbon atoms and additional 1-3 heteroatoms selected from N, $NR^5$, O, and S, and substituted with 0-3 $R^a$;
$R^3$ and $R^4$ are independently selected from: H, $C_{1-4}$ alkyl, phenyl, and pyridyl, wherein said phenyl and pyridyl of $R^3$ and $R^4$ are substituted with 0-2 $R^a$;
alternatively, $R^3$ and $R^4$, together with the carbon atoms to which they are attached, combine to form a 5- to 10-membered fused carbocyclic ring or a 5- to 10-membered fused heterocyclic ring consisting of carbon atoms and 1-3 heteroatoms selected from N, $NR^5$, O, and S; wherein said fused carbocyclic ring and fused heterocyclic ring of $R^3$ and $R^4$ are substituted with 0-2 $R^a$;
$R^5$ is, independently at each occurrence, selected from: H and $C_{1-4}$ alkyl;
$R^6$ is independently selected from: H, halogen, $C_{1-4}$ alkyl, $C_{1-4}$ haloalkyl, $C_{1-4}$ alkoxy, and $C_{1-4}$ haloalkoxy;
$R^7$ is independently selected from: OH, $CO_2H$, $CH_2OH$, $CO_2(C_{1-4}$ alkyl), CN, CONHCN, CONHOH, CONHO ($C_{1-4}$ alkyl), $CONHCH_2CO_2H$, $CONHSO_2(C_{1-4}$ alkyl), $CONHSO_2$(4-halo-Ph), $CONHSO_2N(C_{1-4}$ alkyl)$_2$, and a 5-membered heterocyclic ring consisting of carbon atoms and 1-4 heteroatoms selected from N, $NR^5$, O, and S; wherein said heterocyclic ring of $R^7$ is substituted with 0-2 $R^d$;

$R^8$ is independently selected from: $C_{1-6}$ alkyl substituted with 0-1 $R^b$, $C_{3-6}$ cycloalkyl, phenyl, and a 5- or 6-membered heterocyclic ring consisting of carbon atoms and 1-4 heteroatoms selected from N, $NR^5$, O, and S;

$R^9$ is independently selected from: $C_{3-10}$ carbocycle, phenyl, and 5- to 6-membered heterocyclic ring consisting of carbon atoms and 1-4 heteroatoms selected from N, $NR^5$, O, and S; wherein each moiety of $R^9$ is substituted with 0-3 $R^c$;

$R^{10}$ is independently selected from: halogen and $C_{1-4}$ alkyl;

$R^a$ is, independently at each occurrence, selected from: OH, CN, halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), $C_{3-6}$ cycloalkyl, Bn, and phenyl;

$R^b$ is independently selected from: $N(C_{1-4}$ alkyl)$_2$, $C_{1-4}$ alkoxy, $C_{1-4}$ haloalkyl, phenyl, and a 5- or 6-membered heterocyclic ring consisting of carbon atoms and 1-4 heteroatoms selected from N, $NR^5$, O, and S; wherein said heterocyclic ring of $R^b$ is substituted with 0-2 $R^d$;

$R^c$ is, independently at each occurrence, selected from: OH, halogen, $C_{1-4}$ alkyl, $C_{1-4}$ alkoxy, and $C_{1-4}$ haloalkoxy; and $R^d$ is, independently at each occurrence, selected from: =O, =S, OH, halogen, $C_{1-4}$ alkyl, and $C_{1-4}$ alkoxy.

2. The compound of claim 1, having Formula (II):

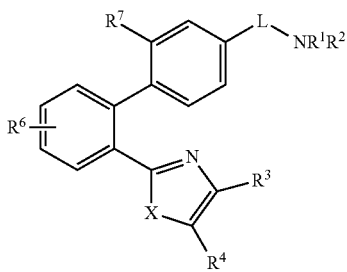

(II)

or a stereoisomer, a tautomer, or a pharmaceutically acceptable salt thereof.

3. The compound of claim 2, having Formula (III):

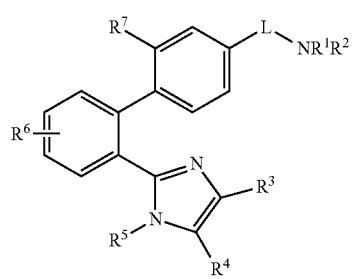

(III)

or a stereoisomer, a tautomer, or a pharmaceutically acceptable salt thereof.

4. The compound of claim 1, or a stereoisomer, a tautomer, or a pharmaceutically acceptable salt thereof, wherein:

L is C=O;

$R^1$ is independently selected from: H and methyl;

$R^2$ is —$(CHR^8)_{0-1}$—$R^9$;

alternatively, $R^1$ and $R^2$, together with the nitrogen atom to which they are attached, combine to form a 5- to 10-membered heterocyclic ring consisting of carbon atoms and additional 1-3 heteroatoms selected from N, $NR^5$, O, and S and substituted with 0-3 $R^a$;

$R^3$ and $R^4$ are independently selected from: H, $C_{1-4}$ alkyl, phenyl, and pyridyl, wherein said phenyl and pyridyl of $R^3$ and $R^4$ are substituted with 0-2 $R^a$;

alternatively, $R^3$ and $R^4$, together with the carbon atoms to which they are attached, combine to form a 5- to 10-membered fused carbocyclic ring or a 5- to 10-membered fused heterocyclic ring consisting of carbon atoms and 1-3 heteroatoms selected from N, $NR^5$, O, and S; wherein said fused carbocyclic ring and fused heterocyclic ring of $R^3$ and $R^4$ are substituted with 0-2 $R^a$;

$R^7$ is independently selected from: OH, $CO_2H$, $CH_2OH$, $CO_2(C_{1-4}$ alkyl), CN, CONHCN, CONHOH, CONHO($C_{1-4}$ alkyl), $CONHCH_2CO_2H$, $CONHSO_2(C_{1-4}$ alkyl), $CONHSO_2$(4-halo-Ph), $CONHSO_2N(C_{1-4}$ alkyl)$_2$, tetrazolyl,

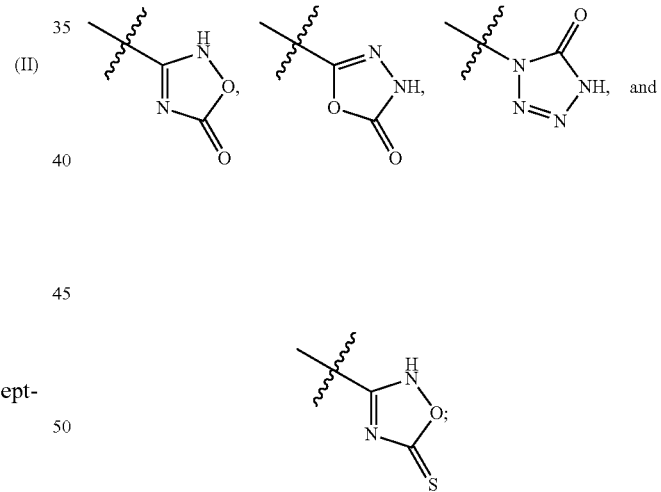

$R^8$ is independently selected from: $C_{1-6}$ alkyl substituted with 0-1 $R^b$, $C_{3-6}$ cycloalkyl, phenyl, and a 5- or 6-membered heterocyclic ring consisting of carbon atoms and 1-4 heteroatoms selected from N, $NR^5$, O, and S;

$R^9$ is independently selected from: $C_{3-10}$ cycloalkyl, phenyl, and 5- to 6-membered heteroaryl consisting of carbon atoms and 1-4 heteroatoms selected from N, $NR^5$, O, and S; wherein each moiety of $R^9$ is substituted with 0-3 $R^c$.

5. The compound of claim 4, having Formula (IV):

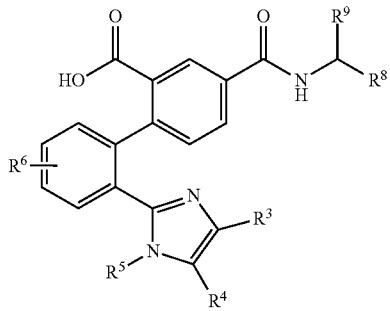
(IV)

or a stereoisomer, a tautomer, or a pharmaceutically acceptable salt.

6. The compound of claim 1, or a stereoisomer, a tautomer, or a pharmaceutically acceptable salt thereof, wherein:

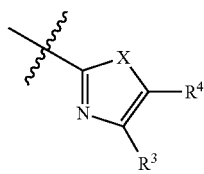

is independently selected from:

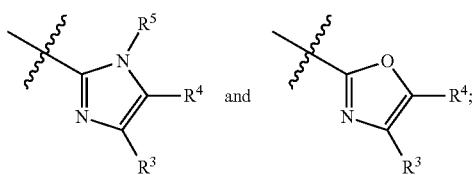

$R^3$ and $R^4$ are independently selected from: H, $C_{1-4}$ alkyl and phenyl substituted with 0-2 $R^a$.

7. The compound of claim 1, or a stereoisomer, a tautomer, or a pharmaceutically acceptable salt thereof, wherein:

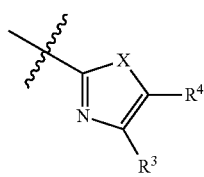

is independently selected from:

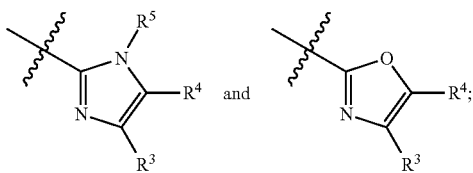

$R^3$ and $R^4$, together with the carbon atoms to which they are attached, combine to form a 5- to 10-membered fused carbocyclic ring or a 5- to 10-membered fused heterocyclic ring consisting of carbon atoms and additional 1-3 heteroatoms selected from N, $NR^5$, O, and S and wherein said fused carbocyclic ring and fused heterocyclic ring of $R^3$ and $R^4$ are substituted with 0-2 $R^a$.

8. The compound of claim 7, or a stereoisomer, a tautomer, or a pharmaceutically acceptable salt thereof, wherein:

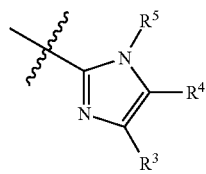

is independently selected from:

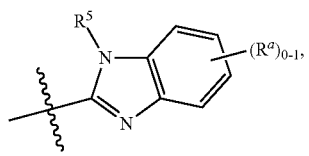

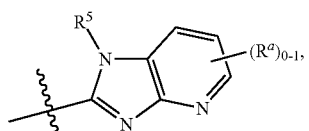

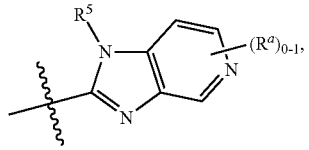

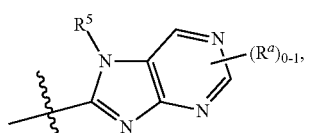

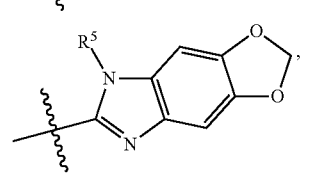

-continued

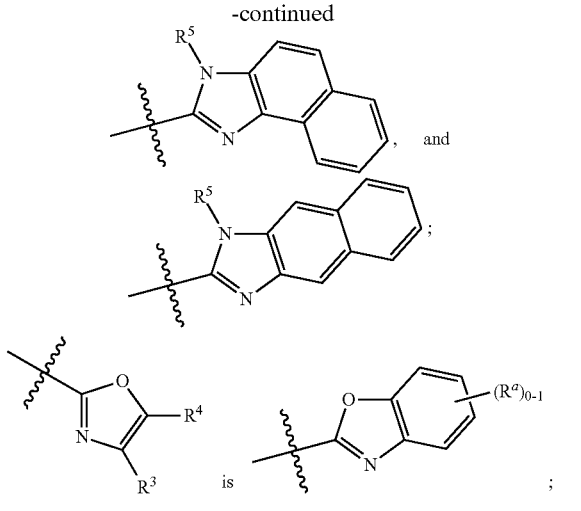

and

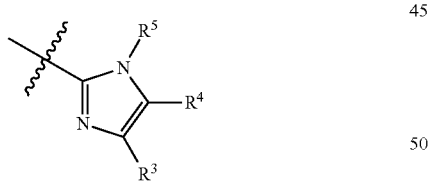

is

R[5] is, independently at each occurrence, selected from: H and $C_{1-4}$ alkyl;

R[6] is, independently at each occurrence, selected from: H, halogen, $C_{1-4}$ alkyl, $C_{1-4}$ haloalkyl, and $C_{1-4}$ alkoxy;

R[8] is independently selected from: $C_{1-6}$ alkyl substituted with 0-1 R[b] and cyclopropyl;

R[9] is independently selected from: phenyl substituted with 0-2 R[c], naphthyl substituted with 0-1 R[c] and pyridyl substituted with 0-1 R[c];

R[a] is, independently at each occurrence, selected from: OH, CN, halogen, $C_{1-4}$ alkyl, $C_{1-4}$ alkoxy, $C_{1-4}$ haloalkyl, $C_{1-4}$ haloalkoxy, $CO_2(C_{1-4}$ alkyl), and $C_{3-6}$ cycloalkyl;

R[b] is independently selected from: $C_{1-4}$ alkoxy, $C_{1-4}$ haloalkyl and morpholinyl; and R[c] is, independently at each occurrence, selected from: OH, halogen, $C_{1-4}$ alkyl, and $C_{1-4}$ alkoxy.

9. The compound of claim 8, or a stereoisomer, a tautomer, or a pharmaceutically acceptable salt thereof, wherein:

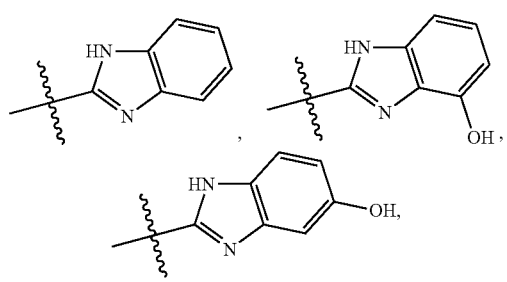

is independently selected from:

-continued

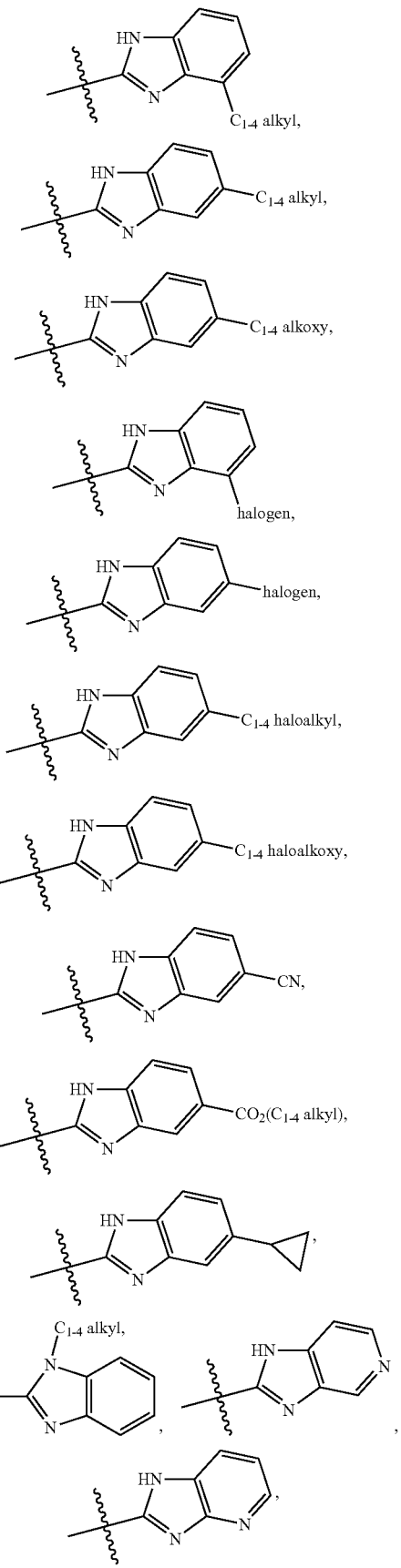

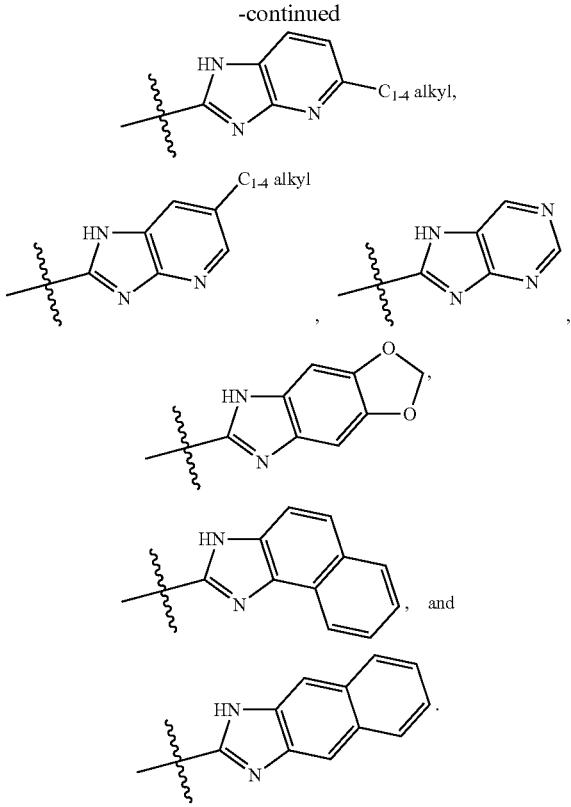

10. The compound of claim 4, or a stereoisomer, a tautomer, or a pharmaceutically acceptable salt thereof, wherein:

$R^9$ is independently selected from: cyclopentyl, cyclohexyl, cycloheptyl, phenyl, thiazolyl and pyridyl, wherein each moiety of $R^9$ is substituted with 0-1 $R^c$; and $R^c$ is, independently at each occurrence, selected from: OH, halogen, $C_{1-4}$ alkyl, $C_{1-4}$ alkoxy, and $C_{1-4}$ haloalkoxy.

11. The compound of claim 1, wherein $R^1$ and $R^2$, together with the nitrogen atom to which they are attached, combine to form;

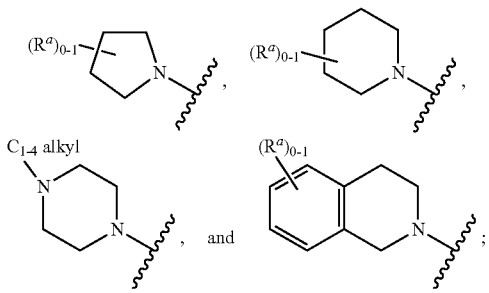

and $R^a$ is, independently at each occurrence, selected from: OH, $C_{1-4}$ alkyl, $C_{1-4}$ alkoxy, $C_{1-4}$ haloalkyl, $C_{1-4}$ haloalkoxy, $CO_2(C_{1-4}$ alkyl), $C_{3-6}$ cycloalkyl, Bn, and phenyl.

12. A compound or a stereoisomer, a tautomer, a pharmaceutically acceptable salt, a solvate or a hydrate thereof, wherein the compound is selected from:

5'-chloro-2'-(5-methoxy-1H-1,3-benzodiazol-2-yl)-4-{[(1R)-1-phenylbutyl]carbamoyl}-[1,1'-biphenyl]-2-carboxylic acid;

2'-(1H-1,3-benzodiazol-2-yl)-5'-chloro-4-{[(1R)-1-phenylbutyl]carbamoyl}-[1,1'-biphenyl]-2-carboxylic acid;

5'-chloro-2'-(5-hydroxy-1H-1,3-benzodiazol-2-yl)-4-{[(1R)-1-phenylbutyl]carbamoyl}-[1,1'-biphenyl]-2-carboxylic acid;

5'-chloro-2'-(5-phenyl-1H-imidazol-2-yl)-4-{[(1R)-1-phenylbutyl]carbamoyl}-[1,1'-biphenyl]-2-carboxylic acid;

2'-(1H-1,3-benzodiazol-2-yl)-5'-chloro-4-{[(1S)-2-(morpholin-4-yl)-1-phenylethyl]carbamoyl}-[1,1'-biphenyl]-2-carboxylic acid;

2'-(1H-1,3-benzodiazol-2-yl)-5'-chloro-N2-cyano-N4-[(1R)-1-phenylbutyl]-[1,1'-biphenyl]-2,4-dicarboxamide;

2'-(1H-1,3-benzodiazol-2-yl)-5'-chloro-2-(hydroxymethyl)-N-[(1R)-1-phenylbutyl]-[1,1'-biphenyl]-4-carboxamide;

5'-chloro-2'-(5-methoxy-1H-1,3-benzodiazol-2-yl)-2-(5-oxo-2,5-dihydro-1,2,4-oxadiazol-3-yl)-N-[(1R)-1-phenylbutyl]-[1,1'-biphenyl]-4-carboxamide;

2'-(1H-1,3-benzodiazol-2-yl)-5'-chloro-2-(5-oxo-4,5-dihydro-1,3,4-oxadiazol-2-yl)-N-[(1R)-1-phenylbutyl]-[1,1'-biphenyl]-4-carboxamide;

5'-chloro-2'-(5-methoxy-1H-1,3-benzodiazol-2-yl)-N-[(1R)-1-phenylbutyl]-2-(5-sulfanylidene-4,5-dihydro-1,2,4-oxadiazol-3-yl)-[1,1'-biphenyl]-4-carboxamide;

2'-(1H-1,3-benzodiazol-2-yl)-5'-chloro-5-methyl-4-{[(1R)-1-phenylbutyl]carbamoyl}-[1,1'-biphenyl]-2-carboxylic acid;

5'-chloro-4-{[(1 S)-2-methoxy-1-phenylethyl]carbamoyl}-2'-(5-methoxy-1H-1,3-benzodiazol-2-yl)-[1,1'-biphenyl]-2-carboxylic acid;

2'-(5-bromo-1H-1,3-benzodiazol-2-yl)-5'-chloro-4-{[(1R)-1-phenylbutyl]carbamoyl}-[1,1'-biphenyl]-2-carboxylic acid;

5'-chloro-2'-(5-methyl-1H-1,3-benzodiazol-2-yl)-4-{[(1R)-1-phenylbutyl]carbamoyl}-[1,1'-biphenyl]-2-carboxylic acid;

5'-chloro-2'-(5-cyclopropyl-1H-1,3-benzodiazol-2-yl)-4-{[(1R)-1-phenylbutyl]carbamoyl}-[1,1'-biphenyl]-2-carboxylic acid;

5'-chloro-4-{[(1R)-1-phenylbutyl]carbamoyl}-2'-[5-(2,2,2-trifluoroethyl)-1H-1,3-benzodiazol-2-yl]-[1,1'-biphenyl]-2-carboxylic acid;

5'-chloro-2'-(4-fluoro-1H-1,3-benzodiazol-2-yl)-4-{[(1R)-1-phenylbutyl]carbamoyl}-[1,1'-biphenyl]-2-carboxylic acid;

5'-chloro-4-{[(1R)-1-phenylbutyl]carbamoyl}-2'-[5-(trifluoromethyl)-1H-1,3-benzodiazol-2-yl]-[1,1'-biphenyl]-2-carboxylic acid;

2'-(5-tert-butyl-1H-1,3-benzodiazol-2-yl)-5'-chloro-4-{[(1R)-1-phenylbutyl]carbamoyl}-[1,1'-biphenyl]-2-carboxylic acid;

5'-chloro-2'-(4-hydroxy-1H-1,3-benzodiazol-2-yl)-4-{[(1R)-1-phenylbutyl]carbamoyl}-[1,1'-biphenyl]-2-carboxylic acid;

5'-chloro-2'[5-(methoxycarbonyl)-1H-1,3-benzodiazol-2-yl]-4-{[(1R)-1-phenylbutyl]carbamoyl}-[1,1'-biphenyl]-2-carboxylic acid;

5'-chloro-4-{[(1R)-1-phenylbutyl]carbamoyl}-2'-[5-(trifluoromethoxy)-1H-1,3-benzodiazol-2-yl]-[1,1'-biphenyl]-2-carboxylic acid;

5'-chloro-2'-{6-methyl-1H-imidazo[4,5-b]pyridin-2-yl}-4-{[(1R)-1-phenylbutyl]carbamoyl}-[1,1'-biphenyl]-2-carboxylic acid;

5'-chloro-2'-{1H-imidazo[4,5-c]pyridin-2-yl}-4-{[(1R)-1-phenylbutyl]carbamoyl}-[1,1'-biphenyl]-2-carboxylic acid;

5'-chloro-2'-{3H-naphtho[1,2-d]imidazol-2-yl}-4-{[(1R)-1-phenylbutyl]carbamoyl}-[1,1'-biphenyl]-2-carboxylic acid;

5'-chloro-2'-{4,6-dioxa-10,12-diazatricyclo[7.3.0.0$^{3,7}$]dodeca-1(9),2,7,10-tetraen-11-yl}-4-{[(1R)-1-phenylbutyl]carbamoyl}-[1,1'-biphenyl]-2-carboxylic acid;

5'-chloro-2'-{1H-naphtho[2,3-d]imidazol-2-yl}-4-{[(1R)-1-phenylbutyl]carbamoyl}-[1,1'-biphenyl]-2-carboxylic acid;

5'-chloro-2'-(5-cyano-1H-1,3-benzodiazol-2-yl)-4-{[(1R)-1-phenylbutyl]carbamoyl}-[1,1'-biphenyl]-2-carboxylic acid;

5'-chloro-4-{[(1R)-1-phenylbutyl]carbamoyl}-2'-(7H-purin-8-yl)-[1,1'-biphenyl]-2-carboxylic acid;

5'-chloro-2'-{5-methyl-1H-imidazo[4,5-b]pyridin-2-yl}-4-{[(1R)-1-phenylbutyl]carbamoyl}-[1,1'-biphenyl]-2-carboxylic acid;

5'-chloro-2'-{1H-imidazo[4,5-b]pyridin-2-yl}-4-{[(1R)-1-phenylbutyl]carbamoyl}-[1,1'-biphenyl]-2-carboxylic acid;

2'-(1H-1,3-benzodiazol-2-yl)-5'-methyl-4-{[(1R)-1-phenylbutyl]carbamoyl}-[1,1'-biphenyl]-2-carboxylic acid;

2'-(1H-1,3-benzodiazol-2-yl)-5'-fluoro-4-{[(1R)-1-phenylbutyl]carbamoyl}-[1,1'-biphenyl]-2-carboxylic acid;

2'-(1H-1,3-benzodiazol-2-yl)-4'-fluoro-4-{[(1R)-1-phenylbutyl]carbamoyl}-[1,1'-biphenyl]-2-carboxylic acid;

2'-(5-methoxy-1H-1,3-benzodiazol-2-yl)-5'-methyl-4-{[(1R)-1-phenylbutyl]carbamoyl}-[1,1'-biphenyl]-2-carboxylic acid;

5'-fluoro-2'-(5-methoxy-1H-1,3-benzodiazol-2-yl)-4-{[(1R)-1-phenylbutyl]carbamoyl}-[1,1'-biphenyl]-2-carboxylic acid;

4'-fluoro-2'-(5-methoxy-1H-1,3-benzodiazol-2-yl)-4-{[(1R)-1-phenylbutyl]carbamoyl}-[1,1'-biphenyl]-2-carboxylic acid;

2'-(5-tert-butyl-1H-1,3-benzodiazol-2-yl)-5'-methyl-4-{[(1R)-1-phenylbutyl]carbamoyl}-[1,1'-biphenyl]-2-carboxylic acid;

2'-(5-tert-butyl-1H-1,3-benzodiazol-2-yl)-5'-fluoro-4-{[(1R)-1-phenylbutyl]carbamoyl}-[1,1'-biphenyl]-2-carboxylic acid;

2'-(5-tert-butyl-1H-1,3-benzodiazol-2-yl)-4'-fluoro-4-{[(1R)-1-phenylbutyl]carbamoyl}-[1,1'-biphenyl]-2-carboxylic acid;

2'-(1H-1,3-benzodiazol-2-yl)-5'-chloro-N2-methoxy-N4-[(1R)-1-phenylbutyl]-[1,1'-biphenyl]-2,4-dicarboxamide;

2'-(1H-1,3-benzodiazol-2-yl)-5'-chloro-N2-hydroxy-N4-[(1R)-1-phenylbutyl]-[1,1'-biphenyl]-2,4-dicarboxamide;

methyl 2'-(1H-1,3-benzodiazol-2-yl)-5'-chloro-4-{[(1R)-1-phenylbutyl]carbamoyl}-[1,1'-biphenyl]-2-carboxylate;

2'-(1H-1,3-benzodiazol-2-yl)-5'-chloro-N2-methanesulfonyl-N4-[(1R)-1-phenylbutyl]-[1,1'-biphenyl]-2,4-dicarboxamide;

2'-(1H-1,3-benzodiazol-2-yl)-5'-chloro-N2-(4-chlorobenzenesulfonyl)-N4-[(1R)-1-phenylbutyl]-[1,1'-biphenyl]-2,4-dicarboxamide;

2'-(1H-1,3-benzodiazol-2-yl)-5'-chloro-N2-(dimethyl sulfamoyl)-N4-[(1R)-1-phenylbutyl]-[1,1'-biphenyl]-2,4-dicarboxamide;

5'-chloro-2'-(5-chloro-1H-1,3-benzodiazol-2-yl)-4-{[(1R)-1-phenylbutyl]carbamoyl}-[1,1'-biphenyl]-2-carboxylic acid;

5'-chloro-4-{[(1R)-1-phenylbutyl]carbamoyl}-2'[5-(propan-2-yl)-1H-1,3-benzodiazol-2-yl]-[1'-biphenyl]-2-carboxylic acid;

5'-chloro-2'-(4-methyl-1H-1,3-benzodiazol-2-yl)-4-{[(1R)-1-phenylbutyl]carbamoyl}-[1,1'-biphenyl]-2-carboxylic acid;

5'-chloro-2'-(4,5-dimethyl-1H-imidazol-2-yl)-4-{[(1R)-1-phenylbutyl]carbamoyl}-[1,1'-biphenyl]-2-carboxylic acid;

2'-(1H-1,3-benzodiazol-2-yl)-4-{[(1R)-1-phenylbutyl]carbamoyl}-5'-(trifluoromethyl)-[1,1'-biphenyl]-2-carboxylic acid;

2'-(1H-1,3-benzodiazol-2-yl)-4-{[(1R)-1-phenylbutyl]carbamoyl}-[1'-biphenyl]-2-carboxylic acid;

2'-(1H-1,3-benzodiazol-2-yl)-5'-methoxy-4-{[(1R)-1-phenylbutyl]carbamoyl}-[1,1'-biphenyl]-2-carboxylic acid;

2'-(1H-1,3-benzodiazol-2-yl)-4'-chloro-4-{[(1R)-1-phenylbutyl]carbamoyl}-[1'-biphenyl]-2-carboxylic acid;

2'-(1H-1,3-benzodiazol-2-yl)-3'-fluoro-4-{[(1R)-1-phenylbutyl]carbamoyl}-[1,1'-biphenyl]-2-carboxylic acid;

2'-(5-methoxy-1H-1,3-benzodiazol-2-yl)-4-{[(1R)-1-phenylbutyl]carbamoyl}-5'-(trifluoromethyl)-[1,1'-biphenyl]-2-carboxylic acid;

4'-chloro-2'-(5-methoxy-1H-1,3-benzodiazol-2-yl)-4-{[(1R)-1-phenylbutyl]carbamoyl}-[1,1'-biphenyl]-2-carboxylic acid;

2'-(5-methoxy-1H-1,3-benzodiazol-2-yl)-4-{[(1R)-1-phenylbutyl]carbamoyl}-[1,1'-biphenyl]-2-carboxylic acid;

5'-methoxy-2'-(5-methoxy-1H-1,3-benzodiazol-2-yl)-4-{[(1R)-1-phenylbutyl]carbamoyl}-[1'-biphenyl]-2-carboxylic acid;

2'-(5-tert-butyl-1H-1,3-benzodiazol-2-yl)-4-{[(1R)-1-phenylbutyl]carbamoyl}-5'-(trifluoromethyl)-[1,1'-biphenyl]-2-carboxylic acid;

2'-(5-tert-butyl-1H-1,3-benzodiazol-2-yl)-5'-methoxy-4-{[(1R)-1-phenylbutyl]carbamoyl}-[1,1'-biphenyl]-2-carboxylic acid;

2'-(5-tert-butyl-1H-1,3-benzodiazol-2-yl)-4-{[(1R)-1-phenylbutyl]carbamoyl}-[1,1'-biphenyl]-2-carboxylic acid;

2'-(5-tert-butyl-1H-1,3-benzodiazol-2-yl)-4'-chloro-4-{[(1R)-1-phenylbutyl]carbamoyl}-[1,1'-biphenyl]-2-carboxylic acid;

4-{[(1 S)-2-methoxy-1-phenylethyl]carbamoyl}-2'-(5-methoxy-1H-1,3-benzodiazol-2-yl)-[1,1'-biphenyl]-2-carboxylic acid;

2'-(5-tert-butyl-1H-1,3-benzodiazol-2-yl)-4-{[(1 S)-2-methoxy-1-phenylethyl]carbamoyl}-[1,1'-biphenyl]-2-carboxylic acid;

2'-(1H-1,3-benzodiazol-2-yl)-4-{[(1 S)-2-methoxy-1-phenylethyl]carbamoyl}-[1,1'-biphenyl]-2-carboxylic acid;

5'-chloro-2'-(5-methoxy-1H-1,3-benzodiazol-2-yl)-5-methyl-4-{[(1R)-1-phenylbutyl]carbamoyl}-[1,1'-biphenyl]-2-carboxylic acid;

2'-(5-tert-butyl-1H-1,3-benzodiazol-2-yl)-5'-chloro-5-methyl-4-{[(1R)-1-phenylbutyl]carbamoyl}-[1,1'-biphenyl]-2-carboxylic acid;

2'-(1H-1,3-benzodiazol-2-yl)-5'-chloro-4-{[(1 S)-2-methoxy-1-phenylethyl]carbamoyl}-[1,1'-biphenyl]-2-carboxylic acid;

2'-(1H-1,3-benzodiazol-2-yl)-5'-chloro-4-{[(1R)-1-(2-methoxyphenyl)ethyl]carbamoyl}-[1,1'-biphenyl]-2-carboxylic acid;

2'-(1H-1,3-benzodiazol-2-yl)-5'-chloro-4-{[(1S)-1-phenylbutyl]carbamoyl}-[1,1'-biphenyl]-2-carboxylic acid;

2'-(1H-1,3-benzodiazol-2-yl)-5'-chloro-4-{[(1R)-1-(3-chlorophenyl)ethyl]carbamoyl}-[1,1'-biphenyl]-2-carboxylic acid;

2'-(1H-1,3-benzodiazol-2-yl)-5'-chloro-4-{[(1R)-1-(naphthalen-1-yl)ethyl]carbamoyl}-[1,1'-biphenyl]-2-carboxylic acid;

2'-(1H-1,3-benzodiazol-2-yl)-5'-chloro-4-{[(1R)-1-(3-methoxyphenyl)ethyl]carbamoyl}-[1,1'-biphenyl]-2-carboxylic acid;

2'-(1H-1,3-benzodiazol-2-yl)-5'-chloro-4-{[(1R)-1-(2-chlorophenyl)ethyl]carbamoyl}-[1,1'-biphenyl]-2-carboxylic acid;

2'-(1H-1,3-benzodiazol-2-yl)-5'-chloro-4-{[(1R)-1-phenylethyl]carbamoyl}-[1,1'-biphenyl]-2-carboxylic acid;

2'-(1H-1,3-benzodiazol-2-yl)-5'-chloro-4-{[(1 S)-2-(dimethylamino)-1-phenylethyl]carbamoyl}-[1,1'-biphenyl]-2-carboxylic acid;

2'-(1H-1,3-benzodiazol-2-yl)-5'-chloro-4-{[(2 S)-1-methoxy-3-phenylpropan-2-yl]carbamoyl}-[1,1'-biphenyl]-2-carboxylic acid;

5'-chloro-2'-(5-chloro-1H-1,3-benzodiazol-2-yl)-4-{[(1 S)-2-methoxy-1-phenylethyl]carbamoyl}-[1,1'-biphenyl]-2-carboxylic acid;

2'-(5-tert-butyl-1H-1,3-benzodiazol-2-yl)-5'-chloro-4-{[(1 S)-2-methoxy-1-phenylethyl]carbamoyl}-[1,1'-biphenyl]-2-carboxylic acid;

(S)-2'-(1H-1,3-benzodiazol-2-yl)-6'-chloro-4-{[(1R)-1-phenylbutyl]carbamoyl}-[1,1'-biphenyl]-2-carboxylic acid;

(S)-2'-(1H-1,3-benzodiazol-2-yl)-6'-chloro-4-{[(1 S)-2-methoxy-1-phenylethyl] carbamoyl}-[1,1'-biphenyl]-2-carboxylic acid;

(S)-methyl 2'-chloro-6'-(6-fluoro-5-methoxy-1H-1,3-benzodiazol-2-yl)-4-{[(1R)-1-phenylbutyl]carbamoyl}-[1,1'-biphenyl]-2-carboxylate;

(S)-2'-chloro-6'-(6-fluoro-5-methoxy-1H-1,3-benzodiazol-2-yl)-4-{[(1R)-1-phenylbutyl]carbamoyl}-[1,1'-biphenyl]-2-carboxylic acid;

(S)-2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylic acid;

(S)-methyl 2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylate;

(S)-2'-chloro-6'-(6-fluoro-5-hydroxy-1H-1,3-benzodiazol-2-yl)-4-{[(1R)-1-phenylbutyl]carbamoyl}-[1,1'-biphenyl]-2-carboxylic acid;

(S)-2'-chloro-6'-(6,7-difluoro-1H-1,3-benzodiazol-2-yl)-4-{[(1R)-1-phenylbutyl]carbamoyl}-[1,1'-biphenyl]-2-carboxylic acid;

(S)-2'-chloro-6'-(5,6-difluoro-1H-1,3-benzodiazol-2-yl)-4-{[(1R)-1-phenylbutyl]carbamoyl}-[1,1'-biphenyl]-2-carboxylic acid;

(S)-2'-chloro-6'-(5,7-difluoro-1H-1,3-benzodiazol-2-yl)-4-{[(1R)-1-phenylbutyl]carbamoyl}-[1,1'-biphenyl]-2-carboxylic acid;

(S)-2'-chloro-6'-(5-chloro-6-methyl-1H-1,3-benzodiazol-2-yl)-4-{[(1R)-1-phenylbutyl]carbamoyl}-[1,1'-biphenyl]-2-carboxylic acid;

(S)-2'-chloro-6'-(7-hydroxy-1H-1,3-benzodiazol-2-yl)-4-{[(1R)-1-phenylbutyl]carbamoyl}-[1,1'-biphenyl]-2-carboxylic acid;

(S)-2'-chloro-6'-(5,6-dimethoxy-1H-1,3-benzodiazol-2-yl)-4-{[(1R)-1-phenylbutyl]carbamoyl}-[1,1'-biphenyl]-2-carboxylic acid;

(S)-2'-chloro-6'-(5,7-dichloro-1H-1,3-benzodiazol-2-yl)-4-{[(1R)-1-phenylbutyl]carbamoyl}-[1,1'-biphenyl]-2-carboxylic acid;

(S)-2'-chloro-6'-(5-chloro-7-methyl-1H-1,3-benzodiazol-2-yl)-4-{[(1R)-1-phenylbutyl]carbamoyl}-[1,1'-biphenyl]-2-carboxylic acid;

(S)-2'-chloro-6'-(5,7-difluoro-1H-1,3-benzodiazol-2-yl)-4-{[(1R)-1-phenylbutyl]carbamoyl}-[1,1'-biphenyl]-2-carboxylic acid;

(S)-2'-chloro-6'-(5-chloro-6-methyl-1H-1,3-benzodiazol-2-yl)-4-{[(1R)-1-phenylbutyl]carbamoyl}-[1,1'-biphenyl]-2-carboxylic acid;

(S)-2'-chloro-6'-(4,7-dimethoxy-1H-1,3-benzodiazol-2-yl)-4-{[(1R)-1-phenylbutyl]carbamoyl}-[1,1'-biphenyl]-2-carboxylic acid;

(S)-2'-chloro-6'-(7-hydroxy-1H-1,3-benzodiazol-2-yl)-4-{[(1R)-1-phenylbutyl]carbamoyl}-[1,1'-biphenyl]-2-carboxylic acid;

(S)-2'-chloro-4-{[(1R)-1-phenylbutyl]carbamoyl}-6'-[5-(2,3,6-trifluorophenyl)-1H-imidazol-2-yl]-[1,1'-biphenyl]-2-carboxylic acid;

(S)-2'-chloro-4-{[(1R)-1-phenylbutyl]carbamoyl}-6'-[5-(pyridin-3-yl)-1H-imidazol-2-yl]-[1,1'-biphenyl]-2-carboxylic acid;

(S)-2'-chloro-6'-(5-phenyl-1H-imidazol-2-yl)-4-{[(1R)-1-phenylbutyl]carbamoyl}-[1,1'-biphenyl]-2-carboxylic acid;

(S)-2'-chloro-6'-[5-(3-methoxyphenyl)-1H-imidazol-2-yl]-4-{[(1R)-1-phenylbutyl]carbamoyl}-[1,1'-biphenyl]-2-carboxylic acid;

(S)-2'-chloro-6'-[5-(3-fluoro-4-methylphenyl)-1H-imidazol-2-yl]-4-{[(1R)-1-phenylbutyl]carbamoyl}-[1,1'-biphenyl]-2-carboxylic acid;

(S)-2'-chloro-6'-[5-(4-methoxyphenyl)-1H-imidazol-2-yl]-4-{[(1R)-1-phenylbutyl]carbamoyl}-[1,1'-biphenyl]-2-carboxylic acid;

(S)-2'-chloro-6'-(4-methyl-5-phenyl-1H-imidazol-2-yl)-4-{[(1R)-1-phenylbutyl]carbamoyl}-[1,1'-biphenyl]-2-carboxylic acid;

(S)-2'-chloro-4-{[(1R)-1-phenylbutyl]carbamoyl}-6'-[5-(pyridin-4-yl)-1H-imidazol-2-yl]-[1,1'-biphenyl]-2-carboxylic acid;

(S)-2'-chloro-6'-(5-chloro-6-fluoro-1H-1,3-benzodiazol-2-yl)-4-{[(1R)-1-phenylbutyl]carbamoyl}-[1,1'-biphenyl]-2-carboxylic acid;

(S)-2'-chloro-6'-(5-fluoro-6-methoxy-1H-1,3-benzodiazol-2-yl)-4-[(propan-2-yl)carbamoyl]-[1,1'-biphenyl]-2-carboxylic acid;

(S)-2'-chloro-6'-(5-fluoro-6-methoxy-1H-1,3-benzodiazol-2-yl)-4-(4-phenylpiperidine-1-carbonyl)-[1,1'-biphenyl]-2-carboxylic acid;

(S)-2'-chloro-6'-(5-fluoro-6-methoxy-1H-1,3-benzodiazol-2-yl)-4-[(2-methoxyethyl)carbamoyl]-[1,1'-biphenyl]-2-carboxylic acid;
(S)-2'-chloro-6'-(5-fluoro-6-methoxy-1H-1,3-benzodiazol-2-yl)-4-[(2-phenylethyl)carbamoyl]-[1,1'-biphenyl]-2-carboxylic acid;
(S)-2'-chloro-6'-(5-fluoro-6-methoxy-1H-1,3-benzodiazol-2-yl)-4-(1,2,3,4-tetrahydroisoquinoline-2-carbonyl)-[1,1'-biphenyl]-2-carboxylic acid;
(S)-2'-chloro-6'-(5-fluoro-6-methoxy-1H-1,3-benzodiazol-2-yl)-4-[(3-methylbutyl)carbamoyl]-[1,1'-biphenyl]-2-carboxylic acid;
(S)-2'-chloro-6'-(5-fluoro-6-methoxy-1H-1,3-benzodiazol-2-yl)-4-{[(4-methoxyphenyl)methyl]carbamoyl}-[1,1'-biphenyl]-2-carboxylic acid;
(S)-2'-chloro-6'-(5-fluoro-6-methoxy-1H-1,3-benzodiazol-2-yl)-4-[(3-methoxy-3-oxopropyl)carbamoyl]-[1,1'-biphenyl]-2-carboxylic acid;
(S)-2'-chloro-4-[(2,2-diphenylethyl)carbamoyl]-6'-(5-fluoro-6-methoxy-1H-1,3-benzodiazol-2-yl)-[1,1'-biphenyl]-2-carboxylic acid;
(S)-2'-chloro-6'-(5-fluoro-6-methoxy-1H-1,3-benzodiazol-2-yl)-4-(4-methylpiperazine-1-carbonyl)-[1,1'-biphenyl]-2-carboxylic acid;
(S)-4-(benzylcarbamoyl)-2'-chloro-6'-(5-fluoro-6-methoxy-1H-1,3-benzodiazol-2-yl)-[1,1'-biphenyl]-2-carboxylic acid;
(S)-2'-chloro-4-{[(4-chlorophenyl)methyl]-[carbamoyl}-6'-[5-fluoro-6-methoxy-1H-1,3-benzodiazol-2-yl)-[1,1'-biphenyl]-2-carboxylic acid;
(S)-2'-chloro-6'-(5-fluoro-6-methoxy-1H-1,3-benzodiazol-2-yl)-4-[(2-methylpropyl)carbamoyl]-[1,1'-biphenyl]-2-carboxylic acid;
(S)-2'-chloro-4-{[3-(dimethylamino)propyl]carbamoyl}-6'-(5-fluoro-6-methoxy-1H-1,3-benzodiazol-2-yl)-[1,1'-biphenyl]-2-carboxylic acid;
(S)-2'-chloro-6'-(5-fluoro-6-methoxy-1H-1,3-benzodiazol-2-yl)-4-(4-hydroxypiperidine-1-carbonyl)-[1,1'-biphenyl]-2-carboxylic acid;
(S)-2'-chloro-6'-(5-fluoro-6-methoxy-1H-1,3-benzodiazol-2-yl)-4-(pyrrolidine-1-carbonyl)-[1,1'-biphenyl]-2-carboxylic acid;
(S)-2'-chloro-6'-(5-fluoro-6-methoxy-1H-1,3-benzodiazol-2-yl)-4-[(4-methoxyphenyl)carbamoyl]-[1,1'-biphenyl]-2-carboxylic acid;
(S)-4-(4-benzylpiperidine-1-carbonyl)-2'-chloro-6'-(5-fluoro-6-methoxy-1H-1,3-benzodiazol-2-yl)-[1,1'-biphenyl]-2-carboxylic acid;
2'-chloro-6'-(6-fluoro-5-methoxy-1H-1,3-benzodiazol-2-yl)-N2-methoxy-N4-[(1R)-1-phenylbutyl]-[1,1'-biphenyl]-2,4-dicarboxamide;
(S)-methyl 2'-chloro-6'-(5-hydroxy-1H-1,3-benzodiazol-2-yl)-4-{[(1R)-1-phenylbutyl]carbamoyl}-[1,1'-biphenyl]-2-carboxylate;
2'-(1H-1,3-benzodiazol-2-yl)-6'-chloro-2-(5-oxo-4,5-dihydro-1,3,4-oxadiazol-2-yl)-N-[(1R)-1-phenylbutyl]-[1,1'-biphenyl]-4-carboxamide;
2'-chloro-6'-(6-fluoro-5-methoxy-1H-1,3-benzodiazol-2-yl)-2-(5-oxo-4,5-dihydro-1,3,4-oxadiazol-2-yl)-N-[(1R)-1-phenylbutyl]-[1,1'-biphenyl]-4-carboxamide;
(S)-2'-chloro-6'-(6-fluoro-5-methoxy-1H-1,3-benzodiazol-2-yl)-2-(hydroxymethyl)-N-(1-phenylbutyl)-[1,1'-biphenyl]-4-carboxamide;
(S)-2'-chloro-6'-(5-methoxy-1H-1,3-benzodiazol-2-yl)-4-{[(1R)-1-phenylbutyl]carbamoyl}-[1,1'-biphenyl]-2-carboxylic acid;
(S)-2'-chloro-6'-{1H-imidazo[4,5-c]pyridin-2-yl}-4-{[(1R)-1-phenylbutyl]carbamoyl}-[1,1'-biphenyl]-2-carboxylic acid;
(S)-2'-[5-(acetyloxy)-1H-1,3-benzodiazol-2-yl]-6'-chloro-4-{[(1R)-1-phenylbutyl]carbamoyl}-[1,1'-biphenyl]-2-carboxylic acid;
(S)-2'-chloro-6'-(5-hydroxy-1H-1,3-benzodiazol-2-yl)-4-{[(1R)-1-phenylbutyl]carbamoyl}-[1,1'-biphenyl]-2-carboxylic acid;
(S)-2'-[5-(acetyloxy)-1H-1,3-benzodiazol-2-yl]-6'-chloro-4-{[(1R)-1-phenylbutyl]carbamoyl}-[1,1'-biphenyl]-2-carboxylic acid;
2'-methyl-6'-(1-methyl-1H-1,3-benzodiazol-2-yl)-4-{[(1R)-1-phenylbutyl]carbamoyl}-[1,1'-biphenyl]-2-carboxylic acid;
5'-chloro-4-{[(1 S)-2-methoxy-1-phenylethyl]carbamoyl}-2'-(1-methyl-1H-1,3-benzodiazol-2-yl)-[1,1'-biphenyl]-2-carboxylic acid;
2'-(1H-1,3-benzodiazol-2-yl)-6'-methyl-4-{[(1R)-1-phenylbutyl]carbamoyl}-[1,1'-biphenyl]-2-carboxylic acid;
2'-(1H-1,3-benzodiazol-2-yl)-6'-fluoro-4-{[(1R)-1-phenylbutyl]carbamoyl}-[1,1'-biphenyl]-2-carboxylic acid;
(R)-2'-(1H-1,3-benzodiazol-2-yl)-6'-chloro-4-{[(1R)-1-phenylbutyl]carbamoyl}-[1,1'-biphenyl]-2-carboxylic acid;
2'-(5-methoxy-1H-1,3-benzodiazol-2-yl)-6'-methyl-4-{[(1R)-1-phenylbutyl]carbamoyl}-[1,1'-biphenyl]-2-carboxylic acid;
2'-fluoro-6'-(5-methoxy-1H-1,3-benzodiazol-2-yl)-4-{[(1R)-1-phenylbutyl]carbamoyl}-[1,1'-biphenyl]-2-carboxylic acid;
2'-(5-tert-butyl-1H-1,3-benzodiazol-2-yl)-6'-methyl-4-{[(1R)-1-phenylbutyl]carbamoyl}-[1,1'-biphenyl]-2-carboxylic acid;
2'-(5-tert-butyl-1H-1,3-benzodiazol-2-yl)-6'-fluoro-4-{[(1R)-1-phenylbutyl]carbamoyl}-[1,1'-biphenyl]-2-carboxylic acid;
(S)-2'-methyl-4-{[(1R)-1-phenylbutyl]carbamoyl}-6'-[5-(trifluoromethyl)-1H-1,3-benzodiazol-2-yl]-[1,1'-biphenyl]-2-carboxylic acid;
(R)-2'-methyl-4-{[(1R)-1-phenylbutyl]carbamoyl}-6'-[5-(trifluoromethyl)-1H-1,3-benzodiazol-2-yl]-[1,1'-biphenyl]-2-carboxylic acid;
2'-(4-hydroxy-1H-1,3-benzodiazol-2-yl)-6'-methyl-4-{[(1R)-1-phenylbutyl]carbamoyl}-[1,1'-biphenyl]-2-carboxylic acid;
2'-{1H-imidazo[4,5-c]pyridin-2-yl}-6'-methyl-4-{[(1R)-1-phenylbutyl]carbamoyl}-[1,1'-biphenyl]-2-carboxylic acid;
(S)-2'-(1H-1,3-benzodiazol-2-yl)-6'-chloro-4-{[(1 S)-2-methoxy-1-phenylethyl] carbamoyl}-[1,1'-biphenyl]-2-carboxylic acid;
(S)-2'-(1H-1,3-benzodiazol-2-yl)-6'-chloro-4-{[(1R)-3-hydroxy-3-methyl-1-phenylbutyl]carbamoyl}-[1,1'-biphenyl]-2-carboxylic acid;
(S)-2'-(1H-1,3-benzodiazol-2-yl)-6'-chloro-4-{[(1 S)-1-phenylbutyl]carbamoyl}-[1,1'-biphenyl]-2-carboxylic acid;
(S)-2'-(1H-1,3-benzodiazol-2-yl)-6'-chloro-4-[(heptan-4-yl)carbamoyl]-[1,1'-biphenyl]-2-carboxylic acid;
(S)-2'-chloro-6'-(6-fluoro-5-methoxy-1H-1,3-benzodiazol-2-yl)-4-{[(1 S)-2-methoxy-1-phenylethyl]carbamoyl}-[1,1'-biphenyl]-2-carboxylic acid;

(S)-2'-chloro-6'-(5-hydroxy-1H-1,3-benzodiazol-2-yl)-4-{[(1R)-1-phenylbutyl]carbamoyl}-[1,1'-biphenyl]-2-carboxylic acid;

(S)-2'-(1H-1,3-benzodiazol-2-yl)-6'-chloro-4-{[(1 S)-2-(morpholin-4-yl)-1-phenylethyl]carbamoyl}-[1,1'-biphenyl]-2-carboxylic acid;

(S)-2'-(1H-1,3-benzodiazol-2-yl)-6'-chloro-4-{[(1 S)-2-ethoxy-1-phenylethyl] carbamoyl}-[1,1'-biphenyl]-2-carboxylic acid;

2'-(1H-1,3-benzodiazol-2-yl)-5'-chloro-4-[(4,4,4-trifluoro-1-phenylbutyl)carbamoyl]-[1,1'-biphenyl]-2-carboxylic acid;

(S)-2'-chloro-4-{[(1R)-1-cyclohexylbutyl] carbamoyl}-6'-(6,7-difluoro-1H-1,3-benzodiazol-2-yl)-[1,1'-biphenyl]-2-carboxylic acid;

(S)-2'-chloro-4-{[(1R)-1-cyclohexylbutyl]carbamoyl}-6'-(6-fluoro-5-methoxy-1H-1,3-benzodiazol-2-yl)-[1,1'-biphenyl]-2-carboxylic acid;

(S)-2'-chloro-6'-(5-chloro-6-fluoro-1H-1,3-benzodiazol-2-yl)-4-{[(1R)-1-cyclohexylbutyl]carbamoyl}-[1,1'-biphenyl]-2-carboxylic acid;

(S)-2'-chloro-4-{[(1R)-1-cyclohexylbutyl]carbamoyl}-6'-(5,6-difluoro-1H-1,3-benzodiazol-2-yl)-[1,1'-biphenyl]-2-carboxylic acid;

(S)-2'-(1H-1,3-benzodiazol-2-yl)-6'-chloro-4-{[1-(2,4,6-trimethylphenyl)butyl] carbamoyl}-[1,1'-biphenyl]-2-carboxylic acid;

(S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid;

(S)-2'-(1H-1,3-benzodiazol-2-yl)-6'-chloro-4-{[1-(4-fluoro-2-methoxyphenyl)butyl]carbamoyl}-[1,1'-biphenyl]-2-carboxylic acid;

(S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid;

(S)-2'-(1H-1,3-benzodiazol-2-yl)-6'-chloro-4-{[1-(3-chlorophenyl)butyl]carbamoyl}-[1,1'-biphenyl]-2-carboxylic acid;

(S)-2'-(1H-1,3-benzodiazol-2-yl)-6'-chloro-4-{[1-(pyridin-4-yl)butyl] carbamoyl}-[1,1'-biphenyl]-2-carboxylic acid;

(S)-2'-(1H-1,3-benzodiazol-2-yl)-6'-chloro-4-{[1-(2-chlorophenyl)butyl] carbamoyl}-[1,1'-biphenyl]-2-carboxylic acid;

(S)-2'-(1H-1,3-benzodiazol-2-yl)-6'-chloro-4-{[1-(4-chloro-2-methoxyphenyl)propyl]carbamoyl}-[1,1'-biphenyl]-2-carboxylic acid;

(S)-2'-(1H-1,3-benzodiazol-2-yl)-6'-chloro-4-{[1-(3-fluorophenyl)butyl]carbamoyl}-[1,1'-biphenyl]-2-carboxylic acid;

(S)-2'-(1H-1,3-benzodiazol-2-yl)-6'-chloro-4-{[1-(4-chlorophenyl)butyl] carbamoyl}-[1,1'-biphenyl]-2-carboxylic acid;

(S)-2'-(1H-1,3-benzodiazol-2-yl)-6'-chloro-4-[(1-cycloheptylbutyl)carbamoyl]-[1,1'-biphenyl]-2-carboxylic acid;

(S)-2'-(1H-1,3-benzodiazol-2-yl)-6'-chloro-4-{[1-(2-fluorophenyl)butyl] carbamoyl}-[1,1'-biphenyl]-2-carboxylic acid;

(S)-2'-(1H-1,3-benzodiazol-2-yl)-6'-chloro-4-{[1-(pyridin-2-yl)butyl] carbamoyl}-[1,1'-biphenyl]-2-carboxylic acid;

(S)-2'-(1H-1,3-benzodiazol-2-yl)-6'-chloro-4-({1-[2-(trifluoromethoxy)phenyl]butyl}carbamoyl)-[1,1'-biphenyl]-2-carboxylic acid;

(S)-2'-(1H-1,3-benzodiazol-2-yl)-6'-chloro-4-[(1-cyclohexylbutyl)carbamoyl]-[1,1'-biphenyl]-2-carboxylic acid;

(S)-2'-(1H-1,3-benzodiazol-2-yl)-6'-chloro-4-{[1-(2-fluoro-6-methoxyphenyl)butyl]carbamoyl}-[1,1'-biphenyl]-2-carboxylic acid;

(S)-2'-(1H-1,3-benzodiazol-2-yl)-6'-chloro-4-{[1-(4-chloro-2-methoxyphenyl)butyl]carbamoyl}-[1,1'-biphenyl]-2-carboxylic acid;

(S)-2'-(1H-1,3-benzodiazol-2-yl)-6'-chloro-4-{[1-(pyridin-2-yl)butyl] carbamoyl}-[1,1'-biphenyl]-2-carboxylic acid;

(S)-2'-(1H-1,3-benzodiazol-2-yl)-6'-chloro-4-({1-[4-chloro-2-(trifluoromethyl)phenyl]butyl}carbamoyl)-[1,1'-biphenyl]-2-carboxylic acid;

(S)-2'-(1H-1,3-benzodiazol-2-yl)-6'-chloro-4-{[1-(4-chloro-2-fluorophenyl)butyl]carbamoyl}-[1,1'-biphenyl]-2-carboxylic acid;

(S)-2'-(1H-1,3-benzodiazol-2-yl)-6'-chloro-4-[(1-cyclopentylbutyl)carbamoyl]-[1,1'-biphenyl]-2-carboxylic acid;

(S)-2'-(1H-1,3-benzodiazol-2-yl)-6'-chloro-4-{[1-(4-chloro-2-fluorophenyl)butyl]carbamoyl}-[1,1'-biphenyl]-2-carboxylic acid;

(S)-2'-(1H-1,3-benzodiazol-2-yl)-6'-chloro-4-{[1-(3-chlorophenyl)butyl]carbamoyl}-[1,1'-biphenyl]-2-carboxylic acid;

(S)-2'-(1H-1,3-benzodiazol-2-yl)-6'-chloro-4-{[1-(1,3-thiazol-5-yl)butyl]carbamoyl}-[1,1'-biphenyl]-2-carboxylic acid;

(S)-2'-(1H-1,3-benzodiazol-2-yl)-6'-chloro-4-{[1-(4-chlorophenyl)butyl] carbamoyl}-[1,1'-biphenyl]-2-carboxylic acid;

(S)-2'-(1H-1,3-benzodiazol-2-yl)-6'-chloro-4-{[1-(pyridin-4-yl)butyl] carbamoyl}-[1,1'-biphenyl]-2-carboxylic acid;

(S)-2'-(1H-1,3-benzodiazol-2-yl)-6'-chloro-4-({1-[2-(trifluoromethyl)phenyl]butyl}carbamoyl)-[1,1'-biphenyl]-2-carboxylic acid;

(S)-2'-(1H-1,3-benzodiazol-2-yl)-6'-chloro-4-{[1-(pyridin-3-yl)butyl]carbamoyl}-[1,1'-biphenyl]-2-carboxylic acid;

(S)-2'-(1H-1,3-benzodiazol-2-yl)-6'-chloro-4-({1-[2-(trifluoromethoxy)phenyl]butyl}carbamoyl)-[1,1'-biphenyl]-2-carboxylic acid;

(S)-2'-(1H-1,3-benzodiazol-2-yl)-6'-chloro-4-{[1-(pyridin-4-yl)butyl] carbamoyl}-[1,1'-biphenyl]-2-carboxylic acid;

(S)-2'-(1H-1,3-benzodiazol-2-yl)-6'-chloro-4-{[1-(pyridin-3-yl)butyl]carbamoyl}-[1,1'-biphenyl]-2-carboxylic acid;

(S)-2'-(1H-1,3-benzodiazol-2-yl)-6'-chloro-4-{[1-(1,3-thiazol-5-yl)butyl]carbamoyl}-[1,1'-biphenyl]-2-carboxylic acid;

(S)-2'-chloro-4-[(1-cyclopentylbutyl)carbamoyl]-6'-(6-fluoro-5-methoxy-1H-1,3-benzodiazol-2-yl)-[1,1'-biphenyl]-2-carboxylic acid;

(S)-2'-chloro-6'-(6-fluoro-5-methoxy-1H-1,3-benzodiazol-2-yl)-4-({1-[2-(trifluoromethyl)phenyl]butyl}carbamoyl)-[1,1'-biphenyl]-2-carboxylic acid;

(S)-2'-chloro-4-{[1-(4-chloro-2-methoxyphenyl)butyl] carbamoyl}-6'-(6-fluoro-5-methoxy-1H-1,3-benzodiazol-2-yl)-[1,1'-biphenyl]-2-carboxylic acid;

(S)-2'-chloro-4-[(1-cyclohexylbutyl)carbamoyl]-6'-(6-fluoro-5-methoxy-1H-1,3-benzodiazol-2-yl)-[1,1'-biphenyl]-2-carboxylic acid;

(S)-2'-chloro-6'-(5-chloro-6-fluoro-1H-1,3-benzodiazol-2-yl)-4-{[1-(pyridin-4-yl)butyl]carbamoyl}-[1,1'-biphenyl]-2-carboxylic acid;
(S)-2'-chloro-4-{[1-(4-chloro-2-methoxyphenyl)butyl]carbamoyl}-6'-(5-chloro-6-fluoro-1H-1,3-benzodiazol-2-yl)-[1,1'-biphenyl]-2-carboxylic acid;
(S)-2'-chloro-6'-(5-chloro-6-fluoro-1H-1,3-benzodiazol-2-yl)-4-{[1-(2,4,6-trimethylphenyl)butyl] carbamoyl}-[1,1'-biphenyl]-2-carboxylic acid;
(S)-2'-chloro-6'-(5-chloro-6-fluoro-1H-1,3-benzodiazol-2-yl)-4-[(1-cycloheptylbutyl)carbamoyl]-[1,1'-biphenyl]-2-carboxylic acid;
methyl 2'-(5-tert-butyl-1H-1,3-benzodiazol-2-yl)-5'-chloro-4-{[1-(2-methoxyphenyl)butyl]carbamoyl}-[1,1'-biphenyl]-2-carboxylate;
(S)-methyl 2'-chloro-4-{[(4-chlorophenyl)(cyclopropyl)methyl] carbamoyl}-6'-(6-fluoro-5-methoxy-1H-1,3-benzodiazol-2-yl)-[1,1'-biphenyl]-2-carboxylate;
(S)-2'-chloro-N-[(4-chlorophenyl)(cyclopropyl)methyl]-6'-(6-fluoro-5-methoxy-1H-1,3-benzodiazol-2-yl)-2-(hydroxymethyl)-[1,1'-biphenyl]-4-carboxamide;
2'-chloro-N4-[(4-chlorophenyl)(cyclopropyl)methyl]-6'-(6-fluoro-5-methoxy-1H-1,3-benzodiazol-2-yl)-N2-methanesulfonyl-[1,1'-biphenyl]-2,4-dicarboxamide;
2'-(1H-1,3-benzodiazol-2-yl)-5'-chloro-4-{[1-(2-methoxyphenyl)butyl]carbamoyl}-[1,1'-biphenyl]-2-carboxylic acid;
2'-(1H-1,3-benzodiazol-2-yl)-5'-chloro-4-{[1-(2-methoxyphenyl)butyl]carbamoyl}-[1,1'-biphenyl]-2-carboxylic acid;
2'-(1H-1,3-benzodiazol-2-yl)-5'-chloro-4-{[1-(4-fluorophenyl)butyl]carbamoyl}-[1,1'-biphenyl]-2-carboxylic acid;
2'-(1H-1,3-benzodiazol-2-yl)-5'-chloro-4-[(3-methyl-1-phenylbutyl)carbamoyl]-[1,1'-biphenyl]-2-carboxylic acid;
2'-(1H-1,3-benzodiazol-2-yl)-5'-chloro-4-{[cyclopropyl(phenyl)methyl]carbamoyl}-[1,1'-biphenyl]-2-carboxylic acid;
2'-(1H-1,3-benzodiazol-2-yl)-5'-chloro-4-[(3,3-dimethyl-1-phenylbutyl)carbamoyl]-[1,1'-biphenyl]-2-carboxylic acid;
2'-(1H-1,3-benzodiazol-2-yl)-5'-chloro-4-{[1-(pyridin-2-yl)propyl]carbamoyl}-[1,1'-biphenyl]-2-carboxylic acid;
2'-(1H-1,3-benzodiazol-2-yl)-5'-chloro-4-{[1-(pyridin-4-yl)propyl]carbamoyl}-[1,1'-biphenyl]-2-carboxylic acid;
2'-(1H-1,3-benzodiazol-2-yl)-5'-chloro-4-{[1-(4-fluorophenyl)butyl]carbamoyl}-[1,1'-biphenyl]-2-carboxylic acid;
2'-(1H-1,3-benzodiazol-2-yl)-5'-chloro-4-{[2-(oxan-4-yl)-1-phenylethyl]carbamoyl}-[1,1'-biphenyl]-2-carboxylic acid;
2'-(1H-1,3-benzodiazol-2-yl)-5'-chloro-4-{[2-(oxan-4-yl)-1-phenylethyl]carbamoyl}-[1,1'-biphenyl]-2-carboxylic acid;
5'-chloro-2'-(5-methoxy-1H-1,3-benzodiazol-2-yl)-4-{[1-(2-methoxyphenyl)butyl]carbamoyl}-[1,1'-biphenyl]-2-carboxylic acid;
(S)-2'-(1H-1,3-benzodiazol-2-yl)-6'-chloro-4-{[cyclopropyl(4-fluorophenyl)methyl]carbamoyl}-[1,1'-biphenyl]-2-carboxylic acid;
(S)-2'-(1H-1,3-benzodiazol-2-yl)-6'-chloro-4-{[cyclopropyl(phenyl)methyl]carbamoyl}-[1,1'-biphenyl]-2-carboxylic acid;
(S)-2'-(1H-1,3-benzodiazol-2-yl)-6'-chloro-4-{[1-(2-methoxyphenyl)butyl]carbamoyl}-[1,1'-biphenyl]-2-carboxylic acid;
(S)-2'-(1H-1,3-benzodiazol-2-yl)-6'-chloro-4-{[1-(4-fluorophenyl)butyl] carbamoyl}-[1,1'-biphenyl]-2-carboxylic acid;
(S)-2'-(1H-1,3-benzodiazol-2-yl)-6'-chloro-4-[(3-methyl-1-phenylbutyl)carbamoyl]-[1,1'-biphenyl]-2-carboxylic acid;
(S)-2'-(1H-1,3-benzodiazol-2-yl)-6'-chloro-4-{[(4-chlorophenyl)(cyclopropyl)methyl]carbamoyl}-[1,1'-biphenyl]-2-carboxylic acid;
(S)-2'-(1H-1,3-benzodiazol-2-yl)-6'-chloro-4-{[1-(2-methoxyphenyl)butyl]carbamoyl}-[1,1'-biphenyl]-2-carboxylic acid;
(S)-2'-(1H-1,3-benzodiazol-2-yl)-6'-chloro-4-[(4,4,4-trifluoro-1-phenylbutyl)carbamoyl]-[1,1'-biphenyl]-2-carboxylic acid;
(S)-2'-(1H-1,3-benzodiazol-2-yl)-6'-chloro-4-{[cyclohexyl(cyclopropyl)methyl]carbamoyl}-[1,1'-biphenyl]-2-carboxylic acid;
(S)-2'-(1H-1,3-benzodiazol-2-yl)-6'-chloro-4-{[1-(4-fluorophenyl)butyl] carbamoyl}-[1,1'-biphenyl]-2-carboxylic acid;
(S)-2'-(1H-1,3-benzodiazol-2-yl)-6'-chloro-4-{[cyclopropyl(phenyl)methyl]carbamoyl}-[1,1'-biphenyl]-2-carboxylic acid;
(S)-2'-(1H-1,3-benzodiazol-2-yl)-6'-chloro-4-[(1-cyclopropyl-2-methoxyethyl)carbamoyl]-[1,1'-biphenyl]-2-carboxylic acid;
(S)-2'-chloro-4-{[(1R)-1-cyclohexylbutyl]carbamoyl}-6'-(5-methoxy-1H-1,3-benzodiazol-2-yl)-[1,1'-biphenyl]-2-carboxylic acid;
(S)-2'-chloro-4-{[cyclopropyl(4-fluorophenyl)methyl] carbamoyl}-6'-(6-fluoro-5-methoxy-1H-1,3-benzodiazol-2-yl)-[1,1'-biphenyl]-2-carboxylic acid;
(S)-2'-chloro-6'-(6-fluoro-5-methoxy-1H-1,3-benzodiazol-2-yl)-4-{[1-(4-fluorophenyl)butyl] carbamoyl}-[1,1'-biphenyl]-2-carboxylic acid;
(S)-2'-chloro-4-{[cyclopropyl(phenyl)methyl]carbamoyl}-6'-(6-fluoro-5-methoxy-1H-1,3-benzodiazol-2-yl)-[1,1'-biphenyl]-2-carboxylic acid;
(S)-2'-chloro-4-{[cyclohexyl(cyclopropyl)methyl]carbamoyl}-6'-(6-fluoro-5-methoxy-1H-1,3-benzodiazol-2-yl)-[1,1'-biphenyl]-2-carboxylic acid;
(S)-2'-chloro-4-{[1-(4-chlorophenyl)butyl]carbamoyl}-6'-(6-fluoro-5-methoxy-1H-1,3-benzodiazol-2-yl)-[1,1'-biphenyl]-2-carboxylic acid;
(S)-2'-chloro-4-{[(4-chlorophenyl)(cyclopropyl)methyl] carbamoyl}-6'-(6-fluoro-5-methoxy-1H-1,3-benzodiazol-2-yl)-[1,1'-biphenyl]-2-carboxylic acid;
(S)-2'-chloro-6'-(6-fluoro-5-methoxy-1H-1,3-benzodiazol-2-yl)-4-{[1-(2-methoxyphenyl)butyl]carbamoyl}-[1,1'-biphenyl]-2-carboxylic acid;
(S)-2'-chloro-6'-(6-chloro-5-fluoro-1H-1,3-benzodiazol-2-yl)-4-{[1-(4-chlorophenyl)butyl]carbamoyl}-[1,1'-biphenyl]-2-carboxylic acid;
(S)-2'-chloro-6'-(6-chloro-5-fluoro-1H-1,3-benzodiazol-2-yl)-4-{[(4-chlorophenyl)(cyclopropyl)methyl]carbamoyl}-[1,1'-biphenyl]-2-carboxylic acid; and
2'-(5-tert-butyl-1H-1,3-benzodiazol-2-yl)-5'-chloro-4-{[1-(2-methoxyphenyl)butyl]carbamoyl}-[1,1'-biphenyl]-2-carboxylic acid.

13. A pharmaceutical composition comprising a pharmaceutically acceptable carrier and a compound of claim 1.

14. A method of treating cardiovascular diseases comprising administering to a patient in need there of a therapeutically effective amount of the pharmaceutical composition of claim 13.

15. The method of claim 14 wherein said cardiovascular disease is selected from coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, and valvular heart diseases.

\* \* \* \* \*

UNITED STATES PATENT AND TRADEMARK OFFICE
CERTIFICATE OF CORRECTION

PATENT NO.         : 11,498,903 B2                    Page 1 of 1
APPLICATION NO.    : 16/639145
DATED              : November 15, 2022
INVENTOR(S)        : Shun Su et al.

It is certified that error appears in the above-identified patent and that said Letters Patent is hereby corrected as shown below:

In the Claims

In Claim 9, Column 190, Lines 56-62, delete " 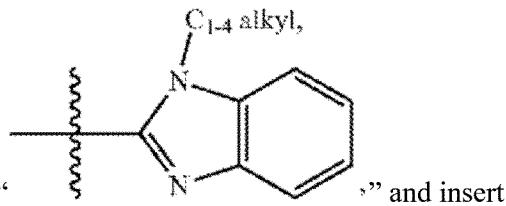 " and insert

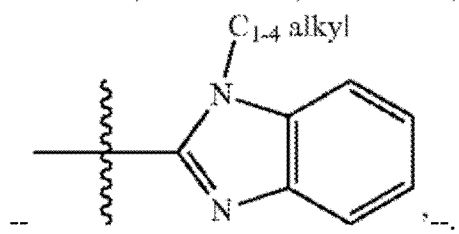

--.

In Claim 12, Column 192, Line 1, delete "compound" and insert -- compound, --.

In Claim 12, Column 194, Line 5, delete "[1'-" and insert -- [1,1'- --.

In Claim 12, Column 194, Line 13, delete "-2'[5-" and insert -- -2'-[5- --.

In Claim 12, Column 194, Line 26, delete "[1'-" and insert -- [1,1'- --.

In Claim 12, Column 194, Line 31, delete "[1'-" and insert -- [1,1'- --.

In Claim 12, Column 194, Line 45, delete "[1'-" and insert -- [1,1'- --.

In Claim 12, Column 197, Line 29, delete "]-[" and insert -- ] --.

In Claim 12, Column 197, Line 30, delete "[5-" and insert -- (5- --.

Signed and Sealed this
Sixth Day of June, 2023

Katherine Kelly Vidal
*Director of the United States Patent and Trademark Office*